US012644891B2

(12) United States Patent
Graige et al.

(10) Patent No.: US 12,644,891 B2
(45) Date of Patent: Jun. 2, 2026

(54) DETERMINATION OF PROTEIN INFORMATION BY RECODING AMINO ACID POLYMERS INTO DNA POLYMERS

(71) Applicant: ABRUS BIO, INC., San Diego, CA (US)

(72) Inventors: Michael Graige, Cardiff by the Sea, CA (US); Christopher MacDonald, San Diego, CA (US)

(73) Assignee: Abrus Bio, Inc., San Diego, CA (US)

( * ) Notice: Subject to any disclaimer, the term of this patent is extended or adjusted under 35 U.S.C. 154(b) by 0 days.

(21) Appl. No.: 18/677,070

(22) Filed: May 29, 2024

(65) Prior Publication Data

US 2025/0052760 A1 Feb. 13, 2025

Related U.S. Application Data

(63) Continuation of application No. 18/365,129, filed on Aug. 3, 2023, now Pat. No. 12,038,443, which is a continuation of application No. PCT/US2023/070077, filed on Jul. 12, 2023.

(60) Provisional application No. 63/467,729, filed on May 19, 2023, provisional application No. 63/439,523, filed on Jan. 17, 2023, provisional application No. 63/399,294, filed on Aug. 19, 2022, provisional application No. 63/388,317, filed on Jul. 12, 2022.

(51) Int. Cl.

| | |
|---|---|
| ***G01N 33/68*** | (2006.01) |
| ***C12Q 1/68*** | (2018.01) |
| ***C12Q 1/6804*** | (2018.01) |
| ***C12Q 1/6869*** | (2018.01) |
| ***G01N 33/58*** | (2006.01) |

(52) U.S. Cl.
CPC ....... *G01N 33/6803* (2013.01); *C12Q 1/6804* (2013.01); *C12Q 1/6869* (2013.01); *G01N 33/58* (2013.01); *G01N 33/6824* (2013.01); *G01N 2458/10* (2013.01)

(58) Field of Classification Search
CPC ............... G01N 33/6803; G01N 33/58; G01N 33/6824; G01N 2458/10; C12Q 1/6804; C12Q 1/6869
See application file for complete search history.

(56) References Cited

U.S. PATENT DOCUMENTS 7,611,834 B2 11/2009 Chhabra et al.
10,287,576 B2 5/2019 Franch et al.
(Continued)

FOREIGN PATENT DOCUMENTS

AU 2018204665 B2 5/2020
CN 112272703 A 1/2021
(Continued)

OTHER PUBLICATIONS (Retrieved Date: Apr. 4, 2024) "4-Azidophenyl Isothiocyanate", Bench Chem, 13 Pages.
(Continued)

*Primary Examiner* — Jezia Riley
(74) *Attorney, Agent, or Firm* — Mintz Levin Cohn Ferris Glovsky and Popeo, P.C.

(57) ABSTRACT

The present disclosure relates to compositions of matter, methods, and systems for analyzing polymeric macromolecules, including polymeric macromolecules such as peptides, polypeptides, and proteins.

19 Claims, 56 Drawing Sheets

Specification includes a Sequence Listing.

(56) References Cited

U.S. PATENT DOCUMENTS

| | | | | |
|---|---|---|---|---|
| 10,697,974 | B2 | 6/2020 | Woo et al. | |
| 10,852,305 | B2 | 12/2020 | Havranek et al. | |
| 11,118,215 | B2 | 9/2021 | Thisted et al. | |
| 11,499,979 | B2 | 11/2022 | Estandian et al. | |
| 11,513,126 | B2 | 11/2022 | Chee et al. | |
| 12,038,443 | B2 | 7/2024 | Graige et al. | |
| 12,188,940 | B2 | 1/2025 | Graige et al. | |
| 12,474,347 | B2 | 11/2025 | Graige et al. | |
| 2014/0273004 | A1 | 9/2014 | Havranek et al. | |
| 2018/0208983 | A1* | 7/2018 | Dambacher | C12Q 1/6806 |
| 2020/0199666 | A1* | 6/2020 | Gatti-Lafranconi | C12Q 1/6869 |
| 2020/0348307 | A1 | 11/2020 | Beierle et al. | |
| 2020/0385432 | A1 | 12/2020 | Tullman et al. | |
| 2021/0079557 | A1 | 3/2021 | Pawlosky et al. | |
| 2021/0147474 | A1 | 5/2021 | Dyer et al. | |
| 2022/0348990 | A1 | 11/2022 | Kishi et al. | |
| 2023/0016396 | A1 | 1/2023 | Gunderson et al. | |
| 2023/0107647 | A1 | 4/2023 | Marcotte et al. | |
| 2023/0193248 | A1 | 6/2023 | Suastegui et al. | |
| 2023/0203562 | A1 | 6/2023 | Okerberg et al. | |
| 2023/0220589 | A1 | 7/2023 | Gunderson et al. | |
| 2023/0236198 | A1 | 7/2023 | Chee et al. | |
| 2023/0305017 | A1 | 9/2023 | Estandian et al. | |
| 2024/0044909 | A1 | 2/2024 | Graige et al. | |
| 2024/0158829 | A1 | 5/2024 | Chee et al. | |
| 2024/0210410 | A1 | 6/2024 | Graige et al. | |
| 2025/0020657 | A1 | 1/2025 | Graige et al. | |

FOREIGN PATENT DOCUMENTS

| | | | |
|---|---|---|---|
| WO | 2010065322 | A1 | 6/2010 |
| WO | 2017192633 | A1 | 11/2017 |
| WO | 2019089836 | A1 | 5/2019 |
| WO | 2019089851 | A1 | 5/2019 |
| WO | 2020146325 | A1 | 7/2020 |
| WO | 2021236716 | A2 | 11/2021 |
| WO | 2022015600 | A2 | 1/2022 |
| WO | 2022132188 | A1 | 6/2022 |
| WO | 2023019148 | A1 | 2/2023 |
| WO | 2023019163 | A1 | 2/2023 |
| WO | 2023114732 | A2 | 6/2023 |
| WO | 2023122698 | A1 | 6/2023 |
| WO | 2023196642 | A1 | 10/2023 |
| WO | 2024015875 | A2 | 1/2024 |
| WO | 2024040236 | A2 | 2/2024 |
| WO | 2024107755 | A1 | 5/2024 |
| WO | 2024159162 | A1 | 8/2024 |
| WO | 2024178395 | A1 | 8/2024 |

OTHER PUBLICATIONS

International Application No. PCT/US2023/070077, Protein recoding & sequencing, filed on Jul. 12, 2023, 1 page.
International Search Report and Written Opinion for International Application No. PCT/US2023/072498, mailed on Mar. 15, 2024, 19 pages.
International Search Report and Written Opinion issued in International Application No. PCT/US2023/070077, mailed on Jan. 23, 2024, 14 pages.
(2018) "Safety Data Sheet", Axis Pharm, 1 page.
Bailey et al. (Jan. 1992) "Automated Carboxy-Terminal Sequence Analysis of Peptides", Protein Science, 1(1):68-80.
Borgo et al. (Apr. 2015) "Computer-aided Design of a Catalyst for Edman Degradation Utilizing Substrate-assisted Catalysis", Protein Science, 24(4):571-579.
Chelius et al. (2003) "Capture of Peptides with N-Terminal Serine and Threonine: A Sequence-Specific Chemical Method for Peptide Mixture Simplification", Bioconjugate Chemistry, 14(1):205-211.
Crook et al. (Apr. 2022) "Challenges and Opportunities for Bayesian Statistics in Proteomics", Journal of Proteome Research, 21(4):849-864.
Database GenBank, "Aminopeptidase From Aeromonasproteolytic A", CAS No. 37288-67-8, 2 pages.
Database GenBank, "Product information "Amino-Modifier C6 dT"", CAS No. 178925-21-8, 4 pages.
Davis et al. (Jun. 2013) "DNA Double Strand Break Repair via Non-Domologous End-Joining", Translational Cancer Research, 2(3):130-143.
Dupont et al. (2000) "The Alkylated Thiohydantoin Method for C-Terminal Sequence Analysis", EXS, 88:119-131.
Gee et al. (1998) "Synthesis, Photochemistry, and Biological Characterization of Photolabile Protecting Groups for Carboxylic Acids and Neurotransmitters", Methods in Enzymology, 291:30-50.
Grzybowski et al. (1993) "Synthesis and Antibody-mediated Detection of Oligonucleotides Containing Multiple 2,4-dinitrophenyl Reporter Groups", Nucleic Acids Res, 21(8):1705-1712.
Gunderson et al. (2004) "Decoding Randomly Ordered DNA Arrays", Genome Research, 14:870-877.
Hong et al. (2009) "Analysis and Optimization of Copper-catalyzed Azide-Alkyne Cydoaddition for Bioconjugation", Angewandte Chemie, 48(52):9879-9883.
Klayman et al. (1979) "2-Acetylpyridine Thiosemicarbazones. 2. N4, N4-Disubstituted Derivatives as Potential Antimalarial Agents", Journal of Medicinal Chemistry, 22(11):1367-1373.
Kluger et al. (2004) "Chemical Cross-Linking and Protein-Protein Interactions—A Review with Illustrative Protocols", Bioorganic chemistry, 32(6):451-472.
Knall et al. (Oct. 20, 2016) "A Trifunctional Linker Suitable for Conducting Three Orthogonal Click Chemistries in One Pot", Organic & Biomolecular Chemistry, 14:10576-10580.
Laursen et al. (1977) "Coupling Methods and Strategies in Solid-Phase Sequencing", Advanced Methods in Protein Sequence Determination, 21-37.
Lohman et al. (2016) "A High-Throughput Assay for the Comprehensive Profiling of DNA Ligase Fidelity", Nucleic Acids Research, 44(2):e14 (11 pages).
Muller, M. Manuel (Jan. 16, 2018) "Post-Translational Modifications of Protein Backbones: Unique Functions, Mechanisms, and Challenges", Biochemistry, 57(2):177-185.
Okuno et al. (Jun. 27, 2000) "Folding Character of Cytochrome c Studied by o-Nitrobenzyl Modification of Methionine 65 and Subsequent Ultraviolet Light Irradiation", Biochemistry, 39(25):7538-7545.
Palm Iero et al. (Aug. 19, 2016) "The Raft Copolymerization of Acrylic Acid and Acrylamide", Polymer, 98:156-164.
Pirrung et al. (Dec. 1992) "Synthesis of Photodeprotectable Serine Derivatives. "Caged Serine"", Bioorganic & Medicinal Chemistry Letters, 2(12):1489-1492.
Poplawski et al. (2009) "[Non-Homologous DNA End Joining—New Proteins, New Functions, New Mechanisms]", Postepy Biochemii, 55(1):36-45.
Presolski et al. (Dec. 1, 2011) "Copper-Catalyzed Azide-Alkyne Click Chemistry for Bioconjugation", Current Protocols in Chemical Biology, 3(4):153-162.
Raza et al. (Jan. 18, 2018) "A Review on Recent Advances in Stabilizing Peptides/Proteins upon Fabrication in Hydrogels from Biodegradable Polymers", Pharmaceutics, 10(1):16 (21 pages).
Saiki et al. (1989) "Genetic Analysis of Amplified DNA with Immobilized Sequence-Specific Oligonucleotide Probes", Proceedings of the National Academy of Sciences, 86(16):6230-6234.
Shamsi et al. (Oct. 1, 2011) "Characterization of Peptide Immobilization on an Acetylene Terminated Surface via Click Chemistry", Surface Science, 605(19-20):1763-1770.
Shashkova et al. (2017) "Single-Molecule Fluorescence Microscopy Review: Shedding New Light on Old Problems", Bioscience Reports, 37(4):BSR20170031 (19 pages).
Tatsu et al. (Oct. 23, 1996) "Solid-Phase Synthesis of Caged Peptides Using Tyrosine Modified with a Photodeavable Protecting Group: Application to the Synthesis of Caged Neuropeptide Y", Biochemical and Biophysical Research Communications, 227(3):688-693.
Tatsu et al. (Aug. 19, 1999) "Synthesis of Caged Peptides Using Caged Lysine: Application to the Synthesis of Caged AIP, A Highly

(56) References Cited

OTHER PUBLICATIONS

Specific Inhibitor of Calmodulin-dependent Protein Kinase II", Bioorganic & Medicinal Chemistry Letters, 9(8):1093-1096.
Watts et al. (Jun. 2009) "Studies on the Hydrolytic Stability of 2'-Fluoroarabinonucleic Acid (2'F-ANA)", Organic & Bimolecular Chemistry, 7(9):1904-1910.
Ionov, Leonid (Dec. 2014) "Hydrogel-based Actuators: Possibilities and Limitations", Materials Today, 17(10):494-503.
Matsudaira, Paul (1993) "A Practical Guide to Protein and Peptide Purification for Microsequencing", Second Edition, 104-123.

* cited by examiner

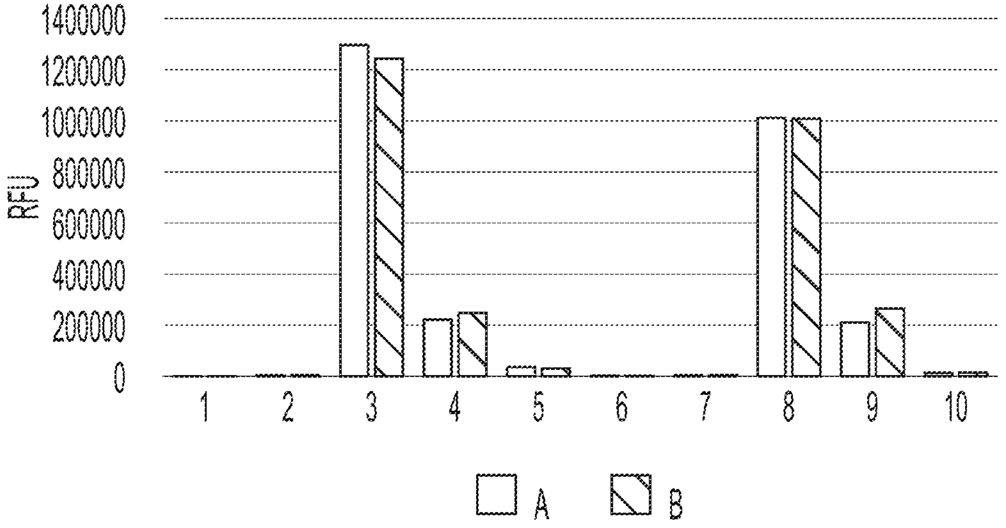

| Label | Sample |
|---|---|
| 1 | Bead Fluorescence after peptide immobilization |
| 2 | Wash supernatant after AF546 Sys1 SOC complement hyb |
| 3 | Beads after AF546 Sys1 SOC complement hyb |
| 4 | Dehybe solution from Sys1 SOC complement hyb |
| 5 | Beads after dehybridization of Sys1 SOC complement |
| 6 | Beads after PPO-Sys3 immobilization |
| 7 | Wash supernatant after TET Sys3 SOC complement hybe |
| 8 | Beads after TET Sys3 SOC complement hyb |
| 9 | Dehybe solution from Sys3 SOC complement hyb |
| 10 | Beads after dehybridization of Sys3 SOC complement |

FIG. 20A

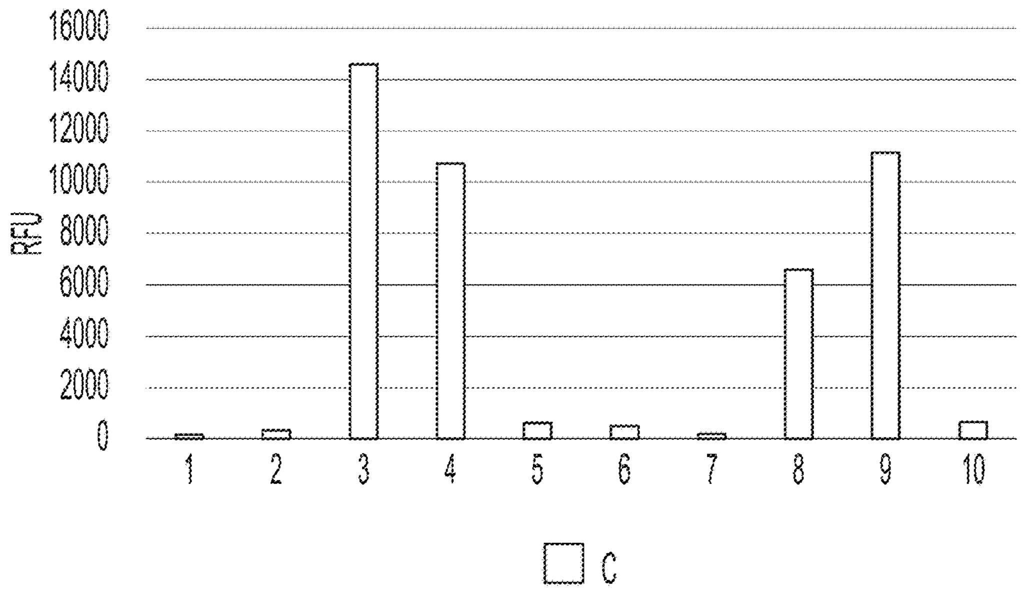

| Label | Sample |
|---|---|
| 1 | Bead Fluorescence after peptide immobilization |
| 2 | Wash supernatant after AF546 Sys1 SOC complement hyb |
| 3 | Beads after AF546 Sys1 SOC complement hyb |
| 4 | Dehybe solution from Sys1 SOC complement hyb |
| 5 | Beads after dehybridization of Sys1 SOC complement |
| 6 | Beads after PPO-Sys3 immobilization |
| 7 | Wash supernatant after TET Sys3 SOC complement hybe |
| 8 | Beads after TET Sys3 SOC complement hyb |
| 9 | Dehybe solution from Sys3 SOC complement hyb |
| 10 | Beads after dehybridization of Sys3 SOC complement |

FIG. 20B

LCMS confirming identity of a trifunctional molecule

Molecular Biology *in situ*

| Sample |
|---|
| ladder dsDNA 1:10 dilution |
| Reaction "Both" products, no dilution |
| Reaction "LO1 only" products, no dilution |
| Reaction "LO2 only" products, no dilution |
| Reaction "Both" mix without T4 ligase (negative control), no dilution |
| Reaction mix with SOC no-tether, no dilution |

PDA

PDON

PPO

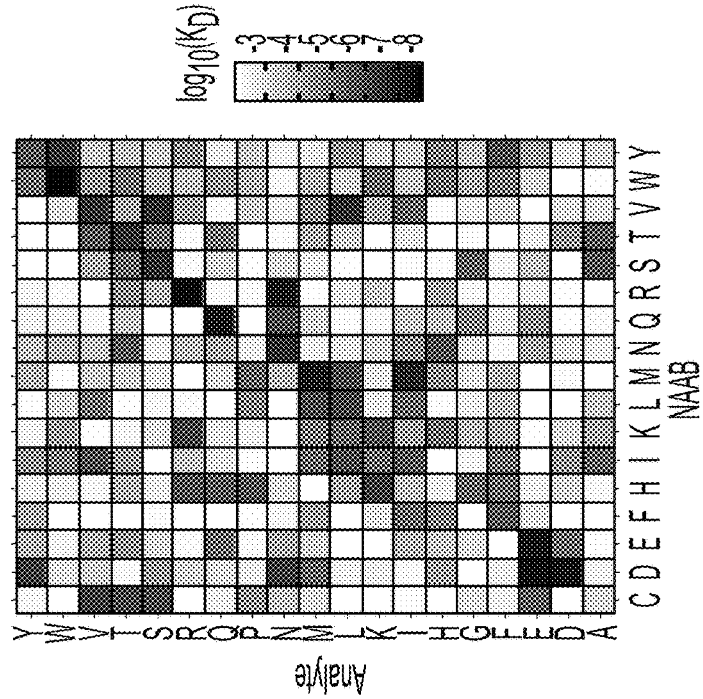
FIG. 36A
| | | |
|---|---|---|
| Original sequence: | MEAGGFLDSL | (SEQ ID NO: 68) |
| Mutated sequence: | MESSQHVDSI | (SEQ ID NO: 69) |
| Closest match: | MEAGGFLDSL | (SEQ ID NO: 68) |
| Second closest match: | MIASQFLSAL | (SEQ ID NO: 70) |
| Original sequence: | METLSQDSLL | (SEQ ID NO: 71) |
| Mutated sequence: | METVVQDSVV | (SEQ ID NO: 72) |
| Closest match: | METLSQDSLL | (SEQ ID NO: 71) |
| Second closest match: | METLLGVSLV | (SEQ ID NO: 73) |
FIG. 36C
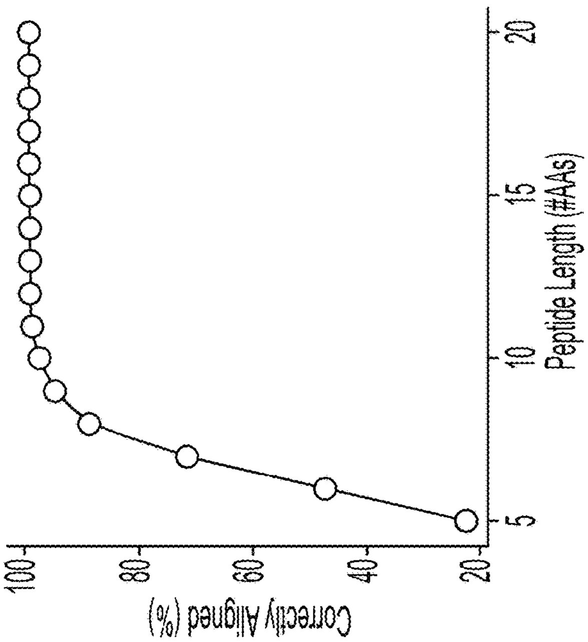
FIG. 36B
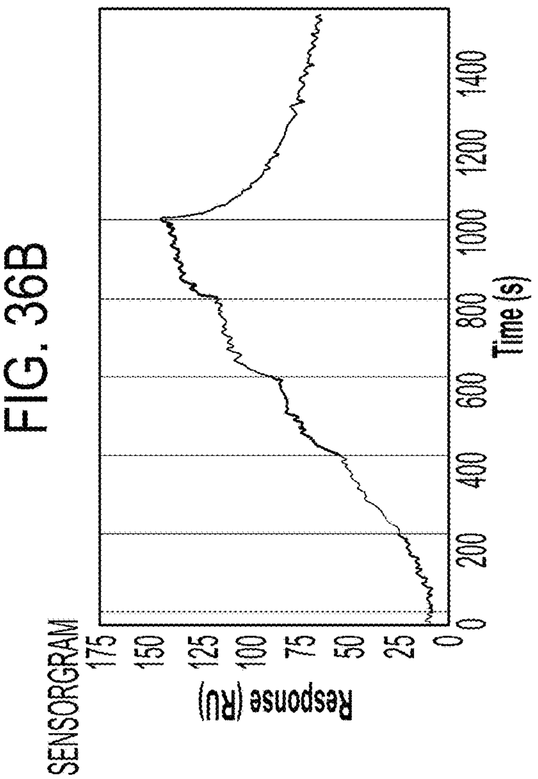
FIG. 36D

DETERMINATION OF PROTEIN INFORMATION BY RECODING AMINO ACID POLYMERS INTO DNA POLYMERS

CROSS-REFERENCE

This application is a continuation of U.S. application Ser. No. 18/365,129 filed Aug. 3, 2023, which is a continuation of PCT Application No. PCT/US2023/070077 filed Jul. 12, 2023, which claims the benefit of U.S. Provisional Application Nos. 63/388,317 filed Jul. 12, 2022, 63/399,294 filed Aug. 19, 2022, 63/439,523 filed Jan. 17, 2023, and 63/467,729 filed May 19, 2023, which applications are incorporated herein by reference.

SEQUENCE LISTING

The instant application contains a Sequence Listing which has been submitted electronically in XML format and is hereby incorporated by reference in its entirety. Said XML copy, created on May 23, 2024, is named 062954-501C03US_SL.xml and is 119,163 bytes in size.

FIELD

The present disclosure relates to compositions of matter, methods, and systems for analyzing polymeric macromolecules, including polymeric macromolecules such as peptides, polypeptides, and proteins.

BACKGROUND

Proteins are fundamental to cellular function. Accordingly, the sequences of the thousands of proteins within each cell, as well as their concentrations, are critical indicators of cell health. Aberrant sequences or concentrations of proteins may signal a disease state. However, tools and technologies are currently lacking for sensitive, accurate, economical, and unbiased characterization of proteomes. Early detection of unusual sequences and/or concentrations is critical to the diagnosis and treatment of many diseases, such as, e.g., cancer. For these and other reasons, better tools to evaluate protein and peptide sequence and concentration in biological samples should be developed.

Once such tools are available, discovery of novel biomarkers, accurate determination of concentrations for even the lowest-abundance proteins, discovery of important post-translational modifications, and monitoring of the dynamics of the proteome are some of the first steps toward improving healthcare. These initial steps toward deeper understanding and earlier detection of important signatures of cancer and other health conditions will allow diagnosis at the earliest stages, facilitate therapeutic discovery, and create beneficial impact on patient care by informing the course of treatment.

There is thus a need in the art for compositions of matter, methods, and systems for highly-parallelized, accurate, sensitive, and high-throughput proteomic analysis. The present disclosure addresses this and other needs.

SUMMARY

The present disclosure relates to compositions of matter, methods, and systems for analyzing polymeric macromolecules, including peptides, polypeptides, and proteins, in a highly-parallel and high-throughput manner via recoding their sequences into DNA polymers.

Disclosed herein, in some embodiments, are methods for determining identity and positional information of an amino acid residue of a peptide coupled to a solid support, the method comprising: (a) providing the peptide to the solid support, the peptide coupled to the solid support such that a N-terminal amino acid residue of the peptide is not directly coupled to the solid support and is exposed to reaction conditions; (b) providing a chemically-reactive conjugate, the chemically-reactive conjugate comprising: (x) a cycle tag comprising a cycle nucleic acid associated with a cycle number, (y) a reactive moiety for binding the N-terminal amino acid residue of the peptide, and (z) an immobilizing moiety for immobilization to the solid support; (c) contacting the peptide with the chemically-reactive conjugate, thereby coupling the chemically-reactive conjugate to the N-terminal amino acid of the peptide to form a conjugate complex; (d) immobilizing the conjugate complex to the solid support via the immobilizing moiety; (e) cleaving and thereby separating the N-terminal amino acid residue from the peptide, thereby providing an immobilized amino acid complex, the immobilized amino acid complex comprising the cleaved and separated N-terminal amino acid residue; (f) contacting the immobilized amino acid complex with a binding agent, the binding agent comprising: a binding moiety for preferentially binding to the immobilized amino acid complex, and a recode tag comprising a recode nucleic acid corresponding with the binding agent, thereby forming an affinity complex, the affinity complex comprising an immobilized amino acid complex and the binding agent and thereby bringing the cycle tag into proximity with the recode tag within the affinity complex; (g) transferring information of the recode nucleic acid to the cycle nucleic acid of the immobilized conjugate complex to generate a recode block; (j) obtaining sequence information of the recode block; and (k) based on the obtained sequence information, determining identity and positional information of an amino acid residue of the peptide. In some embodiments, cleaving the N-terminal amino acid residue from the peptide exposes a next amino acid residue as a N-terminal amino acid residue on the cleaved peptide. In some embodiments, the reactive moiety of the chemically-reactive conjugate cleaves the N-terminal amino acid residue from the peptide. Some embodiments include repeating steps (b) through (k) for each subsequent amino acid of the peptide. Some embodiments include washing the immobilized amino acid complex before said contacting the immobilized amino acid complex with a binding agent. Some embodiments include determining a likely three-dimensional structure of the peptide based on the sequence information. In some embodiments, the recode nucleic acid comprises DNA or RNA. In some embodiments, the cycle nucleic acid comprises DNA or RNA. In some embodiments, obtaining the sequence information for the recode block comprises performing sequencing. In some embodiments, the binding moiety comprises a peptide, antibody, antibody fragment, or antibody derivative. In some embodiments, the binding moiety comprises an aptamer. In some embodiments, the binding moiety binds to a natural amino acid, a post-translationally modified amino acid, a derivatized version of an amino acid, a derivatized or stabilized version of a post-translationally modified amino acid, a synthetic amino acid, an amino acid with a specific side chain, an amino acid with a phosphorylated side chain, an amino acid with a glycosylated side chain, an amino acid with a methylation modification, or a D-amino acid, or binds to a combination thereof. In some embodiments, the solid support comprises a bead, a plate, or a chip. In some embodiments, the solid support comprises glass slide, silica, a resin, a gel, a membrane, polystyrene, a metal, nitrocellulose, a mineral, plastic, polyacrylamide, latex, or ceramic. In some embodiments, the peptide comprises a hormone, neurotransmitter, enzyme, antibody, viral protein, bacterial protein, synthetic peptide, bioactive peptide, peptide hormone, oligopeptide, polypeptide, fusion protein, cyclic peptide, branched peptide, recombinant protein, tumor marker, therapeutic peptide, antigenic peptide, or signaling peptide. In some embodiments, the peptide is derived from a cell lysate, blood sample, plasma sample, serum sample, tissue biopsy, saliva sample, urine sample, cerebrospinal fluid sample, sweat sample, synovial fluid sample, fecal sample, gut microbiome sample, environmental water sample, soil sample, bacterial culture, viral culture, organoid, tumor biopsy, sputum sample, or hair sample. In some embodiments, the peptide is associated with a disease. In some embodiments, said transferring information comprises performing nucleic acid amplification, enzymatic ligation, splint ligation, chemical ligation, template-assisted ligation, use of a ligase enzyme, use of a splint oligonucleotide, use of a catalyst, use of a bridging molecule, use of a condensation agent, use of a coupling reagent, use of a polymerase enzyme, use of a complementary nucleic acid sequence, use of a nicking enzyme, use of a nucleic acid modifying enzyme, use of a recombinase, use of a strand-displacing polymerase, use of a single-strand binding protein, a click chemistry reaction, a phosphodiester bond formation, or a peptide nucleic acid-mediated ligation. In some embodiments, the information of the recode nucleic acid comprises a sequence of the recode nucleic acid or a reverse complement of the sequence of the recode nucleic acid. In some embodiments, said transferring information comprises joining the recode nucleic acid or a reverse complement of the recode nucleic acid with the cycle nucleic acid.

Disclosed herein, in some embodiments, are methods for determining identity and positional information of a plurality of amino acid residues of a peptide, the peptide comprising n amino acid residues, the method comprising: (a) coupling the peptide to a solid support such that a N-terminal amino acid residue of the peptide is not directly coupled to the solid support and is exposed to reaction conditions; (b) providing a chemically-reactive conjugate, the chemically-reactive conjugate comprising: (x) a cycle tag comprising a cycle nucleic acid associated with a cycle number, (y) a reactive moiety for binding and cleaving the N-terminal amino acid residue of the peptide and exposing a next amino acid residue as a N-terminal amino acid residue on the cleaved peptide, and (z) an immobilizing moiety for immobilization to the solid support; (c) contacting the peptide with the chemically-reactive conjugate, thereby coupling the chemically-reactive conjugate to the N-terminal amino acid of the peptide to form a conjugate complex; (d) immobilizing the conjugate complex to the solid support via the immobilizing moiety; (e) cleaving and thereby separating the N-terminal amino acid residue from the peptide, thereby exposing the next amino acid residue as a N-terminal amino acid residue on the cleaved peptide and providing an immobilized amino acid complex, the immobilized amino acid complex comprising the cleaved and separated N-terminal amino acid residue; (f) repeating (b) through (e) n−1 times to assemble n−1 additional immobilized amino acid complexes, each additional immobilized amino acid complex comprising a nucleic acid associated with cycle 2 to n, accordingly; (g) contacting the immobilized amino acid complexes with a binding agent, the binding agent comprising: a binding moiety for preferentially binding to one or to a subset of the immobilized amino acid complexes, and a recode tag comprising a recode nucleic acid corresponding with the binding agent, thereby forming one or more affinity complexes, each affinity complex comprising an immobilized amino acid complex and the binding agent and thereby bringing a cycle tag into proximity with a recode tag within each formed affinity complex; (h) within each formed affinity complex, joining a cycle tag or a reverse complement thereof to a recode tag to form a recode block, thereby creating a plurality of recode blocks, each recode block corresponding with a formed affinity complex; (i) joining two or members of the plurality of recode blocks to form a memory oligonucleotide; (j) obtaining sequence information for the memory oligonucleotide; and (k) based on the obtained sequence information, determining identity and positional information of a plurality of amino acid residues of the peptide. In some embodiments, (g)-(h) are repeated 2, 3, 4, or more times. In some embodiments, n is an integer greater than or equal to 2. In some embodiments, each binding agent comprises recode tags with a unique nucleic acid sequence. In some embodiments, a plurality of binding agents comprises recode tags with the same nucleic acid sequence. In some embodiments, the binding agents comprises recode tags which have a unique sequence portion and a common sequence portion. Some embodiments include deprotecting the cycle tag between (f) and (g).

Some embodiments include washing the immobilized amino acid complex before said contacting the immobilized amino acid complexes with a binding agent. Some embodiments include determining a likely three-dimensional structure of the peptide based on the sequence information. In some embodiments, the recode nucleic acid comprises DNA. In some embodiments, the cycle nucleic acid comprises DNA. Some embodiments that include obtaining the sequence information for the memory oligonucleotide compris performing sequencing. In some embodiments, the binding moiety comprises an antibody or a fragment thereof. In some embodiments, the binding moiety binds to a natural amino acid, a derivatized amino acid, a synthetic amino acid, or a D-amino acid. In some embodiments, the binding moiety binds to a post-translationally modified amino acid. In some embodiments, the solid support comprises a bead, a plate, or a chip. In some embodiments, the solid support comprises glass slide, silica, a resin, a gel, a membrane, polystyrene, a metal, nitrocellulose, a mineral, plastic, polyacrylamide, latex, or ceramic. In some embodiments, determining the identity and positional information of the plurality of amino acid residues of the peptide comprises determining the identity and positional information of all of the amino acid residues of the peptide. In some embodiments, determining the identity and positional information of the plurality of amino acid residues of the peptide comprises determining the identity and positional information of only a subset of the amino acid residues of the peptide. Some embodiments include identifying the peptide by comparing the identity and positional information of the plurality of amino acid residues to a database.

Disclosed herein, in some embodiments, are chemically-reactive conjugates (CRCs) comprising: (A) a nucleic acid sequence tag; (B) a reactive moiety for binding and cleaving a N-terminal amino acid residue from a peptide; and (C) an immobilizing moiety for immobilization to a solid support. Some embodiments include a CRC represented by Formula I:

(Formula I)

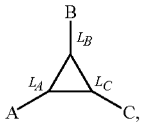

wherein A comprises the cycle tag, B comprises the reactive moiety, C comprises the immobilizing moiety, LA comprises an optional linker, $L_B$, comprises an optional linker, and $L_C$ comprises an optional linker. Some embodiments relate to a CRC of Formula I, wherein A comprises a cycle tag, B comprises a reactive moiety, C comprises an immobilizing moiety, $L_A$ comprises an optional linker, $L_B$, comprises an optional linker, and $L_C$ comprises an optional linker.

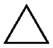

may be or include the central moiety. Some embodiments include a CRC represented by Formula II:

(Formula II)

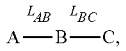

wherein A comprises the cycle tag, B comprises the reactive moiety, C comprises the immobilizing moiety, $L_{AB}$ comprises an optional linker, and $L_{BC}$ comprises an optional linker. Some embodiments relate to a CRC of Formula II, wherein A comprises a cycle tag, B comprises a reactive moiety, C comprises an immobilizing moiety, $L_{AB}$ comprises an optional linker, and $L_{BC}$ comprises an optional linker. In some embodiments, the reactive moiety comprises a phenyl isothiocyanate (PITC), an isothiocyanate (ITC), dansyl chloride, dinitrofluorobenzene (DNFB), an enzyme or peptide, or a combination or derivative thereof. In some embodiments, the reactive moiety specifically cleaves at a specific amino acid. In some embodiments, the reactive moiety cleaves more than a single amino acid or motif. In some embodiments, the immobilizing moiety comprises biotin, streptavidin, a thiol group, an amine group, or a carboxyl group, an azide, an alkyne, an alkene, an aryl boronic acid, an aryl halide, a haloalkyne, a silylalkyne, a Si—H group, a protected or photoprotected reactive group, or a photoactivated reactive group. In some embodiments, the nucleic acid sequence tag generated upon conjugating the nucleic acid sequence to a group for attaching a nucleic acid sequence comprising an oxyamine group, a tetrazine, an azide, an alkyne, an alkene, a trans-cyclooctene, a DBCO, a bicyclononyne, a norbornene, a strained alkyne, or a strained alkene, or a derivative thereof. In some embodiments, the reactive moiety is generated by attaching said reactive moiety to a group on the CRC for attaching the reactive moiety comprising a tetrazine, an azide, an alkene, an alkyne, a trans-cyclooctene, a DBCO, a bicyclononyne, a norbornene, a strained alkyne, or a strained alkene, or a derivative thereof. Some embodiments include a cleavable group between (A) and (B), between (B) and (C), between (A) and (C), between (A) and (B+C), between (B) and (A+C), or between (C) and (A+B), or any combination thereof. Some embodiments include a cleavable group between (A) and (B), between (B) and (C), or a combination thereof. In some embodiments, (A), (B), and (C) are oriented linearly relative to one another in any of the following orders: (A)-(B)—(C), (A)-(C)—(B), or (B)-(A)-(C).

Disclosed herein, in some embodiments, are kits for determining identity and positional information of an amino acid residue of a peptide, comprising: a chemically-reactive conjugate comprising (a) a nucleic acid sequence tag and (b) a reactive moiety that couples to a N-terminal amino acid residue of a peptide, and thereby forms a conjugate complex comprising the chemically-reactive conjugate coupled to the N-terminal amino acid of the peptide; a binding agent comprising a binding moiety for preferentially binding to the conjugate complex, and a recode tag comprising a recode nucleic acid corresponding with the binding agent; and a reagent for transferring information of the recode nucleic acid to the cycle nucleic acid of the conjugate complex to generate a recode block.

Disclosed herein, in some embodiments, are methods for sequencing a subset of the nucleotides of an oligonucleotide, comprising: providing, in a nucleic acid sequencing reaction, a combination reversibly terminated nucleotides and nucleotides that are not reversibly terminated, wherein nucleotides of the nucleic acid being sequenced that correspond with the nucleotides that are not reversibly terminated are not sequenced. Some embodiments include identifying nucleotides of the nucleic acid being sequenced that correspond with the reversibly terminated nucleotides. In some embodiments, the nucleic acid being sequenced comprises a region that includes only a subset of nucleotides selected from A, C, G, and T, and wherein the subset of nucleotides are not sequenced. In some embodiments, the subset of nucleotides selected from A, C, G, and T comprises 2 nucleotides selected from A, C, G, and T. In some embodiments, the subset of nucleotides selected from A, C, G, and T comprises 3 nucleotides selected from A, C, G, and T. In some embodiments, the region comprises a primer sequence. In some embodiments, the region does not include a barcode sequence, recode nucleic acid sequence or a portion thereof, or a cycle nucleic acid sequence or a portion thereof.

Disclosed herein, in some embodiments, are methods, comprising: providing a conjugate comprising a reactive molecule coupled to a protected oligonucleotide; contacting the reactive moiety with a terminal amino acid of a peptide, thereby binding the reactive moiety to the terminal amino acid, and optionally cleaving the terminal amino acid from the peptide; deprotecting the oligonucleotide; and contacting the deprotected oligonucleotide with an enzyme or reagent for ligation or polymerization. Some embodiments include reprotecting the oligonucleotide. In some embodiments, the reactive moiety cleaves the terminal amino acid from the peptide to expose a next terminal amino acid, and wherein the method further comprising contacting the next amino acid with another of the conjugate after reprotecting the oligonucleotide. In some embodiments, the terminal amino acid is N-terminal. In some embodiments, the peptide is immobilized to a solid support. In some embodiments, the conjugate comprises an organic, small molecule. In some embodiments, the conjugate comprises a chemically-reactive conjugate (CRC) comprising: (A) the oligonucleotide; (B) the reactive moiety; and (C) an immobilization moiety. In some embodiments, the oligonucleotide comprises a cycle nucleic acid.

Disclosed herein, in some embodiments, are methods, comprising: providing a conjugate comprising a peptide coupled to a protected oligonucleotide; contacting the terminal amino acid of the peptide, thereby binding a reactive moiety to the terminal amino acid, and optionally cleaving the terminal amino acid from the peptide; deprotecting the oligonucleotide; and contacting the deprotected oligonucleotide with an enzyme or reagent for ligation or polymerization. Some embodiments include reprotecting the oligonucleotide. In some embodiments, the reactive moiety cleaves the terminal amino acid from the peptide to expose a next terminal amino acid, and wherein the method further comprising contacting the next amino acid with another of the conjugate after reprotecting the oligonucleotide. In some embodiments, the terminal amino acid is N-terminal. In some embodiments, the peptide is immobilized to a solid support. In some embodiments, the conjugate comprises an organic, small molecule.

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims. These aspects and other features and advantages of the present disclosure are described below in more detail.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

Accordingly, the foregoing and other features and advantages of the present disclosure will be more fully understood from the following detailed description of illustrative embodiments taken in conjunction with the accompanying drawings in which:

FIG. 20A-20B show PPO functionality. Relative fluorescence units trace binding, cleaving, and immobilization (e.g. steps 1-4 of FIG. 3) by PPO of an N-terminal amino acid residue of an immobilized peptide.

FIG. 36A-36D show example simulations binding of a commercially-available binder to an immobilized PTH-ligand.

It should be understood that the drawings are not necessarily to scale, and that like reference numbers refer to like features. It is contemplated that elements and features of one embodiment may be beneficially incorporated in other embodiments without further recitation.

DETAILED DESCRIPTION

Figure 1:
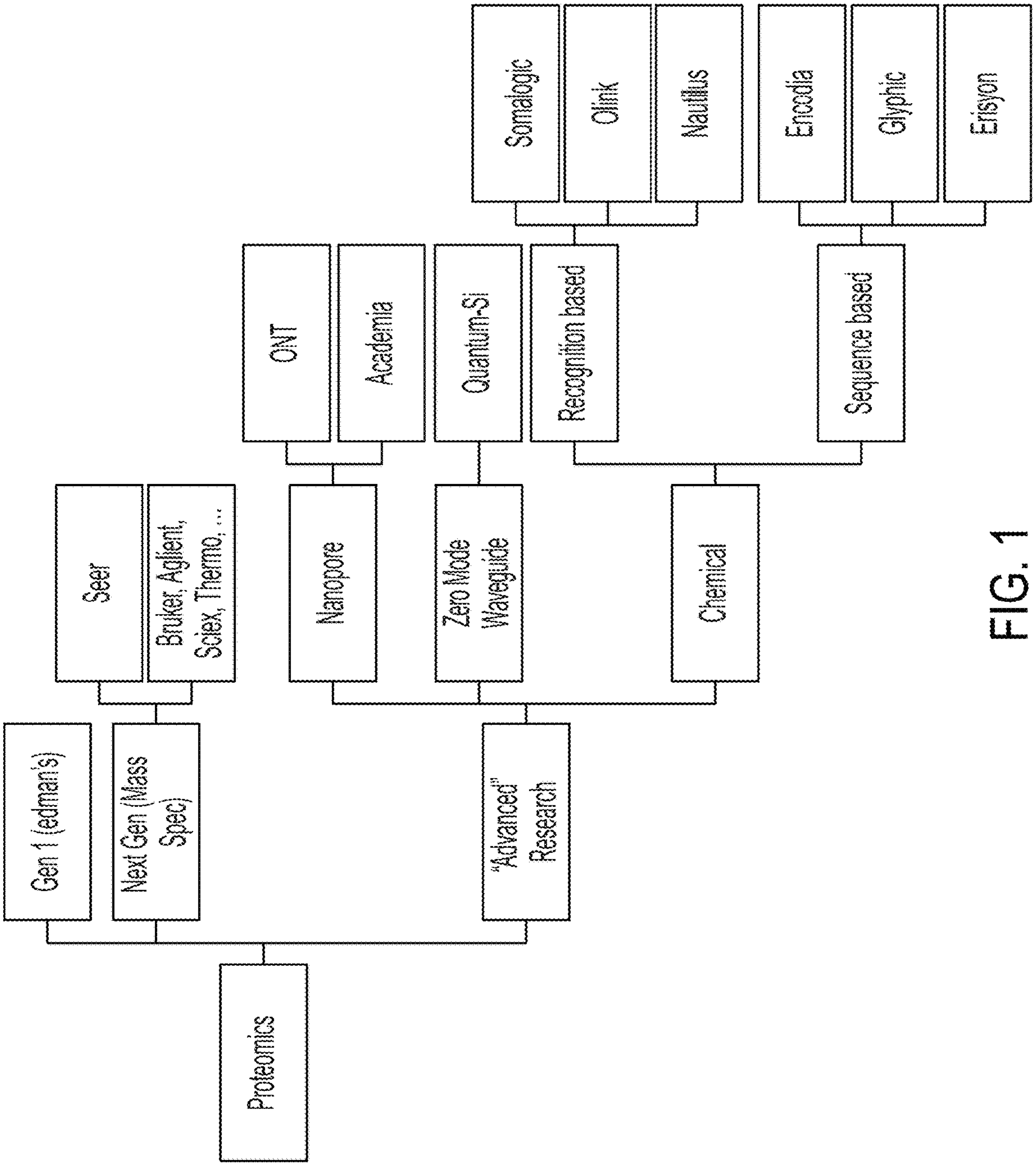
FIG. 1 illustrates an exemplary segmentation of the field of proteomics by technology.

The methods and compositions described herein may be useful for determining identity and positional information of an amino acid residue of a peptide. The peptide may be coupled to a solid support, contacted with a chemically-reactive conjugate which cleaves an N-terminal amino acid of the peptide and couples the N-terminal amino acid to the solid support with a cycle tag. This may then be contacted with a binding agent, such as one specific for the N-terminal amino acid. The binding agent may include a recode tag. The cycle tag and recode tag may include nucleic acid information which may be sequenced to obtain the identity and positional information of the N-terminal amino acid. The process may be repeated for various amino acids of the peptide. Thus, positional and information of amino acid residues of proteins may be recoded using nucleic acids and obtained upon sequencing the nucleic acids.

Disclosed herein, in some embodiments, are methods for determining identity and positional information of an amino acid residue of a peptide coupled to a solid support, the method comprising: (a) providing the peptide to the solid support, the peptide coupled to the solid support such that a N-terminal amino acid residue of the peptide is not directly coupled to the solid support and is exposed to reaction conditions; (b) providing a chemically-reactive conjugate, the chemically-reactive conjugate comprising: (x) a cycle tag comprising a cycle nucleic acid associated with a cycle number, (y) a reactive moiety for binding the N-terminal amino acid residue of the peptide, and (z) an immobilizing moiety for immobilization to the solid support; (c) contacting the peptide with the chemically-reactive conjugate, thereby coupling the chemically-reactive conjugate to the N-terminal amino acid of the peptide to form a conjugate complex; (d) immobilizing the conjugate complex to the solid support via the immobilizing moiety; (e) cleaving and thereby separating the N-terminal amino acid residue from the peptide, thereby providing an immobilized amino acid complex, the immobilized amino acid complex comprising the cleaved and separated N-terminal amino acid residue; (f) contacting the immobilized amino acid complex with a binding agent, the binding agent comprising: a binding moiety for preferentially binding to the immobilized amino acid complex, and a recode tag comprising a recode nucleic acid corresponding with the binding agent, thereby forming an affinity complex, the affinity complex comprising an immobilized amino acid complex and a binding agent and thereby bringing the cycle tag into proximity with the recode tag within the affinity complex; (g) transferring information of the recode nucleic acid to the cycle nucleic acid of the immobilized conjugate complex to generate a recode block; (j) obtaining sequence information of the recode block; and (k) based on the obtained sequence information, determining identity and positional information of an amino acid residue of the peptide. Some embodiments include repeating any or all of steps (b) through (k) for each subsequent amino acid of the peptide.

Disclosed herein, in some embodiments, are methods for determining identity and positional information of an amino acid residue of a peptide coupled to a solid support. The method may include providing the peptide to the solid support. In some embodiments, the peptide is coupled to the solid support, for example such that a N-terminal amino acid residue of the peptide is not directly coupled to the solid support or is exposed to reaction conditions. The method may include providing a chemically-reactive conjugate. The chemically-reactive conjugate may include a cycle tag. The cycle tag may include a cycle nucleic acid associated with a cycle number. The chemically-reactive conjugate may include a reactive moiety. The reactive moiety may be useful for binding the N-terminal amino acid residue of the peptide. The chemically-reactive conjugate may include an immobilizing moiety. The immobilizing moiety may be useful for immobilization to the solid support. The method may include contacting the peptide with the chemically-reactive conjugate. Contacting the peptide with the chemically-reactive conjugate may couple the chemically-reactive conjugate to the N-terminal amino acid of the peptide to form a conjugate complex. The method may include immobilizing the conjugate complex to the solid support, for example via the immobilizing moiety. The method may include cleaving or separating the N-terminal amino acid residue from the peptide. Cleaving or separating the N-terminal amino acid residue from the peptide may provide an immobilized amino acid complex. The immobilized amino acid complex may include the cleaved and separated N-terminal amino acid residue. The method may include contacting the immobilized amino acid complex with a binding agent. The binding agent may include a binding moiety. The binding moiety may be useful for preferentially binding to the immobilized amino acid complex. The binding agent may include a recode tag. The recode tag may include a recode nucleic acid corresponding with the binding agent. Contacting the immobilized amino acid complex with the binding agent may form an affinity complex. The affinity complex may include an immobilized amino acid complex. The affinity complex may include a binding agent. Contacting the immobilized amino acid complex with the binding agent may bring the cycle tag into proximity with the recode tag, for example within the affinity complex. The method may include transferring information of the recode nucleic acid to the cycle nucleic acid. This may generate a recode block. The recode block may be assembled into a memory oligonucleotide. The method may include joining one or more recode blocks created from one or more amino acid residues. The method may include obtaining sequence information of the recode blocks. The method may include obtaining sequence information of the memory oligonucleotide. The method may include, based on the obtained sequence information, determining information of an amino acid residue of the peptide. The information may include identity information. The information may include positional information. In some embodiments, cleaving the N-terminal amino acid residue from the peptide exposes a next amino acid residue as a N-terminal amino acid residue on the cleaved peptide. In some embodiments, the reactive moiety of the chemically-reactive conjugate cleaves the N-terminal amino acid residue from the peptide. Some embodiments include repeating any of the aforementioned steps for each subsequent amino acid of the peptide. In some embodiments, the immobilizing moiety comprises an activatable chemical moiety, alkyne. Some embodiments include joining the chemical moiety to the solid support. In some embodiments, cleaving the N-terminal amino acid residue from the peptide exposes a next amino acid residue as a N-terminal amino acid residue on the cleaved peptide. In some embodiments, the reactive moiety of the chemically-reactive conjugate cleaves the N-terminal amino acid residue from the peptide. Some embodiments include washing away chemically-reactive conjugates that are not joined to the solid support before contacting the next N-terminal amino acid of the peptide with a chemically-reactive complex. Some embodiments include contacting the immobilized amino acid complex with a binding agent to form an affinity complex. Some embodiments include washing the immobilized amino acid complex before said contacting the immobilized amino acid complex with a binding agent. Some embodiments include washing the immobilized amino acid affinity complex after said contacting the affinity complex with one or a set of binding agents.

Disclosed herein, in some embodiments, are methods for determining identity and positional information of a plurality of amino acid residues of a peptide, the peptide comprising n amino acid residues, the method comprising: (a) coupling the peptide to a solid support such that a N-terminal amino acid residue of the peptide is not directly coupled to the solid support and is exposed to reaction conditions; (b) providing a chemically-reactive conjugate, the chemically-reactive conjugate comprising: (x) a cycle tag comprising a cycle nucleic acid associated with a cycle number, (y) a reactive moiety for binding and cleaving the N-terminal amino acid residue of the peptide and exposing a next amino acid residue as a N-terminal amino acid residue on the cleaved peptide, and (z) an immobilizing moiety for immobilization to the solid support; (c) contacting the peptide with the chemically-reactive conjugate, thereby coupling the chemically-reactive conjugate to the N-terminal amino acid of the peptide to form a conjugate complex; (d) immobilizing the conjugate complex to the solid support via the immobilizing moiety; (e) cleaving and thereby separating the N-terminal amino acid residue from the peptide, thereby exposing the next amino acid residue as a N-terminal amino acid residue on the cleaved peptide and providing an immobilized amino acid complex, the immobilized amino acid complex comprising the cleaved and separated N-terminal amino acid residue; (f) repeating (b) through (e) n−1 times to assemble n−1 additional immobilized amino acid complexes, each additional immobilized amino acid complex comprising a nucleic acid associated with cycle 2 to n, accordingly; (g) contacting the immobilized amino acid complexes with a binding agent or a set of binding agents, each binding agent comprising: a binding moiety for preferentially binding to one or to a subset of the immobilized amino acid complexes, and a recode tag comprising a recode nucleic acid corresponding with the binding agent, thereby forming one or more affinity complexes, each affinity complex comprising an immobilized amino acid complex and the binding agent and thereby bringing a cycle tag into proximity with a recode tag within each formed affinity complex; (h) within each formed affinity complex, joining a cycle tag or a reverse complement thereof to a recode tag to form a recode block, or otherwise transferring information of the recode nucleic acid to the cycle nucleic acid of the immobilized conjugate complex, thereby creating a plurality of recode blocks, each recode block corresponding with a formed affinity complex; (i) joining two or more members of the plurality of recode blocks to form a memory oligonucleotide; (j) obtaining sequence information for the memory oligonucleotide; and (k) based on the obtained sequence information, determining identity and positional information of a plurality of amino acid residues of the peptide.

Disclosed herein, in some embodiments, are methods for determining identity and positional information of a plurality of amino acid residues of a peptide. The peptide may include n amino acid residues. The method may include coupling the peptide to a solid support. The coupling may be such that a N-terminal amino acid residue of the peptide is not directly coupled to the solid support or is exposed to reaction conditions. The method may include providing a chemically-reactive conjugate. The chemically-reactive conjugate may include a cycle tag comprising a cycle nucleic acid associated with a cycle number The chemically-reactive conjugate may include a reactive moiety. The reactive moiety may bind and/or cleave the N-terminal amino acid residue of the peptide. The reactive moiety may expose a next amino acid residue as a N-terminal amino acid residue on the cleaved peptide. The chemically-reactive conjugate may include an immobilizing moiety for immobilization to the solid support. The method may include contacting the peptide with the chemically-reactive conjugate. Such contacting may couple the chemically-reactive conjugate to the N-terminal amino acid of the peptide, and may form a conjugate complex. The method may include immobilizing the conjugate complex to the solid support. The immobilization may be via the immobilizing moiety. The method may include cleaving and thereby separating the N-terminal amino acid residue from the peptide. The cleaving may expose the next amino acid residue as a N-terminal amino acid residue on the cleaved peptide. The method may include providing an immobilized amino acid complex. The immobilized amino acid complex may include the cleaved and separated N-terminal amino acid residue. The method may include repeating steps n−1 times to assemble n−1 additional immobilized amino acid complexes. Additional immobilized amino acid complexes may include a nucleic acid associated with cycle 2 to n. The method may include contacting the immobilized amino acid complexes with one or a set of binding agents. The binding agent may include a binding moiety for preferentially binding to one or to a subset of the immobilized amino acid complexes. The binding agent may include a recode tag. The recode tag may include a recode nucleic acid corresponding with the binding agent. Contacting the immobilized amino acid complexes with one or more binding agents may form one or more affinity complexes. The affinity complexes may include an immobilized amino acid complex and the binding agent. Contacting the immobilized amino acid complexes with a binding agent may bring a cycle tag into proximity with a recode tag within the formed affinity complexes. The method may include, within each formed affinity complex, joining a cycle tag or a reverse complement thereof to a recode tag. The joining may form a recode block. The joining or method may include creating a plurality of recode blocks. Each recode block may correspond with a formed affinity complex. The method may include joining two or more members of the plurality of recode blocks to form a memory oligonucleotide. The method may include obtaining sequence information for the memory oligonucleotide. The method may include, based on the obtained sequence information, determining identity and positional information of a plurality of amino acid residues of the peptide. In some embodiments, n is an integer greater than or equal to 2. In some embodiments, each binding agent comprises recode tags with a unique nucleic acid sequence. In some embodiments, a plurality of binding agents comprises recode tags with the same nucleic acid sequence. In some embodiments, binding agents comprises recode tags which may have a unique sequence portion and a common sequence portion.

Disclosed herein, in some embodiments, are chemically-reactive conjugates comprising: (a) a nucleic acid sequence tag; (b) a reactive moiety for binding and cleaving a N-terminal amino acid residue from a peptide; and (c) an immobilizing moiety for immobilization to a solid support.

Disclosed herein, in some embodiments, are chemically-reactive conjugates. The chemically-reactive conjugate may include a nucleic acid sequence tag. The chemically-reactive conjugate may include a reactive moiety. The reactive moiety may be useful for binding a N-terminal amino acid residue. The reactive moiety may be useful for cleaving a N-terminal amino acid residue from a peptide. The chemically-reactive conjugate may include an immobilizing moiety. The immobilizing moiety may be useful for immobilization to a solid support. Also disclosed are kits containing any of the components described herein.

INTRODUCTION

Sequences and concentrations of cellular and secreted proteins are useful indicators of cell health. Aberrant sequences or concentrations may signal a disease state. However, tools and technologies are currently lacking for sensitive, accurate, economical, and unbiased characterization of proteomes. Early detection of unusual sequences and/or concentrations is critical to the diagnosis and treatment of many diseases, such as, e.g., cancer. For these and other reasons, better tools to evaluate protein and peptide sequence and concentration in biological samples must be developed.

Next-generation sequencing (NGS) of DNA and RNA polymers has transformed diagnostic, clinical, and research approaches by enabling clinicians and researchers to analyze billions of DNA sequences at high throughput and low cost. The ability to detect and quantify proteins and peptides, however, has lagged behind that of nucleic acids in large part because there is no equivalent to polymerase chain reaction (PCR) for amino acid polymers. New tools to sensitively quantify proteins and assess their sequences can, similar to NGS, aid in understanding cellular processes, continue to transform research, diagnostics, clinical approaches, and help facilitate precision medicine.

Current state-of-art proteomics toolkits include the following general approaches: 1) Edman degradation followed by conventional chromatography; 2) fragmentation followed by advanced separation and mass spectroscopy (MS) techniques; and 3) recognition of proteins via affinity molecules. These methods provide much useful information. However, none of these approaches creates information at the scale, throughput, reproducibility, access, or cost needed to unlock transformative applications in research, diagnostics, or therapeutics.

Peptide sequencing based on Edman degradation was first proposed and automated by Pehr Edman in the 1950's. The process is analogous to Sanger sequencing. Briefly, stepwise degradation of the N-terminal amino acid on a peptide through a series of chemical reactions and downstream HPLC analyses is used to collect peptide sequence information. First, the N-terminal amino acid is reacted with phenyl isothiocyanate (PITC) under basic conditions (typically NMP/methanol/water) to form a phenylthiocarbamoyl (PTC) derivative. In a second step, the PTC-modified amino group is treated with acid (typically anhydrous TFA) to yield an ATZ-modified (2-anilino-5(4)-thiozolinone) amino acid, separating the amino acid from the polymer and creating a next N-terminus on the polypeptide. The cyclic ATZ-amino acid is converted to a PTH-amino acid derivative and analyzed via chromatography. These steps are then repeated sequentially to determine a peptide sequence. It is effective, but upfront protein sample requirements are high, and the process lacks the throughput and cost to support large scale discovery.

More recently, multiplexed methods and devices for Edman degradation-based peptide sequencing of micro quantities of proteins have been developed. For example, see Chharbra, U.S. Pat. No. 7,611,834 B2. However, such methods and devices are still unsuitable for highly-parallelized, high-throughput proteomic analysis.

In the last 20 years, peptide analysis by fragmentation and analysis via mass spectroscopy (here, LC/MS) has been increasingly used to quantify protein abundance and determine sequence. Additionally, in certain applications, recognition-based proteomics has been employed. In this approach, affinity molecules, such as antibodies or antibody fragments, aptamers, RNA, or modified proteins, are commonly engineered to recognize the tertiary structure of analytes. Often, these are linked to molecular beacons that fluoresce or provide other means of detecting the binding event, such as in ELISA assay. However, like previous approaches, fragmentation and recognition-based methods lack the throughput and efficiency to support large scale discovery.

The present disclosure provides methods for analyzing polymeric macromolecules, such as peptides, polypeptides, and proteins. Accordingly, aspects of the present disclosure relate to the field of proteomics.

FIG. 1 illustrates a segmentation of the field of proteomics by technology. As described above, the current landscape for proteomic analysis includes the following general approaches: 1) Edman degradation followed by conventional chromatography; 2) fragmentation followed by advanced separation and mass spectroscopy techniques; and 3) recognition of proteins via affinity molecules. While these (and other) approaches can provide useful information for researchers, they do not provide such information at the scale, throughput, or cost needed to unlock transformative applications in research, diagnostics, or therapeutics. Some more particular challenges associated with current approaches (e.g., Edman's, LC/MS, and affinity approaches) include:

(a) Protein folding is dynamic, and proteins can lose their characteristic shape. When they do, recognition-based methods become inaccurate. This can happen in the case of labile proteins, or uncontrolled sample treatment prior to analysis.

(b) Recognition-based methods do not inform as to whether the protein sequence is a catalytically-ineffective variant, as often becomes the case in cancer biology.

(c) Biomarkers of interest are likely to be present at fM or lower concentrations, beneath the detection limit of most available tools used to quantify the absolute abundance of multiple proteins.

(d) The universe of protein molecules is extensive. It is much more complex than the RNA transcriptome, due to additional diversity introduced by post-translational modifications (PTMs).

(e) Proteins within a cell dynamically change (in expression level and modification state) in response to the environment, physiological state, and disease state. Thus, proteins contain a vast amount of relevant information that is largely unexplored.

(f) Generating an effective collection of affinity agents having low cross-reactivity between to off-target macromolecules can be time-consuming.

(g) Multiplexing the readout of a collection of affinity agents having minimizing cross-reactivity between the affinity agents and off-target macromolecules is challenging.

(h) Existing methods and the automation around current approaches is slow, expensive, and for the case of Edman's methods, have a limited throughput of only a few peptides per day.

(i) LC/MS suffers from drawbacks including: high instrument cost, requirement for a sophisticated user, poor quantification ability, poor dynamic range. Since proteins ionize at different levels of efficiencies, absolute quantitation and even relative quantitation between samples is challenging.

(j) LC/MS analyzes the more abundant species, so there is a need to employ complex upfront sample preparation, e.g., nanoparticle corona, making characterization of low abundance proteins challenging.

(k) LC/MS sample throughput is typically limited to a few thousand peptides per run.

(l) More recent attempts to develop methodologies suffer from poor discrimination of n-terminal or c-terminal AA and are confounded by "neighbor effects". Still other single molecule methodologies under development will require costly instrumentation because amplification of the analyte is not possible and one must detect small numbers of photons, electrons, or detection elements.

The present disclosure addresses the above challenges as well as other needs by providing methods, systems, and compositions for analyzing polymeric macromolecules via recoding of their sequences into DNA polymers for subsequent DNA sequencing and analysis. Referring to FIG. 1, certain embodiments of the present disclosure fall into the segment: "Proteomics">>"Advanced Research">>"Chemical>>"Sequence-based." The numerous applications of the present disclosure include peptide sequence and quantification determination in synthetically-derived and biologically-derived samples that include a plurality of protein complex, protein, and/or polypeptide components.

Some embodiments of the methods described herein include any of the following steps: 1: binding to substrate; 2: functionalized PITC conjugation to amino acid; 3: immobilization of PITC conjugate to hydrogel substrate; 4: cleavage of amino acid via Edman degradation; 4a: nucleotide deprotection; 5: build recode blocks with binders; 6: memory oligo assembly; and 7: release of oligo for sequencing.

Improved Methods for Determining Protein Sequence and Abundance

Figure 2:
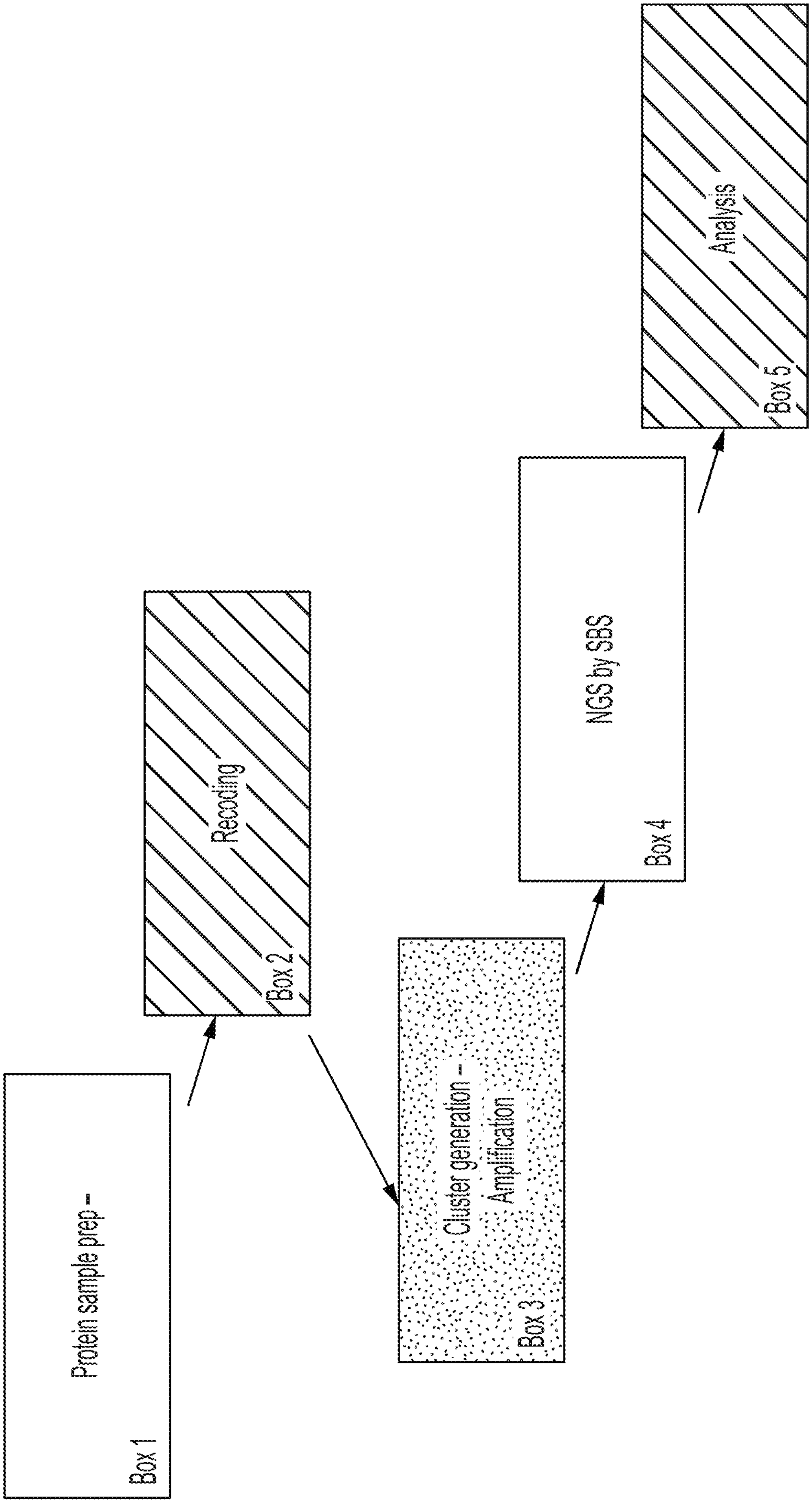
FIG. 2 illustrates a simplified block diagram of an exemplary workflow for analyzing polymeric macromolecules, including polymeric macromolecules such as peptides, and proteins, according to embodiments of the present disclosure.

FIG. 2 illustrates a simplified block diagram of an exemplary workflow 200 for analyzing polymeric macromolecules according to embodiments of the present disclosure. More particularly, the workflow 200 comprises high-level overview of various methods herein, and how such methods fit synergistically with DNA sequencing technologies. As shown, samples of macromolecules, e.g., proteins and peptides, are prepared and immobilized onto solid supports (Box 1). While immobilized, the amino acid sequences of the macromolecules are converted, e.g., "recoded," into DNA sequences (Box 2), and the DNA sequences amplified into libraries for NGS sequencing (Box 3). The DNA libraries are then sequenced (Box 4) and analyzed (Box 5) via high-throughput, high-accuracy methods, thereby enabling low cost.

Figure 3:
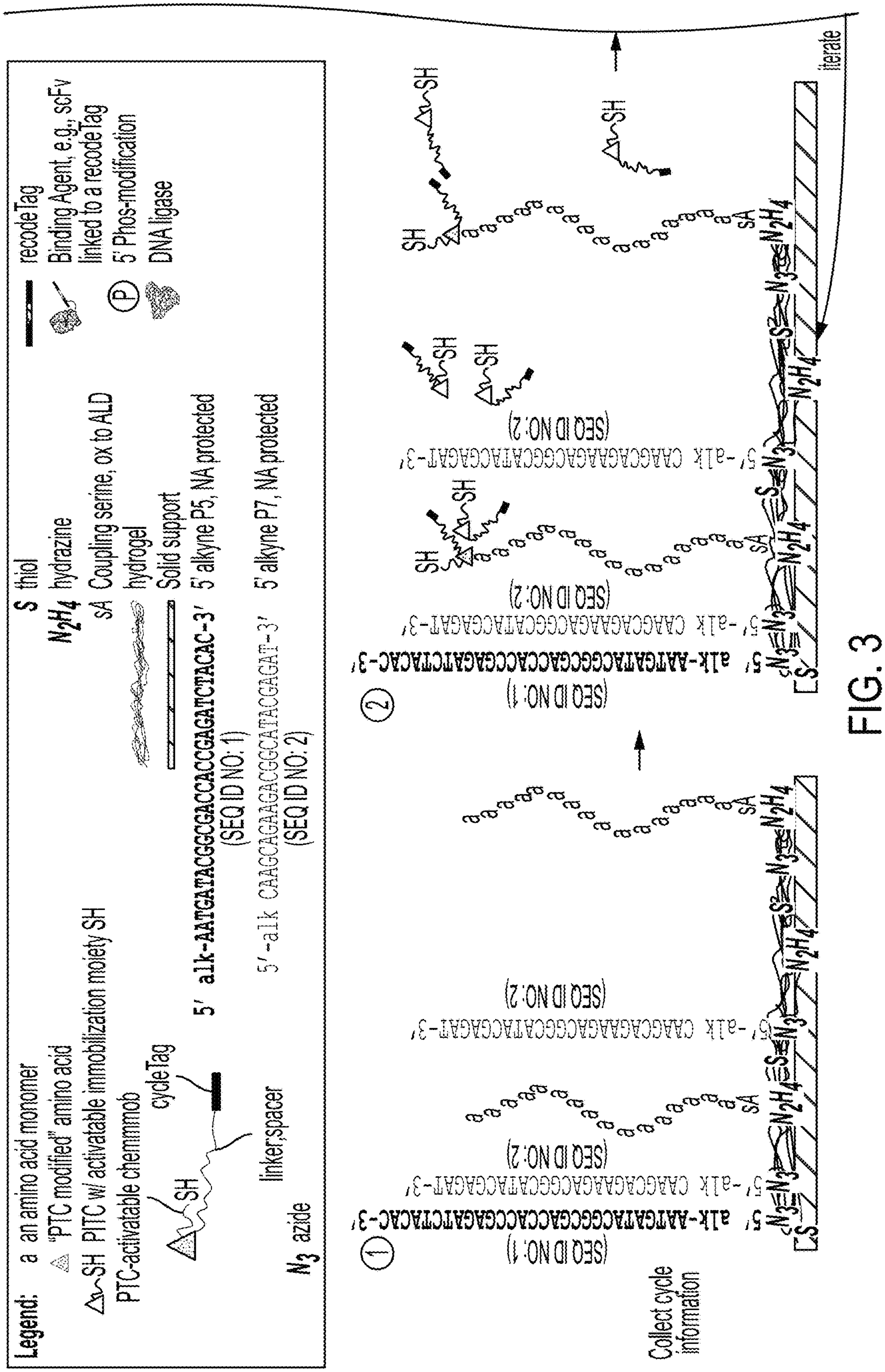
FIG. 3 schematically illustrates a process comprising various operations of the workflow of FIG. 2, according to embodiments of the present disclosure.
Figure 3:
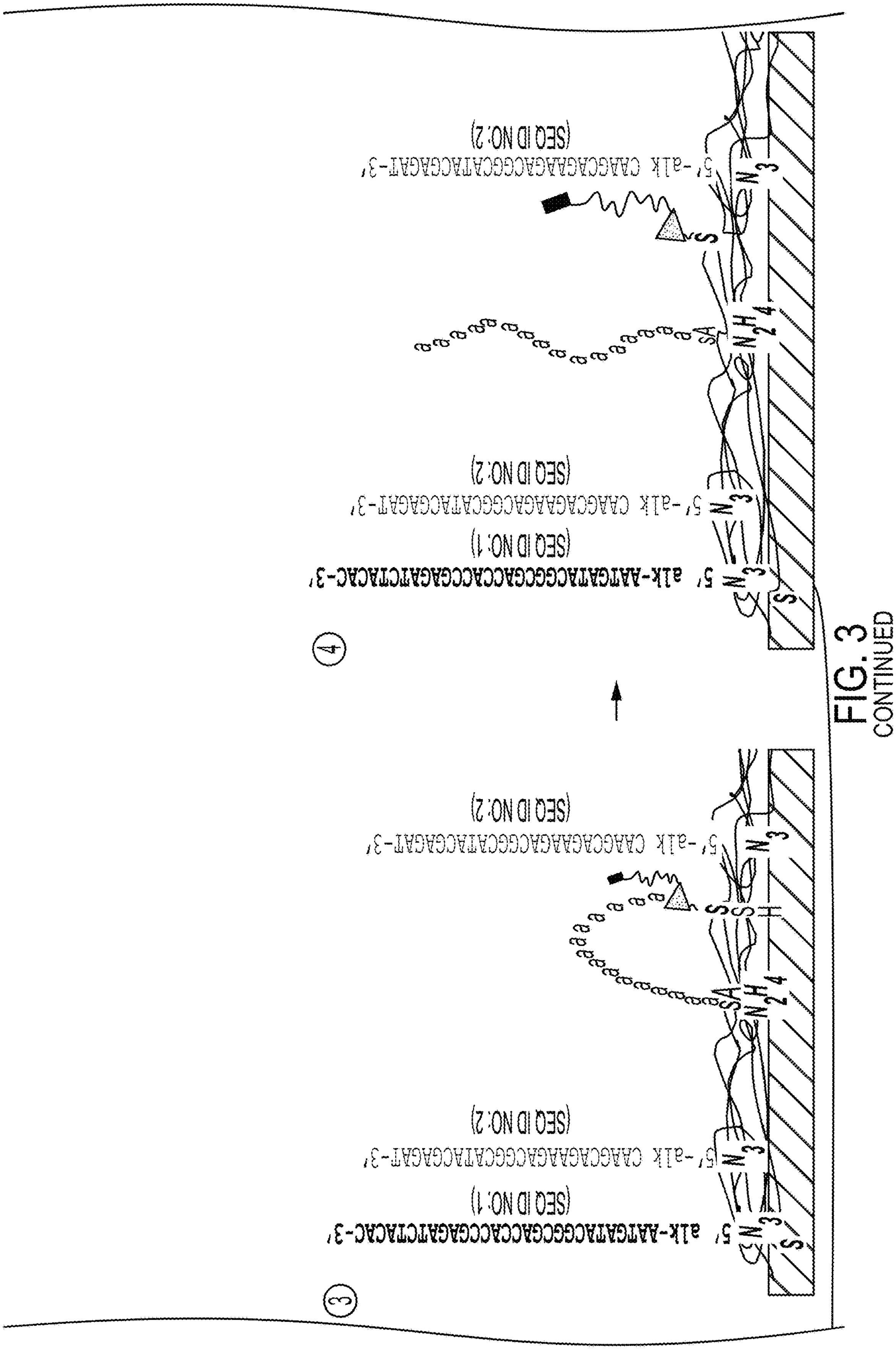
Figure 3:
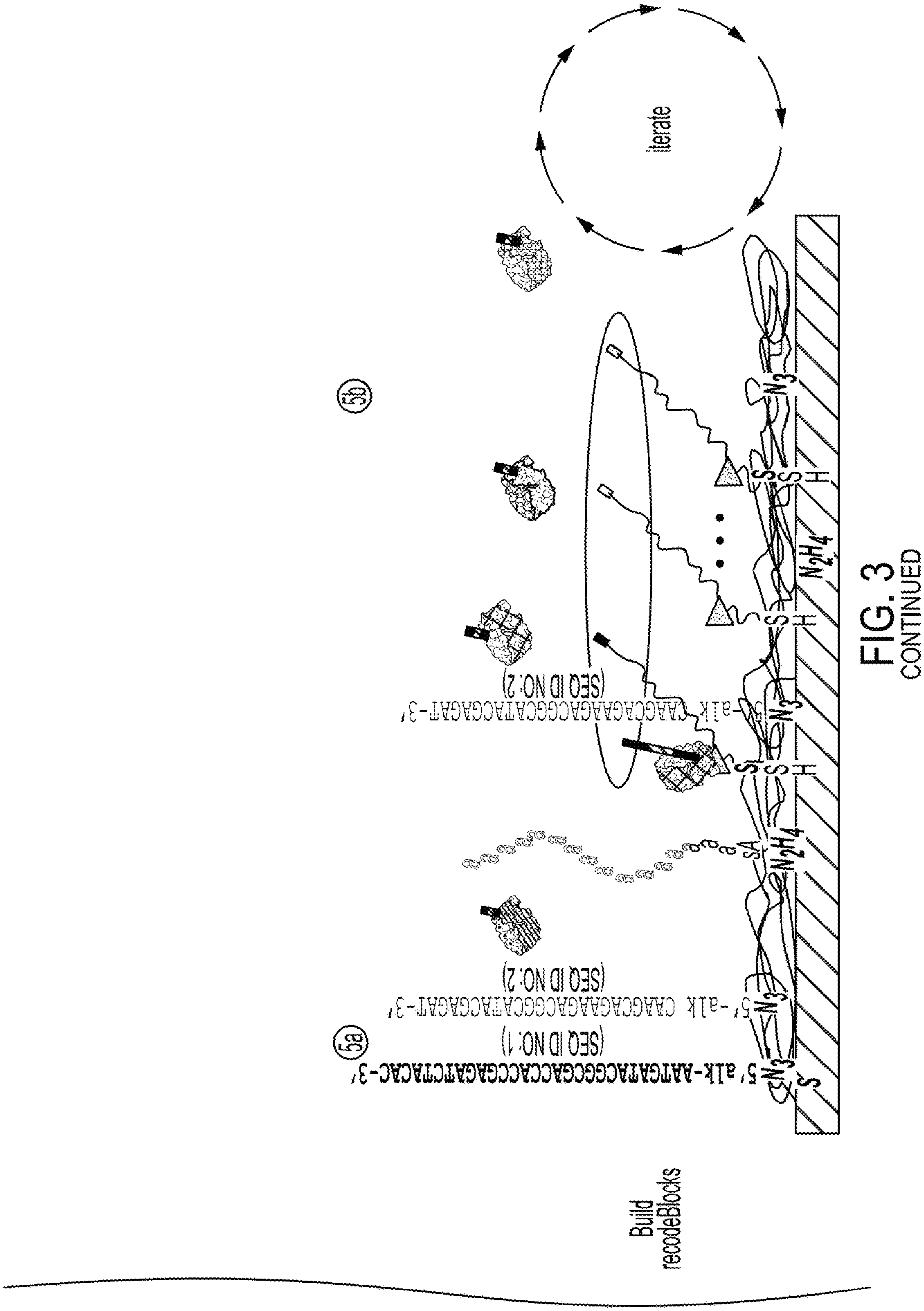
Figure 3:
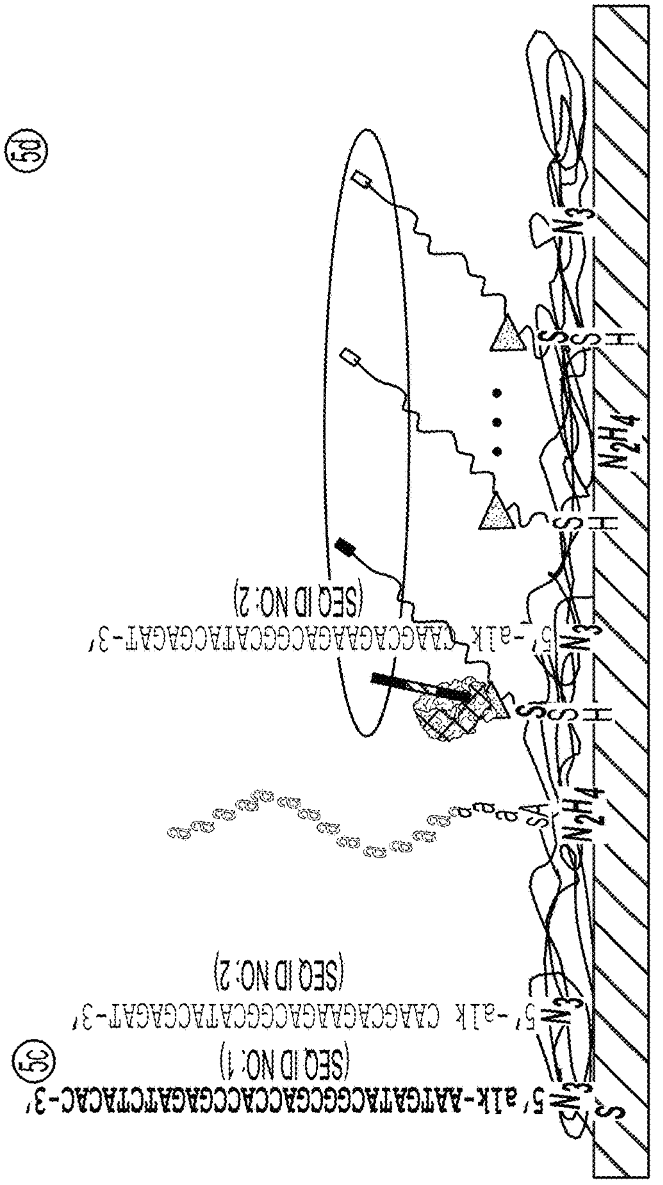
Figure 3:
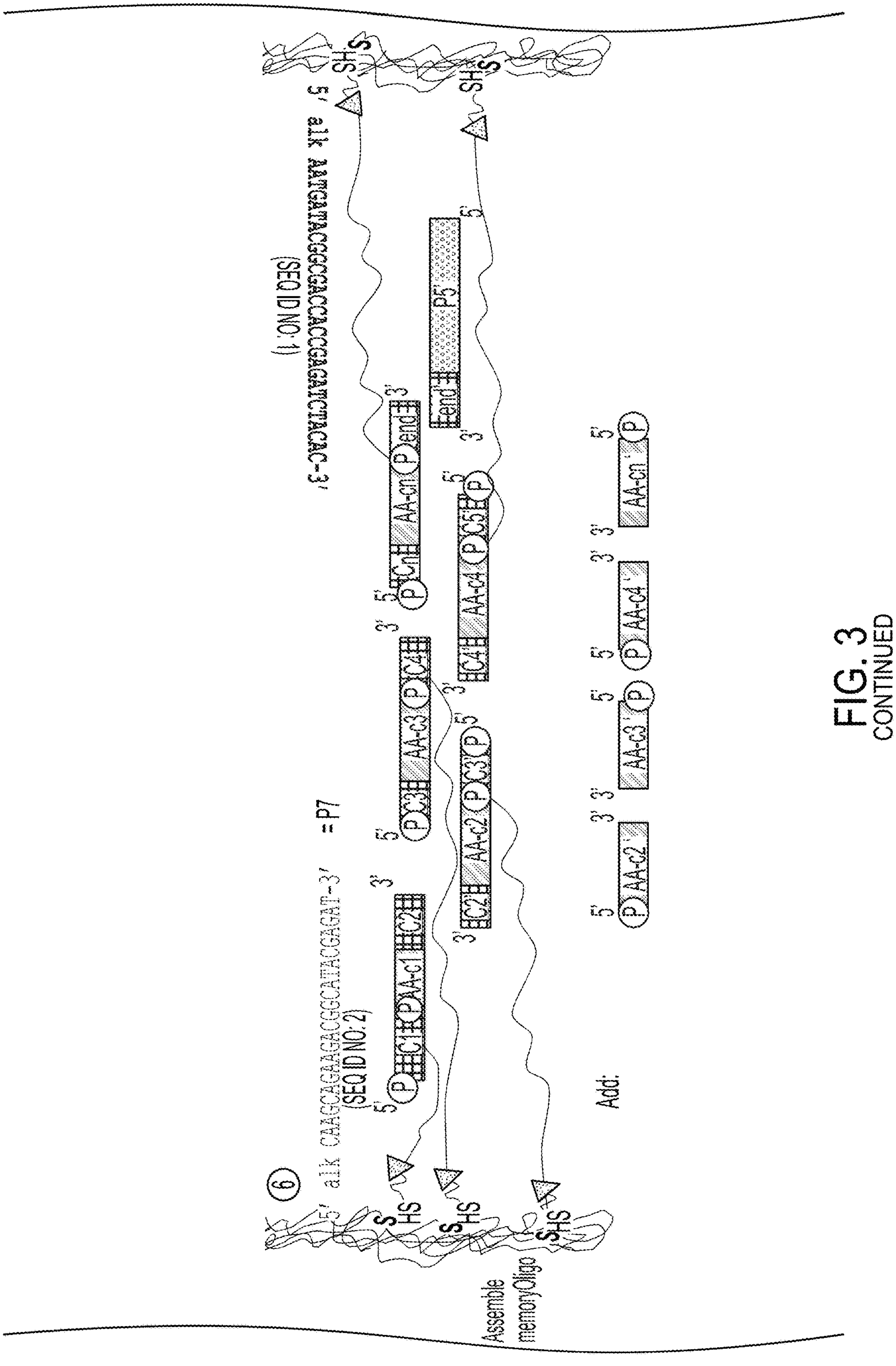
Figure 3:
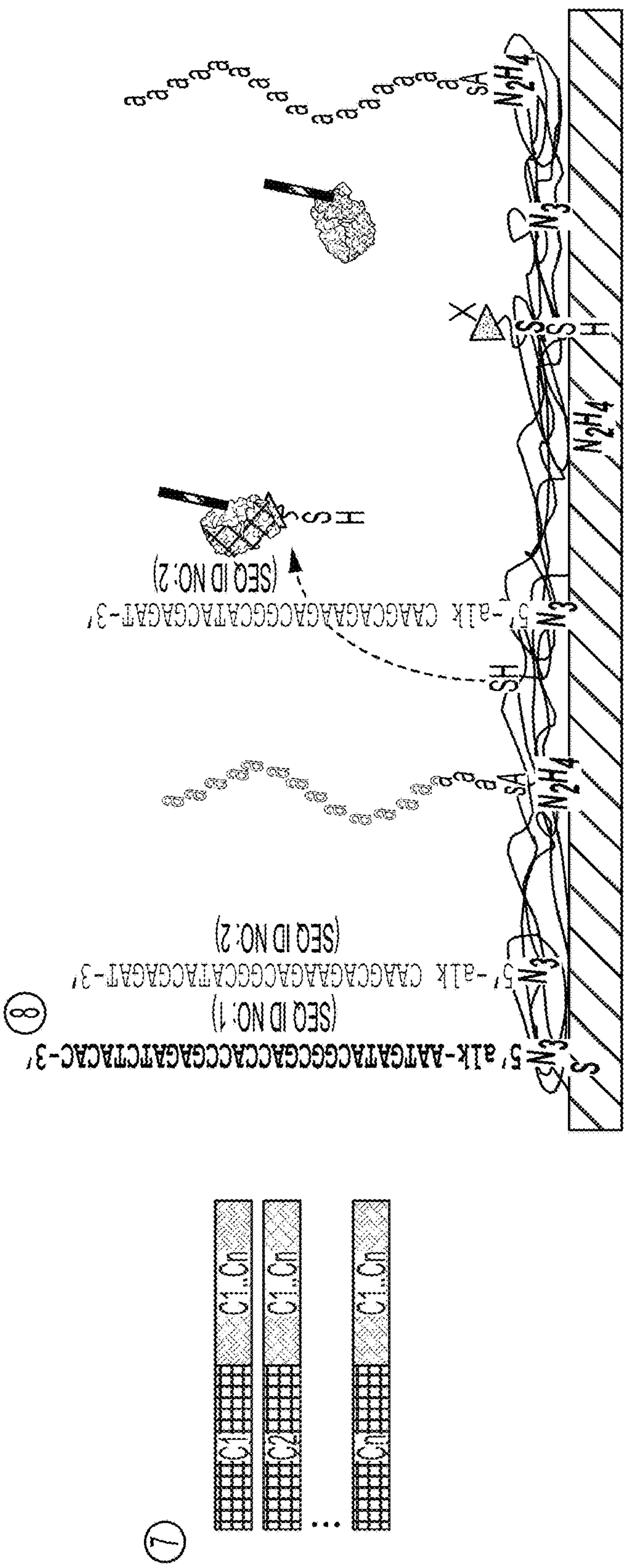

FIG. 3 schematically illustrates various operations of the workflow of FIG. 2, according to embodiments of the present disclosure. More particularly, FIG. 3 illustrates primary stages of the "recoding" operations of FIG. 2 as a process 300. As shown, there are three distinct and separable stages for the recoding process 300, and each stage is depicted in a row of operations.

In a first stage (operations 1-4 in FIG. 3), cycle information is captured. At operation 1, a surface of a solid support is prepared for attachment of: a macromolecular analyte, a set of universal primers, as well as attachment of a trifunctional chemically-reactive conjugate. This can be accomplished by providing 3 (or more) orthogonal chemistries on the surface of the support, shown in FIG. 3 as aldehyde-hydrazine, azide-alkyne, and thiol. Note that multiple conjugation chemistries are possible, including alternative chemistry functional groups to anchor primers, macromolecular analytes, and chemically-reactive conjugates to the solid support, as described below. Using at least one of the support's orthogonally reactive modalities, a plurality of macromolecular analytes, e.g., proteins, protein fragments (i.e., peptides), or other polymers, are immobilized to the support surface.

Operations 2-4 are then performed to immobilize trifunctional chemically-reactive conjugates (as conjugate-AA-cycle tag complexes). As shown, at operation 2, an N-terminal amino acid of the immobilized analytes is contacted with a chemically-reactive conjugate comprising a reactive group to the amino terminus, such as Edman's reagent (phenyl isothiocyanate (PITC)), an orthogonally-reactive group to the support, and a nucleic acid molecule carrying information about the cycle when the conjugate was contacted with the analyte. Under basic conditions the PITC conjugate reacts with the N-terminal amino acid to form a phenylthiocarbamoyl-amino acid (PTC) conjugate. A stringent wash removes unreacted PITC conjugate, and then, at operation 3, activation of an orthogonal chemistry used to tether the conjugate to the support is initiated to immobilize the PTC conjugate in proximity to the anchor point of the associated analyte. For example, by changing redox conditions to induce di-thiol formation, or adding $Cu^{2+}$, stabilizer and redox components to induce a Click reaction, PTC-thiol conjugates or PTC-alkyne conjugates may be immobilized to the solid support. Following immobilization of conjugates to the solid support, a conjugate-reactive scavenger may be added to cap the reactivity of any bound conjugate that was not washed away in the previous step(s), to render it inactive for future n-terminal amino acid reaction. At operation 4, peptide bond cleavage targeting the N-terminal amino acid of the peptide is induced. In examples employing Edman's degradation chemistry, this is facilitated by a change in pH from basic to acidic conditions. Operations 1-4 may then be repeated for n cycles to produce a lawn of n cycle-tagged conjugates localized on a solid support.

In effect, a first iteration through operations 2-4 (i.e., first cycle) provides information related to the terminal monomer of the immobilized polymeric analyte. A second cycle thereof provides information related to the next monomer of the immobilized polymeric analyte, and so on. Iterating through steps 2-4 for n cycles creates a lawn of spatially localized conjugates holding cycle information. With appropriate spacing between anchor points of immobilized macromolecular analytes, conjugates associated with a single analyte are co-located and isolated from those of other analytes.

The second row of FIG. 3 depicts an operation of the iterative process whereby recode blocks are built. In this operation, amino acid information is associated with cycle information. Briefly, a plurality of binding agents that recognize the immobilized conjugate-AA-cycle tag complexes are introduced at operation 5*a* and bind to their cognate target at operation 5*b*. The binding agents are engineered to preferentially recognize specific conjugates based on differences in the cognate amino acid of the immobilized conjugate. Those agents that possess both the cognate AA and the cognate cycle information will thereby direct ligation of AA information to a cycle tag of the corresponding conjugate complex (operations 5*c* and 5d). Repeated binding, washing, and ligation allows multiple attempts to find cognate partners and transfer information to each immobilized conjugate-AA-cycle tag complex to build a recode block. Accordingly, multiple successive binding cycles can be used to drive the yield of information transfer from the binding agents to the immobilized conjugates to an arbitrarily high completion level.

In a third row of FIG. 3, the formed recode blocks are assembled into a memory oligo (e.g. combined into a single memory oligo). This oligo is capable of being amplified on the solid support or in solution, then analyzed using DNA sequencing methods to determine a sequence and/or abundance of the immobilized analytes. Briefly, at operation 6, the co-localized recode blocks interact based on their complementary DNA sequences to assemble a DNA oligonucleotide that represents the sequence of the original macromolecule. The process is similar to g-block assembly of a gene product. Assembly may be facilitated by a polymerase extension-ligation process, or by a ligation process.

Gaps in connectivity between co-localized conjugates may exist, for example, due to a) incomplete information accumulation during the sequential degradation of the peptide and immobilization of a PTC-AA-cycle tag-conjugate complexes, b) incomplete information transfer from a recode tag to a cycle tag during recode block assembly, or c) simply an incomplete ligation of available and existing recode block information during memory oligo assembly. To remedy these gaps and enable high-yield assembly of information into a single oligo that can be analyzed using DNA sequencing, a ligation step employing generic splint oligos may be executed. Thus, at operation 7, incomplete assembly of co-localized recode blocks and/or memory oligos is rectified by adding generic splints that are capable of substituting for recode blocks sequences that were not created at operation 5. In the case of missing recode block information, the amino acid information associated with an errant cycle will be lost, but substantial recode block information will be assembled into the memory oligo. At operation 8, the tethers of the recode blocks are released, and an amplifiable product is generated via polymerase extension. Optionally, the solid support surface may be restored by cleaving conjugates from the surface.

Figure 4:
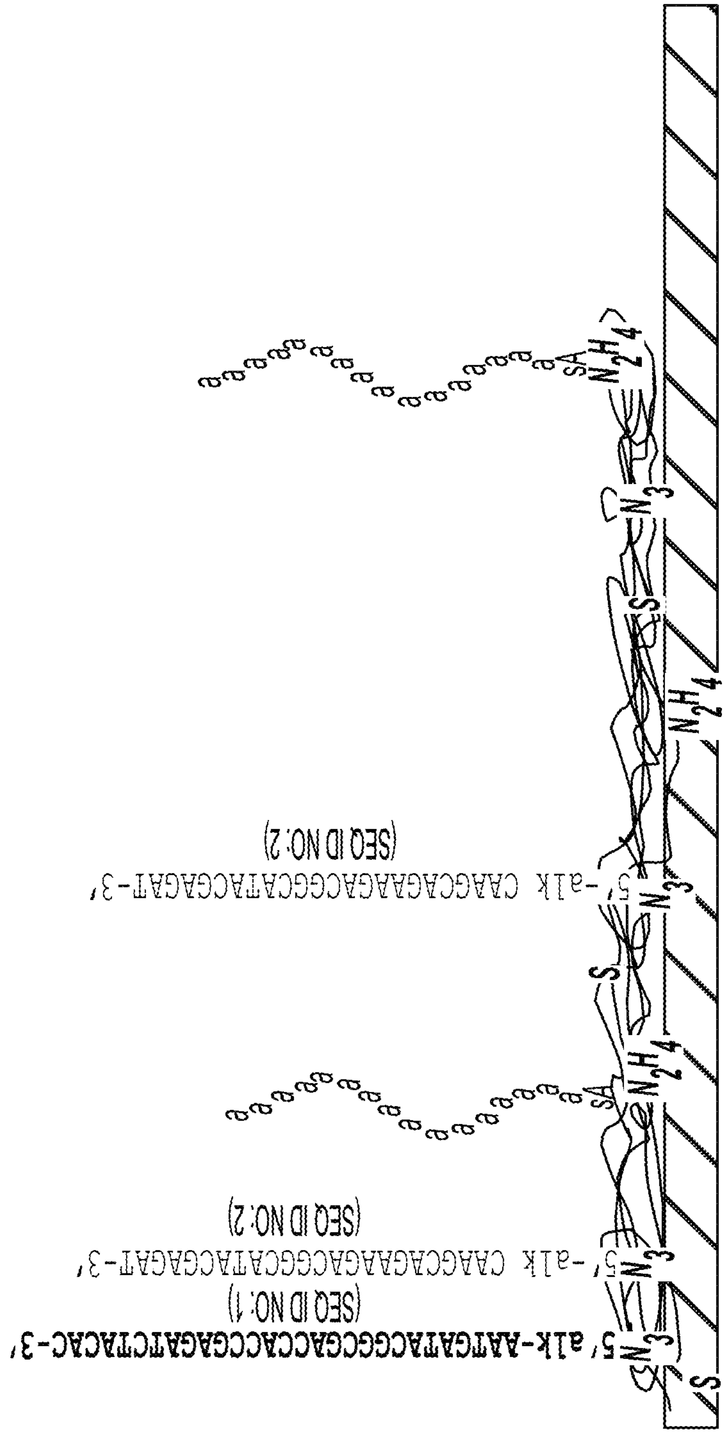
FIG. 4 schematically illustrates an exemplary solid support for spatially supporting macromolecule analytes during the process of FIG. 3, according to embodiments of the present disclosure.

FIG. 4 schematically illustrates an exemplary solid support for spatially supporting macromolecule analytes, according to embodiments of the present disclosure. As shown, the solid support is coated by a hydrogel that supports orthogonal chemistries. Orthogonal chemistries depicted are: aldehyde-hydrazine, azide-alkyne, and thiol. Either a thiol or Click chemistry can be activated for attachment of tri-functional chemically-reactive conjugates, depending on the immobilization scheme chosen. The aldehyde-hydrazine conjugation is an exemplary chemistry that can provide specific and orthogonal immobilization of a macromolecular analyte. The surface is seeded with macromolecule analytes such that, predominantly, they are spatially separated and reactants that interact with one macromolecule do not interact with another. A volume element is defined by the radius circumscribed by the length of the macromolecular polymer, and the lengths of the linkers of the conjugate complexes and the binding agents.

Figure 5:
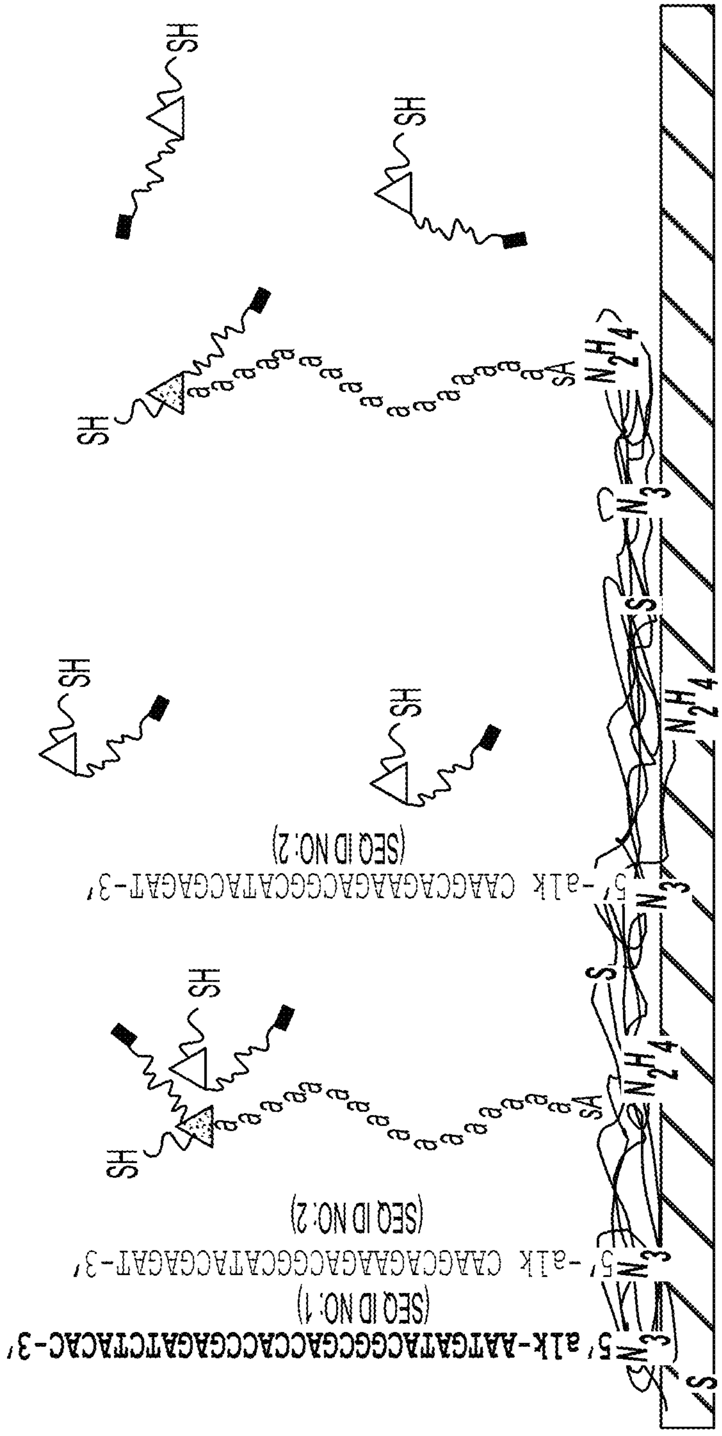
FIG. 5 schematically illustrates the interaction of chemically-reactive conjugates with terminal amino acids of immobilized peptides during the operations of FIG. 3, according to embodiments of the present disclosure.

FIG. 5 schematically illustrates the interaction of chemically-reactive conjugates with terminal amino acids of immobilized peptides during operation 2 of recoding process 300 in FIG. 3, according to embodiments of the present disclosure. Generally, the conjugate has 3 functions: 1) bind to a terminal amino acid and cleave the peptide bond between the terminal amino acid and the next amino acid in the polymer (for N-terminal reactions, this is equivalent to the classical function of Edman's reagent); 2) immobilize the conjugate to the solid support; and 3) carry a cycle tag oligo. Note the 1:1 relationship of an immobilized peptide with a conjugate in a given cycle. Conjugates that react with and become bound to the terminal amino acid in operation 2 of the recoding process 300 are shown as filled triangles in FIG. 5. Under basic conditions, the PITC conjugate reacts with the N-terminal amino acid to form a phenylthiocarbamoyl-amino acid (PTC) conjugate. Unreacted conjugates are shown as open triangles. Any unreacted PITC conjugate can be washed from the surface of the solid support prior to triggering the chemistry that joins the PTC-conjugate to the surface.

Figure 6:
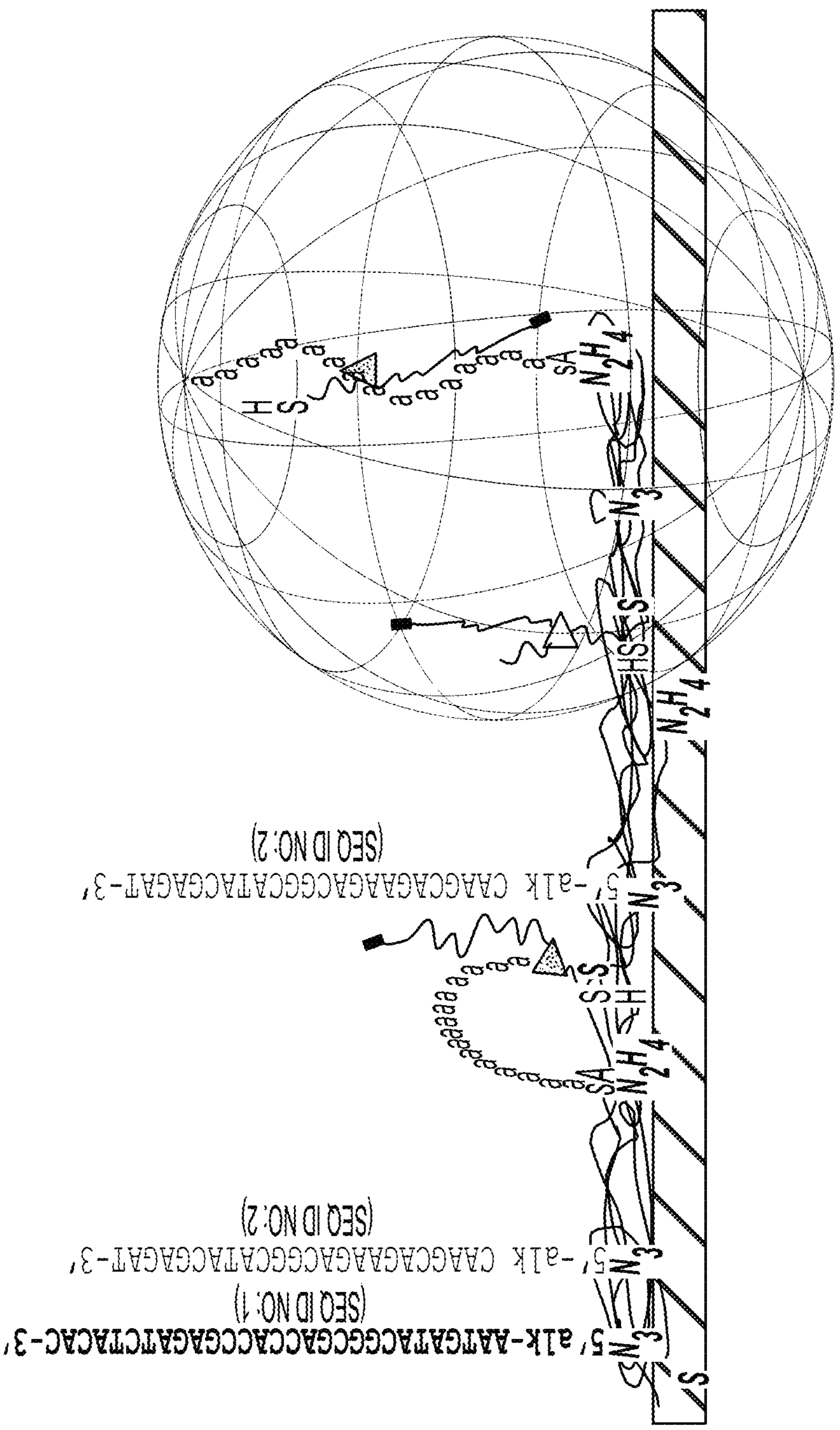
FIG. 6 schematically illustrates the immobilization of chemically-reactive conjugates onto a solid support during the operations of FIG. 3, according to embodiments of the present disclosure.

FIG. 6 schematically illustrates the immobilization of chemically-reactive conjugates onto a solid support during operation 3 of recoding process 300 in FIG. 3, according to embodiments of the present disclosure. Generally, the conjugate immobilization reaction can be triggered by light, catalyst addition, or by modifying the buffer properties or temperature to control the rate of reaction. For example, reducing redox potential allows formation of stable dithiol linkages. A stringent wash removes unreacted PITC conjugate, and then activation of an orthogonal chemistry used to join the conjugate to the solid support is initiated to immobilize PTC conjugate in proximity to the anchor point of an associated peptide. For example, by changing redox conditions to induce di-thiol formation, or adding $Cu^{2+}$, stabilizer and redox components to induce a Click reaction, PTC-thiol conjugates or PTC-alkyne conjugates may be immobilized to the solid support. Note that the length of the peptide defines a volume element around the anchor point with the support, and conjugates associated with the specific peptide are co-localized to that anchor point. Following immobilization of conjugates to the solid support, a conjugate-reactive scavenger may be added to cap the reactivity of residual conjugate that was not reacted to an N-terminal amino acid, was incompletely washed, and became attached to the solid support. In this way, imperfect removal of PITC conjugate is remediated by introducing an amino acid mimic. Unreacted PITC-conjugate may bind to the surface, but its future reactivity to amino acids is quenched, leaving spectator conjugates on the surface that are not able to participate in downstream processes.

Figure 7:
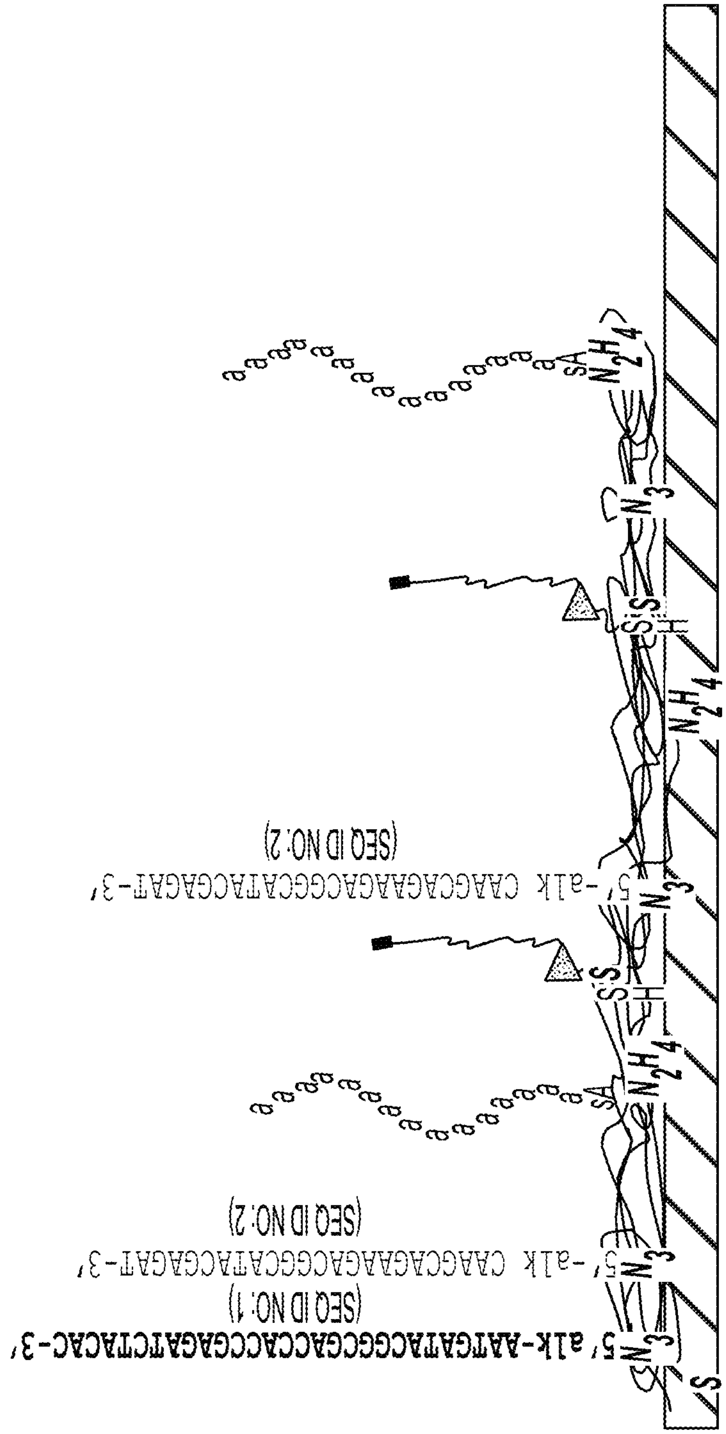
FIG. 7 schematically illustrates the cleavage of terminal amino acids (e.g., the cleavage of peptide bonds) after conjugate immobilization during the operations of FIG. 3, according to embodiments of the present disclosure.

FIG. 7 schematically illustrates the cleavage of terminal amino acids (e.g., the cleavage of peptide bonds) at operation 4 of recoding process 300 in FIG. 3, according to embodiments of the present disclosure. In examples utilizing an Edman's degradation chemistry, this is accomplished by a change in pH from basic to harsh acidic conditions, sometimes in organic solvents. Accordingly, the hydrogel and conjugation reactions are designed to withstand the peptide bond cleavage conditions. Also for this reason, the cycle tag nucleic acids and any other nucleic acids immobilized to the solid support will comprise protecting groups that prevent degradation of amines or other reactive moieties of the nucleic acid. Cleavage of the terminal amino acid results in release of the peptide and provides a new terminal amino acid on the immobilized peptide analyte. In FIG. 7, the immobilized PTC-AA-cycle tag-conjugate complexes are localized near the peptide analyte's anchor point.

Figure 8:
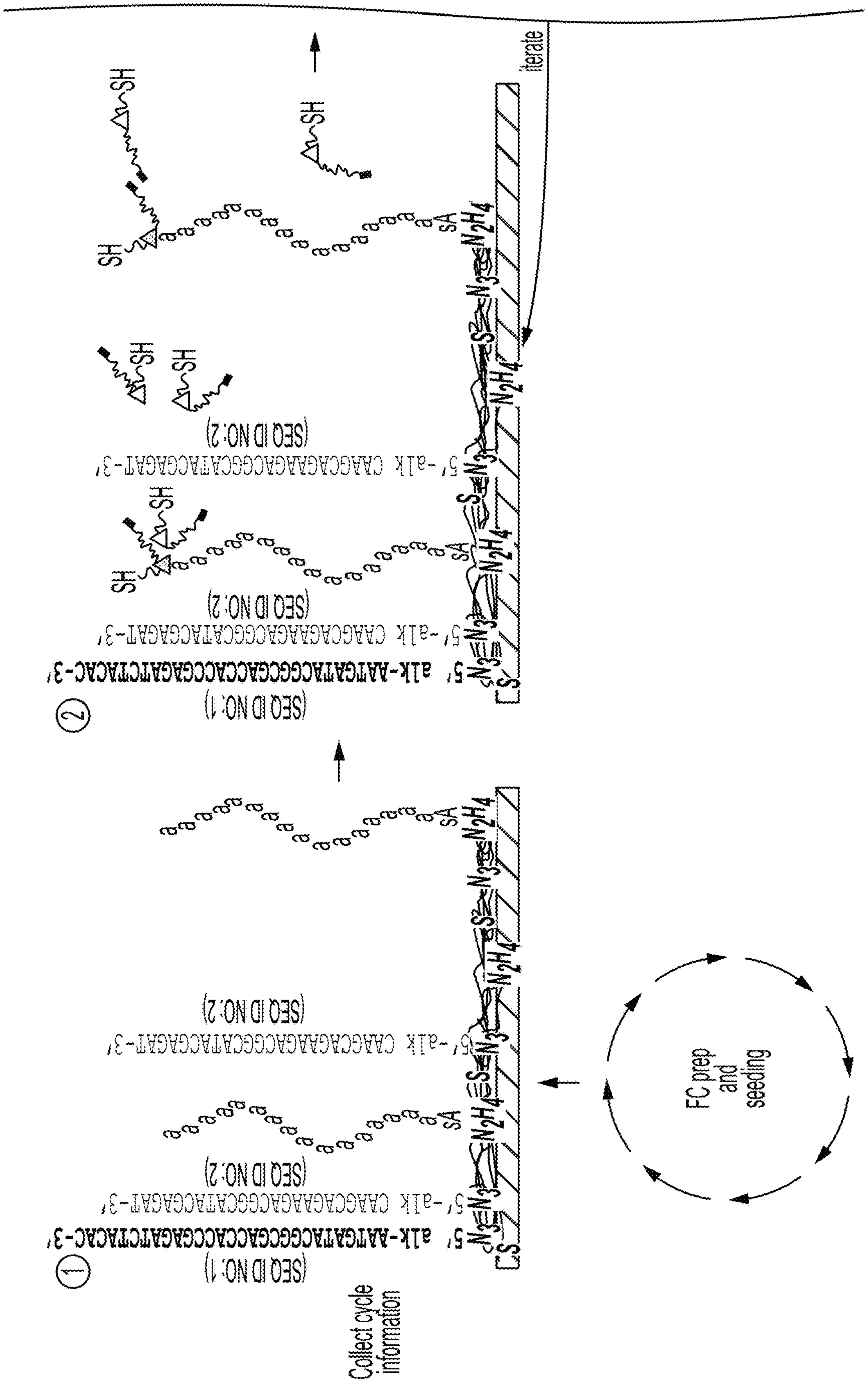
FIG. 8 schematically illustrates the result of iteratively repeating operations of FIG. 5-7, according to embodiments of the present disclosure.
Figure 8:
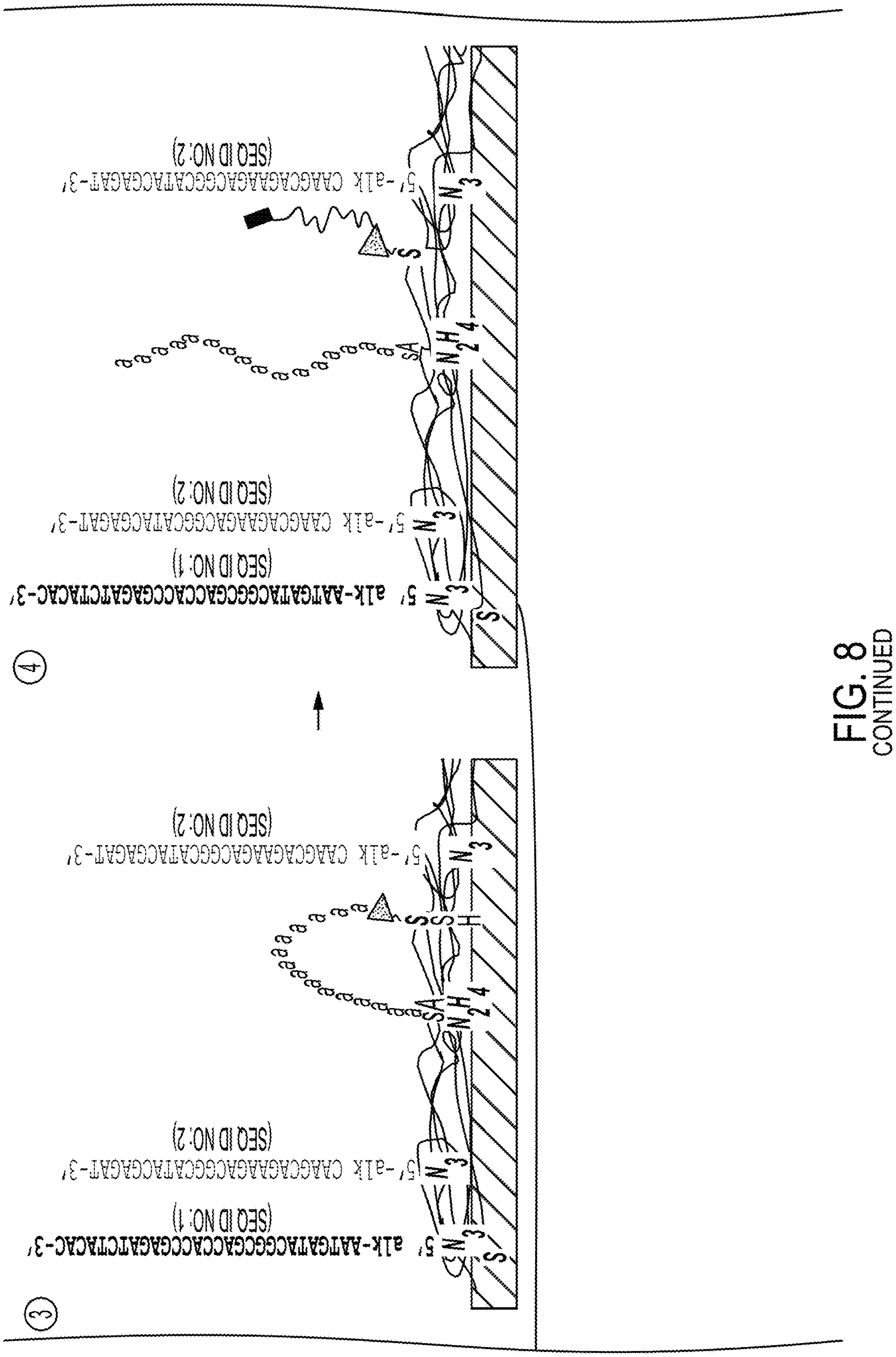
Figure 8:
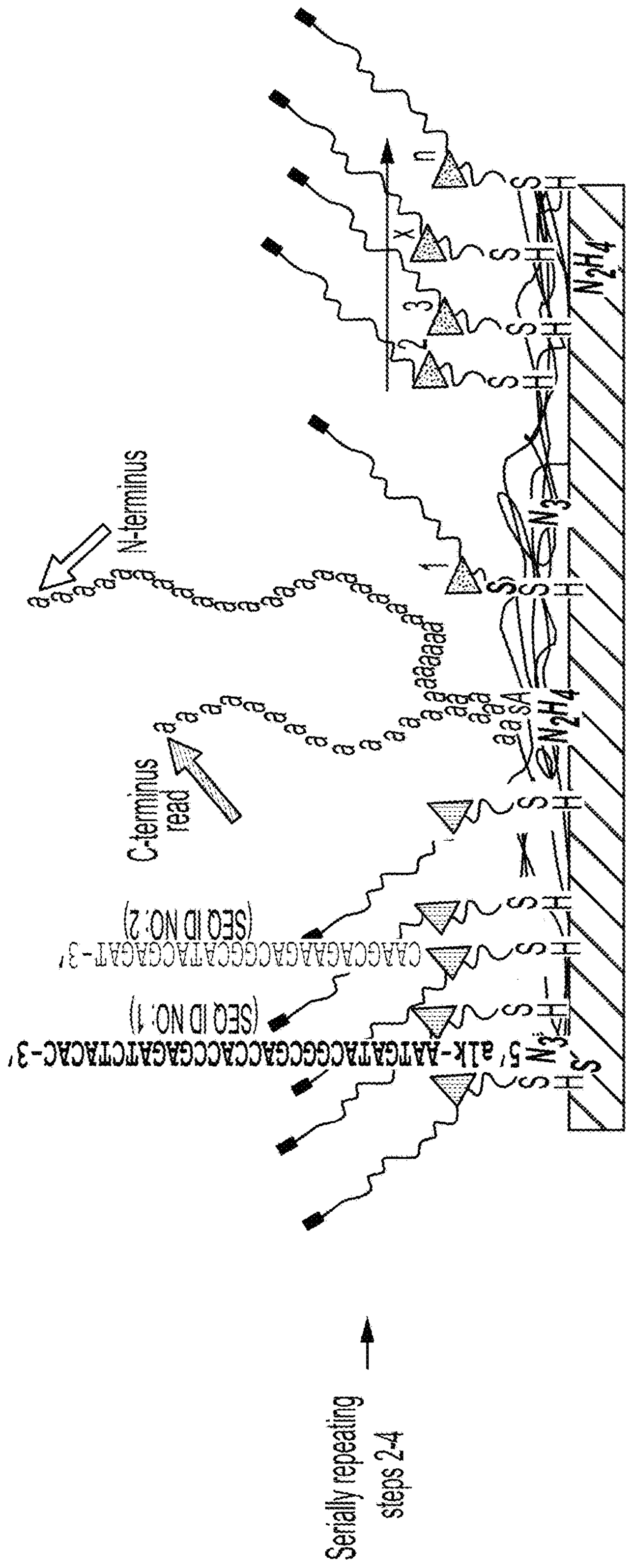

FIG. 8 schematically illustrates the result of iteratively repeating the operations of FIG. 5-7, according to embodiments of the present disclosure. More particularly, FIG. 8 illustrates the iteration of operations 2-4 of the recoding process 300. As shown, a series of co-localized conjugates, each having a cycle tag that carries information related to the relative position of an amino acid in one immobilized peptide analyte, are spatially isolated from the conjugates of other peptide analytes. The details of creation of each conjugate is independent of the information carried by the conjugate. Thus, immobilized conjugates carrying information derived from carboxy-terminus chemistry and immobilized conjugates carrying information derived from amine-terminus chemistry may be combined in downstream steps.

Figure 9:
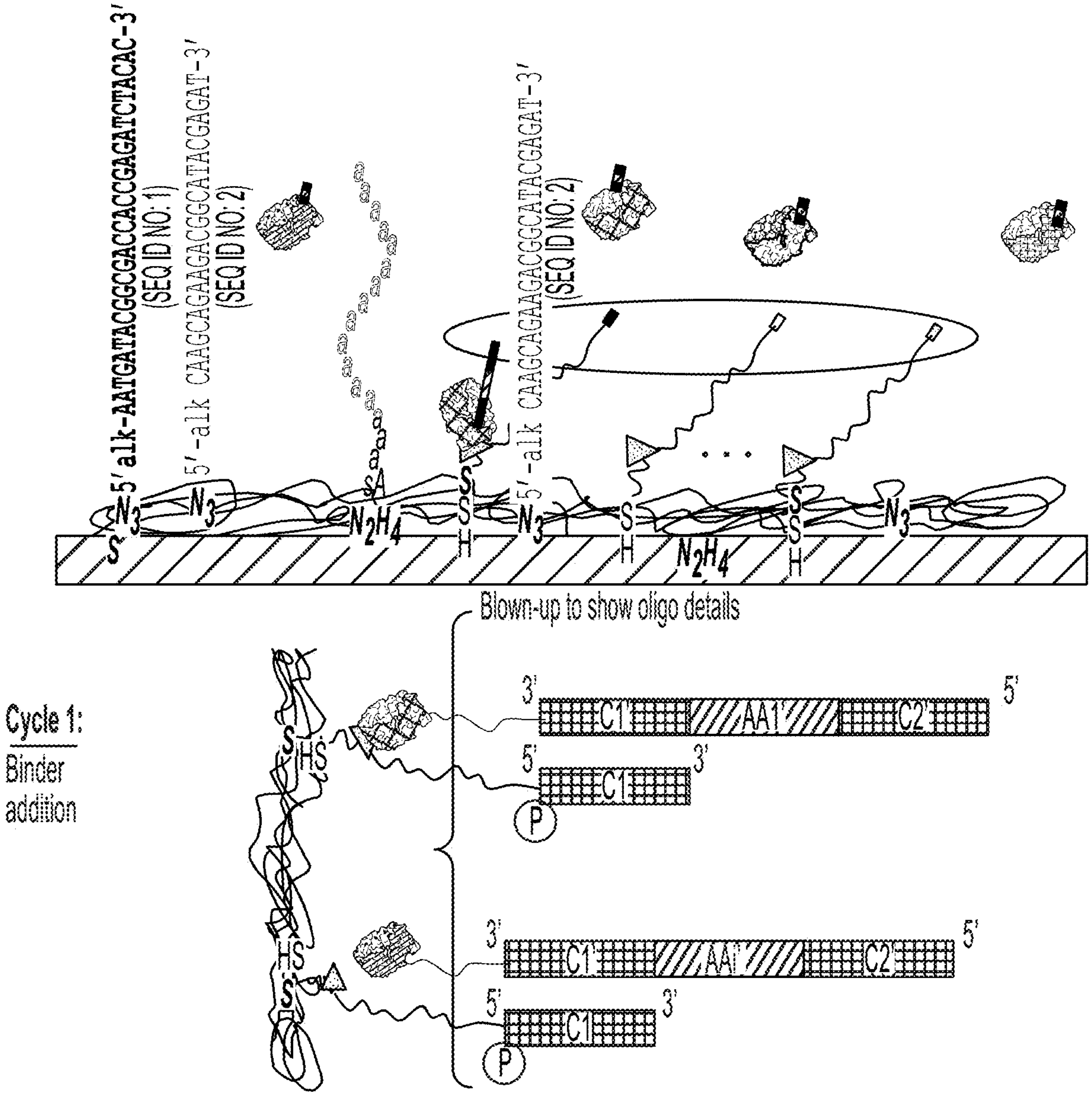
FIG. 9 schematically illustrates the assembly of an exemplary configuration of a recode block, according to embodiments of the present disclosure.

FIG. 9 schematically illustrates the assembly of a recode block, e.g., operations 5*a*-5*b* above, according to embodiments of the present disclosure. In this process of the recoding process 300, the amino acid identity information is aggregated with cycle information. A cognate binding agent interact with an immobilized conjugate as shown in the top panel of FIG. 9. Binding agents are engineered to preferentially recognize specific conjugates based on differences in the cognate amino acid of the immobilized conjugate. The binding energy of the binding agent is a combination of: (a) the binding energy of the affinity binding moiety and the conjugate, and (b) the hybridization energy between the cycle tag oligo of the conjugate and the recode tag oligo of the binding agent. Binding agents that possess both the cognate AA and the cognate cycle information will direct ligation of AA information to the cycle tag, as shown in the bottom panel. In practice, components for recognition of all AA conjugates for all cycles are present simultaneously to concurrently create recode blocks. Discrimination may be enhanced under "competitive" conditions in concert with slow annealing to find global max binding energies for the combined affinity binding moiety and the nucleic acids. Note that recognition of the immobilized PTC-conjugate on the solid support avoids near-neighbor effects from amino acids that were adjacent on the original peptide.

Figure 10:
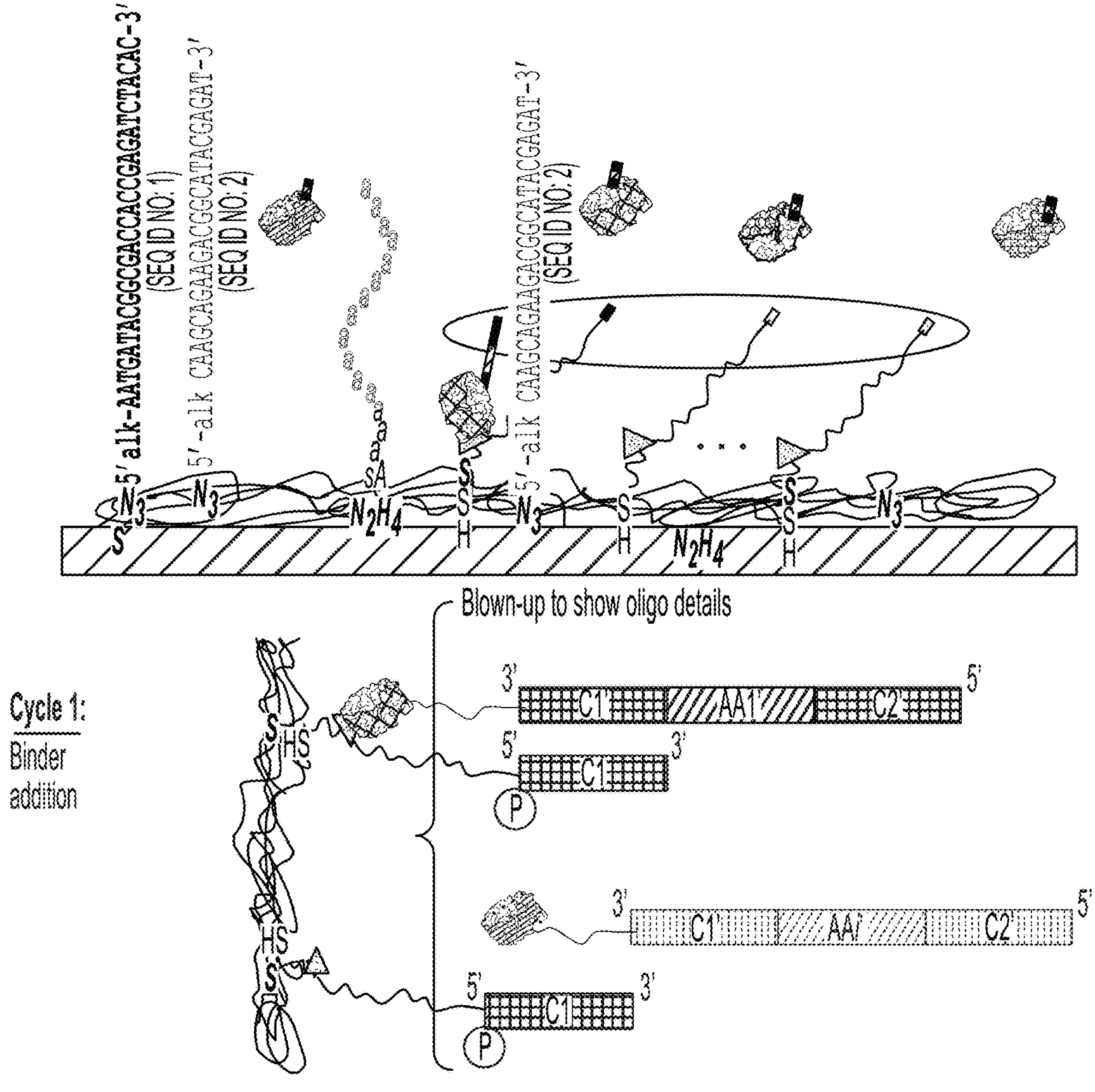
FIG. 10 schematically illustrates the assembly of an exemplary configuration of a recode block, according to embodiments of the present disclosure.

FIG. 10 schematically illustrates preparatory operations of an exemplary process for assembling the recode block of FIG. 9, according to embodiments of the present disclosure. The bottom panel in FIG. 10 shows a binding agent comprising a binding moiety and a recode tag, as well as a conjugate having a cycle tag. There are several possible interactions between binding agents and immobilized conjugates that may exist, since binding agents for recognition of all AA conjugates for all cycles are present simultaneously. They may be classified as: (a) correct cognate AA, correct cognate nucleotide; (b) correct cognate AA, incorrect cognate nucleotide; (c) incorrect cognate AA, correct cognate nucleotide; (d) incorrect cognate AA, incorrect cognate nucleotide; and (e) non-specific binding. Stringent wash conditions remove weakly bound binding agents from the surface. These may be due to cross-reactive binding of binding moieties to non-cognate PTC-AA-cycle tag conjugate complexes, and include interactions classified as either (c), (d) or (e). Interactions classified as (a) are productive during the next step of oligo ligation where information is transferred from a recode tag to a cycle tag to form a recode block. Interactions classified as (b) are not productive during the next step of oligo ligation. The characteristic time ($1/k_{off}$), where $k_{off}$ is the off rate of the cognate binding agent can exceed the time to effectively wash the solid support.

Figure 11:
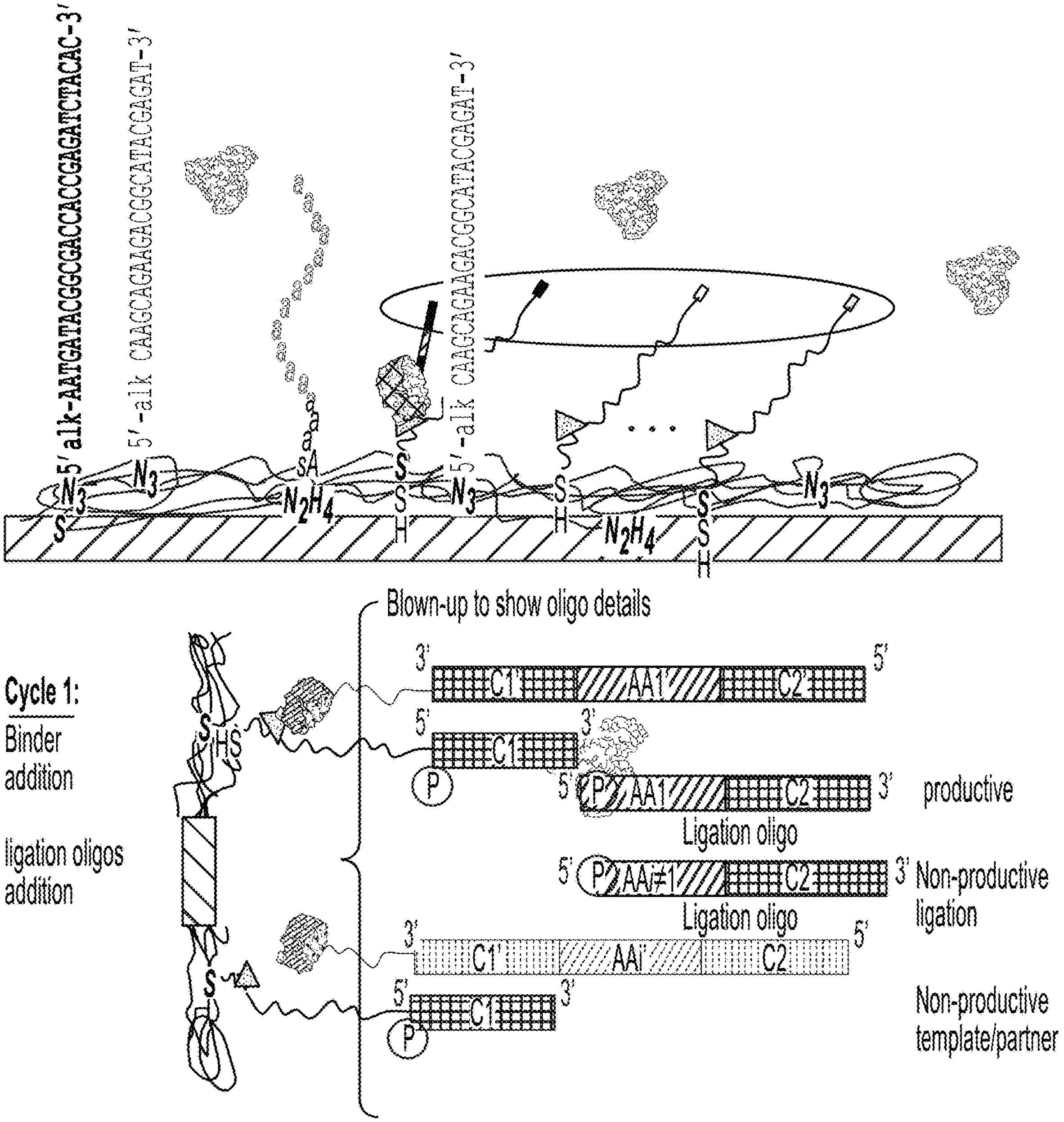
FIG. 11 schematically illustrates the transfer of amino acid identity information from a binding agent's recode tag to an immobilized conjugate's cycle tag to form a recode block via ligation, according to embodiments of the present disclosure.

FIG. 11 schematically illustrates the transfer of amino acid identity information from a binding agent's recode tag to an immobilized conjugate's cycle tag to form a recode block via ligation, e.g., operation 5*c*-5*d* of recoding process 300, according to embodiments of the present disclosure. As shown, complementary ligation oligos and ligase are added in an appropriate buffer to support ligation and undergo information transfer only when cognate amino acid and complementary nucleic acid conditions are met. Binding agents that are cognate to the amino acid, but comprise a recode tag non-complementary to the cycle tag, do not undergo information transfer. Similarly, ligation oligos that are not complementary to the recode tag of the binding agent do not undergo information transfer.

Figure 12:
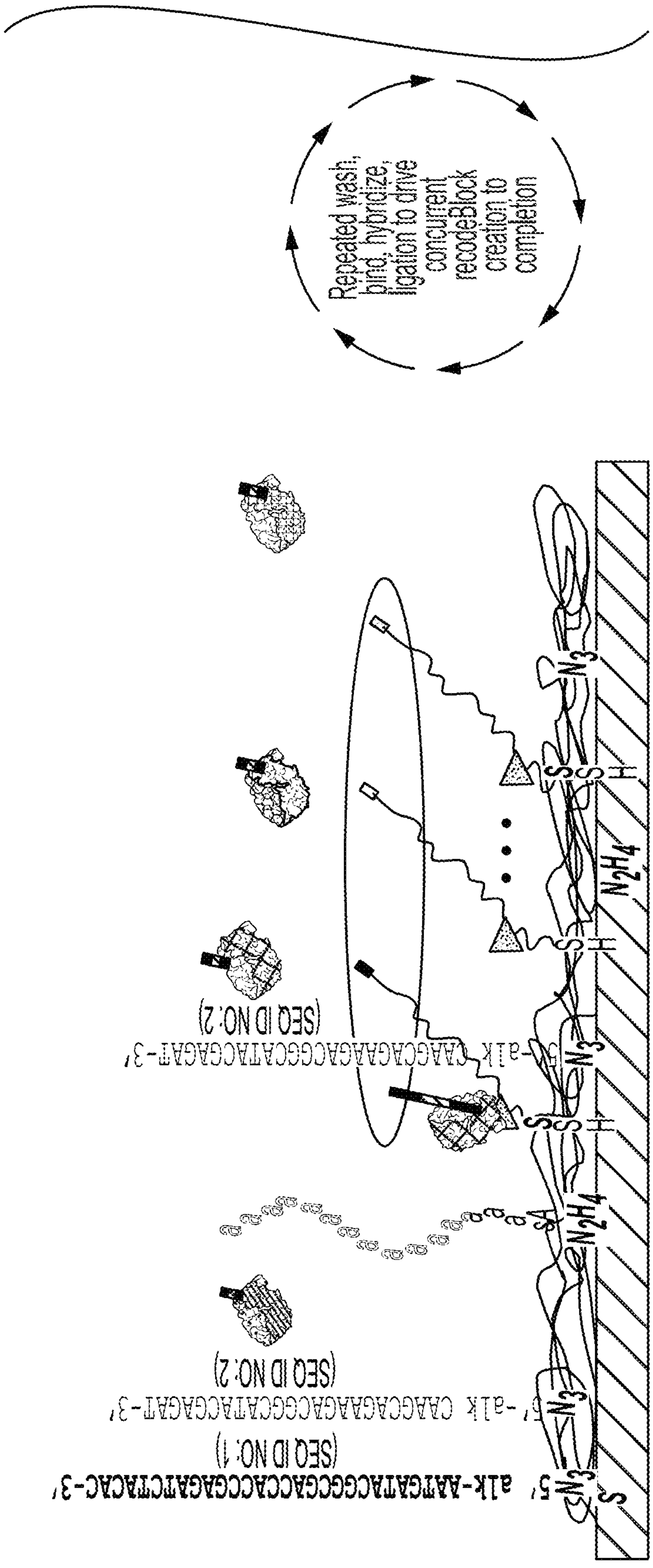
FIG. 12 schematically illustrates an iterative process for assembling recode blocks, according to embodiments of the present disclosure.
Figure 12:
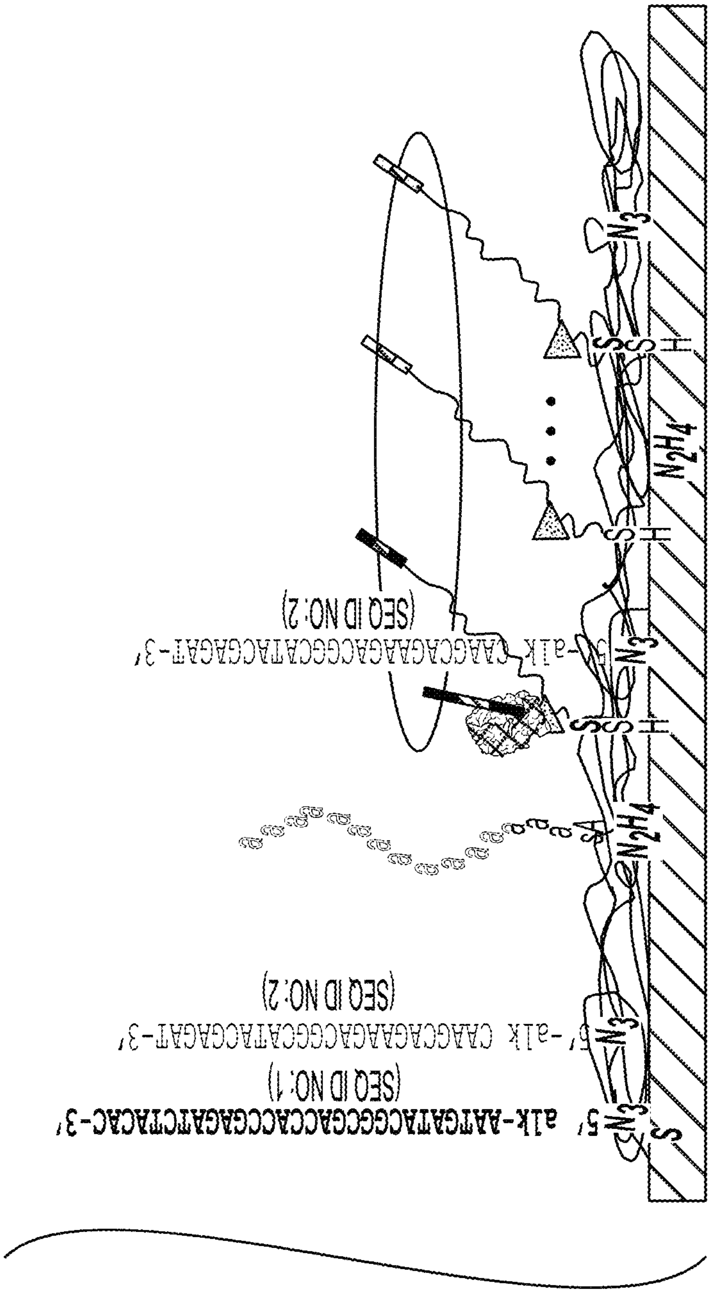

FIG. 12 schematically illustrates iterative performance of the operations 5*a*-5*d* of recoding process 300 for assembling recode blocks, according to embodiments of the present disclosure. During the performance thereof, binding agents for recognition of all AA conjugates for all cycles are present simultaneously. Thus, the efficiency of correct binding of the cognate pair in any one trial may be low. Slow annealing will help to differentiate between interactions with similar binding energies, and drive binding of the cognate pair. However, this may not improve efficiency to desired levels. In addition, steric hinderance due to co-localization of immobilized conjugates may restrict access of binding agents to one or more conjugates in any given trial. To drive a high fraction of recode blocks assembly, multiple trials of bind, wash, and ligation can be employed. In a trial where an unproductive binding event occurs, no ligation occurs. A stringent wash to remove the non-cognate binding agents creates a new opportunity to find and anneal to the cognate agent in the next trial. In principle, assuming there are no systematic effects, repeating trials will drive recode blocks assembly to completion.

Figure 13:
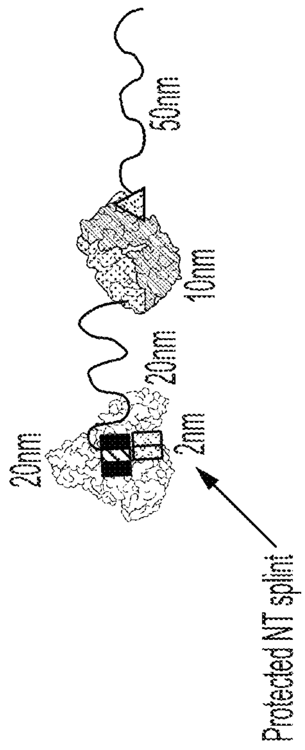
FIG. 13 schematically illustrates the relative sizes of various constituents in the process of FIG. 3, according to embodiments of the present disclosure.

FIG. 13 schematically illustrates the relative sizes of various constituents of the recoding process 300, according to embodiments of the present disclosure. As shown, the relative sizes of the various constituents emphasizes the need to provide linker/spacers that allow ample freedom for constituents to interact, while also maintaining co-localization isolation for each immobilized macromolecular analyte on the solid support.

Figure 14:
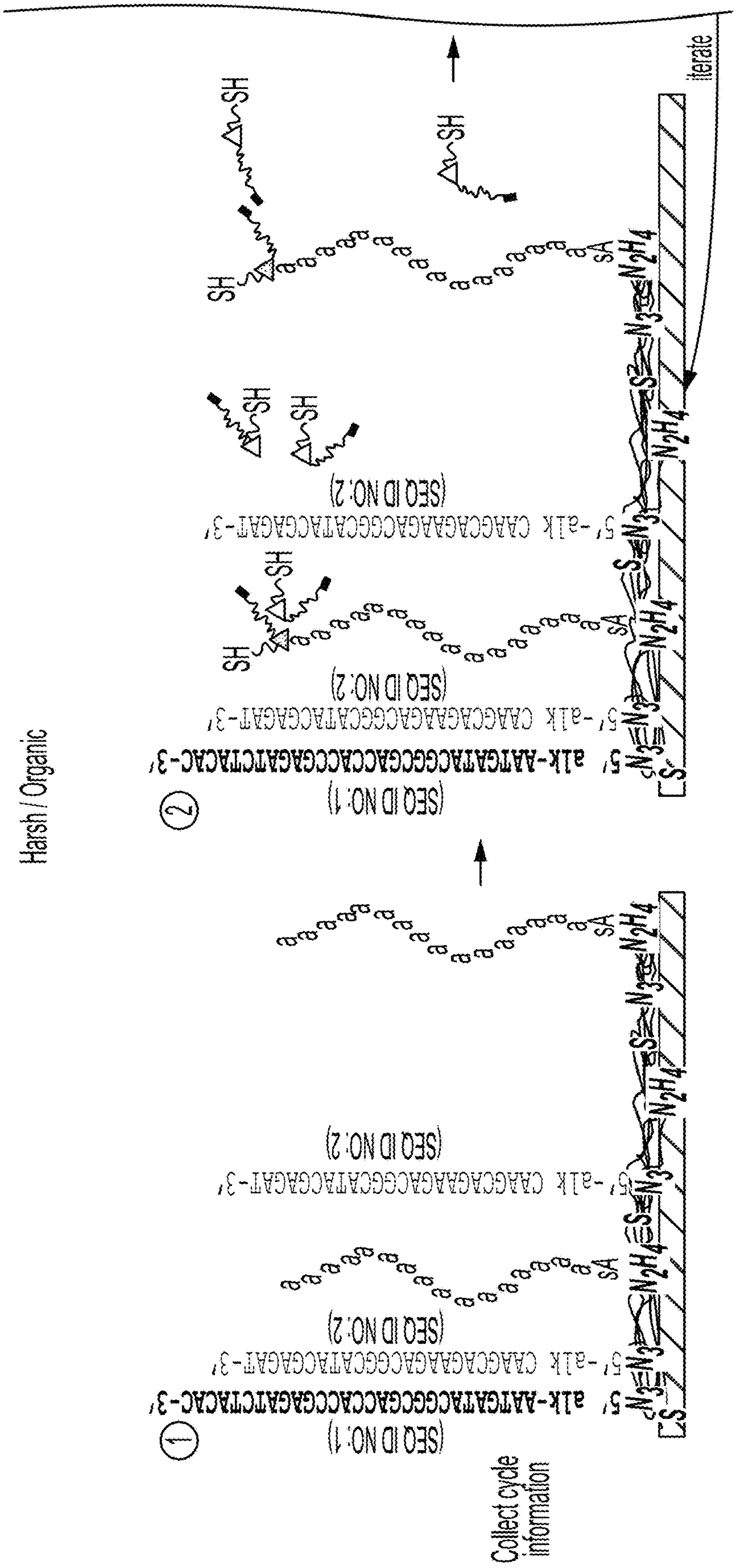
FIG. 14 schematically illustrates the separation of incompatible chemical operations during the process of FIG. 3, according to embodiments of the present disclosure.
Figure 14:
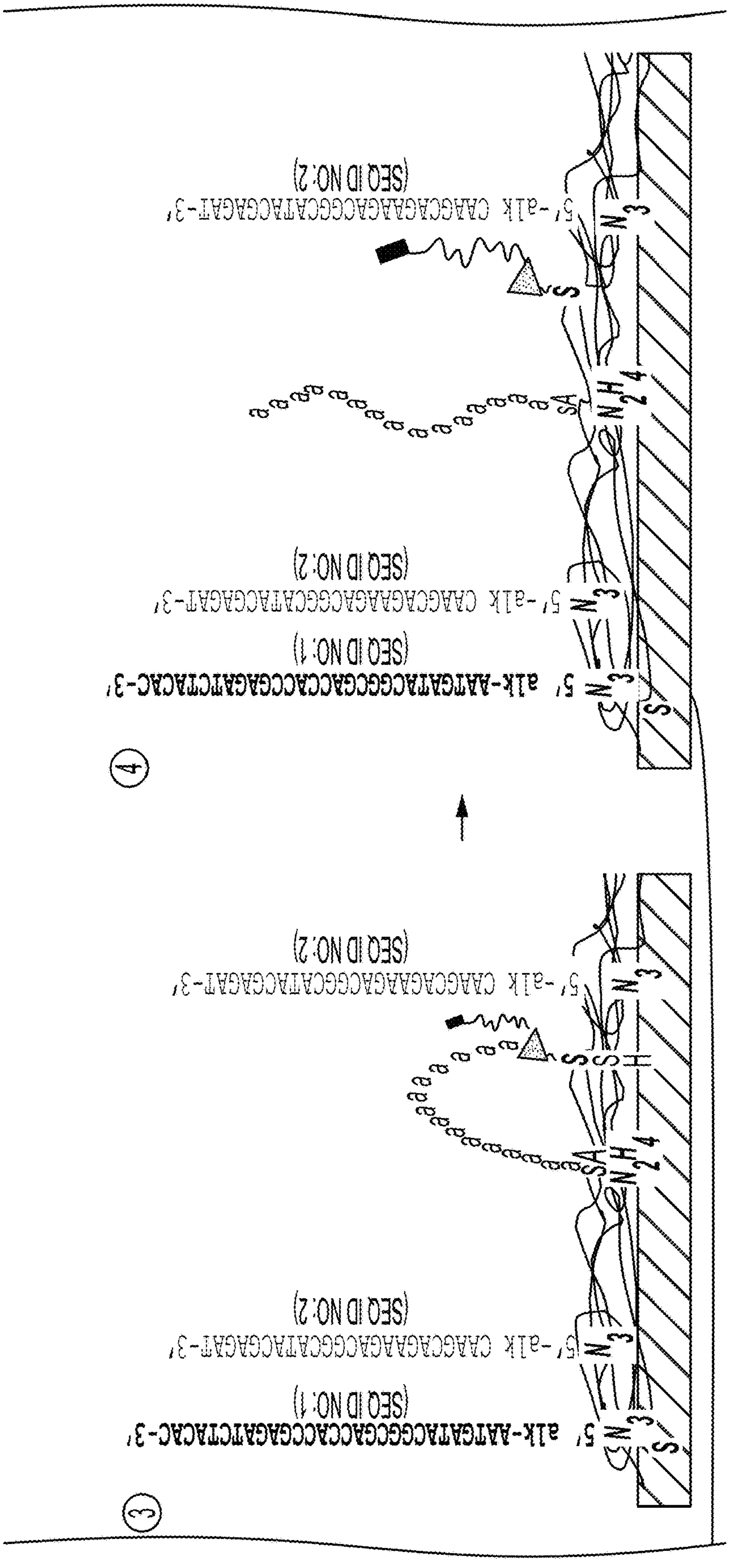
Figure 14:
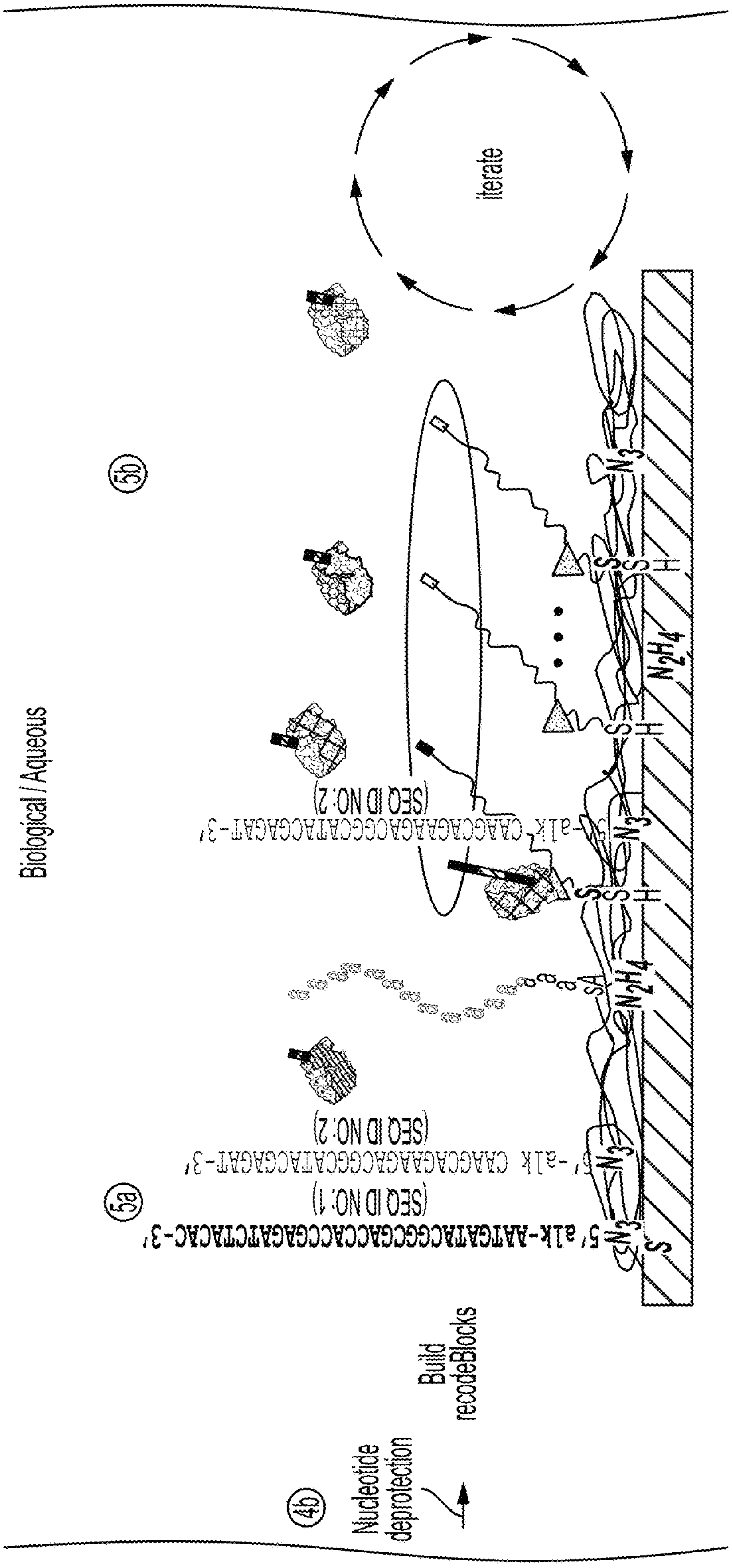
Figure 14:
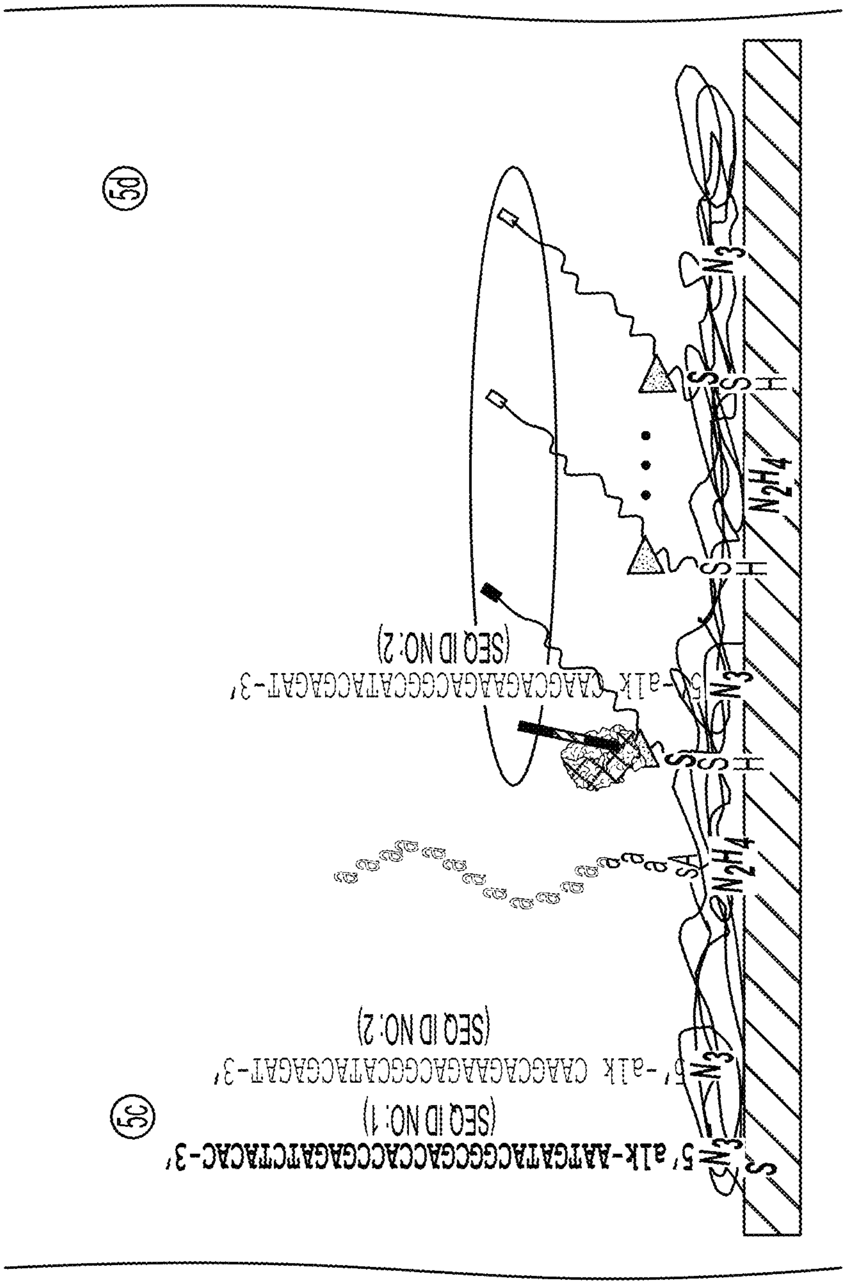
Figure 14:
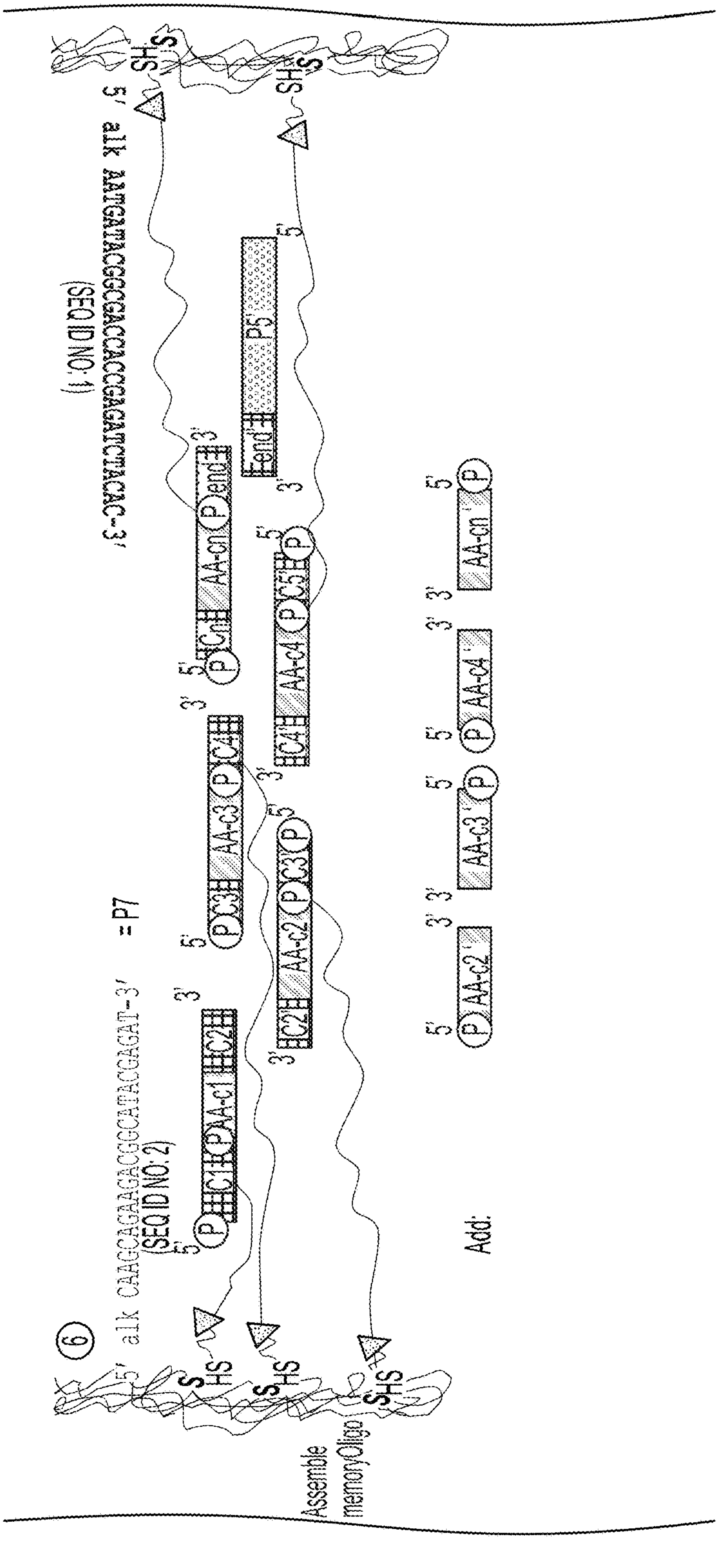
Figure 14:
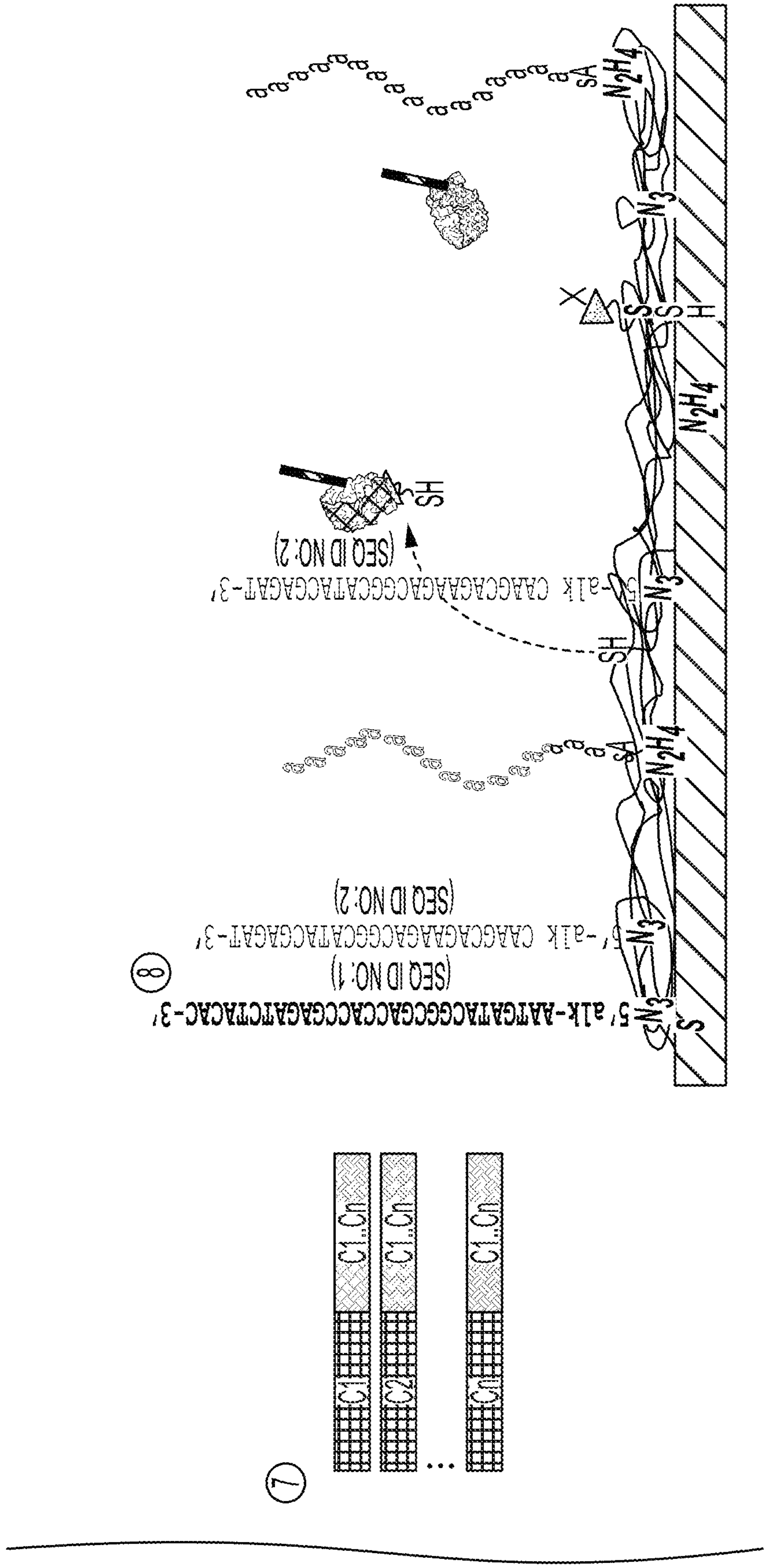

FIG. 14 schematically illustrates the separation of incompatible chemical operations during the recoding process 300, according to embodiments of the present disclosure. As shown, the recoding process 300 lends itself to separating these steps, such that toggling between chemistries to complete a cycle and/or reversible chemistries is not required.

Figure 15:
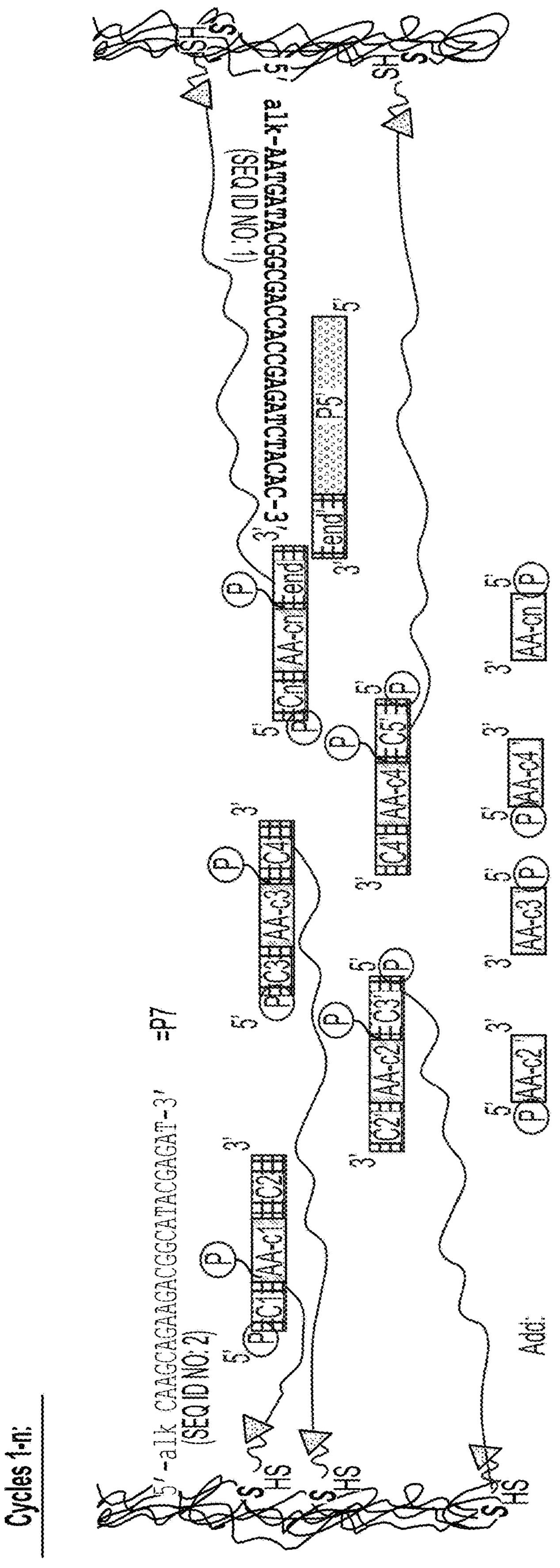
FIG. 15 schematically illustrates the assembly of a single memory oligo for subsequent DNA sequencing analysis, according to embodiments of the present disclosure.

FIG. 15 schematically illustrates the assembly of a memory oligo for subsequent DNA sequencing analysis at operations 6-8 of the recoding process 300, according to embodiments of the present disclosure. As shown, the overlapping and complementary sequences of co-localized recode blocks facilitate assembly thereof into a single oligo (memory oligo) that becomes the seed for analysis using DNA sequencing technologies. Several molecular biology methods may be useful during assembly. For example, a memory oligo may be assembled using extension via polymerase followed by ligation, or simply by using ligation methods. In the case of assembly by ligation, addition of single stranded 5' phosphorylated DNA oligos complementary to the AA tags of the recode blocks facilitate assembly. Ligation directly to primer sequences immobilized to the solid support, such as the P5 and P7 sequences shown in FIG. 15, using chimeric splints having sequence complementary to recode blocks and to P5 or P7 sequence may facilitate memory oligo amplification. Subsequent to memory oligo assembly, the recode block tethers to the solid support may optionally be cleaved, and polymerase extension from the 3' end of immobilized P5 or P7 may initiate cluster generation. Alternately, assembled memory oligo may undergo end-repair, A-tailing, sequencing adapter ligation, and amplification either in situ or in solution.

Figure 16:
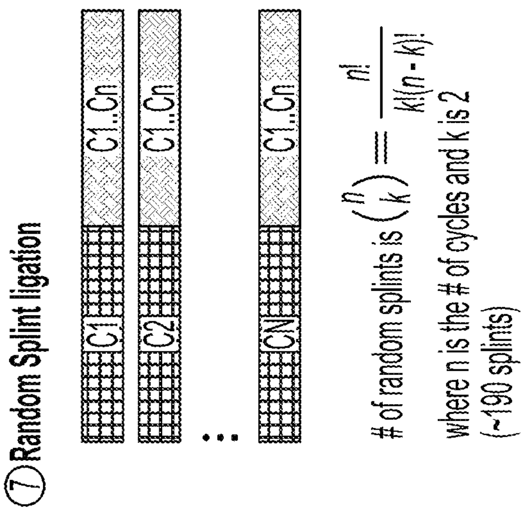
FIG. 16 schematically illustrates the remediation of incomplete recode blocks during memory oligo assembly, according to embodiments of the present disclosure.

FIG. 16 schematically illustrates the remediation of incomplete recode blocks during memory oligo assembly, according to embodiments of the present disclosure. Thus, FIG. 16 illustrates operation 7 of the recoding process 300. As shown, gaps in connectivity between co-localized conjugates may exist, for example, due to a) incomplete information accumulation during the sequential degradation of the peptide and immobilization of a PTC-AA-cycle tag-conjugate complexes, b) incomplete information transfer from a recode tag to a cycle tag during recode block assembly, or c) an incomplete ligation of available and existing recode block information during memory oligo assembly. To remedy these gaps and enable high-yield assembly of information into a single oligo that can be analyzed using DNA sequencing, a ligation step employing generic splint oligos may be executed. Remediation may be accomplished simultaneously for all cycles by using a pool that contains splints capable to assemble any non-ligated recode block with any other non-ligated recode blocks. Alternatively, remediation may be accomplished by stepwise using a subset of the described pool. The " . . . " in FIG. 16 indicates completion of the series and represents intervening linking oligos not explicitly shown. C1 indicates the cycle tag sequence (or its complement sequence) and "n" denotes the total number of cycles.

Figure 17:
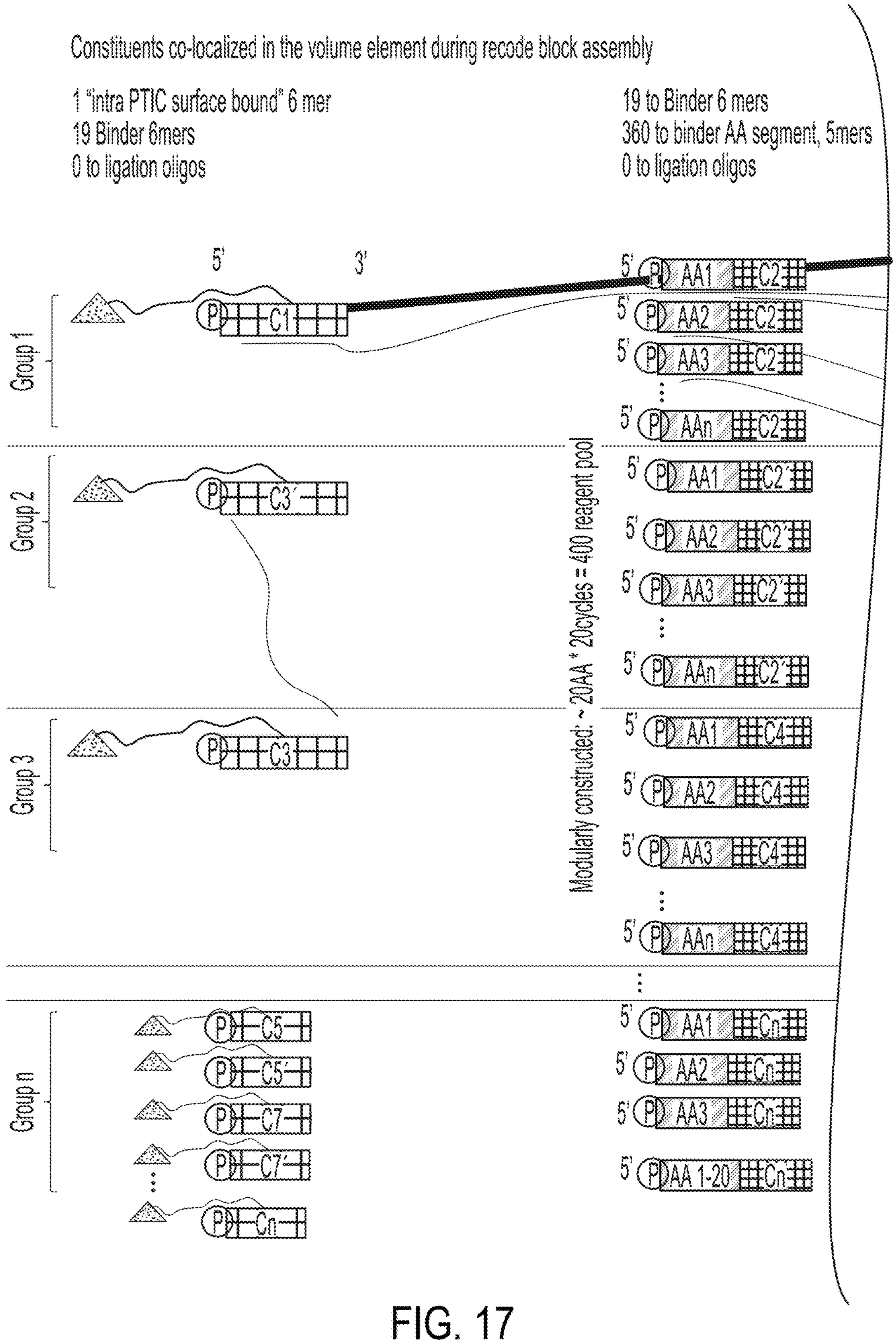
FIG. 17 schematically illustrates various oligonucleotide constituents within a sample volume during recode block assembly, according to embodiments of the present disclosure.
Figure 17:
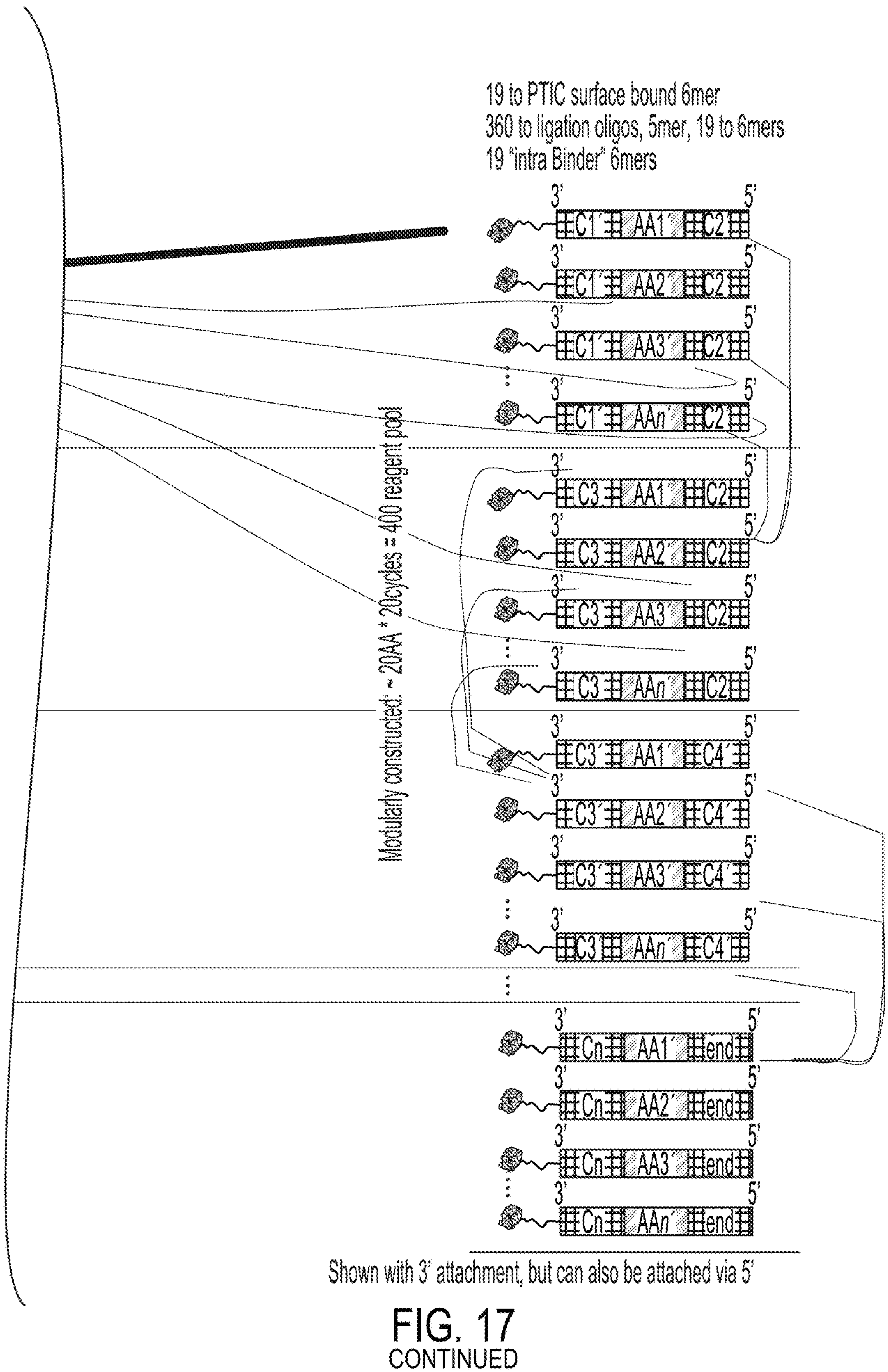

FIG. 17 schematically illustrates various oligonucleotide constituents within a sample volume during recode block assembly, according to embodiments of the present disclosure. Accounting for interactions and tuning reaction conditions facilitates accurate and complete assembly during the recoding process 300. Within any given volume element surrounding the anchor point of a protein or peptide will exist immobilized PTC-AA-cycle tag-conjugate complexes that have: (a) same AA, different cycle information, and (b) different AA, different cycle information, BUT no complexes with (c) different AA, same cycle information or (d) same AA, same cycle information. In FIG. 17, "Group 1" constituents are present to support assembly of cycle 1 information. "Group 2" constituents are present to support assembly of cycle 2 information, and so on through group 3 to group "n". Interactions within and across groups are cataloged at the top of each column. Total numbers of oligo constituents are given for each constituent type. Weak interactions due to hybridization of shortmer oligos is possible. These will be outweighed by the relatively stronger interaction of the binding moiety directing oligos for assembly. The heavyline shows a desired interaction assumed for a given recode block, $AA_1$-$Cycle_1$, and represents the total binding energy of the interaction. The light lines show exemplary possible oligo interactions. The Tm for these interactions is low, and thus erroneous ligation leading to erroneous recode block information is controlled. Recode blocks are shown with various tether sites, e.g., to 5', 3', and to internal nucleosides. The " . . . " in FIG. 17 indicates completion of the series and represents intervening cycle tags, ligation oligos, or recode tags not explicitly shown. C1 indicates the cycle tag sequence (or its complement sequence), AA indicates the amino acid recode sequence, and "n" denotes the total number of cycles.

Figure 18:
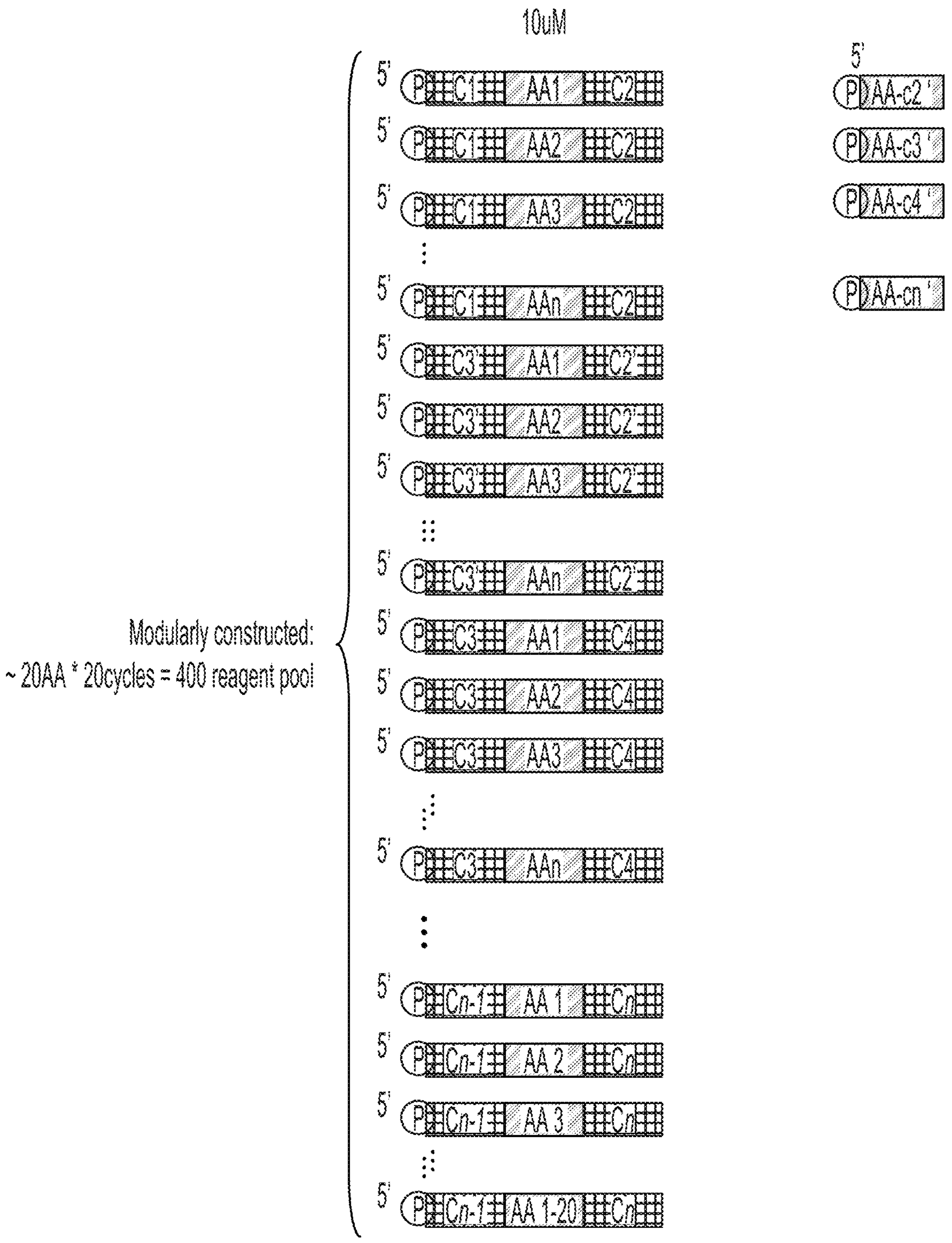
FIG. 18 schematically illustrates various oligonucleotide constituents within a sample volume during memory oligo assembly, according to embodiments of the present disclosure.

FIG. 18 schematically illustrates various oligonucleotide constituents within a sample volume during memory oligo assembly, according to embodiments of the present disclosure. In FIG. 18, the effective concentrations of constituents are high due to the co-localization within the volume element defined by the length of the macromolecular analyte and the length of the linkers of the associated recode blocks. The complexity of oligos, however, is not high. And because cycle codes (C1, C2, . . . Cn) and amino acid codes (AA1, AA2, . . . AAn) are defined using schema based on communication theory, mismatch ligation is unlikely. Note that even "incorrect assembly" that results from mismatch ligation produces an oligo with useful macromolecular analyte sequence information, since the cycle information flanks the amino acid information. Sequential information blocks in the memory oligo are redundant in determining the sequence of a peptide analyte. The " . . . " indicates completion of the series and represents intervening recode blocks or AA'-complements not explicitly shown. The "n" denotes the total number of cycles.

Figure 19:
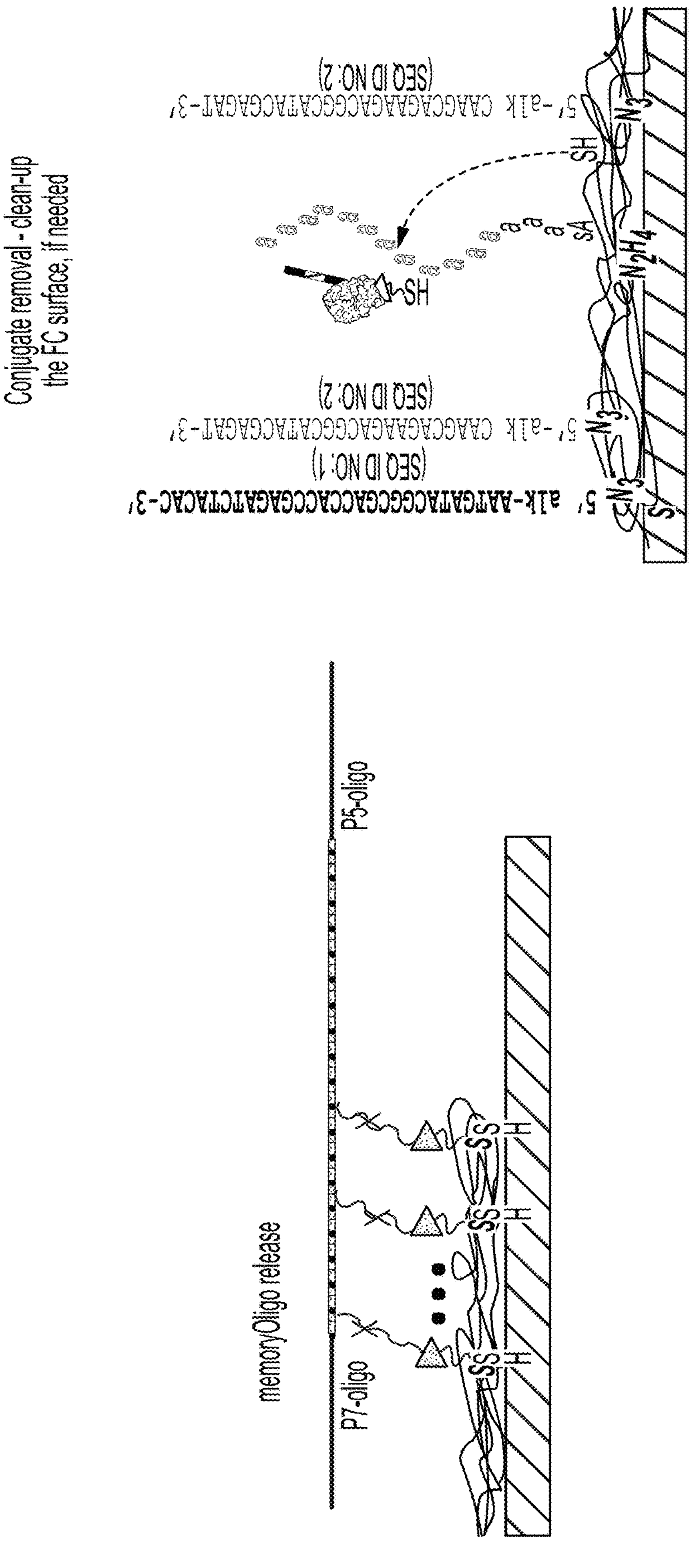
FIG. 19 schematically illustrates the release of memory oligos and conjugate complexes from a solid support, according to embodiments of the present disclosure.

FIG. 19 schematically illustrates the release of memory oligos and conjugate complexes from a solid support at operation 8 of the recoding process 300, according to embodiments of the present disclosure. An exemplary memory oligo is shown in FIG. 19 having p7 and P5 adapters. The memory oligo may also comprise a sample index, a UMI, a CRISPR PAM or spacer sequence, or other identifying nucleic acid sequence that may be incorporated during the NGS library preparation steps. Cleaving the tethers (or a subset of tethers) to the solid support is an optional step to improve the efficiency of PCR extensions involving the memory oligo. Conjugate removal from the surface is an optional process to clean-up the solid support prior to its use for downstream steps such as cluster generation, and NGS sequencing. In FIG. 19, reduction of a disulfide bond is depicted, which can be mediated by addition of dithiothreitol to a solution contacting the support surface.

In certain embodiments, a recode block comprises a sequence that facilitates assembly of a memory oligo, and/or that facilitates target enrichment, target depletion, and/or sequencing sample preparation (e.g. NGS sample preparation), such as a CRISPR PAM or spacer sequence. For example, about 90% of the protein content in human blood plasma is albumin. It would be advantageous to deplete the albumin in plasma to improve the sensitivity to detect lower-abundance proteins that are interacting with albumin therein. Thus, depletion via DNA methods of enrichment or depletion following recoding may provide less biased sample preparation than depletion or enrichment of a protein sample via conventional recognition-based methods of protein enrichment or depletion. Accordingly, oligo designs for a cycle tag, recode tag, recode block, and/or memory oligo may include CRISPR PAM and spacer sequences (or other) specific to albumin, e.g., NGG, C1-AAtag$_{Met}$-C2-AAtag$_{Lys}$, to preferentially deplete recoded albumin peptide sequences via cutting of the memory oligo amplicon with a CRISPR nuclease or other enzyme.

FIG. 20A-20B depict fluorescence values obtained throughout execution of steps 1 through 4 of FIG. 3. Relative fluorescence units (RFU) of fluorescent oligonucleotides complementary to cycle tags mark progress through advancing steps of the method. In FIG. 20A each bar shows a measurement of fluorescence in an advancing step. Bars 1 demonstrate minimal autofluorescence of the peptide and solid support used in the study. Bars 3 demonstrate capture of fluorescent oligonucleotides by CRCs immobilized to the solid support via the reaction of their reactive moiety (PITC) with the N-terminal amino acid of immobilized peptides. Low signal for bars 2 supports that signal is not related to unbound fluorescent oligonucleotides in solution, and is consistent with a signal emanating from fluorescent oligos captured by CRCs reacted to immobilized peptides on solid support. Bars 4 demonstrate the signal from fluorescent oligos released from the surface upon exposing the surface to mild chemical conditions that promote dehybridization of oligonucleotides. Relative values for bars 3 and 4 can be explained by a difference in volume during the measurements. Bars 5 corroborate the dehybridization of fluorescent oligonucleotides from the surface. Between measurement of bars 5 and 6 CRCs of sample B were immobilized to the surface via a Cu-catalyzed Huisgen cycloaddition reaction. Also, between measurement of bars 5 and bars 6, the surface was subjected to anhydrous acid under conditions that support cleavage of the N-terminal amino acid, exposing the next amino acid residue as a N-terminal amino acid residue on the cleaved peptide. Bars 6 show the progression of contacting a second CRC having a different cycle tag sequence to the surface via the reactive moiety (PITC). The CRC will be reactive toward newly exposed N-terminal amino acids of the immobilized peptides following the cleavage of the first N-terminal amino acid with acid. Bars 8 demonstrates capture of the new fluorescent oligo by CRC immobilized to the solid support via the reaction of its reactive moiety (PITC) with the new terminal amino acid of an immobilized peptide. Low signal for bars 7 supports that signal is not related to unbound fluorescent oligonucleotides in solution, and is consistent with a signal emanating from fluorescent oligos captured by the CRC reacted to the immobilized peptide on solid support. Bars 9 demonstrates the signal from fluorescent oligos released from the surface upon exposing the surface to mild chemical conditions that promote dehybridization of oligonucleotides. Relative values for bars 8 and 9 can be explained by difference in volume during the measurements. Bars 10 corroborate the dehybridization of fluorescent oligonucleotides from the surface. The progression of fluorescence signals confirms reaction, capture, and cleavage of a N-terminal amino acid residue of a peptide using matter and methods disclosed within. Strong signals for bars in step 3, 4, 8, and 9 confirm functionality of the CRC to perform steps 2-4 of FIG. 3. In FIG. 20B each bar shows fluorescence in an advancing step of the method. The conditions and conclusion are the same as for bars B of FIG. 20A, with the exception that the starting azide-functionalized silica surface was supplied by a commercial source.

Figure 21:
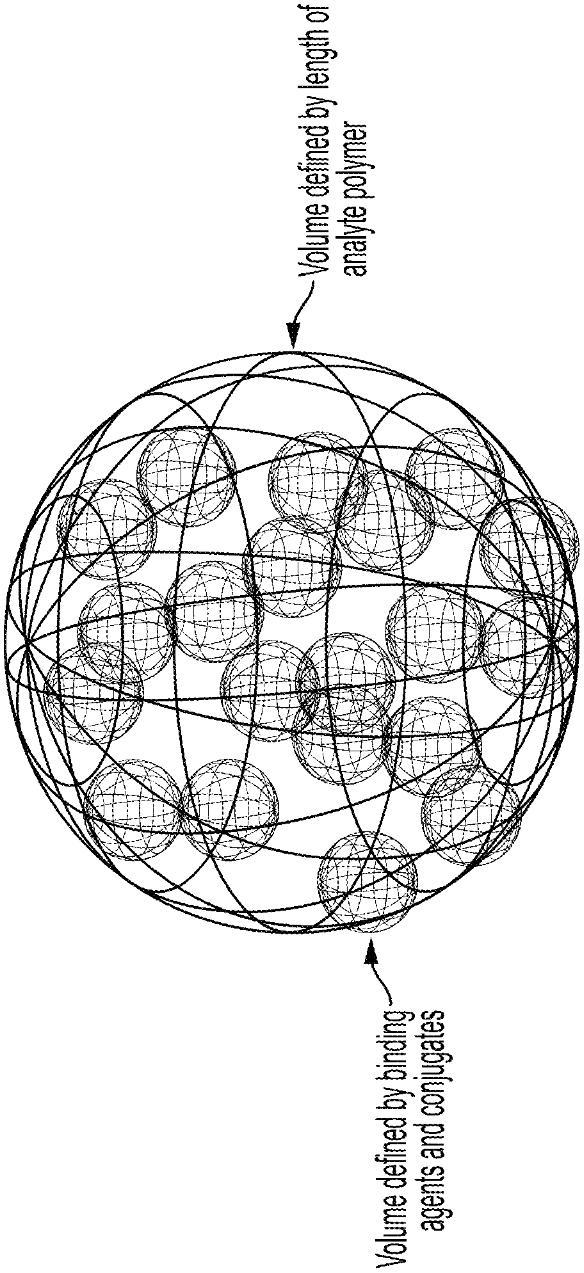
FIG. 21 schematically illustrates the adjustment of access between oligonucleotide constituents during memory oligo assembly according to the methods described herein, according to embodiments of the present disclosure.

FIG. 21 schematically illustrates how efficiency of memory oligo assembly may be adjusted, according to the methods described herein. As shown, the large sphere in FIG. 21 represents a volume as defined by the length of an analyte polymer, e.g., an amino acid polymer. Within the large sphere are many smaller spheres. Each of these smaller spheres may represent a volume as defined by the binding agents and conjugates utilized during the recoding process, and more particularly the binding agents and conjugates utilized during operation 5 described above. Such volume is primarily dependent on the linker lengths of both binding agents and conjugates. Accordingly, to facilitate association of recode blocks during memory oligo assembly, the polymer (representative larger sphere) may be collapsed via known polymer collapse mechanism, such as those described in, e.g., Leonid Lonov, Hydrogel-based actuators: possibilities and limitations, Materials Today, 17, 10, 494 (2014), which is herein incorporated in its entirety. Alternatively, the binding agents and conjugates (representative smaller spheres) may be expanded, e.g., by utilizing expandable spacers, linking oligos, and/or deconvolution of rare events in silico, as described elsewhere herein, thereby facilitating communication of neighboring recode blocks. Note that the recode blocks may be linked in any sequential order to create a memory oligo. Expandable spacers may include molecules that comprise multiple thiol groups. When disulfide bonds are formed, the range of the spacer is shortened, and when the cross-linkers are reduced, e.g., by addition of DTT, the spacer range is increased.

Figure 22:
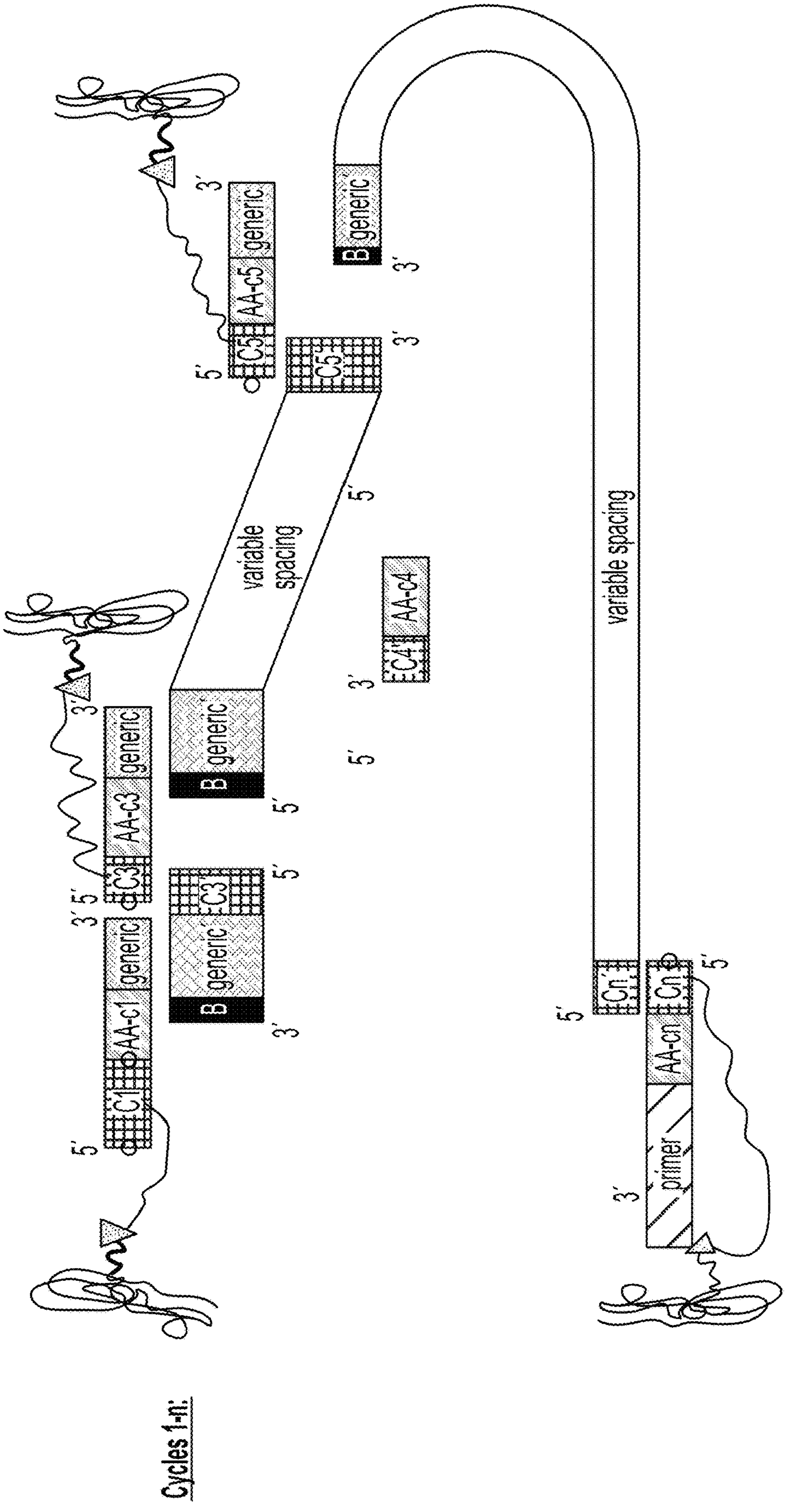
FIG. 22 illustrates the utilization of universal sequences during memory oligo assembly, according to embodiments of the present disclosure.

FIG. 22 illustrates the utilization of universal sequences to facilitate linking of recode blocks during memory oligo assembly without regard to any specific order, according to embodiments of the present disclosure. As described above, recode blocks may be linked in any sequential order to create a memory oligo. This is due to cycle information being immediately adjacent to amino acid information in assembled recode blocks, regardless of whether the recode blocks are in sequential or non-sequential order within a memory oligo. While assembly of recode blocks in the correct sequential order of an analyte may be efficient, the adjacent nature of the cycle and amino acid information in the recode blocks may cause redundancies. Thus, to avoid these redundancies while also relaxing the criteria for memory oligo assembly, the recode blocks may be assembled in random order.

To facilitate the assembly of memory oligos without regard to any specific order, universal assembly sequences may be utilized during the recoding process. Such universal sequences may be attached to the 5' and/or 3' ends of cycle tags and/or recode tags prior to introduction of these tags to the anchored analyte(s). Attaching complementary universal sequences to two or more cycle tags and/or recode tags facilitates the random linking (e.g., ligation) of resulting recode blocks during memory oligo assembly, without regard to sequential order, and a correct macromolecule analyte sequence may be assigned during post-sequencing analysis.

Figure 23:
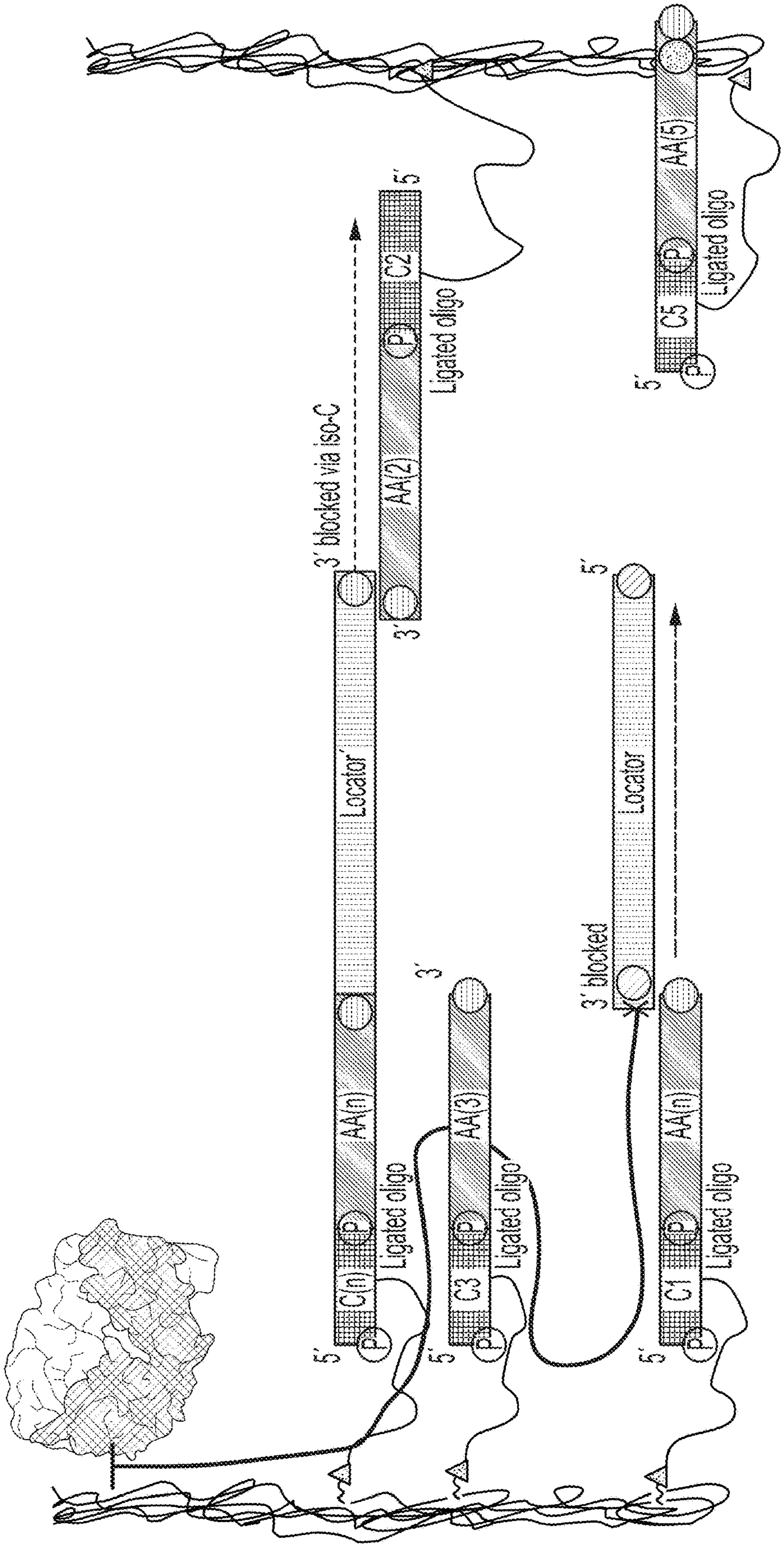
FIG. 23 is a schematic showing transfer of information from a location oligo to a recode block, according to embodiments of the present disclosure.

FIG. 23 schematically illustrates transfer of information from a location oligo to a recode block. In certain embodiments, during the recoding process, a peptide is attached to a solid support via a location linker, which may include any molecule configured to attach the peptide to the solid support, and further configured to bind to a nucleic acid. The nucleic acid can include any suitable type of nucleic acid sequence that carries code information related to the location of immobilized PTC-conjugates isolated on the solid support. The nucleic acid could be directly joined to hydrogel. This nucleic acid may be referred to as the "location oligo." Location oligos may be attached to location linkers before or after binding of the peptide thereto, and/or before or after immobilization of the peptide to the solid support. During the recoding process, after transferring the information of the recode tags to the immobilized conjugate complexes to generate recode blocks, a PCR-like thermal cycling process may be performed to sequentially transfer location oligo information via polymerase extension onto a plurality of proximal recode blocks. Utilization of non-natural nucleotides in the synthetic nucleic acids, denoted in the figure as circles, and polymerase extension with only A,G,C,T and iC in the reaction solution may be used to control undesired polymerase extension.

In sum, the recoding processes described above avoid key challenges associated with 1) incompatible chemistries/protection chemistries, 2) reversible chemistries, and 3) binder molecule specificity. Regarding incompatible chemistries and protection chemistries: Harsh chemical conditions associated with peptide bond breakage are conducted in a single block of processes wherein protecting groups can be utilized to preserve nucleic acid integrity. Regarding reversible chemistries: since information is aggregated in blocks, switching between chemistries, blocking and de-blocking labile chemical moieties, and other complexities is avoided. Because operations may be run in parallel, instead of serially accumulating information, reversible chemistries are not required. This greatly expands the universe of potential chemistries that can be deployed within the workflow. Regarding binder molecule specificity: binder molecule specificity to single amino acids is accomplished by isolating the recognition event for each individual amino acids from the influence of neighboring amino acids of the peptide by recognizing the amino acid within the isolated context of an immobilized PTC conjugate. The amino acid identity is recoded separately from cycle information (position within the polypeptide chain), providing flexibility and simplicity to the workflow/process, and reduction in the complexity of the amino acid recognition event. The DNA library recoded from peptide sequence can be amplified either directly on the solid support or by liberating the nucleic acid library from the solid support and amplifying it using standard NGS library prep reagent kits, or via standard molecular biology techniques. Analysis using any high-throughput NGS method results in millions of reads per run and translates to millions of peptides sequenced in a single run.

Figure 24:
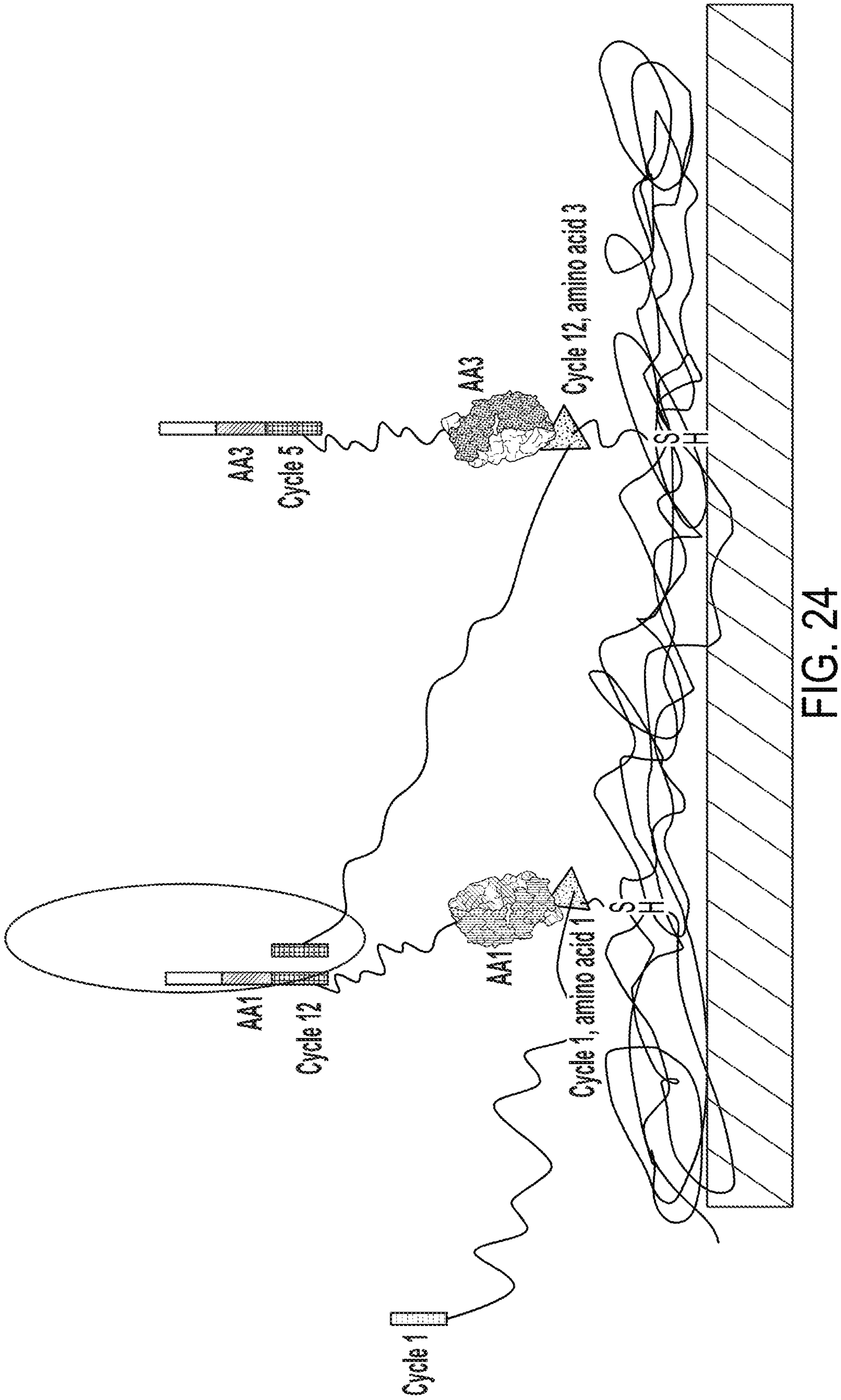
FIG. 24 schematically illustrates an alternative event during performance of the methods described herein, according to embodiments of the present disclosure.

FIG. 24 schematically illustrates an example of an alternative event during performance of the recoding methods described herein, according to embodiments of the present disclosure. More particularly, FIG. 24 depicts the inaccurate association of cycle tag information to a monomer of an analyte as caused by two conjugates being immobilized in close proximity to each other on a solid support. Referring back to operation 5*a* of the recoding process, upon introducing binding agents to immobilized conjugate-AA-cycle tag complexes, the bindings agents that possess both the cognate AA and the cognate cycle information should recognize and bind to their target conjugates. Thereafter, the binding agent should direct ligation of its AA information, in the form of a recode tag, to a cycle tag of the conjugate complex. However, the proximity of immobilized conjugate complexes on a solid support may in rare occasions cause a binding agent that possesses the cognate AA but not the cognate cycle information to bind to a conjugate complex, which leads to an alternative recode tag-cycle tag ligation and thus, inaccurate associate of cycle tag information to a monomer of the analyte.

In FIG. 24, a binding agent "AA1:C12" is shown bound to a conjugate-AA-cycle tag complex "C1:AA1." In this example, the binding agent AA1:C12 correctly recognizes the cognate amino acid (e.g., AA1 is recognized) of CA:AA1. However, because the cycle tag of complex C1:AA1 is non-cognate, the binding agent should not bind to C1:AA1. Yet, the binding agent AA1:C12 recognizes the cycle tag C12 of the nearby conjugate-AA-cycle tag complex "C12:AA3," which facilitates the "alternative" binding of binding agent AA1:C12 to complex C1:AA1. This binding is therefore facilitated by the avidity of the binding moiety of the binding agent AA1:C12 to AA1, in addition to the hybridization energy of the C12:AA3 complex in close proximity to the CA:AA1 complex. As a result of this binding, amino acid 3 (AA3) is "alternatively" assigned to cycle 12 (C12), whereas the correct assignment in in this example would be AA1 to C1. Note that in this example, the binding agent and the nearby conjugate complex must hold the same cycle information in order to allow the alternative event.

The alternative assignment in FIG. 24 may not be remedied by sequentially introducing binding agents to immobilized conjugate-AA-cycle tag complexes in the order of: $AA_{1-n}$:C1, $AA_{1-n}$:C2, $AA_{1-n}$:C3, and so on, for all recode cycles to cycle "n". Similarly, the assignment cannot be remedied by sequentially introducing binding agents to immobilized conjugate-AA-cycle tag complexes in the order of: $AA_1$:C1, $AA_2$:C2, $AA_3$:C3, and so on, for all amino acid binding moieties. Rather, in order to reduce or eliminate the type of interactions in FIG. 24, spatial separation of the conjugate-AA-cycle tag complexes may be promoted.

Short spacers for the conjugate-AA-cycle tag complexes and the binding agents may be used during the recode block assembly steps (e.g., operations 5*a*-5*d* above) to effectively avoid these alternative events. However, such spacers may negatively affect the assembly of memory oligos, since such assembly is facilitated by the interaction of recode blocks. To overcome these conflicting spatial constraints, a spacer molecule that can be controllably lengthened or expanded may be used. For example, a cysteine may be incorporated at both ends of a spacer molecule via a disulfide bridge, thereby facilitating a shortened linker during recode block assembly (e.g., operations depicted in FIG. 24). This spacer may be expanded during memory oligo assembly by reducing the disulfide bonds. Alternatively, a polymer that is controllably expandable can be utilized. For example, a two-part hydrogel configured to collapse or expand based on solution/solvent conditions, or a polymer having reactivity that allows for expansion, can be incorporated in the solid support. During recode block assembly, the polymer may be relaxed, thereby increasing the distance between anchored conjugate-AA-cycle tag complexes; however, during other steps of the recoding process, the polymer may be collapsed.

In still further embodiments, linking oligos with bridging capability may be utilized (e.g., see FIG. 22) to mitigate inaccessibility of recode blocks to one another. For example, as shown in FIG. 22, long linking oligos may be used to bridge gaps via recode blocks via an extension:ligation approach. In other embodiments, a priori information and probabilities may be used to improve the accuracy of identification, since the events as depicted in FIG. 24 are rare and dependent on proximity of conjugate-AA-cycle tag complexes). AI and other computer-based methods may be useful to recognize these events so that they may be corrected in silico.

Figure 25:
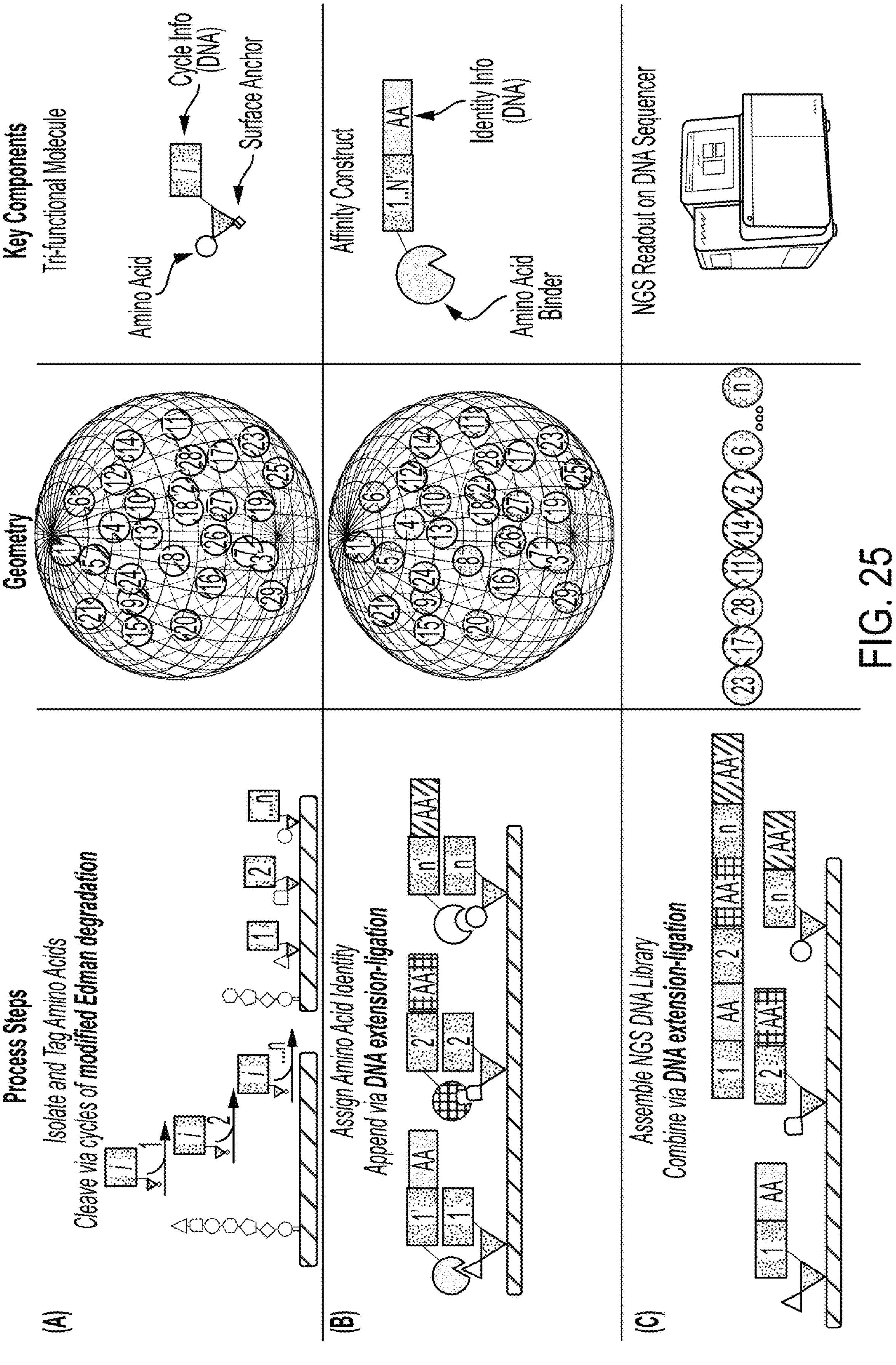
FIG. 25 is a schematic describing useful process steps, system geometry, and components.

FIG. 25A-25C include example methodologies, which may include isolation, assignment, and assembly. FIG. 25A depicts an example of Isolation: N-terminal amino acids may be sequentially removed from a peptide using a trifunctional molecule in a series of cycles, each of which results in immobilization of one amino acid complex adjacent to the anchor point of its cognate peptide. Multiple cycles may create a lawn of spatially localized complexes holding cycle DNA, as depicted in the uppermost Geometry panel, where the large sphere represents a protein localization, and the smaller spheres represent its isolated amino acid localizations. Cycle may be known, but an amino acid identity is not yet determined. FIG. 25B depicts an example of Assignment: following the removal of protecting groups from isolated complexes and transition from an anhydrous to an aqueous environment, amino acid identity may be appended to isolated complexes via recognition by an affinity construct that brings identity information in the form of DNA into proximity of the cycle DNA. 'Identity' and 'cycle' DNA may be ligated in a high-fidelity reaction. FIG. 25C depicts an example of Assembly: extension-ligation of regional DNA into a long construct that reflects the original peptide information, as shown in the lowest geometry panel, may be analyzed using NGS sequencing.

Figure 26:
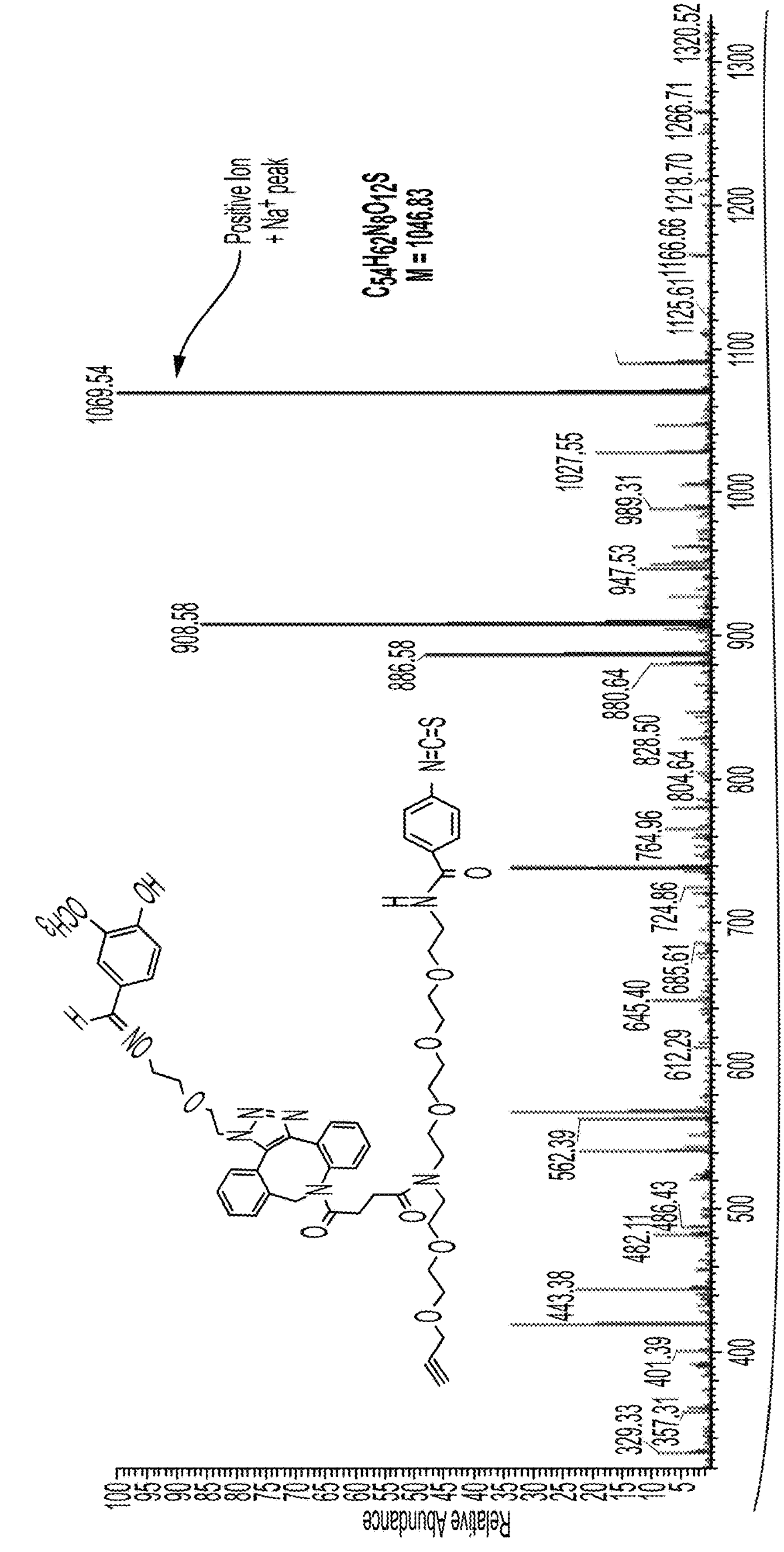
FIG. 26 shows an example model CRC with a model vanillin molecule in place of an oligonucleotide for proof-of-concept analysis showing creation of the three described groups.
Figure 26:
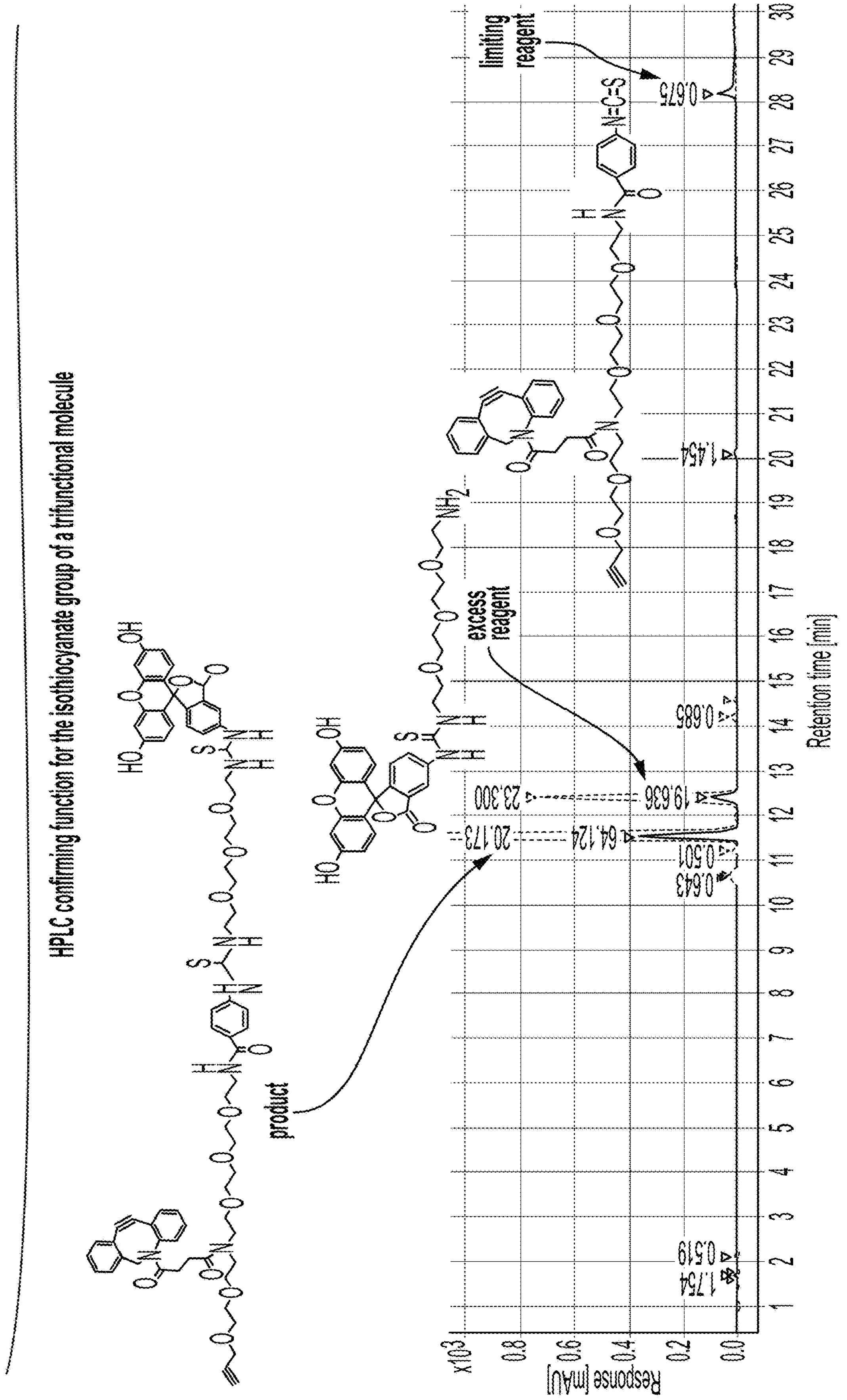

FIG. 26 shows a ~1 kd trifunctional molecule with: (1) phenyl isothiocyanate, (2) propargyl, and (3) model vanillin at the oligo position to simplify analytical characterization of the base structure: NNN-(Propargyl-PEG2) (6-oxo-6-(dibenzo[b,f]azacyclo oct-4-yn-1-yl)-caproic) (PEG3-1-acetamido-4-iso-thiocyanato-benzene). The molecular structure was confirmed using $L_C$ ESI-MS, and its function was tested. The HPLC analysis shows formation of a product with high yield indicating functional activity of the key reactive isothiocyanate moiety.

Figure 27:
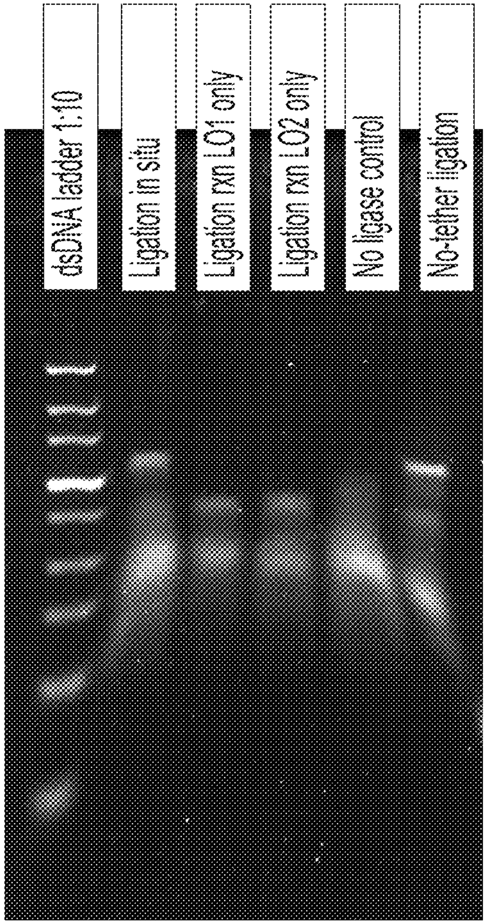
FIG. 27 shows gel data of ligation of a model cycle tag and a recode tag to generate a recode block.

FIG. 27 shows an agarose electrophoresis gel that demonstrates effective in situ ligation of cycle tags and recode tag oligos. In lane 1 is a dsDNA ladder (cat #10597012 from Invitrogen) with the brightest band appearing at 100 base pairs. In lane 2 are the products from ligation of the 45-mer oligo with tether arm with a 30-mer ligation oligo on both the 3' (Sys #001 LO2,30, SEQ ID NO: 85) and 5' (Sys #001,LO1,30, SEQ ID NO: 84) ends. Three bands are visible: the product with both 30-mer oligos ligated, a faint band showing either one or the other 30-mer oligos ligated, and a smeared band showing the unligated 45-mer oligo. Lanes 3 and 4 show the ligation products when only one or the other of the 30-mer ligation oligos is added to the reaction, so a shorter product is generated. Lane 5 shows the ligation mixture without ligase added, the primary band is the 45-mer oligo band. Lane 6 shows the ligation products with a "no tether" version of the 45-mer oligo and the three bands are similar to those in Lane 2 indicating the presence of the double ligation product, the single ligation products, and the unligated 45-mer product.

Figure 28:
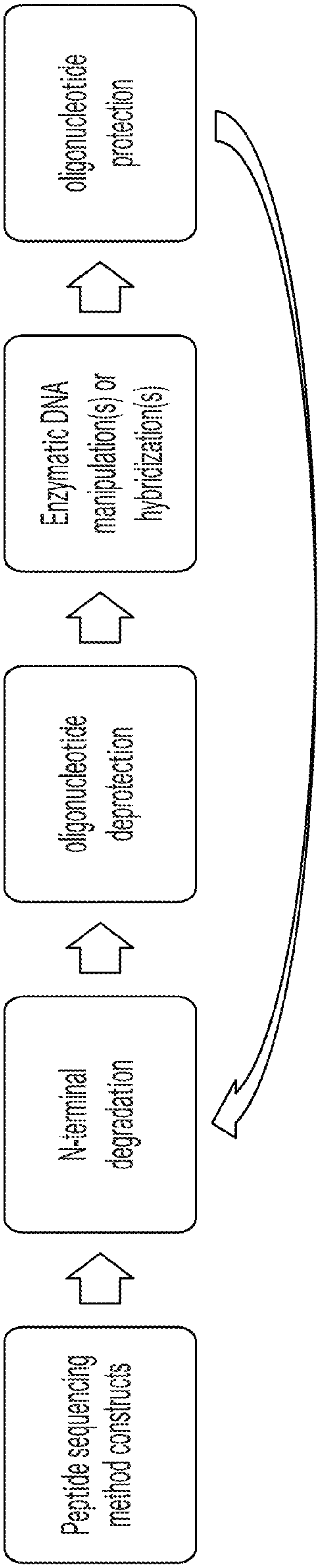
FIG. 28 shows an example of a cyclic protection and deprotection workflow.

FIG. 28 shows a block diagram for steps of a cyclic protection and deprotection workflow.

Figure 29:
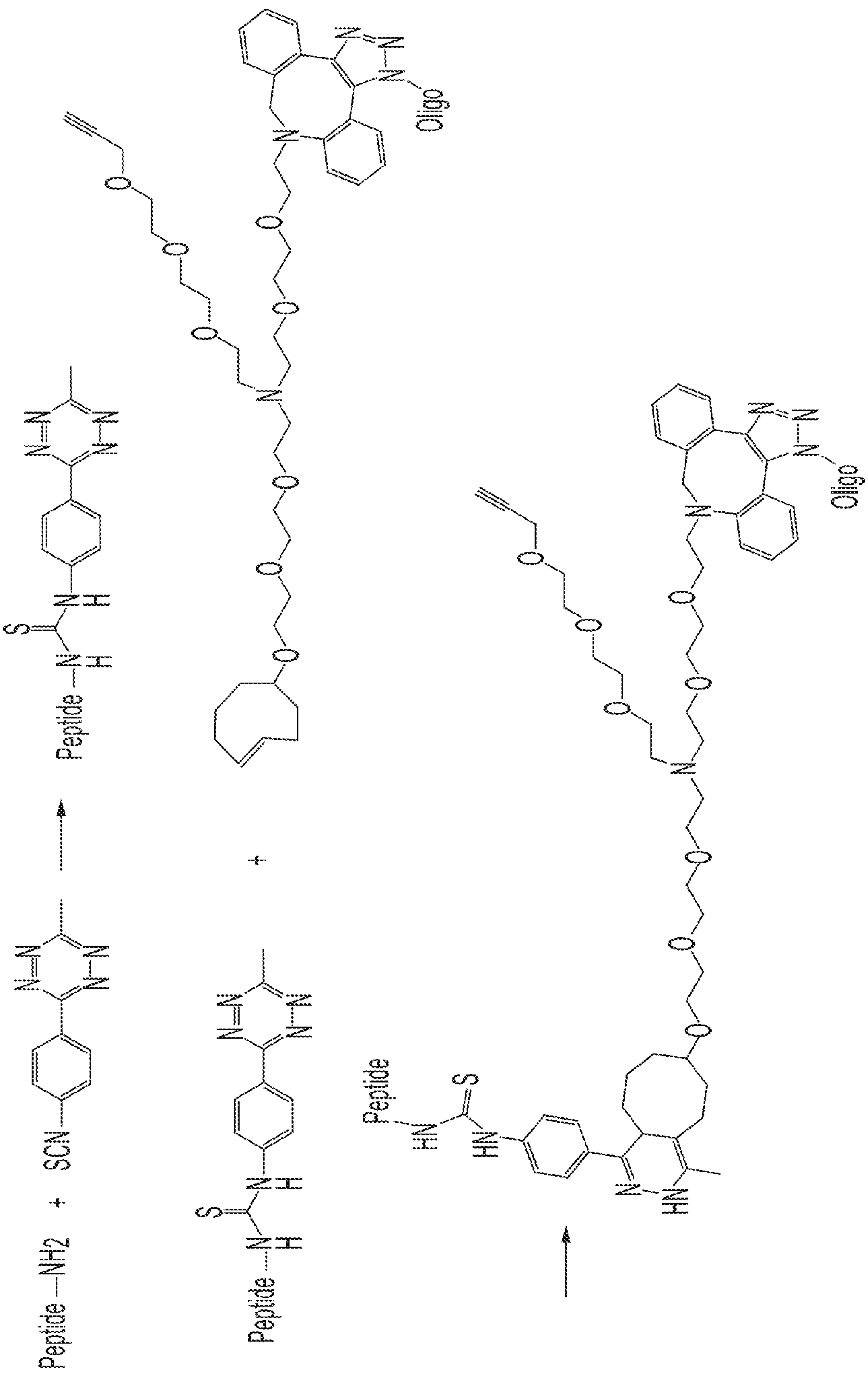
FIG. 29 schematically illustrates a 2-step assembly of a CRC with the N-terminus of a peptide FIG. 30 schematically illustrates a 2-step assembly of a CRC with the N-terminus of a peptide.

FIG. 29 shows a reaction scheme for the stepwise assembly of an immobilized CRC complex, where an N-terminal amino acid is reacted with an amine-reactive molecule possessing a 2nd reactive functional group (e.g. tetrazine). The trifunctional construct possessing a nucleic acid cycle tag and surface immobilization moiety and trans-cyclooctene may be reacted with the tetrazine of the amine-reactive molecule to form a immobilized CRC complex.

Figure 30:
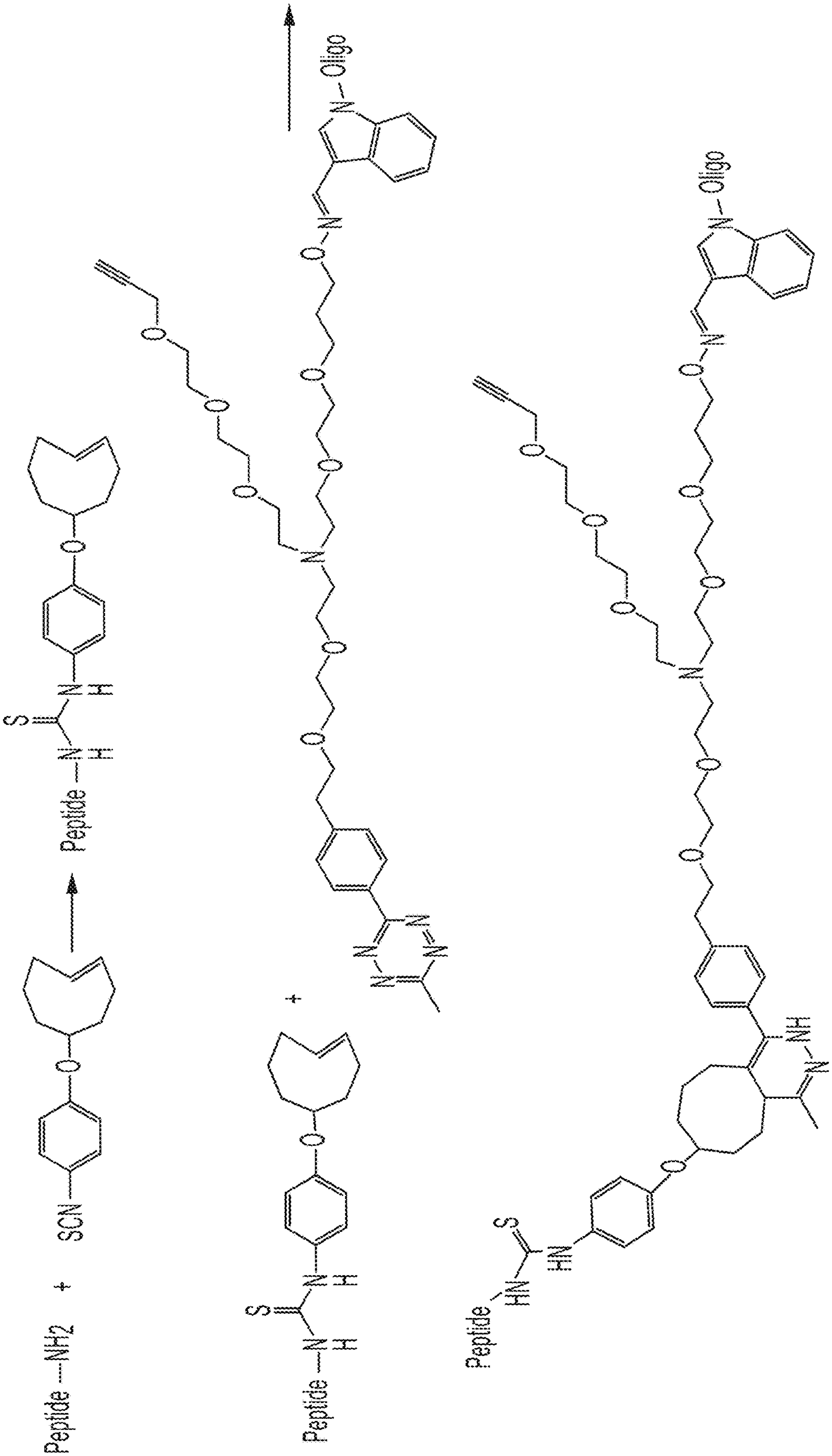

FIG. 30 shows a reaction scheme for the stepwise assembly of an immobilized CRC complex, where an N-terminal amino acid is reacted with an amine-reactive molecule possessing a 2nd reactive functional group (e.g. trans-cyclooctene). The trifunctional construct possessing a nucleic acid cycle tag and surface immobilization moiety may be reacted with the tetrazine functional group of the amine-reactive molecule to form a immobilized CRC complex.

Figure 31:
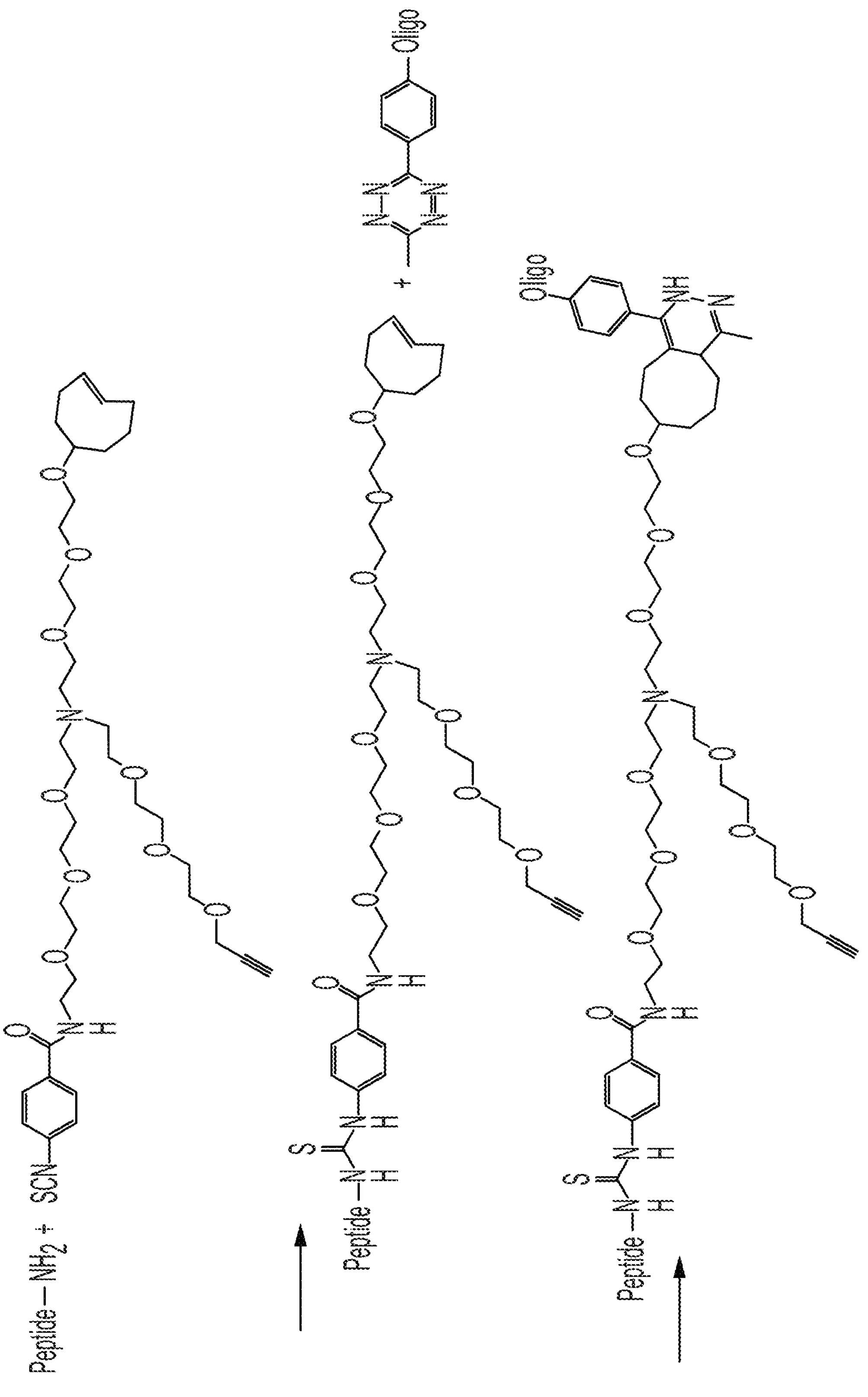
FIG. 31 schematically illustrates a 2-step assembly of a CRC with the N-terminus of a peptide.

FIG. 31 shows a reaction scheme for the stepwise assembly of an immobilized CRC complex, where a tetrazine-labeled oligo is reacted with an a functional group (e.g. trans-cyclooctene) of a trifunctional construct possessing a reactive moiety for binding and cleaving the N-terminal amino acid residue of the peptide and a surface immobilization moiety.

Figure 32A:
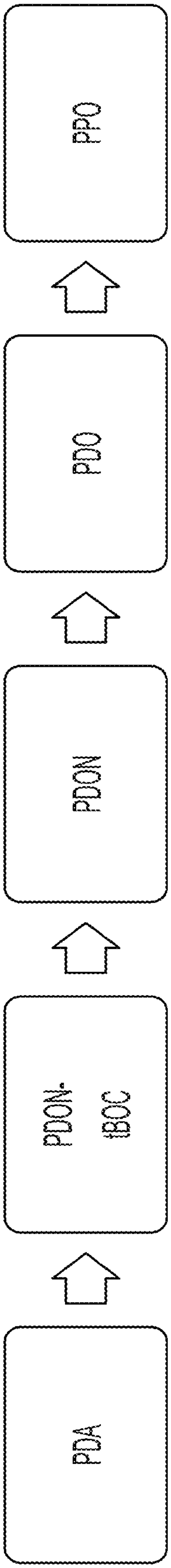
FIG. 32A-32B show a CRC synthesis processes and intermediate molecules.
Figure 32B:
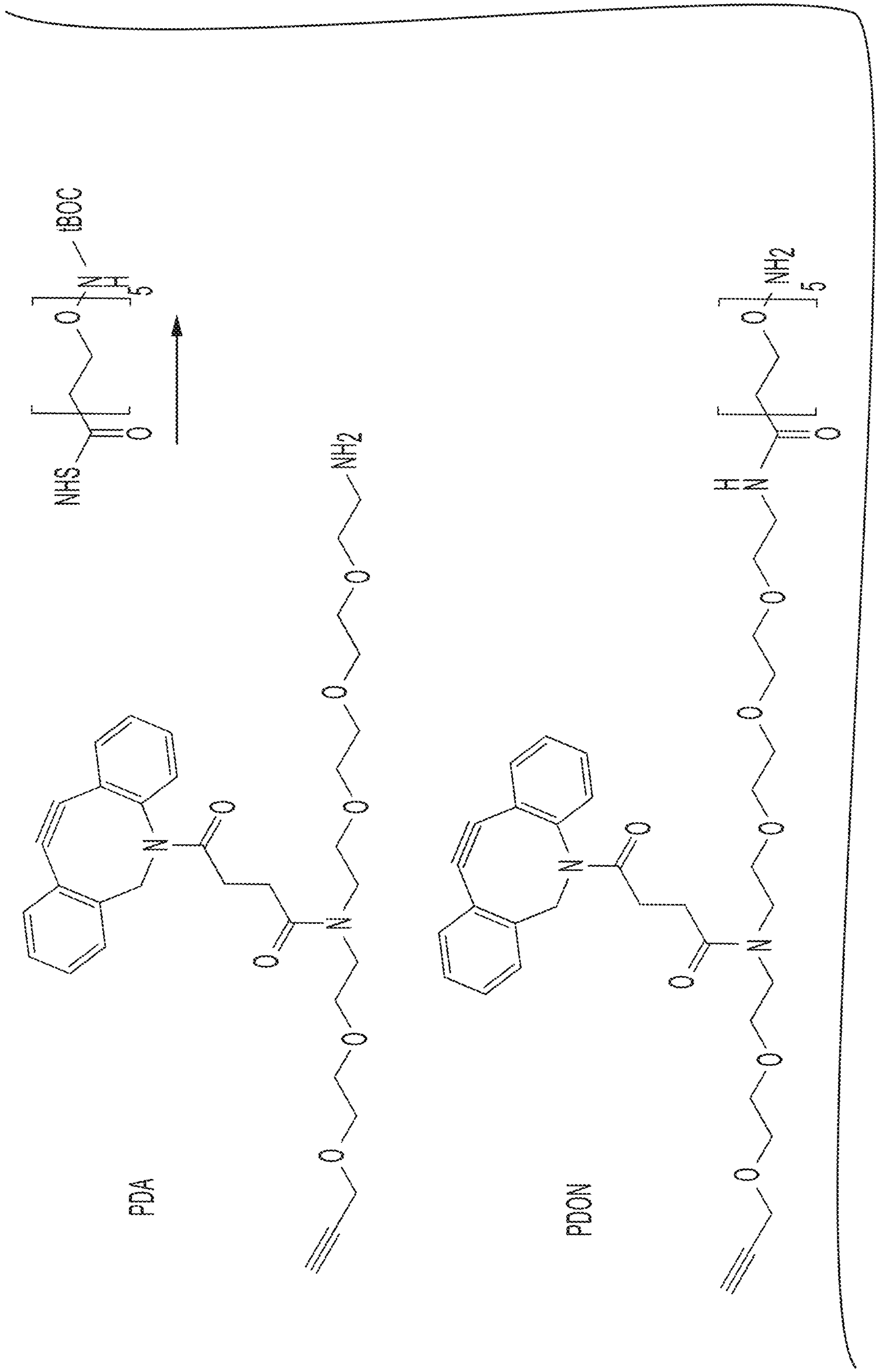
Figure 32B:
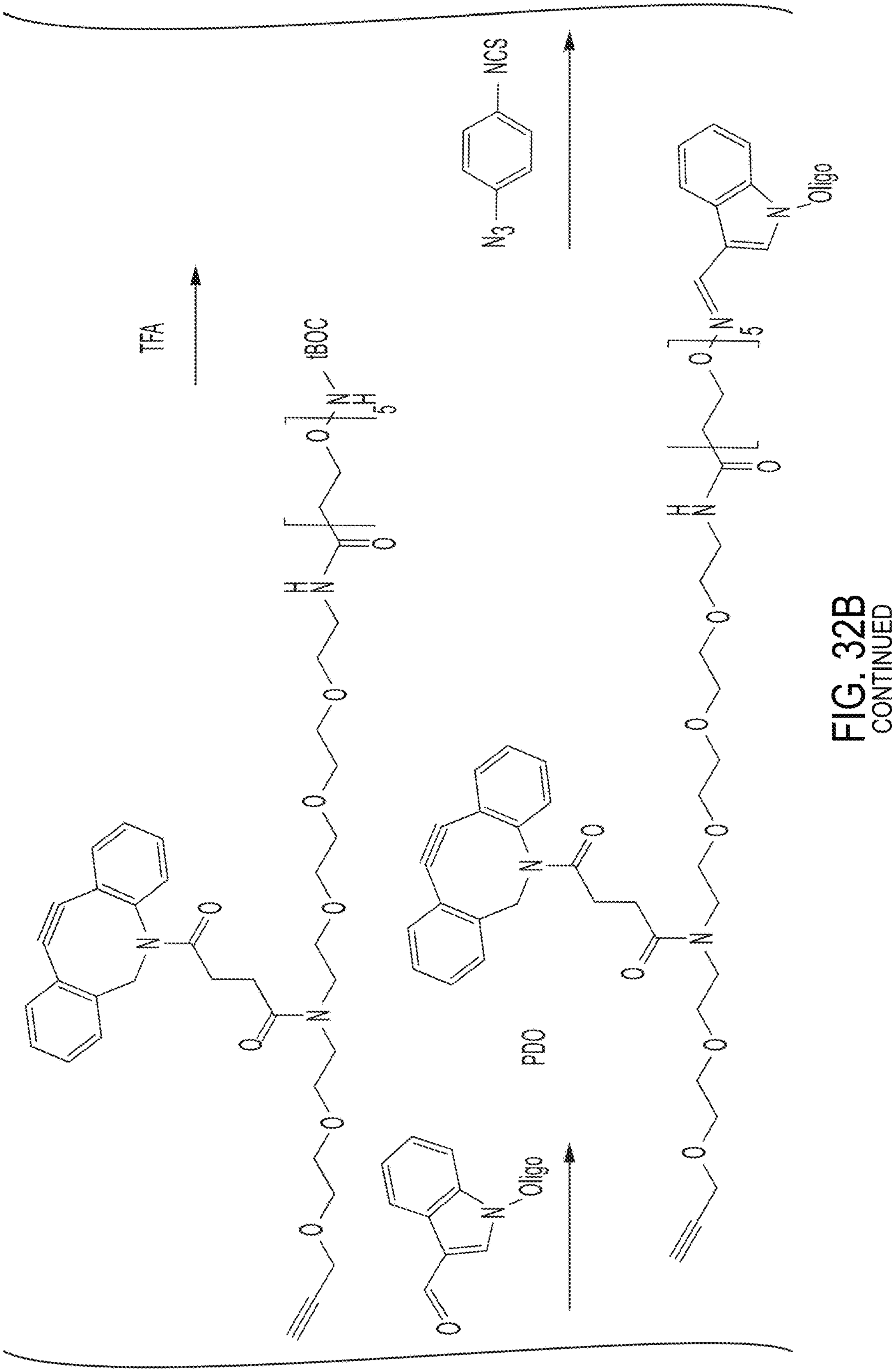
Figure 32B:
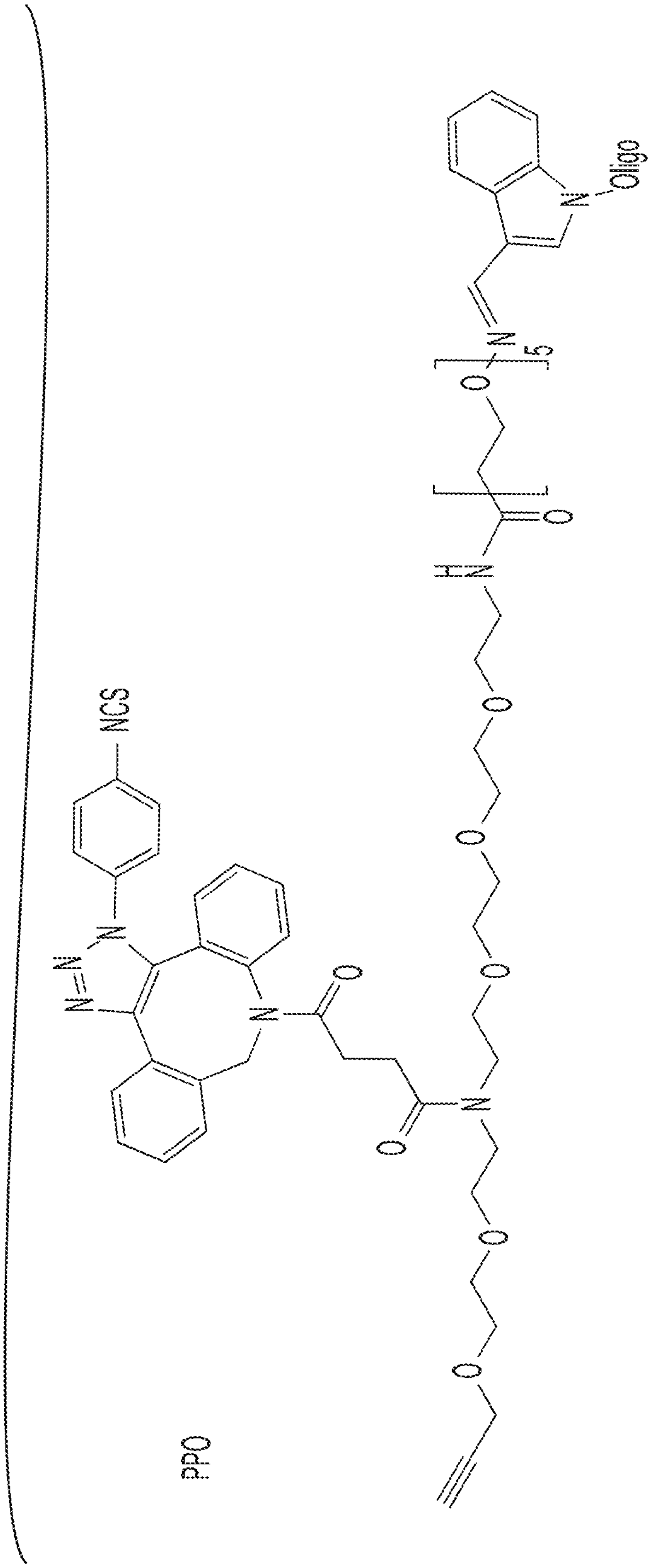

FIG. 32A-32B show a CRC synthesis processes and intermediate molecules. FIG. 32A is a block diagram that illustrates the steps for synthesizing PPO, starting from PDA. It is converted to PDON-tBOC, which may be deprotected to form PDON, then converted to PDO and subsequently converted to PPO. FIG. 32B includes the chemical structure of PPO and intermediates.

Figure 33:
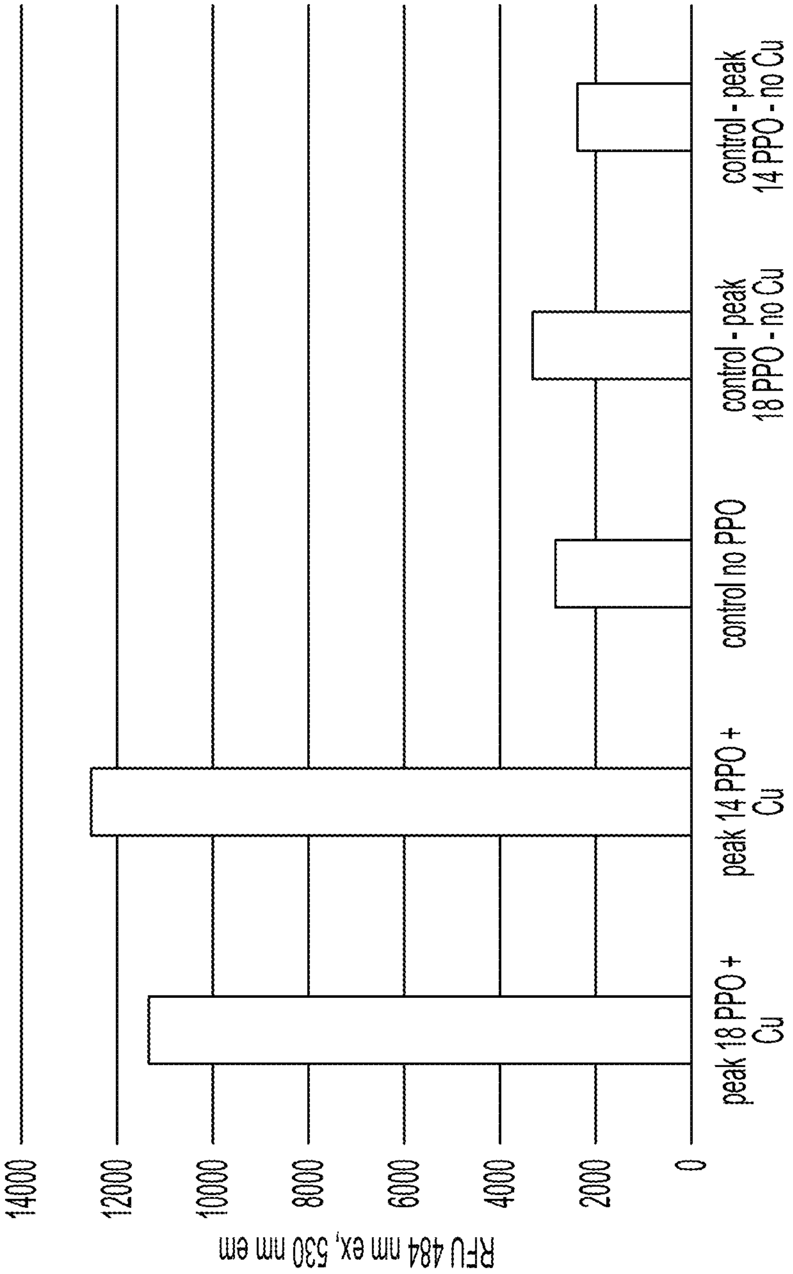
FIG. 33 shows functionality of PPO: Relative fluorescence units (RFU) of of PPO immobilized to an azide-modified surface via Cu-catalyzed Huisgen cycloaddition followed by reaction with amine-labelled fluorescein FIG. 34 Shows functionality of PPO. Relative fluorescence units of a fluorescent oligo complementary to the oligo on PPO immobilized to an azide-modified surface via Cu-catalyzed Huisgen cycloaddition.

FIG. 33 shows the function of PPO. Relative fluorescence units (RFU) of PPO immobilized to an azide-modified surface via Cu-catalyzed Huisgen cycloaddition followed by reaction with amine-labelled fluorescein is shown. Multiple fractions of purified PPO perform similarly. Strong signals above background confirm both the function of the alkyne and ITC chemically-reactive elements of the CRC.

Figure 34:
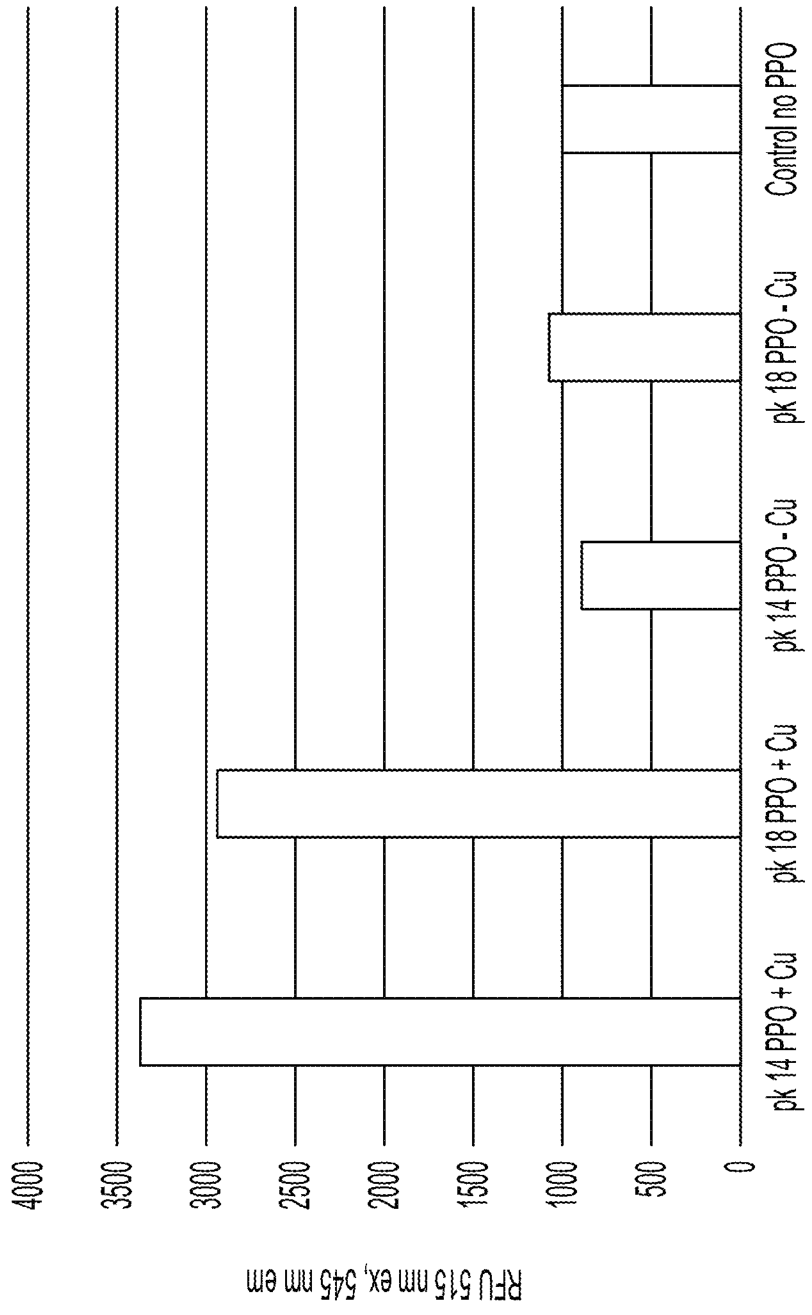

FIG. 34 Shows the function of PPO. Relative fluorescence units of a fluorescent oligo complementary to the oligo on PPO immobilized to an azide-modified surface via Cu-catalyzed Huisgen cycloaddition is shown. Multiple fractions of purified PPO perform similarly. Strong signals above background confirm both the function of the alkyne and oligo elements of the CRC.

Figure 35:
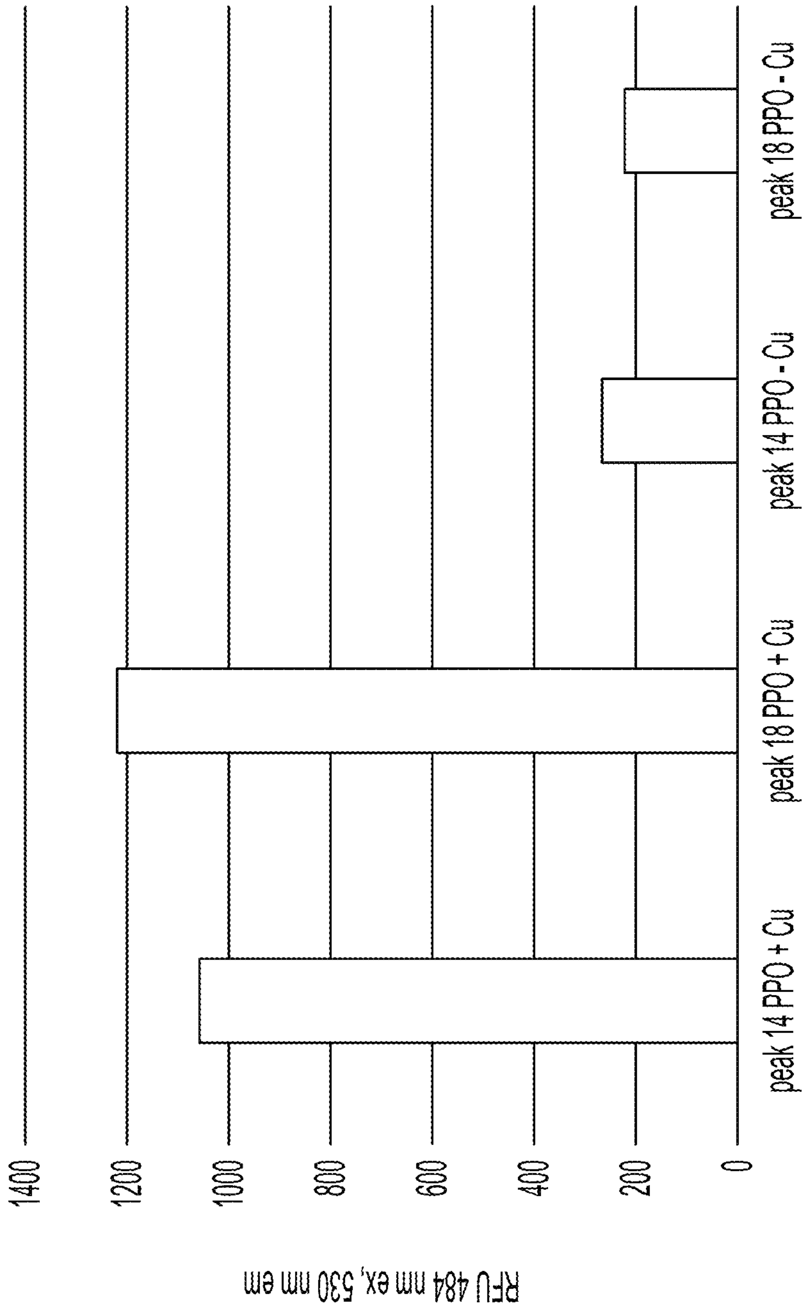
FIG. 35 shows functionality of PPO: Relative fluorescence units (RFU) of of PPO immobilized to a different azide-modified surface via Cu-catalyzed Huisgen cycloaddition followed by reaction with amine-labelled fluorescein

FIG. 35 shows the function of PPO. Relative fluorescence units (RFU) of PPO immobilized to an amine-modified surface via the reactive ITC moiety followed by Cu-catalyzed Huisgen cycloaddition to a azido-labeled fluorescein reagent is shown. Multiple fractions of purified PPO perform similarly. Strong signals above background confirm the function of the alkyne, function of the ITC chemically-reactive elements of the CRC and the capability to use the CRC on multiple embodiments of solid support.

FIG. 36A-36D shows exemplary simulations and the binding kinetics of a commercially-available antibody (Sigma, SAB5200015) to an immobilized phosphotyrosine-PTH-ligand. FIG. 36D shows representative data of strong and reproducible binding curves generated using the Nicoya SPR system.

Figure 37:
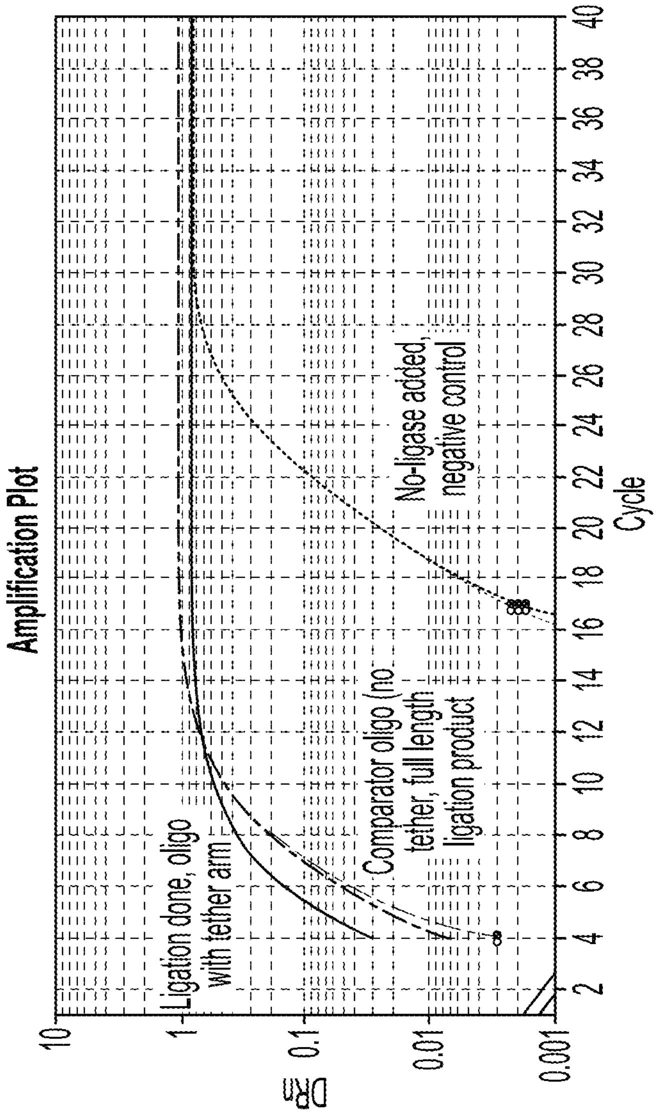
FIG. 37 shows PCR data of ligation of a model cycle tag and a recode tag to generate a recode block.

FIG. 37 shows PCR data of ligated recode block. Amplification of ligated oligos both with and without tethers shows amplification of ligated recode blocks with tethers, thus showing the ability to generate amplicons off of tethered recode blocks for subsequent obtaining of sequence information for a memory oligonucleotide or recode block.

In certain embodiments, a method for analyzing one or more peptides from a sample comprising a plurality of peptides, proteins, and/or protein complexes is provided, the method comprising: (a) providing a peptide of mer length n=2 to 2000 joined to a solid support; (b) providing a first chemically-reactive conjugate, e.g., a PITC-conjugate, wherein the first chemically-reactive conjugate comprises a cycle tag (e.g., a "cycleTag") with identifying information regarding a workflow cycle of the method, a reactive moiety that can bind and cleave a terminal amino acid of the peptide, and a reactive moiety that facilitates immobilization to a solid support, (c) contacting the peptide with the first chemically-reactive conjugate, wherein the first chemically-reactive conjugate binds with a terminal amino acid, or a modified terminal moiety, of the peptide to form a conjugate complex, e.g., a PTC-AA-cycle tag-conjugate complex, (d) immobilizing the conjugate complex to the solid support, (e) cleaving the terminal amino acid from the peptide thereby providing an immobilized conjugate complex, and a new terminal amino acid of the peptide joined to the solid support of (a), (f) contacting the immobilized conjugate complex with a first binding agent capable of binding to the immobilized conjugate complex, wherein the first binding agent comprises a binding moiety and a first recode tag (e.g., a "recodeTag") with identifying information regarding the first binding agent; (g) transferring the information of the first recode tag associated with the first binding agent to the cycle tag of the immobilized conjugate complex, to generate a first recode block (e.g., a "recodeBlock"); (h) optionally repeating steps (b) through (g) to assemble a second recode block having recoding information for the new terminal amino acid of the peptide; (i) optionally repeating step (h) for additional iterative cycles to create additional recode blocks for additional amino acids of the immobilized peptide of step (a); (j) optionally deprotecting nucleic acids of the first, second, and additional recode blocks; (k) contacting the recode blocks with polymerase, nucleotides, ligase, and buffer under conditions that allow extension-ligation to assemble the recode blocks into a memory oligonucleotide (e.g., a "memoryOligo"); and (1) analyzing the memory oligonucleotide.

In some aspects, one or more operations of the method are repeated one or more times to increase a step yield of the method. For example, in specific aspects, operations (e), (f), and/or (g) are repeated one or more times to increase the step yield.

In some aspects, the method further comprises, between operation (h) and (j) and/or after operation (k), contacting the immobilized conjugate complex with a promiscuous binding agent capable of binding to the immobilized conjugate complex independent of the identity of an amino acid (AA) within the conjugate complex, and wherein the promiscuous binding agent comprises a binding moiety that associates with the immobilized conjugate independent of the AA. The promiscuous binding agent may carry specific cycle information, or a promiscuous recode tag (e.g., inosine bases) capable of hybridization to any cycle tag (or subset of cycle tags) and that carries identifying information regarding the promiscuous binding agent. This provides robustness to the binding recognition operation, and may be repeated one or more times to increase the step yield. In such aspects, operation (k) may be repeated after contacting the immobilized conjugate complex with the promiscuous binding agent.

In some aspects, the peptide comprises any suitable macromolecular polymer, including a protein, a peptide, a complex carbohydrate, and the like. In such aspects, a monomeric unit of the macromolecular polymer may comprise an amino acid, a carbohydrate, and/or any monomeric moiety that may be combined into a polymer.

In some aspects, the conjugate complex comprises zero, one, or more reactive moieties (e.g., moieties used to join the complex to a solid support), and the reaction comprises an activatable chemistry. In some aspects, the conjugate complex comprises zero, one, or more reactive moieties (e.g., moieties used to join the complex to a solid support), and the reaction comprises an activatable chemistry. In some aspects, the conjugate complex comprises zero, one, or more reactive moieties (e.g., moieties used to join the complex to a solid support), and the reaction comprises a reversible chemistry and activatable chemistry.

In some aspects, the recode tag linked to the binding agent is a nucleic acid having a sequence corresponding to an (n-1)th cycle tag or (n+/−i)th cycle tag, an amino acid (AA) tag (e.g., an "AAtag"), and an nth cycle tag. Optionally, the recode tag linked to the binding agent is a nucleic acid having a universal sequence for amplification or assembly, a sequence complementary to a cycle tag (e.g., a "cycle tag complement sequence"), and an amino acid (AA) tag (e.g., an "AAtag").

In some aspects, operation (k) comprises contacting the recode blocks with ligase, AA tag oligonucleotide complements, and buffer under conditions that allow ligation to assemble the recode blocks and AA tag oligonucleotide complements into a memory oligo, or create a fragment of a memory oligo.

In certain embodiments, a method for analyzing one or more peptides from a sample comprising a plurality of peptides, proteins, and/or protein complexes is provided, the method comprising: (a) providing a peptide of mer length n=2 to 2000 joined to a solid support; (b) providing a first chemically-reactive conjugate (e.g. a PITC-conjugate), wherein the conjugate comprises a cycle tag with identifying information regarding a workflow cycle of the method, a reactive moiety that can bind and cleave a terminal amino acid of the peptide, and a reactive moiety that facilitates immobilization to a solid support; (c) contacting the peptide with the first chemically-reactive conjugate, wherein the first chemically-reactive conjugate binds with the terminal amino acid, or a modified terminal moiety, of the peptide to form a first conjugate complex, e.g., a PIT-AA-cycle tag-conjugate complex; (d) immobilizing the first conjugate complex to the solid support; (e) cleaving the terminal amino acid from the peptide thereby providing a first immobilized conjugate complex and a new terminal amino acid of the peptide joined to the solid support of (a); (f) optionally repeating (b) through (e) to assemble a second immobilized conjugate complex having cycle information for the new terminal amino acid of the peptide, (g) optionally repeating (f) for additional iterative cycles to create additional immobilized conjugate complexes for additional amino acids of the peptide of step (a); (h) optionally deprotecting nucleic acids of the conjugate complex and/or any protected nucleic acids associated with the solid support; (i) contacting the first immobilized conjugate complex with a first binding agent capable of binding to the first immobilized conjugate complex, wherein the first binding agent comprises a binding moiety and a recode tag with identifying information regarding the first binding agent; (j) transferring the information of the recode tag associated with the first binding agent to the cycle tag of the first immobilized conjugate complex to generate a first recode block; (k) optionally repeating (i) and (j) with a second binding agent comprising a binding moiety and a recode tag with identifying information regarding the second binding agent to transfer the information of the recode tag associated with the second binding agent to the second immobilized conjugate complex to generate a second recode block; (l) optionally repeating (k) for additional cycles to create recode blocks for additional amino acids of the peptide of step (a); (m) contacting the recode blocks with polymerase, nucleotides, ligase, and buffer under conditions that allow extension-ligation to assemble the recode blocks into a memory oligo, or create a fragment of a memory oligo; and (n) analyze the memory oligo.

In some aspects, one or more operations of the method are repeated one or more times to increase a step yield of the method. For example, in specific aspects, operations (e), (i), and/or (j) are repeated one or more times to increase the step yield.

In some aspects, the method further comprises after operation (m), contacting the first immobilized conjugate complex with a promiscuous binding agent capable of binding to the first immobilized conjugate complex independent of the identity of an amino acid within the conjugate complex, wherein the promiscuous binding agent comprises a binding moiety that associates with the immobilized conjugate independent of the amino acid. The promiscuous binding agent may carry specific cycle information, or a promiscuous recode tag (e.g., inosine bases) capable of hybridization to any cycle tag (or subset of cycle tags) and that carries identifying information regarding the promiscuous binding agent. This provides robustness to the binding recognition operation, and may be repeated one or more times to increase the step yield. In such aspects, operation (m) may be repeated after contacting the immobilized conjugate complex with the promiscuous binding agent.

In some aspects, assembly (e.g., joining) of the recode blocks is facilitated by utilization of a permissive polymerase, such as polymerase theta (PolΘ), or by utilization of proteins involved in blunt end DNA ligation processes similar to non-homologous end joining (NHEJ). See, e.g., Poplawski T et al., Postepy Biochem 2009; 55(1):36-45; Davis A J, Chen D J, Transl Cancer Res. 2013 June; 2(3): 130-143.

In some aspects, the peptide comprises any suitable macromolecular polymer, including a protein, a peptide, a polypeptide, and the like. In such aspects, a monomeric unit of the macromolecular polymer may comprise an amino acid, a carbohydrate, and/or any monomeric moiety that may be combined into a polymer.

In certain embodiments, a method for analyzing one or more peptides from a sample comprising a plurality of peptides, proteins, and/or protein complexes is provided, the method comprising: (a) providing a peptide of mer length n=2 to 2000 joined to a solid support using a location linker, wherein the location linker is bound to a location oligo (e.g., "locationOligo"); (b) providing a first chemically-reactive conjugate (e.g. a PITC-conjugate), wherein the conjugate comprises a cycle tag with identifying information regarding a workflow cycle of the method, a reactive moiety that can bind and cleave a terminal amino acid of the peptide, and a reactive moiety that facilitates immobilization to a solid support; (c) contacting the peptide with the first chemically-reactive conjugate, wherein the first chemically-reactive conjugate binds with the terminal amino acid, or a modified terminal moiety, of the peptide to form a first conjugate complex, e.g., a PIT-AA-cycle tag-conjugate complex; (d) immobilizing the first conjugate complex to the solid support; (e) cleaving the terminal amino acid from the peptide thereby providing a first immobilized conjugate complex and a new terminal amino acid of the peptide joined to the solid support of (a); (f) optionally repeating (b) through (e) to assemble a second immobilized conjugate complex having cycle information for the new terminal amino acid of the peptide; (g) optionally repeating (f) for additional iterative cycles to create additional immobilized conjugate complexes for additional amino acids of the peptide of step (a); (h) optionally deprotecting nucleic acids of the conjugate complex and/or any protected nucleic acids associated with the solid support; (i) contacting the first immobilized conjugate complex with a first binding agent capable of binding to the first immobilized conjugate complex, wherein the first binding agent comprises a binding moiety and a recode tag with identifying information regarding the first binding agent; (j) transferring the information of the recode tag associated with the first binding agent to the cycle tag of the first immobilized conjugate complex to generate a first recode block; (k) optionally repeating (i) and (j) with a second binding agent comprising a binding moiety and a recode tag with identifying information regarding the second binding agent to transfer the information of the recode tag associated with the second binding agent to the second immobilized conjugate complex to generate a second recode block; (l) optionally repeating step (k) for additional cycles to create recode blocks for additional amino acids of the peptide of step (a); (m) contacting at least the first recode block and a corresponding location oligo with a polymerase, nucleotides, and buffer under conditions that allow extension to transfer information from the location oligo to the first recode block, thereby creating a memory oligo; (n) optionally repeating step (m) to transfer information from the location oligo to additional recode blocks proximal to the location oligos; (o) releasing the memory oligos from the solid support via tether cleavage, hydrogel dissociation, polymerization, or another means; (p) optionally assembling the memory oligos into longer memory oligos (ex situ); and (q) analyzing the memory oligos.

In some aspects, one or more operations of the method are repeated one or more times to increase a step yield of the method. For example, in specific aspects, operations (e), (i), and/or (j) are repeated one or more times to increase the step yield.

In some aspects, the peptide comprises any suitable macromolecular polymer, including a protein, a peptide, a complex carbohydrate, and the like. In such aspects, a monomeric unit of the macromolecular polymer may comprise an amino acid, a carbohydrate, and/or any monomeric moiety that may be combined into a polymer.

In some aspects, the recode tag linked to the binding agent is a nucleic acid having a sequence corresponding to an (n-1)th cycle tag or (n+/−i)th cycle tag, an amino acid (AA) tag (e.g., an "AAtag"), and an nth cycle tag. Optionally, the recode tag linked to the binding agent is a nucleic acid having a universal sequence for amplification or assembly, a sequence complementary to a cycle tag (e.g., a "cycle tag complement sequence"), and an amino acid (AA) tag (e.g., an "AAtag").

In some aspects, some aspects, the information is transferred from a location oligo to a recode block using a ligase.

In some aspects, each individual memory oligo is analyzed either on its own or randomly assembled with other memory oligos from the same analyte or different analytes of a sample. This approach may facilitate streamlining of the recoding process and allows for more efficient analysis.

In some aspects, the location oligos can be utilized to determine spatial location within a histological tissue section and combined with identification data in silico to enables spatial resolution of individual protein molecules. Determining spatial locations of protein molecules within histological tissue sections enables spatial multiomic analysis. Spatial multiomics is the study of gene/RNA expression and protein abundance with spatial context to elucidate functional biology. Integrating different scales of analysis from spatial multiomics can facilitate an improved understanding of tissue and cellular microenvironments.

In some aspects, the conjugate complex comprises zero, one, or more reactive moieties (e.g., used to join the complex to a solid support), and the reaction comprises an activatable chemistry.

In some aspects, the conjugate complex comprises zero, one, or more reactive moieties (e.g., used to join the complex to a solid support), and the reaction comprises a reversible chemistry.

In some aspects, the conjugate complex comprises zero, one, or more reactive moieties (e.g., used to join the complex to a solid support), and the reaction comprises an activatable and reversible chemistry.

In some aspects, one or more amino acids (or monomer subunits) are removed from the immobilized peptide (or macromolecular analyte) without regard to identifying the amino acid (or monomer) for that cycle. These "skipped" amino acid cycles are recorded in silico, and analysis algorithms account for known translations of the skipped information during alignment to reference sequences. In the case of peptides, this may be accomplished by optionally performing one or more iterations of operations 2-4, described below, where PITC is substituted for the chemically-reactive conjugate (e.g., a PITC-conjugate). This may be referred to as a "strobed" read or "strobed" sequencing. One advantage of this aspect is that an isoform of a protein may be readily determined by reading segments of said protein that are not adjacent to one another to achieve long-range information. This may save time and costs to obtain intervening or redundant information contained in the peptide, or in a combination of peptide and associated genomic information. For example, this aspect may include 5 cycles of peptide degradation using a chemically-reactive conjugate, followed by 30 cycles using PITC or an enzymatic cleavage, then another 5 cycles with the chemically-reactive conjugate, and so on.

In some aspects, utilization of a predetermined subset of binding agents allows identification of a subset of the amino acids of a peptide, polypeptide, protein, or a protein complex. Given that sites of interest (e.g. post-translational modification (PTM) or splice locations) can be different across various proteins in a mixed population, this aspect eliminates the need for measuring/determining the identity for every single amino acid in a sample at every single cycle—a task that would require significantly more sequencing.

In some aspects, the subset of amino acids identified by the subset of binding agents are modified with a post translational modification. Doing so may greatly enrich the information density for the subset of amino acids upon analysis.

In some aspects, one or more amino acids (or monomer subunits) are removed from the immobilized peptide (or macromolecular analyte) without regard to identifying the amino acid (or monomer) for that cycle, using an aminopeptidase (e.g., CAS Number: 37288-67-8) or similar agent/construct. Further, this technique can also be applied to prepare an N-terminus of proteins or peptides protected by acylation for processing by the chemically-reactive conjugate. Further, this method can be used to "strobe" through amino acids, such as proline, which may otherwise not be effectively cleaved under chemical conditions using a chemically-reactive conjugate in some examples.

In some aspects, one or more operations of the method are performed simultaneously. For example, in specific aspects, operations (i) through (1) are performed at the same time.

In some aspects, operation (m) comprises contacting the recode blocks with ligase, AA tag oligonucleotide complements, and buffer under conditions that allow ligation to assemble the recode blocks and AA tag oligonucleotide complements into a memory oligo.

In some aspects, a memory oligo, a cycle tag, a recode block, an AA tag complement, and/or an ligation oligo or component may comprise a DNA molecule, an RNA molecule, another type of nucleic acid molecule, a DNA molecule with pseudo-complementary bases (e.g. Inosine), or a combination or chimera thereof.

In some aspects, the memory oligo or ligation component comprises a universal priming site, and the universal priming site may comprise a priming site for amplification, priming site for sequencing, or both.

In some aspects, the memory oligo comprises a sample index, a spacer, a unique molecular identifier (UMI), a universal priming site, a CRISPR protospacer adjacent motif (PAM) sequence, or any combination thereof.

In some aspects, the memory oligo and/or chemically-reactive conjugate comprises a spacer having a length between 0.1 nm and 500 nm attached at its 3'-terminus, 5'-terminus, or attached to a modified nucleotide base.

In some aspects, the memory oligo is associated with a unique molecule identifier (UMI) or barcode.

In some aspects, a solid support as described herein comprises a solid bead, a porous bead, a solid planar support, a porous planar support, a patterned or non-patterned surface, a nanoparticle, or a inorganic or polymeric microsphere. In some aspects, the support may comprise a glass slide or wafer, a silicon slide or wafer, a PC PTC PE HDPE or other plastic surface, a teflon, nylon, nitrocellulose or other membrane, and particles/beads may be polystyrene, crosslinked polystyrene, agarose, or acrylamide.

In some aspects, the bead or nanoparticle is magnetic or paramagnetic.

In some aspects, a solid support may be passivated with glass, silicon oxide, tantalum pentoxide, DLC diamond-like carbon, or other passivation agents, or a solid supports may comprise membranes that are passivated or activated via, e.g., corona or other plasma treatments methods, etc.

In some aspects, a solid support may or may not be assembled with other components to facilitate fluid transport and/or detection (e.g., flowcell, biochip, a microtitre plate).

In some aspects, a solid support is comprised of a hydrogel that supports joining components for macromolecule recoding and/or analysis workflow.

In some aspects, a hydrogel is formed from synthetic polymers, natural polymers, and/or hybrid polymers. Monomers may include one or more: acrylamide, dihydroxy methacrylates, methacrylic acid, or the like in linear, branched, and/or crosslinked configurations, block co-polymers configurations, or other configurations conducive to sequencing macromolecules In some aspects, a hydrogel comprises at least 3 orthogonal conjugation chemistry modalities.

In some aspects, macromolecule (e.g., protein, peptide) and/or universal primer sequences are covalently joined to the solid support.

In some aspects, the binding agent comprises a polypeptide or protein, e.g., an antibody or portion thereof (e.g., a single-chain variable fragment (scFv), a fragment antigen-binding (FAB) region, a FAB2 region), a nanobody, a DNA aptamer, an RNA aptamer, a modified aptamer, a photo-active or non-photoactive cage compound, an oligo-peptide permease (Opp), an aminoacyl tRNA synthetase (aaRS), a periplasmic binding protein (PBP), a dipeptide permease (Dpp), a proton dependent oligopeptide transporter (POT), a modified aminopeptidase, a modified amino acyl tRNA synthetase, a modified anticalin, or a modified Clp protease adaptor protein (ClpS).In some aspects, the binding agent is capable of selectively binding to an immobilized conjugate complex depending on the AA that is part of the complex.

In some aspects, the binding agent comprises a binding moiety and a recode tag.

In some aspects, the recode tag comprises sequences that represent AA information, and the recode block comprises sequences that represent both workflow cycle and amino acid (or monomer identity) information.

In some aspects, the binding moiety and the recode tag are joined by a linker with length between 0.1 nm and 500 nm.

In some aspects, the chemically reactive conjugate and/or conjugate complex further comprises a spacer, a workflow cycle specific sequence, a unique molecular identifier, a universal priming site, a restriction endonuclease cleavage sequence, or any combination thereof.

In some aspects, the chemically reactive conjugate and/or conjugate complex comprises a spacer associated with a reactive moiety used for immobilization of the chemically-reactive conjugate complex to the hydrogel surface, and the spacer comprises a restriction endonuclease cleavage sequence capable of releasing the PITC-AA moiety and/or cycle tag from the conjugate complex.

In some aspects, the chemically reactive conjugate and/or conjugate complex comprises a spacer associated with the reactive moiety used to bind and cleave terminal amino acids, and that spacer contains a restriction endonuclease cleavage sequence capable to release the cycle tag and/or the reactive moiety used for immobilization from the conjugate complex.

In some aspects the chemically reactive conjugate may be in a pro-form, meaning that it is able, through additions, activations, cleavage reactions or other manipulations, to perform the functions of cycle identification (e.g., cycle tag), binding and cleavage of amino acids (e.g., PITC), and reaction to a surface, such as a hydrogel coated surface.

In some aspects, transferring the information of the recode tag to the recode block is mediated by a DNA ligase and a ligation oligo.

In some aspects, transferring the information of the recode tag to the recode block is mediated by a DNA polymerase, or by a combination of a DNA polymerase and ligase.

In some aspects, transferring the information of the recode tag to the recode block is mediated by chemical ligation.

In some aspects, a plurality of macromolecules and associated conjugate complexes are joined to a solid support.

In some aspects, a plurality of pools with different combinations or compositions of binding agents having completely distinct, or distinct but overlapping, affinities can be introduced to the surface of immobilized chemically-reactive conjugates. By using different pools with distinct binding properties, a more comprehensive and accurate characterization of the immobilized peptides can be achieved.

In some aspects, the plurality of macromolecules are spaced apart on the solid support at an average distance>100 nm.

In some aspects, the reactivity of a residual chemically-reactive conjugate (e.g., a conjugate that is unreacted with amino-acid, but immobilized to the surface, due to insufficient removal by washing prior to initiating the immobilization chemistry) is quenched by an amino acid or amino acid mimic so as to become a bystander in future cycles.

In some aspects, modification of a terminal amino acid of the peptide prior to contacting the peptide with the first chemically-reactive conjugate increases the reactivity of the chemically-active conjugate toward the modified amino acid relative to non-modified amino acids. For example, activation of the C-terminal amino acid with acetic anhydride prior to contacting with trimethylsilylisothiocyanate has been described. Bailey, J. M., Shenoy, N. R., Ronk, M., & Shively, J. E., 1992, Protein Sci. 1, 68-80.

In some aspects, the methods described herein further comprise after contacting the recode blocks with polymerase, nucleotides, ligase, and/or buffer under conditions that allow extension-ligation or ligation to assemble the recode blocks into a memory oligo, contacting a plurality of incompletely ligated memory oligos with linking oligos, polymerase, nucleotides, ligase, and/or buffer under conditions that allow extension-ligation or ligation to assemble the incompletely ligated memory oligos into a memory oligo. Accordingly, the yield during memory oligo assembly may be increased.

In some aspects, the methods described herein further comprise after contacting the recode blocks with polymerase, nucleotides, ligase, and/or buffer under conditions that allow extension-ligation or ligation to assemble the recode blocks into a memory oligo, contacting a plurality of incompletely ligated memory oligo fragments and/or recode blocks with linking oligos, ligase, and buffer under conditions that promote ligation of recode blocks and memory oligo fragments. Accordingly, the yield during memory oligo assembly may be increased.

In some aspects, the linking oligo comprises a sequence complementary to that of the recode blocks, thereby facilitating ligation of recode blocks that were not ligated during contacting with the polymerase, nucleotides, ligase, and buffer.

In some aspects, the linking oligos comprise additional nucleotide sequences coded to carry information related to sample or process, and/or that aid in ligation or extension-ligation.

In some aspects, the memory oligo is amplified prior to analysis, e.g., by bridge amplification, ExAmp NGS clustering, isothermal clustering, solution-based PCR amplification, A-tailing to add primers sequences prior to solution-based amplification, or any suitable DNA amplification method.

In some aspects, a memory oligo optionally comprises a sample index, a spacer, a unique molecular identifier (UMI), a universal priming site, a CRISPR protospacer adjacent motif (PAM) sequence, or any combination thereof.

In some aspects, a plurality of memory oligos are enriched prior to analysis, e.g., via a depletion process or a normalization process to remove or reduce the fraction of oligos associated with abundant protein, peptides, or macromolecules. In some aspects, enrichment or depletion may be carried out via commercially available kits, such as Agilent SureSelect, or via custom enrichment or depletion methods using oligonucleotides partially complementary to a memory oligo sequence, e.g., complementary to AA tag sequences of the target memory oligo.

In some aspects, a plurality of memory oligos representing a plurality of macromolecules are analyzed in parallel.

In some aspects, analyzing the memory oligo(s) comprises a nucleic acid sequencing method.

In some aspects, analyzing the memory oligo(s) comprises analysis via a multiplex PCR method.

In some aspects, the nucleic acid sequencing method comprises sequencing by synthesis, sequencing by ligation, sequencing by hybridization, or pyrosequencing.

In some aspects, the nucleic acid sequencing method comprises single molecule microscopy sequencing or nanopore sequencing.

In some aspects, the memory oligo is configured to be analyzed using commercially available NGS technology, such as the NGS methods exemplified by Illumina, Element Bio, and Singular Genomics.

In some aspects, the chemically reactive conjugate and/or conjugate complex comprises a cleavable group flanked by matched unique molecular identifiers (UMIs) within the cycle tag to facilitate cleavage of memory oligos at designated positions. In these aspects, one or more restriction endonuclease sequences carried by one or more cycle tag sequences assembled into a memory oligo are cleaved to create one or more oligonucleotides (memory oligos). The oligonucleotides are short enough to be read completely using short-read DNA sequencing technology, including those short-read DNA sequencing methods and devices commercialized by Illumina, Element Bio, and Singular Genomics.

In some aspects, helicase may be utilized during assembly of memory oligos. The use or strobing of helicase during one or more assembly processes may, in some examples, improve access of DNA blocks to facilitate longer memory oligo assembly.

In some aspects, the memory oligo or recode blocks thereof are configured to be analyzed using a decode-based methodology. More information regarding decode-based techniques may be found in Gunderson et al., Decoding Randomly Ordered DNA Arrays, Genome Res., 2004 May; 14(5):870-7, which is herein incorporated in its entirety by reference for all purposes.

In some aspects, fragments of memory oligos, or recode blocks, or any such spatially-confined set of constructs that contains sequence and identity information associated with a given peptide, protein, protein complex, or polymer, are analyzed using a decode-based methodology. See Gunderson et al.

In some aspects, identifying components are selected from UMIs, sample indexes, recode tags, recode blocks, ligation oligos, AA tags, their complements, or any combination thereof.

In some aspects, the N-terminal AA of the peptide is removed by chemical cleavage alternatives to Edman cleavage.

In some aspects, one or more chemically-reactive conjugates binds to a terminal amino acid residue of the peptide.

In some aspects, one or more binding agents bind to the conjugate complex.

In some aspects, the conjugate complex comprises a post-translationally modified amino acid.

In some aspects, the identifying components of a recode tag, recode block, or both comprise error detection and/or correction bits.

In some aspects, the error detection/correcting sequence is derived from Hamming distance theory, or other modern digital code space theories (e.g., Lee, Levenshtein-Tenengolts, Reed-Solomon, or others).

In some aspects, the constituents of a recode tag, recode block, or both, comprise 2, 3, 4, 5, 6 or more different types of nucleotides.

In some aspects, the code (or codes) (e.g., sequences) associated with a recode tag or recode block via analysis of the memory oligo are derived from 2, 3, 4, 5, 6 or more types of nucleotides.

In some aspects, the number of different types of nucleotides used to create a recode code do not equal the number of nucleotide types that comprise the recode tag, cycle tag, or either, or both.

In some aspects, a macromolecule, fragment, or peptide activation comprises a functional moiety NHS group, aldehyde group, azide group, alkyne group, maleimide group, thiol group, tetrazine and trans-cyclooctene, or the like.

In some aspects, an immobilized peptide is linearized (denatured) using detergent(s), surfactant(s), chaotropic agent(s), reducing agent(s), and/or alkylation agent(s).

In some aspects, a chemically-reactive conjugate reacts and cleaves from a C-terminus of the peptide rather than the N-terminus to create recode blocks that can be assembled using any of the methods described herein.

In some aspects, "paired-end read" information may be collected from an immobilized protein complex, protein, or peptide, by creating recode blocks using chemically-reactive conjugates operating on both the N-terminus and C-terminus of a given protein complex, protein, or peptide sequentially or in parallel to create recode blocks that can be assembled using methods described herein.

In certain embodiments, a method for acquiring a priori defined code information via sequencing of a subset of nucleotides types in an oligonucleotide or oligonucleotide cluster is provided. Such is particularly beneficial when considering readouts of information stored in DNA (e.g., DNA data storage information technology readout).

In some aspects, information recoded into a memory oligos is acquired via sequencing of a subset of the nucleotides types in the memory oligo. For example, a subset of nucleotide types may be identified and a subset of nucleotide types may not be identified in the sequencing readout, e.g., by introducing non-fluorescent, non-reversibly-terminated nucleotides into an SBS sequencing reagent mixture. In certain embodiments, the subset is 2 of the 4 natural nucleotides.

In certain embodiments, a method for preparing a peptide or a plurality of peptides of mer length n=2 to 2000 to be joined to a solid support is provided, the method comprising: (a) fragmenting peptides, protein, and/or protein complexes in one or more samples; (b) activating zero, 1, 2, or more moieties of each fragmented peptide, protein, and/or protein complex; (c) optionally joining a sample-specific nucleotide index sequence to the activated peptides, proteins, and/or protein complexes; and (d) joining the peptides to a solid support.

In some aspects, one or more of the operations of the method are performed in any suitable sequential order, or are simultaneously performed.

In some aspects, subunits of a given protein are co-immobilized directly or through their interaction with native subunits on the surface. Subsequently, the one or more subunits may be simultaneously recoded by processes (b)-(m), including alternate aspects associated with the method, within the same localized region. Information of the memory oligo may contain an admixture of subunits (protein and native) which can be deconvoluted in silico.

In certain embodiments, a method for preparing interacting peptides, or a plurality of interacting peptides, to be joined to a solid support is provided, the method comprising: (a) cross-linking peptides, protein, and/or protein complexes in one or more samples (for example, using homo-bifunctional, heterobifunctional, or photoreactive methods as described in Kluger, et al., (2004) Bioorganic Chemistry v32:6, 451); (b) activating zero, 1, 2, or more moieties of each cross-linked peptide, protein, and/or protein complex for immobilization to a solid support; (c) optionally joining a sample-specific nucleotide index sequence to the activated peptides, proteins, and/or protein complexes; and (d) joining the complexes to the solid support. In some aspects, one or more of the operations of the method are performed in any suitable sequential order, or are simultaneously performed. Generally, the method enables the analysis of in vivo associated proteins and their interactions, and thus, facilitates discovery, identification, and investigation of protein interactomes.

In certain embodiments, a method for preparing interacting DNA-peptides, or a plurality of interacting DNA-peptides complexes, to be joined to a solid support is provided, the method comprising: (a) cross-linking peptides, protein, and/or protein complexes with native DNA with which the protein was associated in biological context for one or more samples (for example, using formaldehyde, or other methods known in the art); (b) activating zero, 1, 2, or more moieties of each cross-linked peptide-DNA, protein, and/or protein complex-DNA complexes; (c) optionally joining a sample-specific nucleotide index sequence to the activated peptides-DNA, and/or protein-DNA complexes; and (d) joining the complexes to a solid support. In some aspects, one or more of the operations of the method are performed in any suitable sequential order, or are simultaneously performed. Generally, the method provides for the analysis of vivo interactions between proteins and DNA.

In some aspects, fragmentation comprises physical sheering, endopeptidase activity, modified endopeptidase activity, protease, metalloprotease, and/or other suitable fragmenting methods.

In some aspects, a peptide comprises any suitable macromolecular polymer, including a protein, a peptide, and the like. In such aspects, a monomeric unit of the macromolecular polymer may comprise an amino acid, a carbohydrate, and/or any monomeric moiety that may be combined into a polymer.

In some aspects, the method further comprises depletion of one or more abundant proteins from the sample prior to any of operations (a) (b) (c), and/or (d).

In certain embodiments, the utilization of chemically-reactive conjugates with cleavable spacers allows rejuvenation of a surface of a substrate for a second round of recoding. For example, in certain embodiments, a method for analyzing one or more residual immobilized analytes from a surface having a plurality of peptides, proteins, and/or protein complexes is provided, the method comprising: (a) providing a surface used in a previous round of recoding operations (b)-(d) described below, and which has been rejuvenated by cleaving the spacers of a first chemically-reactive conjugate, (b) providing a second chemically-reactive conjugate (e.g. a PITC-conjugate), wherein the conjugate comprises a cycle tag with identifying information regarding a workflow cycle of the method, a reactive moiety that can bind and cleave a terminal amino acid of the peptide, and a reactive moiety that facilitates immobilization to a solid support; (c) contacting the peptide with the second chemically-reactive conjugate, wherein the second chemically-reactive conjugate binds with the terminal amino acid, or a modified terminal moiety, of the peptide to form a second conjugate complex, e.g., a PIT-AA-cycle tag-conjugate complex; (d) immobilizing the second conjugate complex to the solid support; (e) cleaving the terminal amino acid from the peptide thereby providing a second immobilized conjugate complex and a new terminal amino acid of the peptide joined to the solid support of (a); (f) optionally repeating (b) through (e) to assemble a second immobilized conjugate complex having cycle information for the new terminal amino acid of the peptide, (g) optionally repeating (f) for additional iterative cycles to create additional immobilized conjugate complexes for additional amino acids of the peptide of step (a); (h) optionally deprotecting nucleic acids of the conjugate complex and/or any protected nucleic acids associated with the solid support; (i) contacting the second immobilized conjugate complex with a binding agent capable of binding to the second immobilized conjugate complex, wherein the binding agent comprises a binding moiety and a recode tag with identifying information regarding the binding agent; (j) transferring the information of the recode tag associated with the binding agent to the cycle tag of the second immobilized conjugate complex to generate a recode block; (k) optionally repeating (i) and (j) with a second binding agent comprising a binding moiety and a recode tag with identifying information regarding the second binding agent to transfer the information of the recode tag associated with the second binding agent to the second immobilized conjugate complex to generate a second recode block; (l) optionally repeating (k) for additional cycles to create recode blocks for additional amino acids of the peptide of step (a); (m) contacting the recode blocks with polymerase, nucleotides, ligase, and buffer under conditions that allow extension-ligation to assemble the recode blocks into a memory oligo, or create a fragment of a memory oligo; and (n) analyze the memory oligo.

In some aspects, previously described aspects associated with a first round of operations are applied to a second round of operations.

In some aspects, one or more of the operations of the method are performed in any suitable sequential order, or are simultaneously performed.

In some aspects, a rejuvenation process is repeated one of more times.

In some aspects, only a fraction of the chemically-reactive conjugates are cleaved from a surface, as it may be desirable to retain a fraction of the recode blocks to facilitate in silico mapping and assembly across iterative cycles of memory oligo assembly.

In some aspects, surface rejuvenation may include 'strobing' the protein using either chemical (e.g., phenylisothiocyanate (PITC)) or biological (e.g., aminopeptidase) methods.

In some aspects, the amine groups of residual non-cleaved recode blocks nucleic acid bases are protected by reaction with fluorenylmethyloxycarbonyl (FMOC) or other standard protection chemistries.

In some aspects, following process (m) of the method, a plurality of assembly oligos containing all or some of the possible assembly oligos are hybridized to the memory oligo, ligated, and dehybridized to form a solution-phase memory oligo.

Disclosed herein, in some embodiments, are methods method for analyzing one or more peptides from a sample comprising a plurality of peptides, proteins, and/or protein complexes, comprising: (a) providing a peptide of mer length n=2 to 2000 joined to a solid support; (b) providing a first chemically-reactive conjugate, wherein the conjugate comprises a cycle tag, a reactive moiety that can bind and cleave a terminal amino acid of the peptide, and a reactive moiety that facilitates immobilization to a solid support; (c) contacting the peptide with the first chemically-reactive conjugate, wherein the first chemically-reactive conjugate binds with the terminal amino acid, or a modified terminal moiety, of the peptide to form a first conjugate complex; (d) immobilizing the first conjugate complex to the solid support; (e) cleaving the terminal amino acid from the peptide thereby providing a first immobilized conjugate complex and a new terminal amino acid of the peptide joined to the solid support of (a); (f) optionally repeating processes (b) through (e) to assemble a second immobilized conjugate complex having cycle information for the new terminal amino acid of the peptide; (g) optionally repeating (f) for additional iterative cycles to create additional immobilized conjugate complexes for additional amino acids of the peptide of step (a); (h) optionally deprotecting nucleic acids of the conjugate complex and/or any protected nucleic acids associated with the solid support; (i) contacting the first immobilized conjugate complex with a first binding agent capable of binding to the first immobilized conjugate complex, wherein the first binding agent comprises a binding moiety and a recode tag with identifying information regarding the first binding agent; (j) transferring the information of the recode tag associated with the first binding agent to the cycle tag of the first immobilized conjugate complex to generate a first recode block; (k) optionally repeating (i) and (j) with a second binding agent comprising a binding moiety and a recode tag with identifying information regarding the second binding agent to transfer the information of the recode tag associated with the second binding agent to the second immobilized conjugate complex to generate a second recode block; (l) optionally repeating (k) for additional cycles to create recode blocks for additional amino acids of the peptide of step (a); (m) contacting the recode blocks with polymerase, nucleotides, ligase, and buffer under conditions that allow extension-ligation to assemble the recode blocks into a memory oligo, or create a fragment of a memory oligo; and (n) analyzing the memory oligo. Any of the aforementioned method steps may be used alone or in combination with other steps or methods described herein. In some embodiments, (e), (i), and (j) are repeated one or more times to increase a step yield of the method. Some embodiments include: after (m) and/or (l), contacting the first immobilized conjugate complex with a promiscuous binding agent capable of binding to the first immobilized conjugate complex independent of the identity of an amino acid within the conjugate complex, wherein the promiscuous binding agent comprises a binding moiety that associates with the immobilized conjugate independent of the amino acid, and a promiscuous recode tag capable of hybridization to any cycle tag and that carries identifying information regarding the promiscuous binding agent. In some embodiments, the conjugate complex comprises zero, one, or more reactive moieties, and the reaction comprises an activatable chemistry and/or reversible chemistry. In some embodiments, the recode tag associated with the first binding agent is a nucleic acid having a sequence corresponding to an (n-1)th cycle tag, an amino acid (AA) tag, and an nth cycle tag. In some embodiments, (i) through (l) are performed simultaneously. In some embodiments, (m) comprises contacting the recode blocks with ligase, AA tag oligonucleotide complements, and buffer under conditions that allow ligation to assemble the recode blocks and AA tag oligonucleotide complements into a memory oligo. In some embodiments, the memory oligo, the cycle tag, and the recode block each comprise a nucleic acid molecule. In some embodiments, the memory oligo comprises a universal priming site, the universal priming site comprising a priming site for amplification or a priming site for sequencing, or both. In some embodiments, the binding agent comprises a polypeptide or protein.

Disclosed herein, in some embodiments, are methods for determining identity and positional information of an amino acid residue of a peptide coupled to a solid support, the method comprising: (a) providing the peptide to the solid support, the peptide coupled to the solid support such that a N-terminal amino acid residue of the peptide is not directly coupled to the solid support and is exposed to reaction conditions; (b) providing a chemically-reactive conjugate, the chemically-reactive conjugate comprising: (x) a cycle tag comprising a cycle nucleic acid associated with a cycle number; (y) a reactive moiety for binding and cleaving the N-terminal amino acid residue of the peptide and exposing a next amino acid residue as a N-terminal amino acid residue on the cleaved peptide; and (z) a immobilizing moiety for immobilization to the solid support; (c) contacting the peptide with the chemically-reactive conjugate, thereby coupling the chemically-reactive conjugate to the N-terminal amino acid of the peptide to form a conjugate complex; (d) immobilizing the conjugate complex to the solid support via the immobilizing moiety; (e) cleaving and thereby separating the N-terminal amino acid residue from the peptide, thereby providing an immobilized amino acid complex, the immobilized amino acid complex comprising the cleaved and separated N-terminal amino acid residue; (f) contacting the immobilized amino acid complex with a binding agent, the binding agent comprising: a binding moiety for preferentially binding to the immobilized amino acid complex; and a recode tag comprising a recode nucleic acid corresponding with the binding agent, thereby forming an affinity complex, the affinity complex comprising an immobilized amino acid complex and a binding agent and thereby bringing a cycle tag into proximity with a recode tag within each formed affinity complex; (g) transferring the information of the nucleic acid recode tag associated with the first binding agent to the cycle tag of the first immobilized conjugate complex to generate a first recode block; (j) obtaining sequence information for the recode block; and (k) based on the obtained sequence information, determining identity and positional information of an amino acid residue of the peptide. In some embodiments, the immobilized amino acid complex is washed before contacting with the binding agent. In some embodiments, the sequence information is used to determine the likely three-dimensional structure of the peptide. Some embodiments include repeating steps (b) through (k) for each subsequent amino acid in the peptide.

Disclosed herein, in some embodiments, are methods for determining identity and positional information of an amino acid residue of a peptide coupled to a solid support, the method comprising: (a) providing the peptide to the solid support, the peptide coupled to the solid support such that a N-terminal amino acid residue of the peptide is not directly coupled to the solid support and is exposed to reaction conditions; (b) providing a chemically-reactive conjugate, the chemically-reactive conjugate comprising: (x) a cycle tag comprising a cycle nucleic acid associated with a cycle number; (y) a reactive moiety for binding and cleaving the N-terminal amino acid residue of the peptide and exposing a next amino acid residue as a N-terminal amino acid residue on the cleaved peptide; and (z) an immobilizing moiety for immobilization to the solid support; (c) contacting the peptide with the chemically-reactive conjugate, thereby coupling the chemically-reactive conjugate to the N-terminal amino acid of the peptide to form a conjugate complex; (d) immobilizing the conjugate complex to the solid support via the immobilizing moiety; (e) cleaving and thereby separating the N-terminal amino acid residue from the peptide, thereby providing an immobilized amino acid complex, the immobilized amino acid complex comprising the cleaved and separated N-terminal amino acid residue; (f) contacting the immobilized amino acid complex with a binding agent, the binding agent comprising: a binding moiety for preferentially binding to the immobilized amino acid complex, and a recode tag comprising a recode nucleic acid corresponding with the binding agent, thereby forming an affinity complex, the affinity complex comprising an immobilized amino acid complex and a binding agent and thereby bringing the cycle tag into proximity with the recode tag within the affinity complex; (g) joining the recode nucleic acid or a sequence of the recode nucleic acid with the cycle nucleic acid or a sequence of the cycle nucleic acid to generate a recode block; (j) obtaining sequence information of the recode block; and (k) based on the obtained sequence information, determining identity and positional information of an amino acid residue of the peptide. Some embodiments include repeating steps (b) through (k) for the next amino acid of the peptide. Some embodiments include repeating steps (b) through (k) for each subsequent amino acid of the peptide. Some embodiments include washing the immobilized amino acid complex before said contacting the immobilized amino acid complex with a binding agent. Some embodiments include determining a likely three-dimensional structure of the peptide based on the sequence information.

Disclosed herein, in some embodiments, are methods for determining identity and positional information of a plurality of amino acid residues of a peptide, the peptide comprising n amino acid residues, the method comprising: (a) coupling the peptide to a solid support such that a N-terminal amino acid residue of the peptide is not directly coupled to the solid support and is exposed to reaction conditions; (b) providing a chemically-reactive conjugate, the chemically-reactive conjugate comprising: (x) a cycle tag comprising a cycle nucleic acid associated with a cycle number; (y) a reactive moiety for binding and cleaving the N-terminal amino acid residue of the peptide and exposing a next amino acid residue as a N-terminal amino acid residue on the cleaved peptide; and (z) a immobilizing moiety for immobilization to the solid support; (c) contacting the peptide with the chemically-reactive conjugate, thereby coupling the chemically-reactive conjugate to the N-terminal amino acid of the peptide to form a conjugate complex; (d) immobilizing the conjugate complex to the solid support via the immobilizing moiety; (e) cleaving and thereby separating the N-terminal amino acid residue from the peptide, thereby exposing the next amino acid residue as a N-terminal amino acid residue on the cleaved peptide and providing an immobilized amino acid complex, the immobilized amino acid complex comprising the cleaved and separated N-terminal amino acid residue; (f) repeating (b) through (e) n−1 times to assemble n−1 additional immobilized amino acid complexes, each additional immobilized amino acid complex comprising a nucleic acid associated with cycle 2 to n, accordingly; (g) contacting the immobilized amino acid complexes with a binding agent, the binding agent comprising: a binding moiety for preferentially binding to one or to a subset of the immobilized amino acid complexes; and a recode tag comprising a recode nucleic acid corresponding with the binding agent, thereby forming one or more affinity complexes, each affinity complex comprising an immobilized amino acid complex and a binding agent and thereby bringing a cycle tag into proximity with a recode tag within each formed affinity complex; (h) within each formed affinity complex, joining a cycle tag to a recode tag to form a recode block, thereby creating a plurality of recode blocks, each recode block corresponding with a formed affinity complex; (i) joining two or members of the plurality of recode blocks to form a memory oligonucleotide; (j) obtaining sequence information for the memory oligonucleotide; and (k) based on the obtained sequence information, determining identity and positional information of a plurality of amino acid residues of the peptide. In some embodiments, n is an integer greater than or equal to 2. In some embodiments, each binding agent comprises recode tags with a unique nucleic acid sequence. In some embodiments, a plurality of binding agents comprises recode tags with the same nucleic acid sequence. In some embodiments, binding agents comprises recode tags which may have a unique sequence portion and a common sequence portion.

In some embodiments, determining the identity and positional information of the plurality of amino acid residues of the peptide comprises determining the identity and positional information of all of the amino acid residues of the peptide. In some embodiments, determining the identity and positional information of the plurality of amino acid residues of the peptide comprises determining the identity and positional information of only a subset of the amino acid residues of the peptide. Some embodiments include identifying the peptide, for example by comparing the identity and positional information of the plurality of amino acid residues to a database.

Disclosed herein, in some embodiments, are methods for determining identity and positional information of an amino acid residue of a peptide coupled to a solid support, the method comprising: (a) providing the peptide to the solid support, the peptide coupled to the solid support such that a N-terminal amino acid residue of the peptide is not directly coupled to the solid support and is exposed to reaction conditions; (b) providing a chemically-reactive conjugate, the chemically-reactive conjugate comprising: (x) a cycle tag associated with a cycle number; (y) a reactive moiety for binding and cleaving the N-terminal amino acid residue of the peptide and exposing a next amino acid residue as a N-terminal amino acid residue on the cleaved peptide; and (z) an immobilizing moiety for immobilization to the solid support; (c) contacting the peptide with the chemically-reactive conjugate, thereby coupling the chemically-reactive conjugate to the N-terminal amino acid of the peptide to form a conjugate complex; (d) immobilizing the conjugate complex to the solid support via the immobilizing moiety; (e) cleaving and thereby separating the N-terminal amino acid residue from the peptide, thereby providing an immobilized amino acid complex, the immobilized amino acid complex comprising the cleaved and separated N-terminal amino acid residue; (f) contacting the immobilized amino acid complex with a binding agent, the binding agent comprising: a binding moiety for preferentially binding to the immobilized amino acid complex; and a recode tag comprising a recode nucleic acid corresponding with the binding agent, thereby forming an affinity complex, the affinity complex comprising an immobilized amino acid complex and a binding agent and thereby bringing the cycle tag into proximity with the recode tag within the affinity complex; (g) transferring information of the recode nucleic acid associated with the binding agent to the cycle tag of the immobilized conjugate complex to generate a recode block; (j) obtaining sequence information for the recode block; and (k) based on the obtained sequence information, determining identity and positional information of an amino acid residue of the peptide.

Recode Tags

Disclosed herein, in some embodiments, are recode tags. The recode tag may be a part of a binding agent. The recode tag may correspond with a binding agent. For example, the recode tag may convey information about a molecule (e.g. an amino acid or PTM) to which the binding agent binds. The recode tag may include a nucleic acid such as a recode nucleic acid. In some embodiments, the recode nucleic acid comprises DNA or RNA. In some embodiments, the recode tag is a DNA sequence. In some embodiments, the recode tag is an RNA sequence. The recode nucleic acid may be useful to encode amino acid information in a nucleic acid. The recode tag may be used in a method described herein, such as a method for determining protein information such as amino acid location or identity.

Recode Blocks

Disclosed herein, in some embodiments, are recode blocks. The recode block may include a cycle tag, and a recode tag or a reverse complement thereof. The recode block may include a cycle tag or a reverse complement thereof, and a recode tag. The recode block may include a cycle tag or a reverse complement thereof, and a recode tag or a reverse complement thereof. The recode block may include a cycle tag and a recode tag, or information corresponding to the cycle tag and the recode tag. For example, the recode block may include a cycle nucleic acid, a cycle nucleic acid sequence, or a reverse complement thereof, and may include a recode nucleic acid, a recode nucleic acid sequence, or a reverse complement thereof. The recode block may be useful for joining into a memory oligonucleotide, either of which may convey information about amino acid location and identity within a protein. The recode block may be used in a method described herein, such as a method for determining protein information such as amino acid location or identity.

In some embodiments, the recode block comprises the recode nucleic acid, a sequence of the recode nucleic acid, or a reverse complement of the sequence of the recode nucleic acid joined or combined with the cycle nucleic acid, a sequence of the cycle nucleic acid, or a reverse complement of the sequence of the cycle nucleic acid. In some embodiments, the recode block comprises the recode nucleic acid or a reverse complement of the sequence of the recode nucleic acid joined with the cycle tag. In some embodiments, the recode block comprises the recode nucleic acid, a sequence of the recode nucleic acid, or a reverse complement of the sequence of the recode nucleic acid. In some embodiments, the recode block comprises the cycle nucleic acid, a sequence of the cycle nucleic acid, or a reverse complement of the sequence of the cycle nucleic acid.

Transfer of Information

Disclosed herein, in some embodiments, are methods which include transferring information. For example, a method may include transferring information of the recode nucleic acid to the cycle nucleic acid of the immobilized conjugate complex to generate a recode block. The transfer of information may form a recode block, or may be used to form a memory oligonucleotide. The transfer of information may be included in a method described herein, such as a method for determining protein information such as amino acid location or identity.

In some embodiments, said transferring information comprises performing a nucleic acid sequence-based amplification, for example to generate the sequence of the recode nucleic acid or the sequence of the cycle nucleic acid. In some embodiments, said transferring information comprises performing polymerase chain reaction (PCR) to generate the sequence of the recode nucleic acid or the sequence of the cycle nucleic acid. In some embodiments, the PCR comprises real-time PCR, digital PCR, multiplex PCR, nested PCR, hot-start PCR, touchdown PCR, or quantitative PCR. In some embodiments, said transferring information comprises performing or conducting a ligase chain reaction, a helicase-dependent amplification, a strand displacement amplification, a loop-mediated isothermal amplification, a rolling circle amplification, a recombinase polymerase amplification, a nicking enzyme amplification reaction, a whole genome amplification, a transcription-mediated amplification, a multiple displacement amplification, or multiple annealing and looping-based amplification cycles, for example to generate the sequence of the recode nucleic acid or the sequence of the cycle nucleic acid. The amplification or other procedure may be to generate the sequence of the recode nucleic acid, the sequence of the cycle nucleic acid, a reverse complement, or a combination thereof. In some embodiments, the information of the recode nucleic acid comprises a sequence of the recode nucleic acid or a reverse complement of the sequence of the recode nucleic acid.

In some embodiments, the transfer of information involves a polymerase chain reaction. In some embodiments, the transfer of information involves a reverse transcription polymerase chain reaction. In some embodiments, the transfer of information involves a real-time polymerase chain reaction. In some embodiments, the transfer of information involves a digital polymerase chain reaction. In some embodiments, the transfer of information involves a multiplex polymerase chain reaction. In some embodiments, the transfer of information involves a nested polymerase chain reaction. In some embodiments, the transfer of information involves a hot-start polymerase chain reaction. In some embodiments, the transfer of information involves a touchdown polymerase chain reaction. In some embodiments, the transfer of information involves a quantitative polymerase chain reaction. In some embodiments, the transfer of information involves a ligase chain reaction. In some embodiments, the transfer of information involves a helicase-dependent amplification. In some embodiments, the transfer of information involves a strand displacement amplification. In some embodiments, the transfer of information involves a loop-mediated isothermal amplification. In some embodiments, the transfer of information involves a rolling circle amplification. In some embodiments, the transfer of information involves a recombinase polymerase amplification. In some embodiments, the transfer of information involves a nicking enzyme amplification reaction. In some embodiments, the transfer of information involves a whole genome amplification. In some embodiments, the transfer of information involves a transcription-mediated amplification. In some embodiments, the transfer of information involves a multiple displacement amplification. In some embodiments, the transfer of information involves a multiple annealing and looping-based amplification cycles. In some embodiments, the transfer of information involves a nucleic acid sequence-based amplification.

In some embodiments, said transferring information comprises joining the recode nucleic acid or a reverse complement of the recode nucleic acid with the cycle nucleic acid.

Joining

Disclosed herein, in some embodiments, are methods which include joining. For example a recode nucleic acid or a reverse complement thereof may be joined with a cycle nucleic acid or a reverse complement thereof. The joining may form a recode block, or may be used to form a memory oligonucleotide. The joining may be included in a method described herein, such as a method for determining protein information such as amino acid location or identity.

In some embodiments, joining comprises enzymatic ligation. In some embodiments, joining comprises splint ligation. In some embodiments, joining comprises chemical ligation. In some embodiments, joining comprises template-assisted ligation. In some embodiments, joining comprises the use of a ligase enzyme. In some embodiments, joining comprises the use of a splint oligonucleotide. In some embodiments, joining comprises the use of a catalyst. In some embodiments, joining comprises the use of a bridging molecule. In some embodiments, joining comprises the use of a condensation agent. In some embodiments, joining comprises the use of a coupling reagent. In some embodiments, joining comprises the use of a polymerase enzyme. In some embodiments, joining comprises the use of a complementary nucleic acid sequence. In some embodiments, joining comprises the use of a nicking enzyme. In some embodiments, joining comprises the use of a nucleic acid modifying enzyme. In some embodiments, joining comprises the use of a recombinase. In some embodiments, joining comprises the use of a strand-displacing polymerase. In some embodiments, joining comprises the use of a single-strand binding protein. In some embodiments, joining comprises a click chemistry reaction. In some embodiments, joining comprises a phosphodiester bond formation. In some embodiments, joining comprises a peptide nucleic acid-mediated ligation. In some embodiments, each binding agent comprises recode tags with a unique nucleic acid sequence. In some embodiments, a plurality of binding agents comprises recode tags with the same nucleic acid sequence. In some embodiments, binding agents comprises recode tags which may have a unique sequence portion and a common sequence portion.

In some embodiments, joining the recode nucleic acid or a sequence of the recode nucleic acid with the cycle nucleic acid or a sequence of the cycle nucleic acid to generate a recode block comprises: (i) joining the recode nucleic acid with the cycle nucleic acid, (ii) joining the recode nucleic acid with a sequence of the cycle nucleic acid, (iii) joining a sequence of the recode nucleic acid with the cycle nucleic acid, or (iv) joining a sequence of the recode nucleic acid with a sequence of the cycle nucleic acid. Some embodiments include performing a nucleic acid sequence-based amplification to generate the sequence of the recode nucleic acid or the sequence of the cycle nucleic acid. Some embodiments include performing polymerase chain reaction (PCR) to generate the sequence of the recode nucleic acid or the sequence of the cycle nucleic acid. In some embodiments, the PCR comprises real-time PCR, digital PCR, multiplex PCR, nested PCR, hot-start PCR, touchdown PCR, or quantitative PCR. Some embodiments include performing or conducting a ligase chain reaction, a helicase-dependent amplification, a strand displacement amplification, a loop-mediated isothermal amplification, a rolling circle amplification, a recombinase polymerase amplification, a nicking enzyme amplification reaction, a whole genome amplification, a transcription-mediated amplification, a multiple displacement amplification, or multiple annealing and looping-based amplification cycles, to generate the sequence of the recode nucleic acid or the sequence of the cycle nucleic acid.

In some embodiments, the joining comprises enzymatic ligation, splint ligation, chemical ligation, template-assisted ligation, use of a ligase enzyme, use of a splint oligonucleotide, use of a catalyst, use of a bridging molecule, use of a condensation agent, use of a coupling reagent, use of a polymerase enzyme, use of a complementary nucleic acid sequence, use of a nicking enzyme, use of a nucleic acid modifying enzyme, use of a recombinase, use of a strand-displacing polymerase, use of a single-strand binding protein, a click chemistry reaction, a phosphodiester bond formation, or a peptide nucleic acid-mediated ligation.

Some embodiments include contacting an additional immobilized amino acid complex with a second binding agent. In some embodiments, the binding agent and the second binding agent comprise distinct recode tags having different recode nucleic acids from each other. In some embodiments, the binding agent and the second binding agent comprise recode tags having identical recode nucleic acids as each other. In some embodiments, the binding agent and the second binding agent comprise distinct recode tags having recode nucleic acids that have different sequences from each other, and that have a portion of the recode nucleic acids that are identical.

In some embodiments, said transferring information comprises joining or combining the recode nucleic acid, a sequence of the recode nucleic acid, or a reverse complement of the sequence of the recode nucleic acid with the cycle nucleic acid, a sequence of the cycle nucleic acid, or a reverse complement of the sequence of the cycle nucleic acid, to generate a recode block.

Memory Oligo Readout

Disclosed herein, in some embodiments, are methods that include a memory oligonucleotide. The memory oligonucleotide may include multiple recode blocks, reverse complement of multiple recode blocks, or one or more recode blocks and the reverse complement of one or more recode blocks. The memory oligonucleotide may be used in a method described herein, such as a method for determining protein information such as amino acid location or identity.

In some embodiments, obtaining the sequence information for the recode block comprises performing sequencing. In some embodiments, obtaining the sequence information for the memory oligonucleotide comprises performing sequencing. The memory oligonucleotide may include a recode block or multiple recode blocks. In some embodiments, the sequencing comprises Sanger sequencing. In some embodiments, the sequencing comprises Next-Generation Sequencing. In some embodiments, the sequencing comprises pyrosequencing, sequencing by synthesis, sequencing by ligation, Illumina sequencing, Ion Torrent sequencing, Pacific Biosciences sequencing, Oxford Nanopore sequencing, SOLiD sequencing, nanopore sequencing, Single Molecule Real-Time (SMRT) sequencing, 454 sequencing, Complete Genomics sequencing, Helicos sequencing, MinION sequencing, direct RNA sequencing, Linked-Read sequencing, mate-pair sequencing, or targeted gene sequencing.

In some embodiments, the sequence information for the memory oligonucleotide is obtained by sequencing. In some embodiments, the sequence information for the memory oligonucleotide is obtained by Sanger sequencing. In some embodiments, the sequence information for the memory oligonucleotide is obtained by Next-Generation Sequencing. In some embodiments, the sequence information for the memory oligonucleotide is obtained by pyrosequencing. In some embodiments, the sequence information for the memory oligonucleotide is obtained by sequencing by synthesis. In some embodiments, the sequence information for the memory oligonucleotide is obtained by sequencing by ligation. In some embodiments, the sequence information for the memory oligonucleotide is obtained by Illumina sequencing. In some embodiments, the sequence information for the memory oligonucleotide is obtained by Ion Torrent sequencing. In some embodiments, the sequence information for the memory oligonucleotide is obtained by Pacific Biosciences sequencing. In some embodiments, the sequence information for the memory oligonucleotide is obtained by Oxford Nanopore sequencing. In some embodiments, the sequence information for the memory oligonucleotide is obtained by SOLiD sequencing. In some embodiments, the sequence information for the memory oligonucleotide is obtained by nanopore sequencing. In some embodiments, the sequence information for the memory oligonucleotide is obtained by Single Molecule Real-Time (SMRT) sequencing. In some embodiments, the sequence information for the memory oligonucleotide is obtained by 454 sequencing. In some embodiments, the sequence information for the memory oligonucleotide is obtained by Complete Genomics sequencing. In some embodiments, the sequence information for the memory oligonucleotide is obtained by Helicos sequencing. In some embodiments, the sequence information for the memory oligonucleotide is obtained by MinION sequencing. In some embodiments, the sequence information for the memory oligonucleotide is obtained by direct RNA sequencing. In some embodiments, the sequence information for the memory oligonucleotide is obtained by Linked-Read sequencing. In some embodiments, the sequence information for the memory oligonucleotide is obtained by mate-pair sequencing. In some embodiments, the sequence information for the memory oligonucleotide is obtained by targeted gene sequencing.

Some embodiments include aggregation of information from only a subset of cycles. Some embodiments include analysis of peptide information that does not include all amino acids of a peptide, for example using sequencing information generated through a recode process (e.g. from a memory oligonucleotide formed from sequences of recode tags and cycle tags) that does not include all amino acids of the peptide. In some embodiments, only some amino acids of a protein are recoded into recode blocks.

A memory oligo may include recode blocks corresponding to all, or only some of the amino acids, of a peptide. The missing amino acid information may be taken into account when reconstructing a peptide, or identifying a peptide. Some memory oligonucleotides include recode blocks with recode tag and cycle tag sequences.

Binding Agent

Disclosed herein, in some embodiments, are binding agents. The binding agent may include a recode tag and a binding moiety. The recode tag may include a recode nucleic acid. The binding agent may be used in a method described herein, such as a method for determining protein information such as amino acid location or identity.

In some embodiments, the binding moiety comprises a peptide. In some embodiments, the binding moiety comprises an antibody. In some embodiments, the antibody comprises a monoclonal antibody, polyclonal antibody, an antibody fragment, an antibody derivative, a bispecific antibody, a nanobody, or a single-domain antibody. In some embodiments, the antibody comprises an antibody fragment comprising a Fab, F(ab')2, or scFv. In some embodiments, the binding moiety comprises an antibody derivative comprising an antibody-drug conjugate, a synthetic antibody, an antibody mimic, an engineered protein binder comprising a DARPin or Affibody, an aptamer, a ligand for a peptide receptor, a small molecule, a lectin, an enzyme substrate, a RNA molecule, or a DNA molecule.

In some embodiments, the binding agent includes an antibody. In some embodiments, the binding agent includes a monoclonal antibody. In some embodiments, the binding agent includes a polyclonal antibody. In some embodiments, the binding agent includes an antibody fragment, such as Fab, F(ab')2, or scFv. In some embodiments, the binding agent includes an antibody derivative, such as an antibody-drug conjugate. In some embodiments, the binding agent includes a bispecific antibody. In some embodiments, the binding agent includes a synthetic antibody or antibody mimic. In some embodiments, the binding agent includes an aptamer. In some embodiments, the binding agent includes a nanobody or single-domain antibody. In some embodiments, the binding agent includes an engineered protein binder, such as a DARPins or Affibodies. In some embodiments, the binding agent includes a peptide. In some embodiments, the binding agent includes a ligand for a peptide receptor. In some embodiments, the binding agent includes a small molecule. In some embodiments, the binding agent includes a lectin. In some embodiments, the binding agent includes an enzyme substrate. In some embodiments, the binding agent includes a RNA molecule. In some embodiments, the binding agent includes a DNA molecule.

In some embodiments, the binding agent further comprises a second tag. In some embodiments, the second tag comprises a fluorescent tag for visualization, a biotin tag for interaction with streptavidin, a radioactive tag for detection, a quantum dot for visualization, a mass spectrometry-based detection tag, a chromogenic tag for visualization, a chemiluminescent tag for detection, a photoacoustic imaging tag, a single-molecule imaging tag, or a dual-modality imaging tag.

In some embodiments, the binding agent is labeled with a second tag for visualization. In some embodiments, the binding agent is labeled with a fluorescent tag for visualization. In some embodiments, the binding agent is labeled with a biotin tag for subsequent interaction with streptavidin. In some embodiments, the binding agent is labeled with a radioactive tag for detection. In some embodiments, the binding agent is labeled with a quantum dot for visualization. In some embodiments, the binding agent is labeled with a second tag for mass spectrometry-based detection. In some embodiments, the binding agent is labeled with a chromogenic tag for visualization. In some embodiments, the binding agent is labeled with a chemiluminescent tag for detection. In some embodiments, the binding agent is labeled with a second tag for photoacoustic imaging. In some embodiments, the binding agent is labeled with a second tag for single-molecule imaging. In some embodiments, the binding agent is labeled with a second tag for dual-modality imaging.

In some embodiments, the binding moiety binds to any of the following amino acids: Ala, Arg, Asn, Asp, Cys, Gln, Glu, Gly, His, Ile, Leu, Lys, Met, Phe, Pro, Ser, Thr, Trp, Tyr, or Val. In some embodiments, the binding moiety binds to Ala. In some embodiments, the binding moiety binds to Arg. In some embodiments, the binding moiety binds to Asn. In some embodiments, the binding moiety binds to Asp. In some embodiments, the binding moiety binds to Cys. In some embodiments, the binding moiety binds to Gln. In some embodiments, the binding moiety binds to Glu. In some embodiments, the binding moiety binds to Gly. In some embodiments, the binding moiety binds to His. In some embodiments, the binding moiety binds to Ile. In some embodiments, the binding moiety binds to Leu. In some embodiments, the binding moiety binds to Lys. In some embodiments, the binding moiety binds to Met. In some embodiments, the binding moiety binds to Phe. In some embodiments, the binding moiety binds to Pro. In some embodiments, the binding moiety binds to Ser. In some embodiments, the binding moiety binds to Thr. In some embodiments, the binding moiety binds to Trp. In some embodiments, the binding moiety binds to Tyr. In some embodiments, the binding moiety binds to Val. In some embodiments, the binding moiety binds to a combination of any of the aforementioned amino acids. Multiple binding agents may be used, with various binding agents having binding moieties that bind to distinct amino acids, and having distinct recode tags that correspond with the distinct amino acids. Multiple binding agents may be used, with various binding agents having binding moieties that bind to multiple amino acids, groups of amino acids, or marginally preferential binding to some amino acids over others. Multiple binding agents may be used with binding agents having a combination of properties including some binding to distinct amino acids, and other binding to groups of amino acids.

In some embodiments, the binding moiety binds to a dipeptide. In some embodiments, the binding moiety binds to tripeptide. In some embodiments, the binding moiety binds to any of the following: a natural amino acid, a post-translationally modified (PTM) amino acid, a derivatized version of an amino acid, a derivatized or stabilized version of a post-translationally modified amino acid, a synthetic amino acid, an amino acid with a specific side chain, an amino acid with a phosphorylated side chain, an amino acid with a glycosylated side chain, an amino acid with a methylation modification, or a D-amino acid. In some embodiments, the binding moiety binds to a combination of any of the aforementioned amino acids. In some embodiments, the binding moiety binds to a group of amino acids. For example, a binding moiety may bind to multiple of many amino acids, e.g. all positively charges, or phosphorylated PTMS. In some embodiments, the binding moiety is weakly specific for an amino acid or group of amino acids. For example, in some embodiments, the binding moiety has only a mild preference for one amino acid or group of amino acids over another. In some embodiments, a PTM such as phosphotyrosine, phosphothreonine, or phosphoserine is recognized. The binding moiety may bind to a phosphorylated amino acid. The binding moiety may bind to a glycosylated amino acid. The binding moiety may bind to a methylated amino acid. The binding moiety may bind to a ubiquitinylated amino acid. Multiple different binding moieties may be used in a plurality of binding agents, and each binding agent may include a recode tag corresponding with each of the multiple different binding moieties. The binding moiety may bind to a derivatized or stabilized version of an amino acid, post-translationally modified amino acid, of other natural or synthetic amino acid. The binding moiety may bind to an amino acid that has undergone sumoyloation, prenylation, nitrosylation, sulfation, ADP-ribosylation, palmitoylation, myristoylation, carboxylation, hydroxylation, or other modification. The binding moiety may bind to a group or class of said modifications or amino acids with similar modifications. For example, the binding moiety may bind to a group such as any amino acid having a certain PTM, such as all phosphorylated amino acids.

Solid Support

Disclosed herein, in some embodiments, are solid supports. A peptide may be coupled to the solid support. A chemically-reactive conjugate may bind to the solid support. The solid support may be used in a method described herein, such as a method for determining protein information such as amino acid location or identity.

In some embodiments, the solid support comprises a bead, a plate, or a chip. In some embodiments, the solid support comprises glass slide, silica, a resin, a gel, a membrane, polystyrene, a metal, nitrocellulose, a mineral, plastic, polyacrylamide, latex, or ceramic. In some embodiments, the solid support comprises a magnetic bead, a glass slide, a microarray chip, a nanoparticle, a silica gel, a resin, a polystyrene bead, a gold plate, a silicon chip, a nitrocellulose membrane, a quartz slide, a multiwell plate, a cellulose paper, an agarose bead, a plastic bead, a polyacrylamide gel, a magnetic nanoparticle, a latex bead, or a ceramic bead. In some embodiments, the solid support is contained within a flow cell or within a well plate.

In some embodiments, the solid support is a bead, a plate, or a chip. In some embodiments, the solid support is a magnetic bead. In some embodiments, the solid support is a glass slide. In some embodiments, the solid support is a microarray chip. In some embodiments, the solid support is a nanoparticle. In some embodiments, the solid support is a silica gel. In some embodiments, the solid support is a resin. In some embodiments, the solid support is a polystyrene bead. In some embodiments, the solid support is a gold plate. In some embodiments, the solid support is a silicon chip. In some embodiments, the solid support is a nitrocellulose membrane. In some embodiments, the solid support is a quartz slide. In some embodiments, the solid support is a multi-well plate. In some embodiments, the solid support is a cellulose paper. In some embodiments, the solid support is an agarose bead. In some embodiments, the solid support is a plastic bead. In some embodiments, the solid support is a polyacrylamide gel. In some embodiments, the solid support is a magnetic nanoparticle. In some embodiments, the solid support is a latex bead. In some embodiments, the solid support is a ceramic bead. In some embodiments, the solid support is contained within a flow cell. In some embodiments, the solid support is contained within well plate.

In some embodiments, the solid support comprises a bead, plate, chip, polymer, metal, or glass. In some embodiments, the solid support is a bead. In some embodiments, the solid support is a plate. In some embodiments, the solid support is a chip. In some embodiments, the solid support is composed of a polymer.

In some embodiments, the solid support is composed of a metal. In some embodiments, the solid support is composed of glass.

Peptides

Disclosed herein, in some embodiments, are peptides. The peptide may be the subject of a method which seeks to obtain information about the peptide, such as information on an identity or location of one or more amino acids of the peptide. The peptide may be included in a method described herein, such as a method for determining protein information such as amino acid location or identity.

In some embodiments, the peptide comprises a polypeptide or a protein. In some embodiments, the peptide comprises a hormone, neurotransmitter, enzyme, antibody, viral protein, bacterial protein, synthetic peptide, bioactive peptide, peptide hormone, oligopeptide, polypeptide, fusion protein, cyclic peptide, branched peptide, recombinant protein, tumor marker, therapeutic peptide, antigenic peptide, or signaling peptide.

In some embodiments, the peptide is a polypeptide or a protein. In some embodiments, the peptide is a hormone. In some embodiments, the peptide is a neurotransmitter. In some embodiments, the peptide is an enzyme. In some embodiments, the peptide is an antibody. In some embodiments, the peptide is a viral protein. In some embodiments, the peptide is a bacterial protein. In some embodiments, the peptide is a synthetic peptide. In some embodiments, the peptide is a bioactive peptide. In some embodiments, the peptide is a peptide hormone. In some embodiments, the peptide is an oligopeptide. In some embodiments, the peptide is a polypeptide. In some embodiments, the peptide is a fusion protein. In some embodiments, the peptide is a cyclic peptide. In some embodiments, the peptide is a branched peptide. In some embodiments, the peptide is a recombinant protein. In some embodiments, the peptide is a tumor marker. In some embodiments, the peptide is a therapeutic peptide. In some embodiments, the peptide is an antigenic peptide. In some embodiments, the peptide is a signaling peptide.

Disclosed herein, in some embodiments, are peptides coupled to a solid support. In some embodiments, the peptide is coupled to the solid support such that a N-terminal amino acid residue of the peptide is not directly coupled to the solid support. For example, the peptide may be coupled directly by a C-terminal amino acid residue to the solid support, or may be coupled directly by an internal (e.g. non-N-terminal and non-C-terminal) amino acid residue to the solid support. In some embodiments, the N-terminus of the peptide is linked or coupled indirectly to the solid support via a chain of other amino acids of the peptide.

In some embodiments, the peptide coupled to the solid support such that a N-terminal amino acid residue is exposed to reaction conditions. For example, the N-terminal amino acid residue may be on an exterior of the peptide. In some embodiments, the N-terminal amino acid residue exposed to reaction conditions is exposed to a solvent.

In some embodiments, the peptide is derived from a human, plant, bacterium, fungus, animal, virus, mammal, bird, marine organism, insect, reptile, amphibian, synthetic source, protist, yeast, primate, cell culture, parasite, patient sample, environmental sample, or genetically modified organism.

In some embodiments, the peptide is derived from a cell lysate, blood sample, plasma sample, serum sample, tissue biopsy, saliva sample, urine sample, cerebrospinal fluid sample, sweat sample, synovial fluid sample, fecal sample, gut microbiome sample, environmental water sample, soil sample, bacterial culture, viral culture, organoid, tumor biopsy, sputum sample, or hair sample.

In some embodiments, the peptide is derived from a human. In some embodiments, the peptide is derived from a plant. In some embodiments, the peptide is derived from a bacterium. In some embodiments, the peptide is derived from a fungus. In some embodiments, the peptide is derived from an animal. In some embodiments, the peptide is derived from a virus. In some embodiments, the peptide is derived from a mammal. In some embodiments, the peptide is derived from a bird. In some embodiments, the peptide is derived from a marine organism. In some embodiments, the peptide is derived from an insect. In some embodiments, the peptide is derived from a reptile. In some embodiments, the peptide is derived from an amphibian. In some embodiments, the peptide is derived from a synthetic source. In some embodiments, the peptide is derived from a protist. In some embodiments, the peptide is derived from a yeast. In some embodiments, the peptide is derived from a primate. In some embodiments, the peptide is derived from a cell culture. In some embodiments, the peptide is derived from a parasite. In some embodiments, the peptide is derived from a patient sample. In some embodiments, the peptide is derived from an environmental sample. In some embodiments, the peptide is derived from a genetically modified organism.

In some embodiments, the peptide is derived from a cell lysate. In some embodiments, the peptide is derived from a plasma sample. In some embodiments, the peptide is derived from a tissue biopsy. In some embodiments, the peptide is derived from a serum sample. In some embodiments, the peptide is derived from a saliva sample. In some embodiments, the peptide is derived from a urine sample. In some embodiments, the peptide is derived from a cerebrospinal fluid sample. In some embodiments, the peptide is derived from a sweat sample. In some embodiments, the peptide is derived from a synovial fluid sample. In some embodiments, the peptide is derived from a fecal sample. In some embodiments, the peptide is derived from a gut microbiome sample. In some embodiments, the peptide is derived from an environmental water sample. In some embodiments, the peptide is derived from a soil sample. In some embodiments, the peptide is derived from a bacterial culture. In some embodiments, the peptide is derived from a viral culture. In some embodiments, the peptide is derived from an organoid. In some embodiments, the peptide is derived from a tumor biopsy. In some embodiments, the peptide is derived from a sputum sample. In some embodiments, the peptide is derived from a hair sample.

In some embodiments, the peptide is associated with a disease state. In some embodiments, the peptide is associated with a cancerous disease state, an autoimmune disease state, a neurodegenerative disease state, a cardiovascular disease state, a metabolic disease state, a genetic disease state, a viral infection, a bacterial infection, a fungal infection, a parasitic infection, an inflammatory condition, an endocrine disorder, an immunodeficiency, a respiratory disorder, a skin disorder, a gastrointestinal disorder, a psychiatric disorder, an aging process, a muscular disorder, or a renal disorder.

In some embodiments, the peptide is associated with a specific disease state. In some embodiments, the peptide is associated with a cancerous disease state. In some embodiments, the peptide is associated with an autoimmune disease state. In some embodiments, the peptide is associated with a neurodegenerative disease state. In some embodiments, the peptide is associated with a cardiovascular disease state. In some embodiments, the peptide is associated with a metabolic disease state. In some embodiments, the peptide is associated with a genetic disease state. In some embodiments, the peptide is associated with a viral infection. In some embodiments, the peptide is associated with a bacterial infection. In some embodiments, the peptide is associated with a fungal infection. In some embodiments, the peptide is associated with a parasitic infection. In some embodiments, the peptide is associated with an inflammatory condition. In some embodiments, the peptide is associated with an endocrine disorder. In some embodiments, the peptide is associated with an immunodeficiency. In some embodiments, the peptide is associated with a respiratory disorder. In some embodiments, the peptide is associated with a skin disorder. In some embodiments, the peptide is associated with a gastrointestinal disorder. In some embodiments, the peptide is associated with a psychiatric disorder. In some embodiments, the peptide is associated with an aging process. In some embodiments, the peptide is associated with a muscular disorder. In some embodiments, the peptide is associated with a renal disorder.

In some embodiments, the peptide is a biomarker for a disease or condition, a drug target for a disease or condition, an antigen for the development of a vaccine, used for patient stratification in a clinical trial, a therapeutic agent for a disease or condition, used in the production of a biosimilar or generic drug, used for evaluating the efficacy of a drug treatment, used in personalized medicine for a specific disease or condition, used in immuno-oncology research, used in the validation of a diagnostic test, used in the development of a peptide-based therapeutic, a component of a cell signaling pathway, used in a structure-activity relationship study, used in the development of an immunoassay, used in the study of protein-protein interactions, used in the design of a drug delivery system, used in a high-throughput screening assay, used in a pharmacokinetic study, used in the formulation of a nutraceutical product, used in the development of a probiotic product, or used in a proteomics study.

In some embodiments, the peptide is a biomarker for a disease or condition. In some embodiments, the peptide is a drug target for a specific disease or condition. In some embodiments, the peptide is an antigen for the development of a vaccine. In some embodiments, the peptide is used for patient stratification in a clinical trial. In some embodiments, the peptide is a therapeutic agent for a specific disease or condition. In some embodiments, the peptide is used in the production of a biosimilar or generic drug. In some embodiments, the peptide is used for evaluating the efficacy of a drug treatment. In some embodiments, the peptide is used in personalized medicine for a specific disease or condition. In some embodiments, the peptide is used in immuno-oncology research. In some embodiments, the peptide is used in the validation of a diagnostic test. In some embodiments, the peptide is used in the development of a peptide-based therapeutic. In some embodiments, the peptide is a component of a cell signaling pathway. In some embodiments, the peptide is used in a structure-activity relationship study. In some embodiments, the peptide is used in the development of an immunoassay. In some embodiments, the peptide is used in the study of protein-protein interactions. In some embodiments, the peptide is used in the design of a drug delivery system. In some embodiments, the peptide is used in a high-throughput screening assay. In some embodiments, the peptide is used in a pharmacokinetic study. In some embodiments, the peptide is used in the formulation of a nutraceutical product. In some embodiments, the peptide is used in the development of a probiotic product. In some embodiments, the peptide is used in a proteomics study.

Deprotection and Reprotection of Oligonucleotides

Disclosed herein, in some embodiments, are methods that comprise protection and/or deprotection. For example, some embodiments include any or all aspects shown in FIG. 28. Some embodiments include serially repeated deprotection and reprotection of oligonucleotides during a protein sequencing method to minimize the effect of peptide cleavage chemical conditions on molecular structure of oligonucleotides. Protection, deprotection, or reprotection may be used in a method described herein, such as a method for determining protein information such as amino acid sequence, identity, or location.

Some embodiments include methods that comprise serially protecting and deprotecting oligonucleotides. The serial protection and deprotection may mitigate DNA damage. Some embodiments include a method for cyclically protecting and deprotecting oligonucleotides bound directly or indirectly to solid support in the presence of peptides bound directly or indirectly to solid support. This may be useful for mitigating DNA damage during cyclic n-terminal degradation of said peptide and subsequent biochemistry within each cycle. Some embodiments include a method for cyclically protecting and deprotecting oligonucleotides in a method of peptide sequencing where the nucleic acid is not bound directly or indirectly to solid support.

Any or all of the following steps may be included within a peptide sequencing method described herein:

(1) Deprotect an oligonucleotide associated with cycle or amino acid or peptide identity to enable polymerization, ligation, or DNA manipulation by enzymes known in the art to modify, extend, amplify, convert, or ligate DNA (2) Reprotect the oligonucleotide;

(3) Cleave the terminal amino acid (4) Repeat

Cleavage may be performed with a chemically-reactive conjugate (CRC). In some aspects, serially repeated protection and deprotection of oligonucleotides is performed in a context of a protein sequencing protocol, for example within a protein sequencing method, or within a barcode creation and/or detection method.

In some embodiments, protection and deprotection steps can be iterated. Cycle tags may be deprotected. In some embodiments, Location oligos may be protected, deprotected, and/or reprotected.

Oligonucleotides may be protected using protection chemistries developed for and utilized during phosphoramidite oligonucleotide synthesis. These protecting groups may withstand anhydrous TCA, which is central to synthesis. For example, N(6)-benzoyl A, N(4)-benzoyl C, and N(2)-isobutyryl G, may be employed during DNA synthesis, and may be amenable to protection within protein sequencing methods.

Also, protecting groups that are removable under mild alkaline conditions, e.g., phenoxyacetyl (Pac) protected dA and 4-isopropyl-phenoxyacetyl (iPr-Pac) protected dG, along with acetyl protected dC, may be employed. As a non-limiting example, protecting the individual bases A, G, and C can be achieved through acylation reactions with the appropriate acid chlorides. The specific acid chlorides used may be benzoyl chloride for adenine and cytosine, isobutyryl chloride for guanine. Solutions of benzoyl chloride in a solvent such as dimethylformamide (DMF) and isobutyl chloride in DMF may be prepared and applied to re-protect the oligonucleotides bound to solid support. In some embodiments, thymine is not protected, but if needed may be protected, for example using diphenylcarbamoyl chloride.

Disclosed herein, in some embodiments, are methods, comprising: (a) protecting an oligonucleotide of a binding or reactive molecule; (b) contacting said molecule with the N-terminus of a peptide bound to a solid support; (c) cleaving one or more amino acid residues from said peptide; (d) deprotecting the oligonucleotide of the binding or reactive molecule; (e) contacting the deprotected oligo with reagent(s) to transfer information by enzymatic ligation, polymerase extension, chemical ligation. Some embodiments include repeating any of the aforementioned steps. The chemically reactive species may include a chemically reactive conjugate described herein.

Disclosed herein, in some embodiments, are methods, comprising: (a) protecting an oligonucleotide joined to a peptide; (b) contacting the N-terminus of said peptide with reagent(s) to cleave one or more amino acid residues from said peptide; (c) deprotecting the oligonucleotide bound to the peptide; (d) contacting the deprotected oligonucleotide with reagent(s) to transfer information by enzymatic ligation, polymerase extension, chemical ligation. Some embodiments include repeating any of the aforementioned steps. The chemically reactive species may include a chemically reactive conjugate described herein.

Disclosed herein, in some embodiments, are methods, comprising: (a) protecting an oligonucleotide associated with location or identity of a peptide; (b) contacting the N-terminus of said peptide with reagent(s) to cleave one or more amino acid residues from said peptide; (c) deprotecting the oligonucleotide bound to the peptide; (d) contacting the deprotected oligonucleotide with reagent(s) to transfer information by enzymatic ligation, polymerase extension, chemical ligation. Some embodiments include repeating any of the aforementioned steps. The chemically reactive species may include a chemically reactive conjugate described herein.

Disclosed herein, in some embodiments, are methods, comprising: (a) protecting an oligonucleotide coupled to a solid support; (b) binding a chemically reactive species to a terminal amino acid of a peptide coupled to the solid support; (c) deprotecting the oligonucleotide; (d) reacting a reagent with the oligonucleotide; and (e) reprotecting the oligonucleotide. Some embodiments include cleaving the terminal amino acid of the peptide after reprotecting the oligonucleotide. Some embodiments include deprotecting the oligonucleotide after cleaving the terminal amino acid of the peptide, and then reacting a second reagent with the oligonucleotide. Some examples include a washing step before or after (a), (b), (c), (d), or (e). Washing may include changing a solution, removing an excess reagent or solution. Any of the aforementioned steps (e.g. step (e)), or a combination of said steps, may be optional in some embodiments.

Disclosed herein, in some embodiments, are methods, comprising: (a) protecting an oligonucleotide coupled to a solid support; (b) cleaving a terminal amino acid of a peptide coupled to the solid support; (c) deprotecting the oligonucleotide; (d) reacting a reagent with the oligonucleotide; and (e) reprotecting the oligonucleotide. Some embodiments include binding a chemically reactive species to a terminal amino acid of the peptide after reprotecting the oligonucleotide. Some embodiments include deprotecting the oligonucleotide after binding the chemically reactive species to the terminal amino acid of the peptide, and then reacting a second reagent with the oligonucleotide. Some examples include a washing step before or after (a), (b), (c), (d), or (e). Washing may include changing a solution, removing an excess reagent or solution. Any of the aforementioned steps (e.g. step (e)), or a combination of said steps, may be optional in some embodiments.

Some embodiments relate to a method. The method may include providing a conjugate comprising a reactive molecule coupled to a protected oligonucleotide. The method may include contacting the reactive moiety with a terminal amino acid of a peptide, for example thereby binding the reactive moiety to the terminal amino acid. The method may include optionally cleaving the terminal amino acid from the peptide.

The method may include deprotecting the oligonucleotide. The method may include contacting the deprotected oligonucleotide with an enzyme or reagent for ligation or polymerization. Disclosed herein, in some embodiments, are methods, comprising: providing a conjugate comprising a reactive molecule coupled to a protected oligonucleotide; contacting the reactive moiety with a terminal amino acid of a peptide, thereby binding the reactive moiety to the terminal amino acid, and optionally cleaving the terminal amino acid from the peptide; deprotecting the oligonucleotide; and contacting the deprotected oligonucleotide with an enzyme or reagent for ligation or polymerization. Some embodiments include reprotecting the oligonucleotide. In some embodiments, the reactive moiety cleaves the terminal amino acid from the peptide to expose a next terminal amino acid, and wherein the method further comprising contacting the next amino acid with another of the conjugate after reprotecting the oligonucleotide. In some embodiments, the terminal amino acid is N-terminal. In some embodiments, the peptide is immobilized to a solid support. In some embodiments, the conjugate comprises an organic, small molecule. In some embodiments, the conjugate comprises a chemically-reactive conjugate (CRC) comprising: (A) the oligonucleotide; (B) the reactive moiety; and (C) an immobilization moiety. In some embodiments, the oligonucleotide comprises a cycle nucleic acid.

Some embodiments relate to a method. The method may include providing a conjugate comprising a peptide coupled to a protected oligonucleotide. The method may include contacting the terminal amino acid of the peptide, e.g. thereby binding a reactive moiety to the terminal amino acid. The method may include optionally cleaving the terminal amino acid from the peptide. The method may include deprotecting the oligonucleotide. The method may include contacting the deprotected oligonucleotide with an enzyme or reagent for ligation or polymerization. Disclosed herein, in some embodiments, are methods, comprising: providing a conjugate comprising a peptide coupled to a protected oligonucleotide; contacting the terminal amino acid of the peptide, thereby binding a reactive moiety to the terminal amino acid, and optionally cleaving the terminal amino acid from the peptide; deprotecting the oligonucleotide; and contacting the deprotected oligonucleotide with an enzyme or reagent for ligation or polymerization. Some embodiments include reprotecting the oligonucleotide. In some embodiments, the reactive moiety cleaves the terminal amino acid from the peptide to expose a next terminal amino acid, and wherein the method further comprising contacting the next amino acid with another of the conjugate after reprotecting the oligonucleotide. In some embodiments, the terminal amino acid is N-terminal. In some embodiments, the peptide is immobilized to a solid support. In some embodiments, the conjugate comprises an organic, small molecule.

Subset Sequencing

Disclosed herein, are methods for sequencing a subset of nucleotides or nucleotides, or excluding a subset of nucleotides or nucleotides from sequencing. The method for sequencing a subset of nucleotides may be included as part of a method for determining protein information such as amino acid sequence, identity, or location. The method may be useful in a distinct methods involving DNA sequencing. In some embodiments, only subset of nucleotides are sequenced. In some embodiments, some nucleotides are not sequenced. For example, in some embodiments, only two nucleotides of a sequence (such as A and C) are sequenced, and the other nucleotides are not sequenced. This may reduce sequencing costs as it reduces the need for sequencing reagents.

Subset sequencing may be particularly useful when an oligonucleotide is required to function during a physiochemical activity, such as a primer for PCR or a spacer oligo, and function to store information. In some embodiments nucleotides of a sequence that is functional during physiochemical activities provide redundant stored information. An aspect such as a barcode nucleic acid or recode nucleic acid may include nucleotides such as A, G, C, and T, whereas information content of the physiochemically functional sequence may be represented by a subset of the nucleotides (such as A and C, or T and G). In some embodiments, a recode tag, cycle tag, and/or recode block nucleic acids include sequence that is useful to obtain. In some aspects this information can be obtained by sequencing a subset of the nucleotides that comprise the nucleic acid. When an oligonucleotide that includes the redundant information sequenced, a subset of nucleotides may be skipped during sequencing.

Disclosed herein, in some embodiments, are methods for sequencing a subset of the nucleotides of an oligonucleotide. The method may include (a) providing, in a nucleic acid sequencing reaction, a combination reversibly terminated nucleotides and nucleotides that are not reversibly terminated. In some embodiments, reversibly terminated nucleotides are fluorescent. In some embodiments, non-reversibly terminated nucleotides are fluorescent. In some embodiments, nucleotides of the nucleic acid being sequenced that correspond with the nucleotides that are not reversibly terminated are not sequenced. In some embodiments, only a subset of nucleotides of the nucleic acid are sequenced. In some embodiments, a subset of nucleotides of the nucleic acid are excluded from sequencing. The method may include providing, in a nucleic acid sequencing reaction, a combination reversibly terminated nucleotides and nucleotides that are not reversibly terminated, wherein nucleotides of the nucleic acid being sequenced that correspond with the nucleotides that are not reversibly terminated are not sequenced. The method may include identifying nucleotides of the nucleic acid being sequenced that correspond with the reversibly terminated nucleotides. In some embodiments, the nucleic acid being sequenced comprises a region that includes only a subset of nucleotides selected from A, C, G, and T, and wherein the subset of nucleotides are not sequenced. In some embodiments, the subset of nucleotides selected from A, C, G, and T comprises 2 nucleotides selected from A, C, G, and T. In some embodiments, the subset of nucleotides selected from A, C, G, and T comprises 3 nucleotides selected from A, C, G, and T. In some embodiments, the region comprises a primer sequence. In some embodiments, the region does not include a barcode sequence, recode nucleic acid sequence or a portion thereof, or a cycle nucleic acid sequence or a portion thereof. The region that is not sequenced may comprise 1, 2, 3, 4, 5, 10, 15, 20, 25, 30, 40, 50, 60, 70, 80, 90, 100, 150, 200, 250, 500, 750, 1000, or more nucleotides, or a range of nucleotides defined by any two or more of the aforementioned integers. The part that is sequenced may comprise 1, 2, 3, 4, 5, 10, 15, 20, 25, 30, 40, 50, 60, 70, 80, 90, 100, 150, 200, 250, 500, 750, 1000, or more nucleotides, or a range of nucleotides defined by any two or more of the aforementioned integers.

In some embodiments, the subset includes a combination of A, G, C, or T. In some embodiments, the subset of nucleotide constituents identified through DNA sequencing is 2 of 4 natural nucleotides (e.g. 2 of A, G, C and T). The subset may include A and G, A and C, A and T, G and C, G and T, or C and T. The subset may exclude A and G, A and C, A and T, G and C, G and T, or C and T. In some embodiments, the subset of nucleotides identified through DNA sequencing is A and C.

In some embodiments, the subset being sequenced includes all four natural nucleotides, wherein non-natural nucleotides are incorporated and are not sequenced and are skipped by non reversibly-terminated nucleotides In some embodiments, the subset of nucleotide constituents identified through DNA sequencing is 3 of 4 natural nucleotides (e.g. 3 of A, G, C and T). The subset may include A, G and C; A, G, and T; A, C, and T; or G, C and T. The subset may exclude A, G and C; A, G, and T; A, C, and T; or G, C and T.

The subset of nucleotides may be sequenced through the use of modified nucleotides (e.g. dideoxy (ddNTPs) such as may be used in Sanger sequencing). The modified nucleotides may include reversible terminated chemistry. The modified nucleotides may include a dye or tag such as a fluorescent dye or tag. The modified nucleotides may be provided in a sequencing reaction. In some embodiments, other nucleotides not included in the subset are not sequenced (e.g. are skipped). The nucleotides not included in the subset may exclude the modification. For example, unmodified nucleotides corresponding to the nucleotides that are skipped or not included in the subset may be used in a sequencing reaction mix.

Disclosed herein, in some embodiments, are methods may include sequencing a subset of nucleotides of an oligonucleotide molecule, comprising: (a) providing a solution that includes oligonucleotides to be sequenced; (b) providing a sequencing reagent comprising one or more nucleotides as predominantly reversibly terminated nucleotides and one or more nucleotides as predominantly non-terminated nucleotides; (c) preparing (a) for sequencing according to protocols for a sequencing system; (d) sequencing the prepared solution of (a) using as at least one component of the sequencing reagents the sequencing reagent of (b) for at least one cycle of DNA sequencing; and (e) obtaining a sequence order for a subset of the nucleotides in the original oligonucleotide sequence. In some embodiments, the oligonucleotides have been designed to contain information about the composition of a peptide or amino acid from a peptide. In some embodiments, the oligonucleotide is a memory oligo, a recode tag, a recode block, or a cycle tag. In some embodiments, the oligonucleotide is derived from a protein sequencing method that creates barcoded nucleic acid information representing protein sequence and/or protein identity. In some embodiments, the oligonucleotides is any nucleic acid sequence that embodies information related to peptide or amino acid sequence or composition. In some embodiments, information of a memory oligo is acquired via DNA sequencing of a subset of the nucleotides that comprise the memory oligo. In some embodiments, any suitable subset of nucleotides is identified through a DNA sequencing process. In some embodiments, the DNA sequencing method is next-generation sequencing (NGS). In some embodiments, the DNA sequencing is a sequencing by synthesis approach using an Illumina Sequencer or a PacBio sequencer. In some embodiments, the DNA sequencing is by ligation approach, a sequence hybridization approach, and/or a ligation-based approach is used. In some embodiments, the subset of nucleotides identified through DNA sequencing is A and C. In some embodiments, the subset of nucleotide constituents identified through DNA sequencing is 2 of the 4 natural nucleotides. In some embodiments, the subset is one of a combination of A, G, C, or T. Some embodiments include introducing non-fluorescent, non-reversibly-terminated nucleotides into NGS sequencing reagent mixtures. In some embodiments, the nucleotides in the oligonucleotide are natural nucleotides (e.g. A, C, G, and/or T). In some embodiments, the nucleotides in the oligonucleotide comprise non-natural nucleotides.

Disclosed herein, in some embodiments, are methods for analyzing one or more peptides from a sample comprising a plurality of peptides, proteins, and/or protein complexes, the method comprising: (a) designing oligonucleotides that include 2, 3, 4, 5, 6 or more different types of nucleotide constituents and that employ a subset of the nucleotide constituents to represent cycle, amino acid, location, and/or protein information; (b) utilizing the physicochemical properties the designed oligonucleotides within a protein sequencing method, such as may be described herein; (c) collecting DNA sequence information for the nucleotides that represent protein information; and (d) analyzing DNA sequence information of a subset of nucleotides to infer protein information. In some embodiments, the oligonucleotide is a memory oligo, a recode tag, a recode block, or a cycle tag. In some embodiments, the oligonucleotide is derived from a protein sequencing method that creates barcoded nucleic acid information representing protein sequence and/or protein identity. In some embodiments, the oligonucleotides is any nucleic acid sequence that embodies information related to peptide or amino acid sequence or composition. In some embodiments, information of a memory oligo is acquired via DNA sequencing of a subset of the nucleotides that comprise the memory oligo. In some embodiments, the DNA sequencing method is NGS. In some embodiments, the DNA sequencing is a sequencing by synthesis approach using an Illumina Sequencer or a PacBio sequencer. In some embodiments, the DNA sequencing is by ligation approach, a sequence hybridization approach, and/or a ligation-based approach is used. In some embodiments, the subset of nucleotides identified through DNA sequencing is A and C. In some embodiments, the subset of nucleotide constituents identified through DNA sequencing is 2 of the 4 natural nucleotides. In some embodiments, the subset is one of a combination of A, G, C, or T. In some embodiments, any suitable subset of nucleotides is identified through a DNA sequencing process. In some embodiments, the method includes introducing non-fluorescent, non-reversibly-terminated nucleotides into NGS sequencing reagent mixtures.

Disclosed herein, in some embodiments, are SBS sequencing reagent mixes. Some embodiments include an SBS sequencing reagent mix comprising one or more nucleotides as predominantly reversibly terminated nucleotides and one or more nucleotides as predominantly non-terminated nucleotides.

Chemically-Reactive Conjugates

Disclosed herein, in some embodiments, are chemically-reactive conjugates (CRCs). The CRC may be used in a method described herein, such as a method for determining protein information such as amino acid sequence, identity, or location. The chemically-reactive conjugate (CRC) may include a nucleic acid sequence tag. The chemically-reactive conjugate may include a reactive moiety. The reactive moiety may bind and cleave a N-terminal amino acid residue from a peptide. The chemically-reactive conjugate may include an immobilizing moiety. The immobilizing moiety may bind to a solid support, and thus may be useful for immobilization to a solid support. The chemically-reactive conjugate may include (A) a cycle tag; (B) a reactive moiety for binding and cleaving a N-terminal amino acid residue from a peptide; and (C) an immobilizing moiety for immobilization to a solid support.

The CRC may include the following structure:

(Formula I)

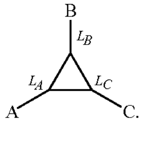

The CRC may include the following structure:

(Formula II)

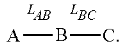

The CRC may include the structure of Formula I or Formula II, or any suitable structure connecting A, B, and C. In either formula, A is, or includes, a cycle tag, B is, or includes, a reactive moiety (e.g. for binding and cleaving a N-terminal amino acid residue from a peptide), and C is, or includes, an immobilizing moiety (e.g. for immobilization to a solid support). $L_A$, $L_B$, and $L_C$ are optional linkers in Formula I. Further, in Formula I,

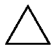

may comprise a central moiety. $L_{AB}$ and $L_B$c are optional linkers in Formula II. Additional arms or aspects may be included or added to Formula I or II.

The chemically reactive conjugate may include a central moiety. The central moiety may be or include a central carbon. The central carbon may be attached to other carbons, such as to 3 other carbons, and link to the arms of the chemically-reactive conjugate. The central moiety may include a heterocycle, a carbocycle, or a trivalent nitrogen. The trivalent nitrogen may include an amine. The amine may include a tertiary amine. The central moiety may include a trivalent boron, a tri- or higher valency phosphorus, a tetravalent silicon, a polyhedral oligomeric silsesquioxane (POSS), a siloxane, a branched siloxane, a polyether, a phosphazene, a phosphonium, an ammonium, an imidazolium, a methane, a propane, a butane, a pentane, a hexane, a C1-C24 alkyl, a benzene, a toluene, a xylene, a phenol, an N,N-disubstituted aniline, an anisole, a trihydroxybenzene, a benzenetricarboxylic acid, a phthalic acid, a trimesic acid, a cyclopropane, a glycol, a glycerol, an ethylene glycol, an oligoethylene glycol, a branched oligoethylene glycol, a multi-arm oligoethylene glycol, a dendrimer, a propylene glycol, an oligopropylene glycol, a trimethylolpropane, a pentaerythritol, a dipentaerythritol, a sugar, a glycoside, a saccharide, a glucose, a fructose, a furanose, a galactose, a mannose, a cyclohexane, a cyclooctane, a cycloheptane, a cyclopentane, a cyclobutene, a cyclononane, a cyclohexene, a cyclobutene, a cyclopentene, a cyclooctene, a cyclononane, an adamantane, a naphthalene, an anthracene, a pyrene, an annulene, a pyridine, a N-substituted piperadine, a N,N-disubstituted piperazine, a thiophene, an indole, a pyrazine, an isoquionline, a pyran, a furan, a pyrimidine, a purine, an oxazole, a benzofuran, a carbazole, a xanthene, a coumarin, an oxazine, a benzothiophene, a benzoxazole, an acridine, a dibenzofuran, a fluorene, an N-substituted azepine, an N-substituted azocine, a thiocane, an N-substituted azonane, a spiro compound, an indolizine, a benzimidazole, an isoindole, an azoindole, a cyclotrisiloxane, a cyclotetrasiloxane, a polycyclic aromatic hydrocarbon, an alkene, a biphenyl, a terphenyl, a triphenylmethane, a decalin, a phenanthrene, a phosphonate, a trisubstituted phosphine, a phosphonic acid, a phosphite, a borate, a norbornane, an oxanorbornene, a norbornene, an oxanorbornene, a dioxane, a di-tertiaryamine, a tri-tertiaryamine, a tetra-tertiary amine, an amide, an N,N-dialkylamide, a sulfonamide, a phosphonamide, a phthalimide, a gallate, an ether, a thioether, a thioamide, a mesitylene, a carboxylic acid functional molecule, a diene, a cyanurate, a guanidine, a urea, a substituted urea, a thiourea, a hydrazone, an oxime, a dibenzocyclooctene, a triazole, or an ester. The central moiety may join the A, B, and C elements of the chemically-reactive conjugate.

In some embodiments, the chemically-reactive conjugate is prepared by an organic synthesis method. Some examples of multicomponent reaction schemes are shown in FIG. 29-32B.

Disclosed herein, in some embodiments, are chemically-reactive conjugate comprising (A) a cycle tag; (B) a reactive moiety; and (C) an immobilizing moiety. In some embodiments, (A), (B), and (C) are oriented linearly in relation to each other. In some embodiments, (A), (B), and (C) are oriented in any of the following orders: (A)-(B)—(C) (like Formula II), (A)-(C)—(B), or (B)-(A)-(C). In some embodiments, (A), (B), and (C) are linearly like Formula II and include optional linkers between (A), (B), and (C), but in the following order: (A)-(C)—(B). In some embodiments, (A), (B), and (C) are linearly like Formula II and include optional linkers between (A), (B), and (C), but in the following order: (B)-(A)-(C). In some embodiments, each of (A), (B) and (C) are on independent arms in relation to each other.

In some embodiments, the CRC is linear in the order (A)-(B)—(C). In some embodiments, the CRC is linear in the order (A)-(C)—(B). In some embodiments, the CRC is linear in the order (B)-(A)-(C). In some embodiments, the CRC each of (A), (B) and (C) are on independent arms.

Some embodiments include a cleavable group between (A) and (B), between (B) and (C), between (A) and (C), between (A) and (B+C), between (B) and (A+C), or between (C) and (A+B), or any combination thereof. Some embodiments include a cleavable group between (A) and (B). Some embodiments include a cleavable group between (B) and (C). Some embodiments include a cleavable group between (A) and (C). Some embodiments include a cleavable group between (A) and (B+C). Some embodiments include a cleavable group between (C) and (A+C). Some embodiments include a cleavable group between (C) and (A+B).

Some embodiments include a non-nucleic acid label (e.g. element A). In some embodiments, the detectable label comprises a fluorophore, a radioactive label, an isotopic label, a mass tag, a chemiluminescent tag, or an imaging tag. Some embodiments include a detectable label. In some embodiments, the detectable label is a fluorophore. In some embodiments, the detectable label is a radioactive label.

In some embodiments, the CRC comprises a pre-nucleic acid sequence tag comprising a group for attaching a nucleic acid sequence. In some embodiments, said group for attaching a nucleic acid sequence comprises an oxyamine group, a tetrazine, an azide, an alkyne, an alkene, a trans-cyclooctene, a DBCO, a bicyclononyne, a norbornene, a strained alkyne, a strained alkene, or derivative thereof. In some embodiments, said group for attaching a nucleic acid sequence is subsequently used to attach a nucleic acid sequence. In some embodiments, the nucleic acid sequence tag is generated upon conjugating the nucleic acid sequence to a group for attaching a nucleic acid sequence comprising an oxyamine group, a tetrazine, an azide, an alkyne, an alkene, a trans-cyclooctene, a DBCO, a bicyclononyne, a norbornene, a strained alkyne, or a strained alkene, or a derivative thereof. In some embodiments, the nucleic acid sequence tag is generated upon conjugating the nucleic acid sequence to a group for attaching a nucleic acid sequence comprising a protected oxyamine group, a protected thiol, a protected amine, a protected hydrazine, a tetrazine, an azide, an alkyne, an alkene, a trans-cyclooctene, a DBCO, a bicyclononyne, a norbornene, a strained alkyne, or a strained alkene, or a derivative thereof. In some embodiments, the conjugation occurs prior to the peptide sequencing steps. In some embodiments, the conjugation occurs after the CRC is reacted to the N-terminal amino acid. In some embodiments, the conjugation occurs after the CRC is reacted to and then cleaved from the N-terminal amino acid, but prior to initiation of the next cycle.

In some embodiments, the CRC comprises a pre-reactive moiety comprising a group for joining said reactive moiety (e.g. as element B). In some embodiments, said pre-reactive moiety for attaching the reactive moiety comprises a tetrazine, an azide, an alkene, an alkyne, a trans-cyclooctene, a DBCO, a bicyclononyne, a norbornene, a strained alkyne, a strained alkene, or a derivative thereof. In some embodiments, said group for attaching the reactive moiety is subsequently used to attach a reactive moiety for binding and cleaving an N-terminal amino acid. In some embodiments, said group for attaching the reactive moiety is used to join the CRC to a reactive moiety that is bound to an N-terminal amino acid.

Some examples of chemically-reactive conjugates are included in Table 1.

TABLE 1

| Examples of PITC embodiments |
| --- |
| 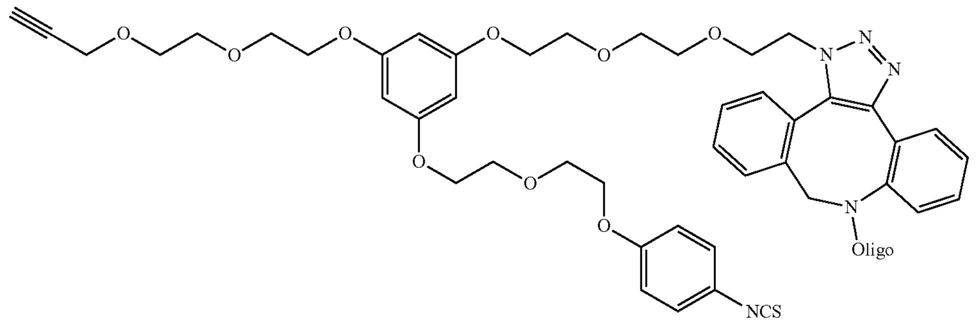 |

TABLE 1-continued
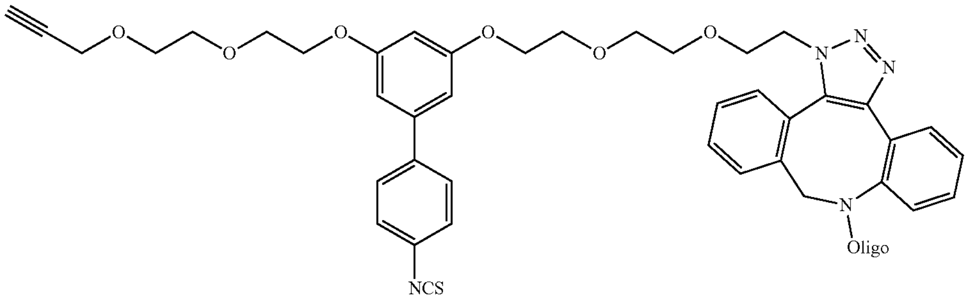
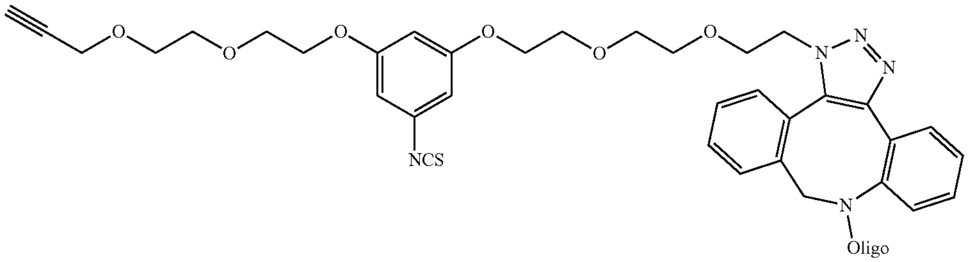
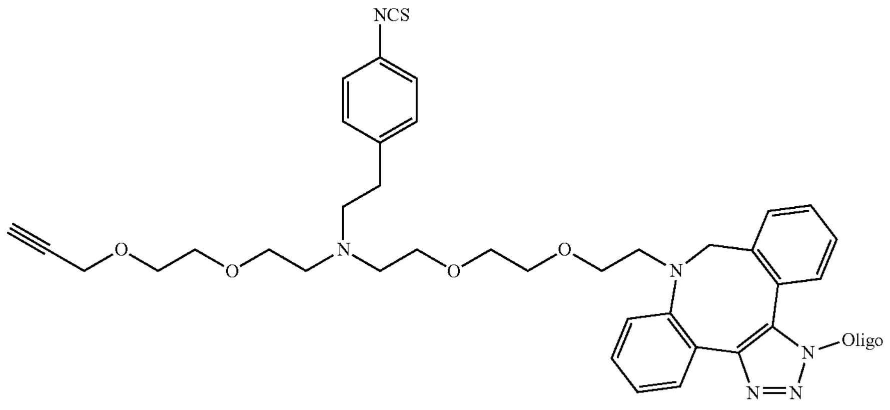
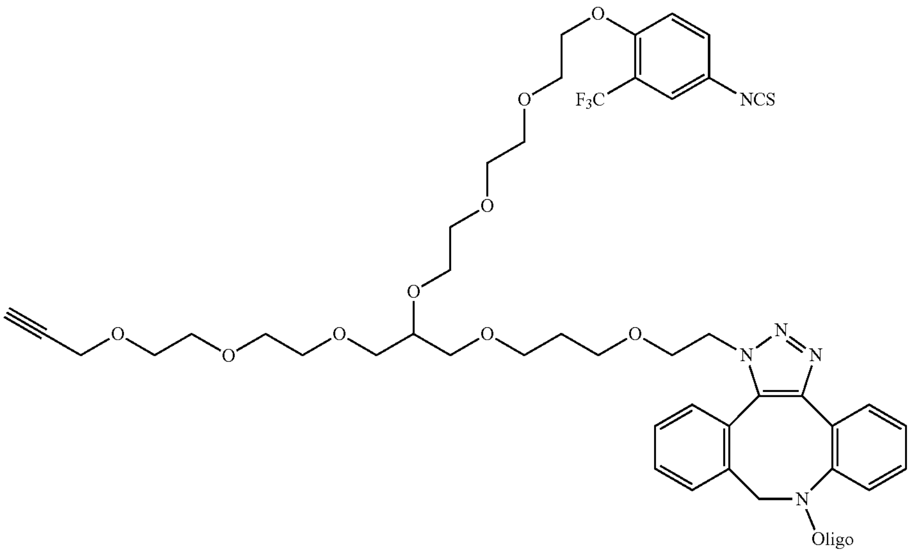

TABLE 1-continued
| Examples of PITC/oligo attachment embodiments |
| --- |
| 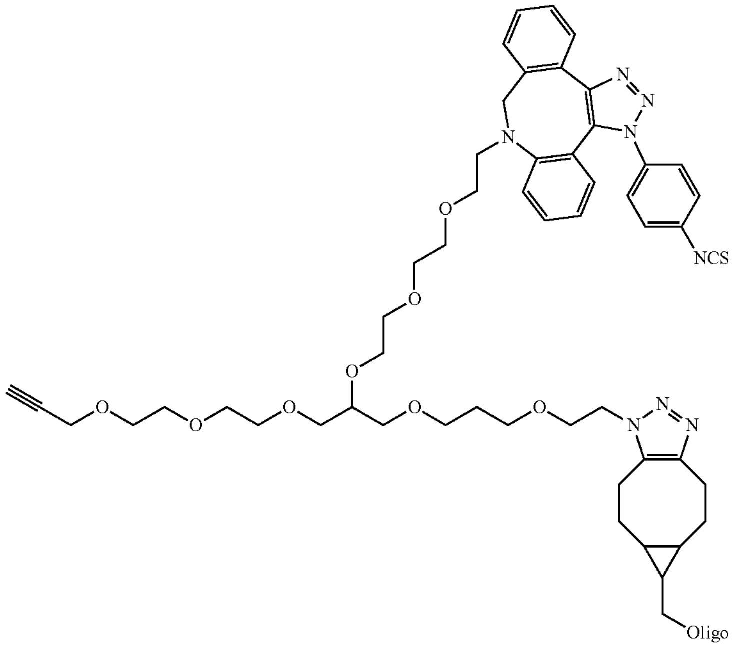 |
| 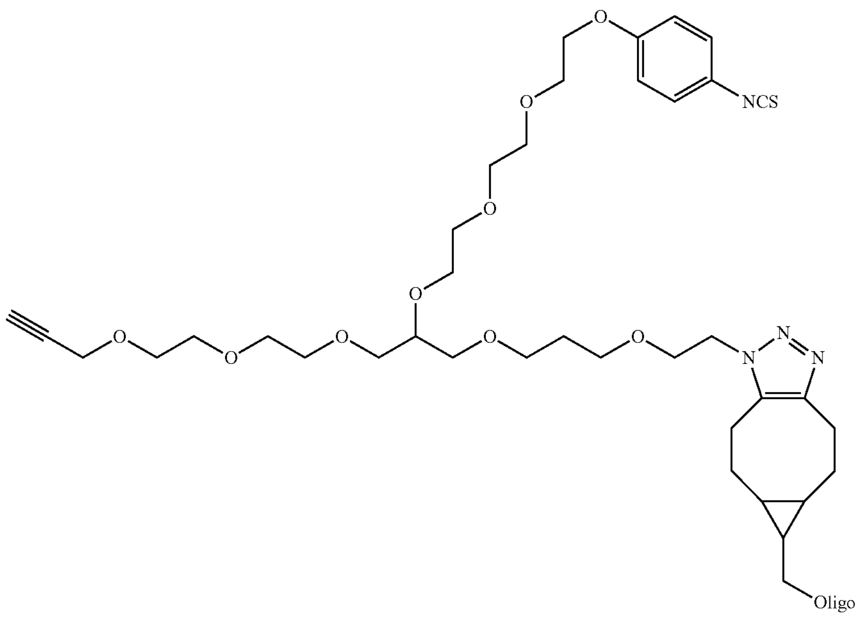 |

TABLE 1-continued
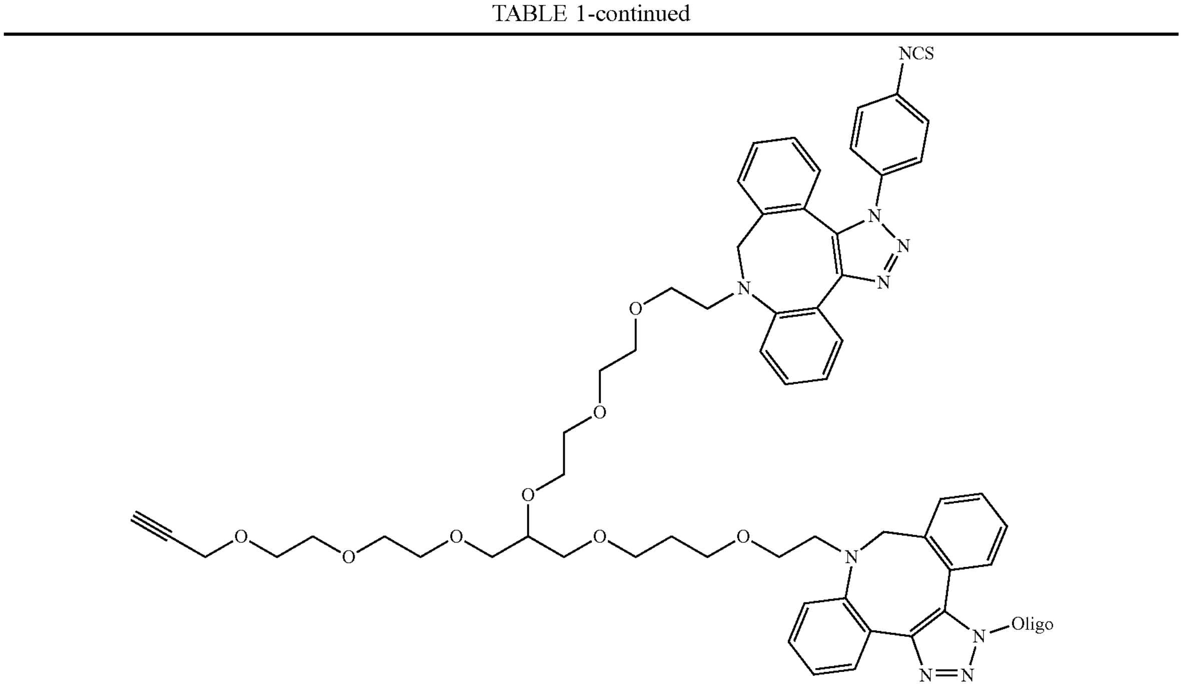
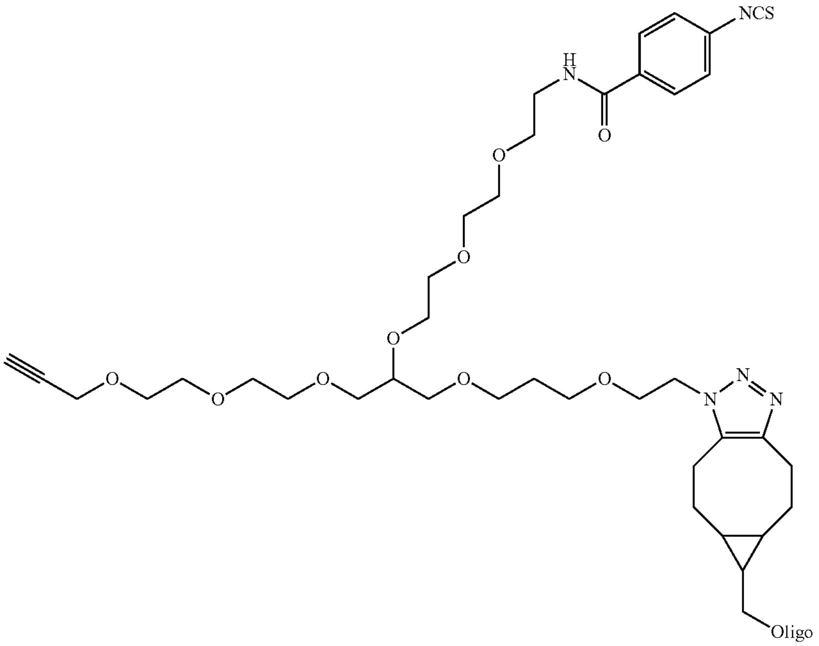

TABLE 1-continued
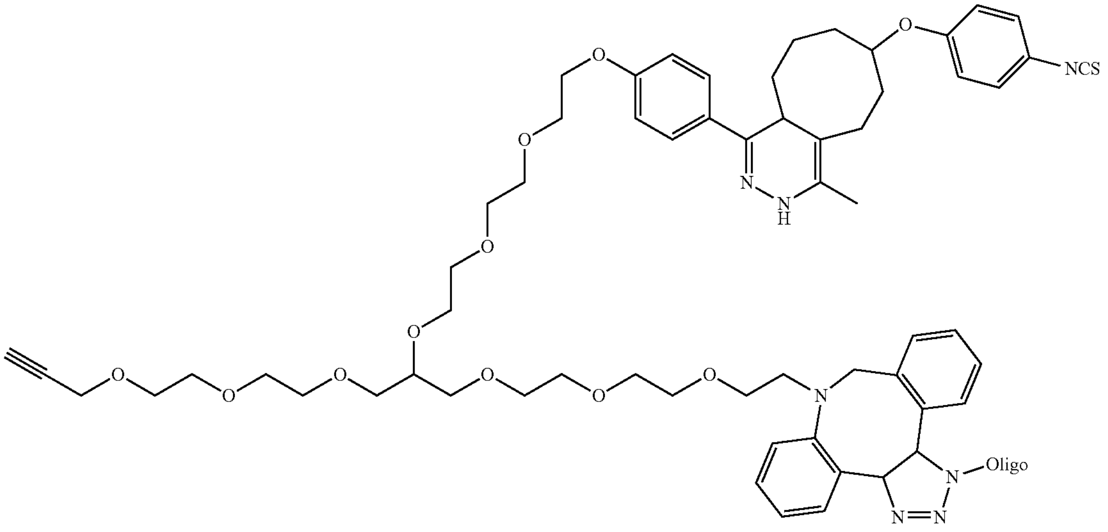
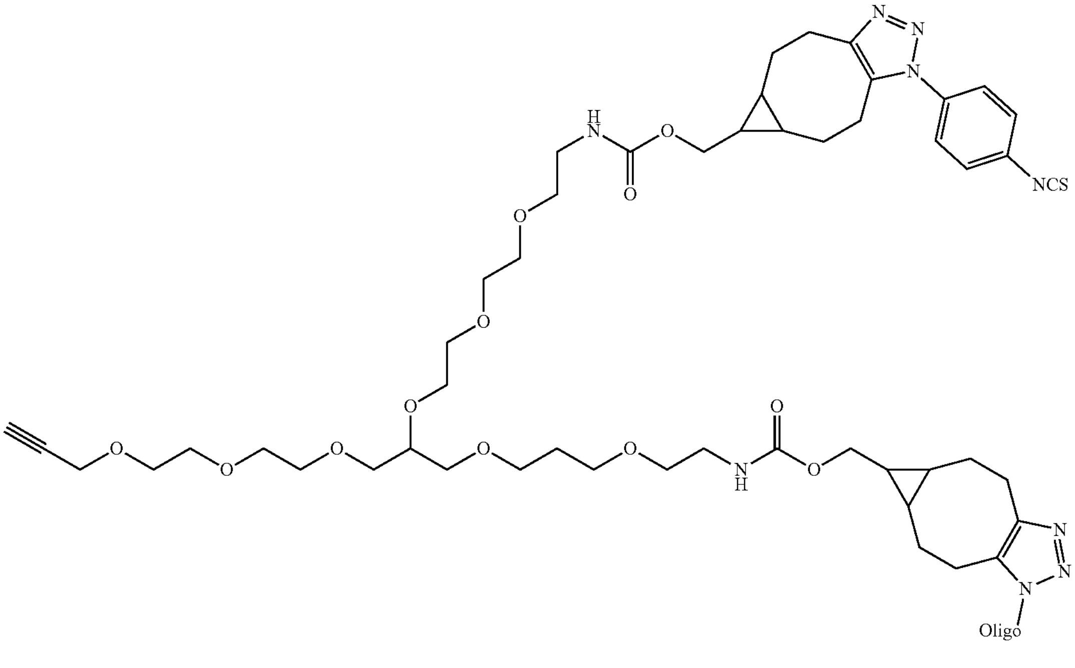

TABLE 1-continued
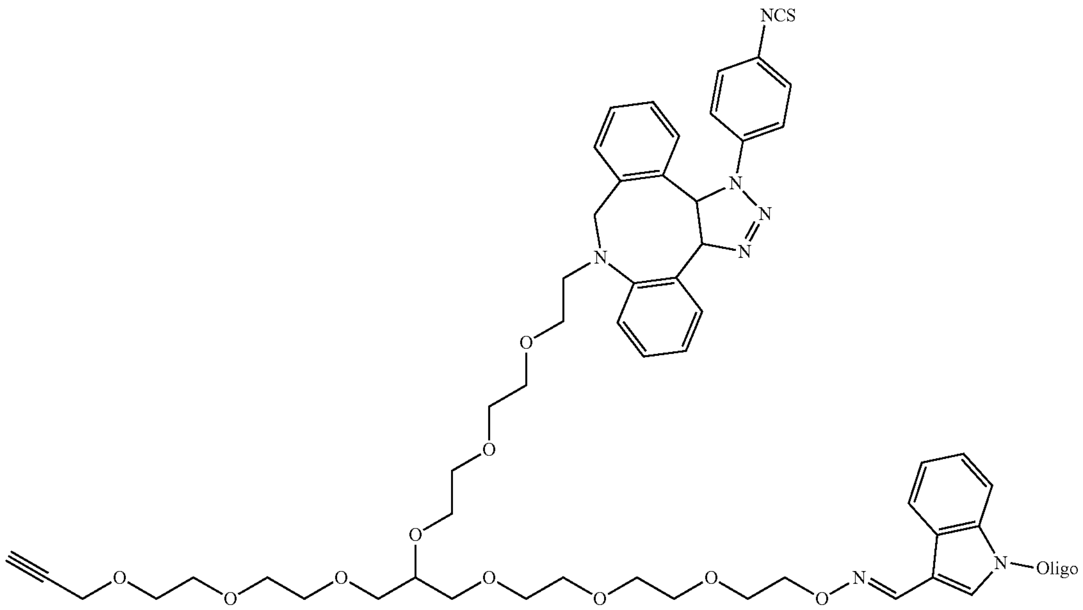
Examples with different immobilization moiety options
Example with photoactivated azirine:
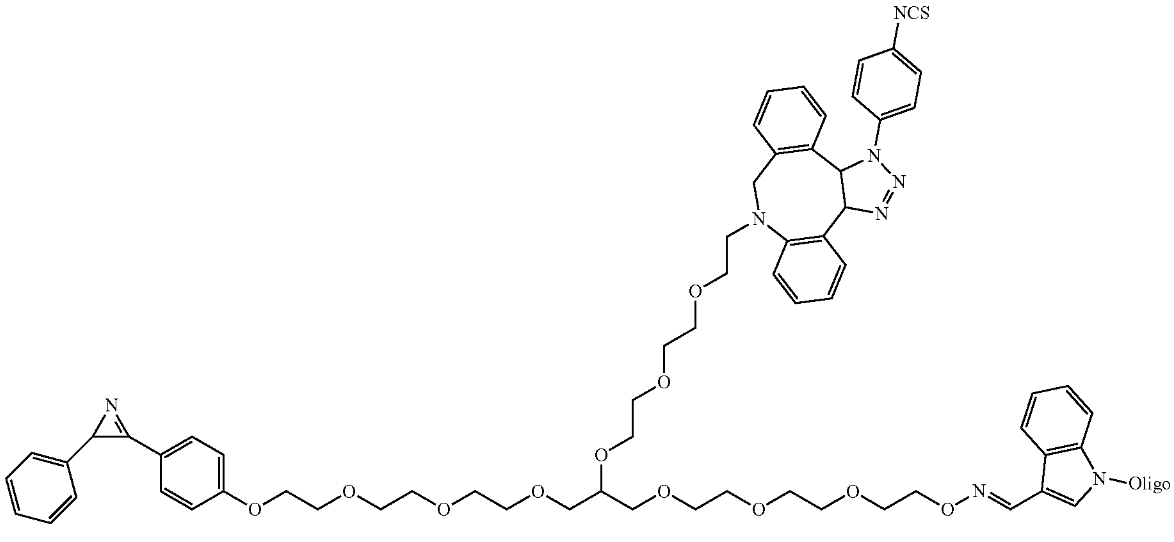
Example with photocaged DBCO:

TABLE 1-continued
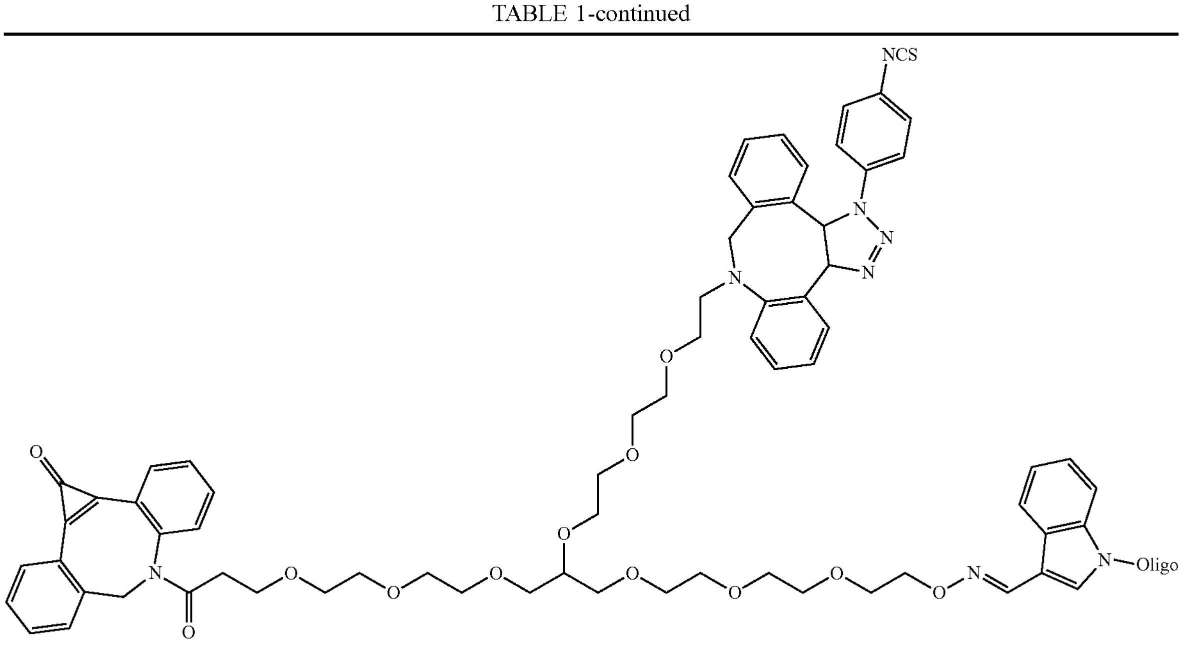
Example with photoactivated tetrazole:
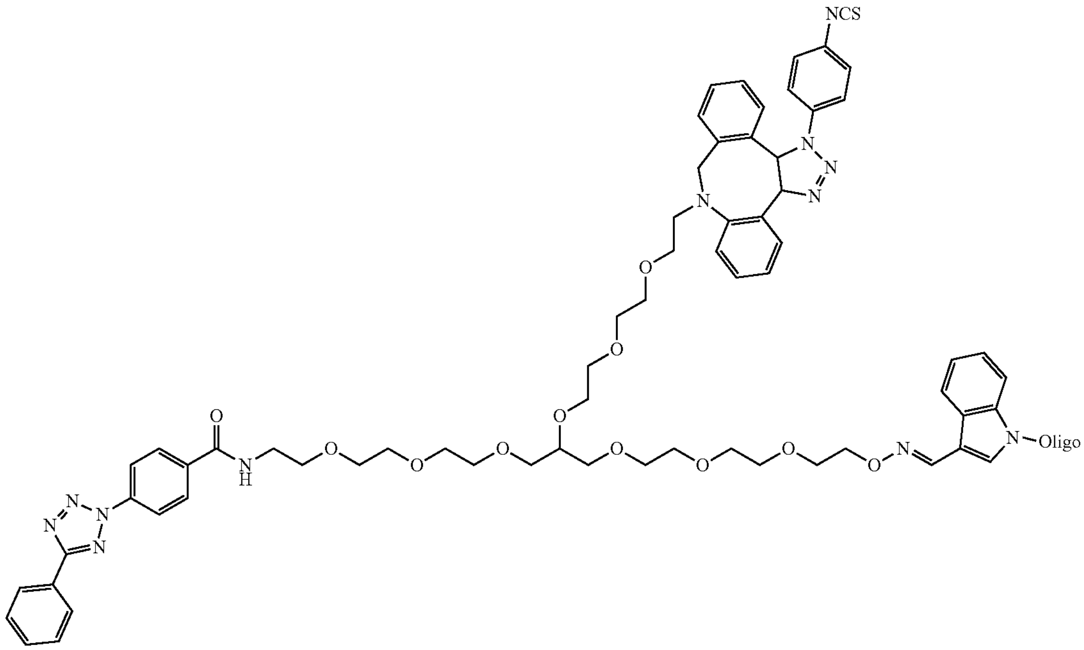

TABLE 1-continued
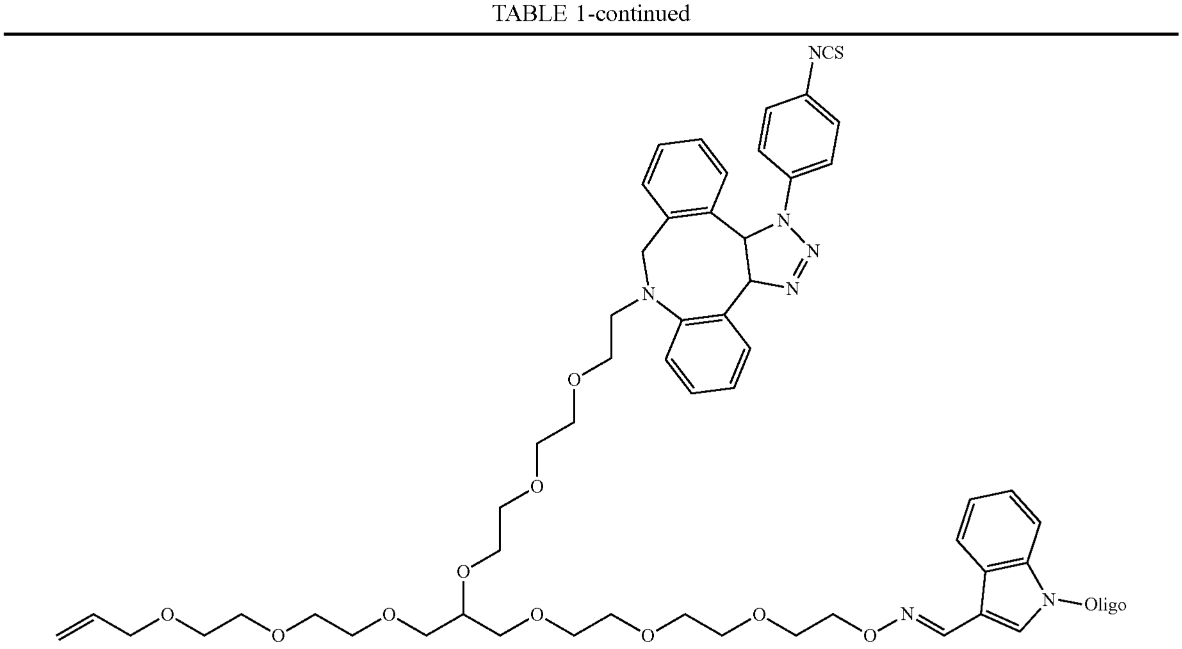
Example with photocaged thiol:
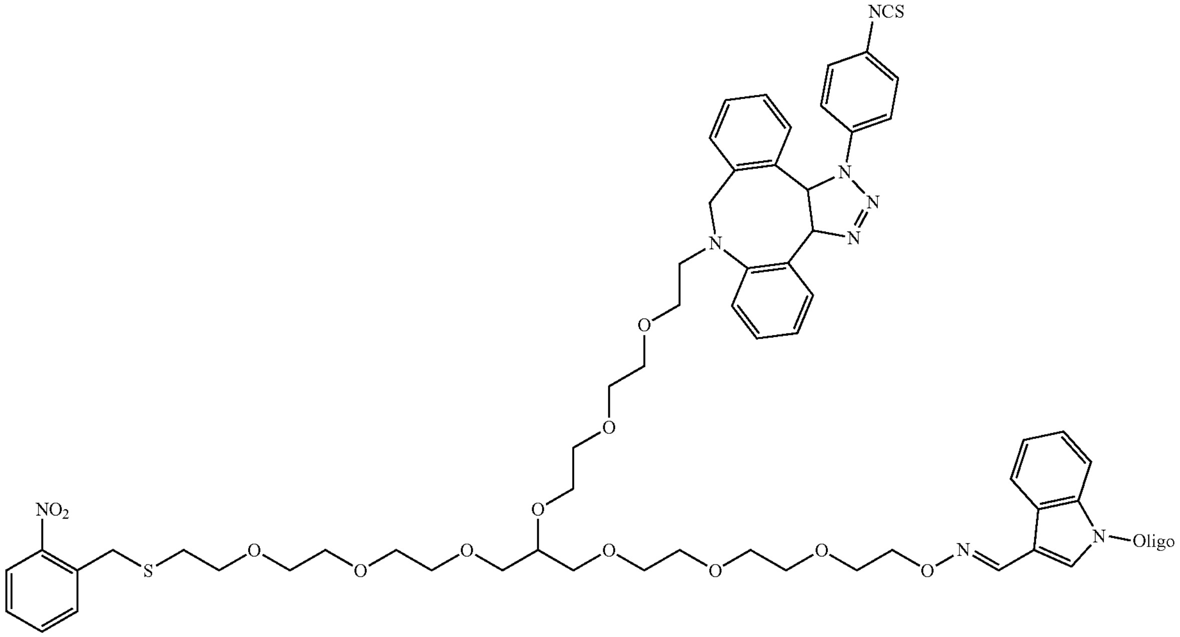
Example with protected thiol via pyridyl disulfide:

TABLE 1-continued
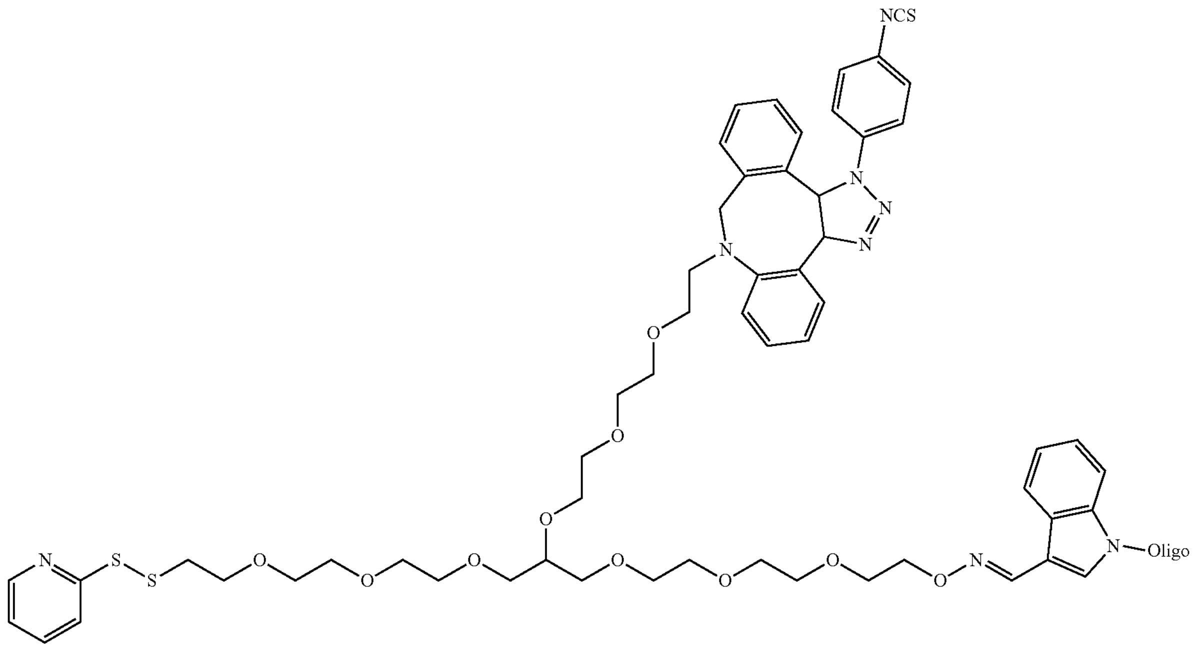
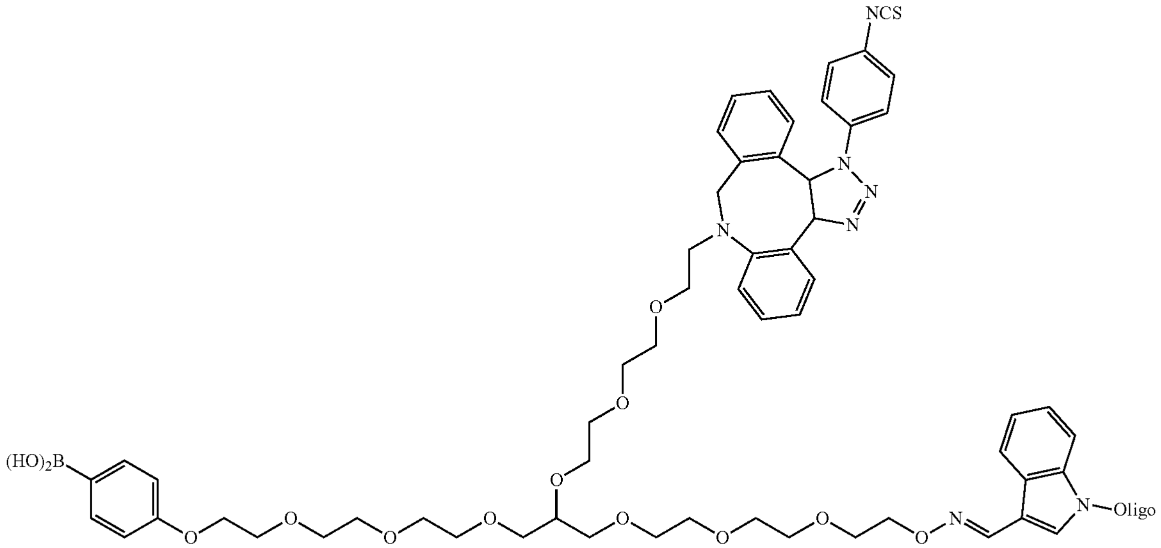

TABLE 1-continued
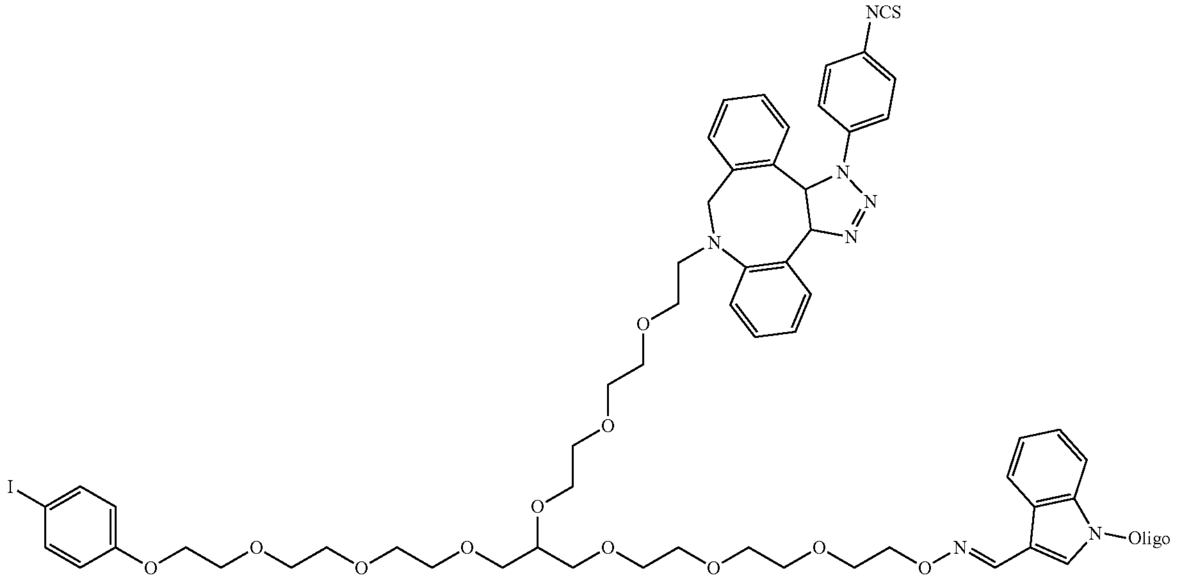
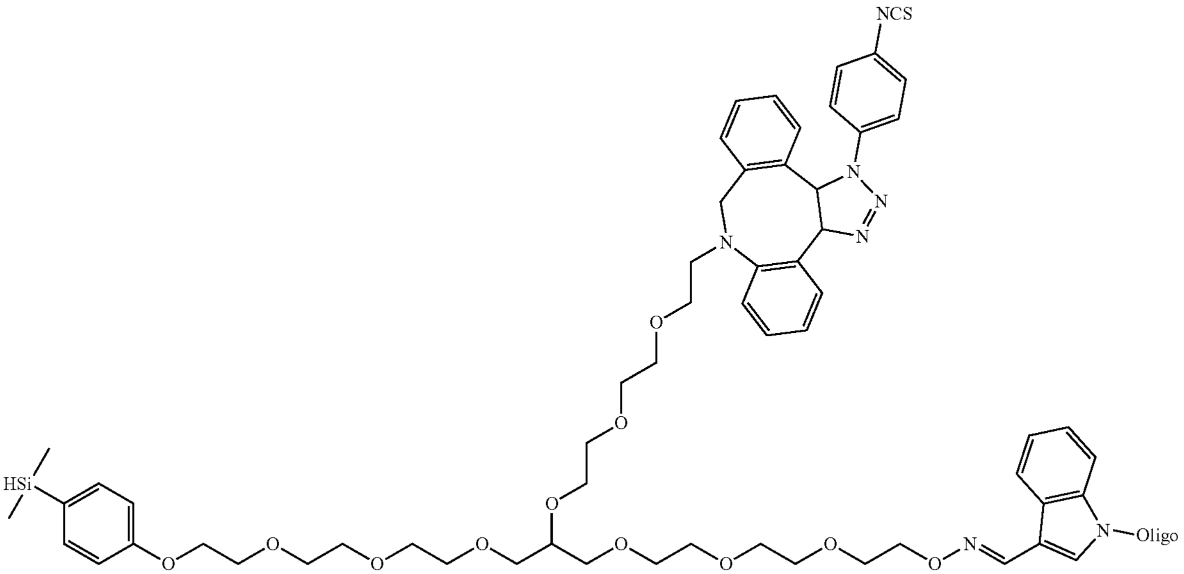

TABLE 1-continued
| Example with different core molecule option |
|---|
| 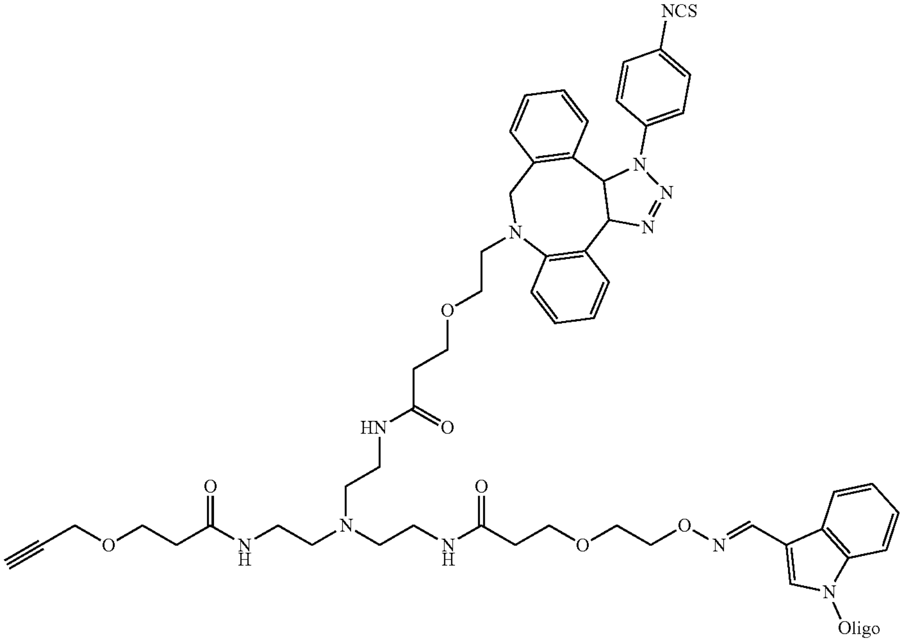 |
| Examples with different configurations |
| 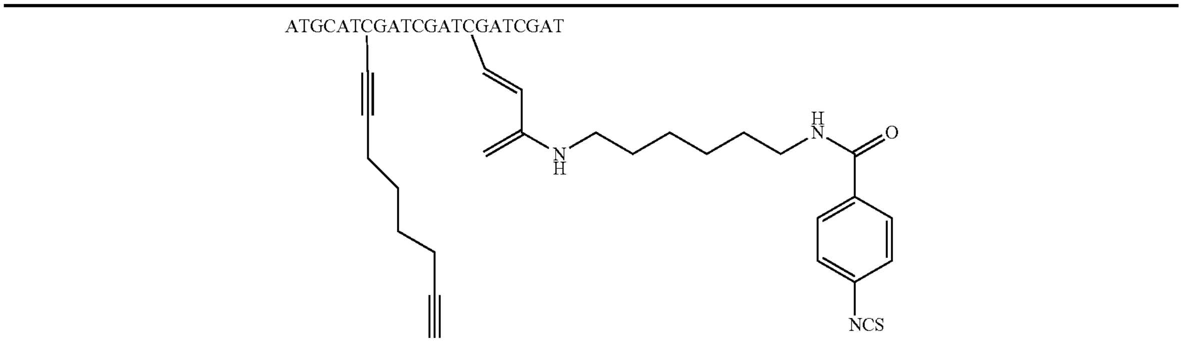 |
| 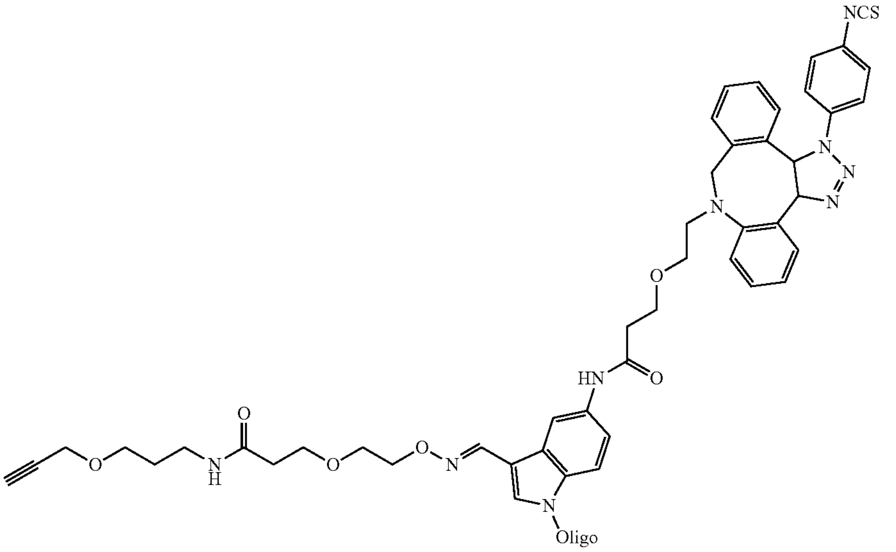 |

Cycle Tag's

Disclosed herein, in some embodiments, are cycle tags. The cycle tag may be associated with a cycle number. The cycle number may correspond with an amino acid number, for example an amino acid number of a peptide when numbered from N to C. The cycle tag may be a part of a chemically-reactive conjugate.

The cycle tag may include a cycle nucleic acid. In some embodiments, the cycle nucleic acid comprises DNA or RNA. In some embodiments, the cycle tag nucleic acid includes RNA, peptide, synthetic small molecule, or peptide nucleic acid. In some embodiments, the cycle tag is a fluorescent tag.

In some embodiments, the cycle tag comprises a peptide. In some embodiments, the cycle tag comprises a peptide nucleic acid. In some embodiments, the cycle tag comprises a fluorescent tag. In some embodiments, the cycle tag comprises a small molecule. In some embodiments, the cycle tag comprises nucleic acid. In some embodiments, the cycle tag is synthetic.

Disclosed herein, in some embodiments, are nucleic acid tags. The nucleic acid tag may be included within a chemically reactive conjugate. The nucleic acid tag of the chemically reactive conjugate may be referred to, or be included as an example of a cycle nucleic acid tag. In some embodiments, the nucleic acid sequence tag comprises a DNA or RNA sequence. In some embodiments, the nucleic acid sequence tag comprises at least 10 nucleotides. In some embodiments, the nucleic acid sequence tag is ligated or bound to an additional oligonucleotide.

In some embodiments, the nucleic acid sequence tag is a DNA sequence. In some embodiments, the nucleic acid sequence tag is an RNA sequence. In some embodiments, the nucleic acid sequence tag is a sequence of at least 10 nucleotides. In some embodiments, the nucleic acid sequence tag is a site for ligating or binding further oligonucleotides and may not include nucleic acids itself.

Reactive Moieties

Disclosed herein, in some embodiments, are reactive moieties. The reactive moiety may be included as part of a chemically-reactive conjugate.

In some embodiments, the reactive moiety comprises an Edman degradation reagent. In some embodiments, the reactive moiety comprises a phenyl isothiocyanate (PITC). In some embodiments, the reactive moiety comprises an isothiocyanate (ITC) or some derivative thereof. In some embodiments, the reactive moiety comprises dansyl chloride or some derivative thereof. In some embodiments, the reactive moiety comprises dinitrofluorobenzene (DNFB) or some derivative thereof.

In some embodiments, the reactive moiety comprises an enzyme or peptide. In some embodiments, the reactive moiety is an enzyme. In some embodiments, the reactive moiety is a peptide. In some embodiments, the reactive moiety specifically cleaves at a specific amino acid. In some embodiments, the reactive moiety specifically cleaves at a specific amino acid that is not N-terminal. In some embodiments, the reactive moiety specifically cleaves at a specific amino acid that is not be the N-terminal acid. In some embodiments, the enzyme or peptide has aminopeptidase activity. In some embodiments, the enzyme or peptide is a modified aminopeptidase. In some embodiments, the reactive moiety cleaves more than a single amino acid. In some embodiments, the reactive moiety cleaves 2, 3, 4, 5 or more amino acids. In some embodiments, the reactive moiety cleaves amino acids at a specific motif. In some embodiments, the motif is at the carboxyl side of lysine (K) and arginine (R) amino acid residues, as long as the next residue is not proline. In some embodiments, the reactive moiety binds and cleaves to a c-terminal amino acid. In some embodiments, the reactive moiety that binds and cleaves to a c-terminal amino acid comprises a modified carboxypeptidase. In some embodiments, the reactive moiety cleaves more than a single amino acid. Examples of reactive moieties that may bind and cleave more than a single amino acid may include a peptidyldipeptidase, or a modified peptidyldipeptidase, such as a modified angiotensin-converting enzyme (ACE). The reactive moiety may include ACE or a modified ACE.

Some embodiments comprise C-terminal peptide degradation, for example following the alkylated thiohydantoin method described by DuPont et al. Dupont D R, Bozzini M, Boyd V L. The alkylated thiohydantoin method for C-terminal sequence analysis. EXS. 2000; 88:119-31.https://doi.org/10.1007/978-3-0348-8458-7_8. The C-terminal carboxyl may be converted to a thiohydantoin via treatment with acetic anhydride followed by thiocyanate ion under acidic conditions. Optionally, the C-terminus can be converted to a thiohydantoin via reaction with diphenyl phosphoroisothiocyanatidate (DPP-ITC). Alkylation of the thiohydantoin can be achieved via reaction with an alkyl halide functional chemically reactive conjugate under basic conditions, resulting in alkylation at the sulfur of the thiohydantoin. This is useful for linking the C-terminus with the CRC. The cleavage of the C-terminal amino acid conjugate may be achieved with thiocyanate ion under acidic conditions.

In some embodiments, the reactive moiety comprises a group on the CRC for attaching to a cleavable derivatized N-terminal amino acid, comprising a tetrazine, an azide, an alkene, an alkyne, a trans-cyclooctene, a DBCO, a bicyclononyne, a norbornene, a strained alkyne, or a strained alkene, or a derivative thereof.

Immobilizing Moieties

Disclosed herein, in some embodiments, are immobilizing moieties. The immobilizing moiety may be included as part of a chemically-reactive conjugate.

In some embodiments, the immobilizing moiety comprises a thiol group, an amine group, or a carboxyl group. In some embodiments, the immobilizing moiety comprises a protected thiol group, a protected amine group, or a carboxyl group, an azide, an alkyne, an alkene, an aryl boronic acid, an aryl halide, a haloalkyne, a silylalkyne, a Si—H group, a protected or photoprotected reactive group, or a photoactivated reactive group. In some embodiments, the immobilizing moiety is an azide, an alkyne, an alkene, an aryl boronic acid, an aryl halide, a haloalkyne, a silylalkyne, a Si—H group, a protected or photoprotected reactive group, or a photoactivated reactive group. The immobilizing moiety may include a thiol. The immobilizing moiety may include an amine. The immobilizing moiety may include an alkyne. The immobilizing moiety may include an azide. The immobilizing moiety may include an alkene. The immobilizing moiety may include an aryl boronic acid. The immobilizing moiety may include an aryl halide. The immobilizing moiety may include a haloalkyne. The immobilizing moiety may include a silylalkyne. The immobilizing moiety may include a Si—H group. The immobilizing moiety may include a protected or photoprotected reactive group (such as a pyridyl disulfide, a phenylacyl protected thiol, a nitrobenzyl protected thiol, a photocaged DBCO). The immobilizing moiety may include a photoactivated reactive group (such as an azirine, a tetrazole, a sydnone, a 3-hydroxynapthalen-2-ol). In some embodiments, the immobilizing moiety is a thiol group. In some embodiments, the immobilizing moiety is a amine group. In some embodiments, the immobilizing moiety is a carboxyl group. In some embodiments, the moiety includes a protected amine, a protected oxyamine, a protected hydrazine, or a blocked isocyanate.

Linkers

Any of the components of the CRC may be linked. The linkage may be through a linker. The components may have the same or different linkers. When the CRC includes the structure of Formula I, $L_A$, $L_B$, or $L_C$ may include a linker. $L_A$ may include a linker. $L_B$ may include a linker. When the CRC includes the structure of Formula II, $L_{AB}$ or $L_{BC}$. $L_A$ may include a linker. $L_{AB}$ may include a linker. $L_{BC}$ may include a linker. In some embodiments, the CRC comprises a linker located at $L_A$, $L_B$, and/or $L_C$.

In some embodiments, the linker comprises polyethylene glycol (PEG), a hydrocarbon, an ether, a carboxyl, an amine, an amide, an azide, a thiol, an azide-thiol, an alkylene, a heteroalkylene, a cyclic group, phenyl, or a combination thereof. The linker may include polyethylene glycol (PEG). The PEG may comprise $PEG_n$, such as $PEG_{1-20}$.

In some cases, the linker comprises an alkylene. In some instances, the alkylene is a C1-C20 alkylene or a derivative thereof. In some instances, the C1-C20 alkylene may optionally be substituted variants thereof. In some instances, the alkylene is a C1-C10 alkylene or a derivative thereof. In some cases, the linker comprises an heteroalkylene. In some instances, the heteroalklyene comprises a $PEG_{1-n}$, wherein n is any suitable integer. In some instances, n is an integer from 2-100. In some instances, n is an integer from 2-50. In some instances, n is an integer from 2-25. In some instances, n is an integer form 2-20. In some instances, the heteroalkylene comprises a PEG1-20 (e g. 1 to 20 units of polyethene glycol) or a derivative thereof. In some instances, the PEG1-20 may optionally be substituted variants thereof. The linker may comprise an oliegoethylene glycol, a peptide, an oligopropylece glycol, an oligoamide, an oligosaccharide, a siloxane, a fully-alkylated polyamine, a polyol, an oliyomeric polyester, a nucleic acid, or an oligomeric poly(tetramethylene oxide). In some aspects, the linker may be modified, for example, with one or more of the following: a heterocycle, a carbocycle, a thioester, an ether, a thioether, a tertiary amine, an amide, a carbamate, a sulfonamide, a dibenzocyclooctyne, a triazole, a thioamide, an oxime, a hydrazone, a urea, a thiourea, a carbonyl (such as an ester or amide), or a carbonate. The number of PEG units in a PEG linker or carbon atoms in an alkylene linker can be decreased or increased as needed. Varying the number of PEGs or carbon atoms in the linker may have varying effects chemical reactive arm reach. For example, longer PEG arms may be useful for allowing greater flexibility or promiscuity, while and shorter PEG arms may provide more rigidity or specificity.

The linker may include a —C(O)—, —O—, —S(O)—, —C(O)O—, —C(O)C1-C10 alkyl, —C(O)C1-C10 alkyl-O—, —C(O)C1-C10 alkyl-CO2-, —C(O)C1-C10 alkyl-S—, —C(O)C1-10 alkyl-NH—C(O)—, —C1-C10 alkyl-C1-C10 alkyl-O—, —C1-C10 alkyl-CO2-, —C1-C10 alkyl-S—, —C1-C10 alkyl-NH—C(O)—, —CH2CH2SO2-C1-C10 alkyl-, CH2C(O)—C1-C1-10 alkyl-, =N—(O or N)—C1-C10 alkyl-O—, =N—(O or N)—C1-C10 alkyl-CO2-, =N—(O or N)—C1-C10 alkyl-S—,

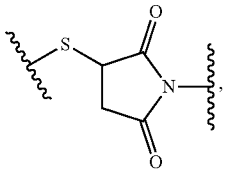,
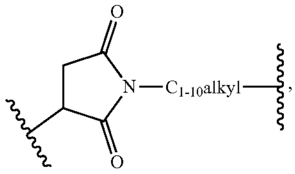, or
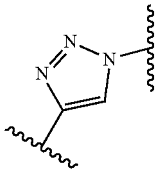.

Any or all of the linkers, such as $L_A$, $L_B$, $L_C$, $L_{AB}$, or $L_{BC}$, may independently include or be selected from any of the aforementioned linkers. $L_A$ may be cleavable. $L_B$ may be cleavable. $L_C$ may be cleavable. $L_{AB}$ may be cleavable. $L_B$C may be cleavable. Any combination of the aforementioned linkers may be used.

A linker may be included between a cycle tag and a reactive moiety (e.g. in a linear version of the CRC), and said linker may be cleavable. A linker may be included between a cycle tag and an immobilizing moiety (e.g. in a linear version of the CRC), and said linker may be cleavable. A linker may be included between a reactive moiety and an immobilizing moiety (e.g. in a linear version of the CRC), and said linker may be cleavable. Any combination of the aforementioned linkers may be used.

In some embodiments, one or more of the linker(s) are cleavable. In some embodiments, one or more cleavable linker(s) comprises a disulfide. The linker may include a cleavable moiety. In some aspects, the cleavable moiety is cleaved by light, an enzyme, or a combination thereof. In some aspects, the light comprises UV light, visible light, IR light, laser, or a combination thereof. In some aspects, the cleavable moiety comprises a photocleavable moiety. In some aspects, the photocleavable moiety comprises an o-nitrobenzyloxy group, o-nitrobenzyl amino group, o-nitrobenzyl group, o-nitroveratryl group, phenacyl group, p-alkoxyphenacyl group, benzoin group, or a pivaloyl group. In some aspects, the photocleavable moiety comprises the o-nitrobenzyl group. In some aspects, the o-nitrobenzyl group is substituted with a methoxy group or an ethoxy group.

A cleavable moiety may be cleaved by light, under acidic conditions, under basic conditions, an enzyme, or a combination thereof. In some cases, the light may comprise UV light, visible light, IR light, laser, or a combination thereof. In such cases, the cleavable moiety may be a photocleavable moiety. The photocleaveable moiety may comprise an electron withdrawing group, such as, but not limited to a nitro group or halide group. In alternative cases, the cleavable moiety may be an enzymatically cleavable moiety.

The cleavable moiety may include a pH sensitive cleavable bond which can be cleaved under acidic or basic conditions. In some non-limiting examples, the cleavable moiety may include a pH sensitive cleavable bond which is cleaved by acidifying the solution. In some non-limiting examples, the cleavable moiety may include a pH sensitive cleavable bond which is cleaved by making the solution basic. The pH sensitive cleavable bond is advantageous because the molecule can be delivered, but would not react until it was under a slightly acidified environment which can be beneficial for the method of protein sequencing.

The cleavable moiety may include a disulfide bond. The disulfide bond may be chemically or enzymatically formed. The disulfide bond may be cleaved by a reducing agent. The disulfide bond may be enzymatically cleavable. The cleavable moiety may include a protein or peptide sequence that is recognized and cleaved by the enzyme. For example, the cleavable moiety may include the peptide sequence ENLYFQ*S (where * denotes a cleavage site). The disulfide bond may be included as part of a peptide.

An enzyme that cleaves a cleavable moiety may include an enzyme that cleaves a disulfide bond, Some examples of enzymes that may cleave disulfide bonds include thioredoxin or glutaredoxin. The enzyme nay include trypsin. The enzyme may include a virus that cleaves a specific peptide sequence. For example, a tobacco etch virus (TEV) protein that specially cleaves the peptide sequence ENLYFQ*S (where * denotes a cleavage site) may be used. This or another peptide sequence may be present in between the central moiety and one (or any) of the arms' After linkage and enrichment, may bond could be cleaved, thereby releasing the molecule of interest.

The photocleavable moiety may be cleaved by UV light. The UV light may have a wavelength in the range of about 100 nm to about 400 nm, about 200 nm to about 400 nm, about 250 nm to about 400 nm, about 280 nm to about 400 nm, about 100 nm to about 370 urn, about 200 nm to about 370 n m, about 250 nm to about 370 nm, or about 280 nm to about 370 nm. In some instances, the photocleavable moiety comprises a nitrobenzyl oxy group, nitrobenzylamino group, nitrobenzyl group, nitroveratryl group, phenacyl group, alkoxyphenacyl group, benzoin group, or a pivaloyl group. In some examples, the nitro group may be in the ortho position of the benzyl, veratryl, phenacyl, benzoin, or pivaloyl group relative to site of cleavage (e.g., 0-nitrobenzyloxy group, o-nitrobenzylamino group, o-nitrobenzyl group, o-nitroveratryl group) In some examples, the alkoxy group may be in the para position of the benzyl, veratryl, phenacyl, benzoin, or pivaloyl group relative to the site of cleavage (e.g. p-alkoxyphenacyl group). In one aspect, the photocleavable moiety comprises a nitrobenzyl group. The nitro group may be ortho to the benzyl group relative to the site of cleavage (o-nitrobenzyl group). The o-nitrobenzyl group may be substituted with a methoxy or an ethoxy, in some cases, the methoxy or ethoxy may be substituted in the para position relative to the nitro of the o-nitrobenzyl group. In further examples, the o-nitrobenzyl group may comprise a linkage connecting to a linker, such as those described herein, that further connects to the central moiety. The linkage may be in the meta positon relative to the nitro group. The linkage may comprise an ester, an ether, an amine, an amide, a carbamate, —O— C1-C10 alkyl-, or any other linkage described herein. In some examples, the photocleavable moiety may comprise the structure represented by the formula:

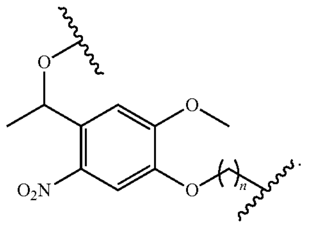

In such examples, n may be 0, 1, 2, 3, 4, 5, 6, 7, 8, 9, or 10.

Any or all of the linkers, such as $L_A$, $L_B$, $L_C$, $L_{AB}$, or $L_{BC}$, may independently include or be selected from any of the aforementioned cleavable linkers or non-cleavable linkers or a combination of cleavable and non cleavable linkers.

Kits

Disclosed herein, in some embodiments are kits. The kit may include any component herein, or any aspect which is described. The kit may be useful for analyzing polymeric macromolecules, including polymeric macromolecules such as peptides, polypeptides, and proteins.

Some embodiments include instructions such as written instructions for use. For example, the kit may include instructions for use in a method of determining identity and positional information of amino acid residues of peptides.

In some embodiments, the kit includes a chemically-reactive conjugate.

In some embodiments, the kit includes a binding agent.

In some embodiments, the kit includes a reagent for transferring information of the recode nucleic acid to the cycle nucleic acid of the conjugate complex to generate a recode block.

Some embodiments include a for analyzing polymeric macromolecules such as polymeric macromolecules such as peptides, polypeptides, or proteins, comprising: a chemically-reactive conjugate comprising (a) a nucleic acid sequence tag and (b) a reactive moiety that couples to a N-terminal amino acid residue of a peptide, and thereby forms a conjugate complex comprising the chemically-reactive conjugate coupled to the N-terminal amino acid of the peptide; a binding agent comprising a binding moiety for preferentially binding to the conjugate complex, and a recode tag comprising a recode nucleic acid corresponding with the binding agent; and a reagent for transferring information of the recode nucleic acid to the cycle nucleic acid of the conjugate complex to generate a recode block.

In some embodiments, the kit includes any or all of the following aspects: (a) a solid support for coupling the peptide to the solid support such that a N-terminal amino acid residue of the peptide is not directly coupled to the solid support and is exposed to reaction conditions; (b) one or more reagents having chemically-reactive conjugates, the chemically-reactive conjugates comprising: (x) a cycle tag comprising a cycle nucleic acid associated with a cycle number, (y) a reactive moiety for binding the N-terminal amino acid residue of the peptide, and (z) an immobilizing moiety for immobilization to the solid support; (c) a reagent for coupling the chemically-reactive conjugate to the N-terminal amino acid of the peptide to form a conjugate complex, when the peptide is contacted with the chemically-reactive conjugate; (d) one or more reagents for immobilizing the conjugate complex to the solid support via the immobilizing moiety; (e) one or more reagents for cleaving and thereby separating the N-terminal amino acid residue from the peptide, thereby providing an immobilized amino acid complex, the immobilized amino acid complex comprising the cleaved and separated N-terminal amino acid residue; (f) one or more reagents having one or more binding agents comprising: (i) a binding moiety for preferentially binding to the immobilized amino acid complex, and (ii) a recode tag comprising a recode nucleic acid corresponding with the binding agent, wherein upon contact of the immobilized amino acid complex with the binding agent, immobilized amino acid complex and the binding agent form an affinity complex, the affinity complex comprising an immobilized amino acid complex and a binding agent; (g) one or more reagents for transferring information of the recode nucleic acid to the cycle nucleic acid of the immobilized conjugate complex to generate a recode block; one or more reagents for joining two or members of the plurality of recode blocks to form a memory oligonucleotide; and/or (j) one or more sequencing reagents for obtaining sequence information of the recode block.

The kit may be used for sequencing a subset of nucleotides of an oligonucleotide, and may include one or more reagents for sequencing a subset of nucleotides of an oligonucleotide. Some embodiments include an SBS sequencing reagent mix comprising one or more nucleotides as predominantly reversibly terminated nucleotides and one or more nucleotides as predominantly non-terminated nucleotides.

The kit may include any reagent or aspect described herein.

Definitions

As used in the present disclosure, the term “amino acid” and notation “AA” refer to natural d-, 1-, non-natural, and post-translationally modified amino acids. An “N-terminal amino acid” refers to an amino acid that has a free amine group, and is linked to only one other amino acid of the peptide through an amide bond. Similarly, a “C-terminal amino acid” refers to an amino acid that has a free carboxyl group, and is linked to only one other amino acid of the peptide through an amide bond.

The term “AA tag” refers to a nucleic acid molecule of any length, but typically in the range 5-20 bases, that contains a sequence that is defined to represent a particular amino acid or class of amino acids that share structural or functional similarity. If recoding a polymer that does not comprise amino acids, then the AA tag sequence may be defined to represent a particular monomer or class of monomers that share structural or functional similarity. It may also refer to any construct that enables a method of subsequent identification of the cycle information, such as a mass tag.

The terms “analyze” and “analyzing” refer to assigning a sequence, and/or quantification, and/or identity to the macromolecule, or a part of the macromolecule analyte.

The term “assembly oligo” (e.g., an assemblyOligo) refers to a nucleic acid capable of hybridizing to a memory oligo tethered to a solid support and/or hydrogel. Assembly oligos may be utilized to facilitate ligation assembly of a complementary DNA strand to a memory oligo that is tethered to the hydrogel surface and or solid support as a template. Ligation assembly of a complementary strand avoids the need for polymerase extension through tethered nucleic acids to create a solution phase nucleic acid representative of the analyte sequence. An assembly oligo comprises a sequence complementary to a cycle tag sequence and a sequence complementary to an amino acid sequence.

The term “binding agent” refers to an entity comprised of a binding moiety joined with a recode tag. The binding moiety and recode tag may be joined by a linker.

The term “binding moiety” refers to a molecule or macromolecule that recognizes and binds with a target analyte or a feature of the target analyte. Exemplary binding moieties include: antibodies, F(ab')2, Fab, and scFv regions, nanobodies, DNA aptamers, RNA aptamers, modified aptamers, photo-active or non-photoactive cage compounds, oligo peptide permease (Opp), amino-acyl t-RNA synthetase (aaRS), periplasmic binding proteins (PBP), dipeptide permease (Dpp), proton dependent oligopeptide transporters (POT), modified aminopeptidases, modified amino acyl tRNA synthetases, modified anticalins, modified ClpS, Lectin, or clathrates. A binding moiety may form a covalent association or non-covalent association with target analytes, which include immobilized conjugate complexes, such as an immobilized PTC-AA-cycle tag-conjugate complex. The binding moiety may exhibit preferential binding to one conjugate complex over another one depending on the amino acid of the complex. The binding moiety may bind preferentially to classes of amino acids that are structurally or functionally similar within the conjugate complex.

In addition to caged drugs and bioactive small molecules, amino acids and derivatized amino acids offer a number of possibilities for caging. For example, amines, carboxylates, and amino acid side chains offer a number of easily caged functional groups. More particularly, caged serine, threonine, tyrosine, cysteine, methionine, aspartate, glutamate, and lysine have all been reported; see Pirrung et al., Synthesis of photodeprotectable serine derivatives—caged serine, Bioorg. Med. Chem. Lett. 2, 1489-1492 (1992); Tatsu et al., Solid-phase synthesis of caged peptides using tyrosine modified with a photocleavable protecting group, Biochem. Biophys. Res. Comm. 227, 688-693 (1996); Gee, K. R., Carpenter, B. K., and Hess, G. P., Synthesis, photochemistry, and biological characterization of photolabile protecting groups for carboxylic acids and neurotransmitters, Met. Enz. 291, 30-50 (1998); Tatsu et al., Synthesis of caged peptides using caged lysine: Application to the synthesis of caged AIP, a highly specific inhibitor of calmodulin-dependent protein kinase II, Bioorg. Med. Chem. Lett. 9, 1093-1096 (1999); Okuno, T., Hirota, S., and Yamauchi, Ol., Folding character of cytochrome c studied by onitrobenzyl modification of methionine 65 and subsequent ultraviolet light irradiation, Biochem. 39, 7538-7545 (2000).

The terms “biochip” and “microarray” refer to consumable devices that support fluidic operations and further support a recode workflow. In some embodiments, these could include a flowcell used directly by an NGS sequencing instrument in a DNA sequencing process.

The term “biologically or synthetically-derived sample” refers to a sample of macromolecules that has its origins from a biological process, such as a cell lysate solution, or has origins from a sample created using synthetic biology techniques, or a sample of macromolecules created using purely chemical synthesis, for example a solution of synthetic peptides, synthetic nucleic acids, or chemically-synthesized polymers.

The term “chemically-reactive conjugate” refers to a conjugate comprising (a) a reactive moiety(ies) that can bind and cleave a terminal amino acid, (b) a reactive moiety that allows immobilization to a solid support, and (c) a cycle tag with identifying information regarding the workflow cycle.

The term “codespace” refers to the universe of codes that are associated with cycle tags and AA tags and are used to represent workflow cycle and monomer identity information, respectively. Codespace is defined by a set of rules that provide practical separation distance between codes and improve fidelity and accuracy while reading information. For example, Hamming distance theory, or other modern digital code space theories (e.g., Lee, Levenshtein-Tenengolts, Reed-Solomon, or others) may be applied to assign codes and enable error detection and error correction capability and account for: 1) NGS sequencing errors during analysis, 2) errors in oligonucleotide synthesis, 3) errors in reagents used in the recoding process, 3) errors that occur during assembly of recode blocks, 4) errors that occur during assembly of memory oligos, or combinations of errors that may occur during any step in the determination of protein sequence and protein abundance by recoding amino acid polymers into DNA polymers and analyzing.

The term "cognate binding agent" refers to a binding agent that was designed to, and that binds with high relative affinity to, a cognate target analyte or a feature or portion of the cognate target analyte. This is contrasted with a "non-cognate binding agent", that was not designed to bind to, and thus interacts with low relative affinity to, a non-cognate target analyte or a feature or portion of the non-cognate target analyte, such that the non-cognate binding agent does not effectively transfer recode tag information to the recode block under conditions appropriate for recode block assembly by cognate binding agents.

The terms "conjugate complex" and "immobilized conjugate complex" refer to a chemically-reactive conjugate having been joined optionally as appropriate within the context to: an amino acid (e.g., a monomer of the macromolecular analyte), a peptide, a linker, a solid support, and/or a cycle tag.

The term "complementary" refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence.

The term "cycle tag" (e.g., "cycleTag") refers to a nucleic acid molecule of any length, but typically in the range 5-20 bases, having a sequence that is defined to represent a particular cycle of the recode workflow. The length of a cycle tag may differ for different cycles of the workflow. The cycle tag may optionally comprise additional nucleic acid sequences that direct assembly of memory oligos in subsequent steps, such as universal assembly sequences which facilitate recode block assembly irrespective of the order of assembly. In certain examples, a cycle tag may optionally comprise a restriction endonuclease sequence. The term, "cycle tag" may also refer to any construct that enables a method of subsequent identification of the cycle information, such as a mass tag.

The term "deprotecting" refers to removing protecting moieties that preserve the integrity of a functional group during exposure to conditions and potential reactants that may otherwise react to alter the functional group. Exemplary protecting agents for nucleic acids include: FMOC, acetyl (Ac), benzoyl (Bz), dimethylformamidine (DMFA), and phenoxyacetyl (PAC). See, Radhakrishnan P. Iyer, Current Protocols in Nucleic Acid Chemistry.

The terms "homology" or "identity" or "similarity" refer to sequence similarity between two peptides or between two nucleic acid molecules.

The term "hydrogel" refers to synthetic polymers, natural polymers, and/or hybrid polymers. Exemplary monomers that may form the hydrogel include one or more: acrylamide, acrylate, vinyl pyridine, dihydroxy methacrylates, other methacrylates, HEMA, PHEMA, PVA, HPMC, PLGA, PEG, etc., in linear, branched, and crosslinked configurations, block co-polymers configurations, or other configurations conducive to sequencing macromolecules. See, Faisal Raza, Hajra Zafar, Ying Zhu, Yuan Ren, Aftab-Ullah, Asif Ullah Khan, Xinyi He, Han Han, Md Aquib, Kofi Oti Boakye-Yiadom and Liang Ge, A Review on Recent Advances in Stabilizing Peptides/Proteins upon Fabrication in Hydrogels from Biodegradable Polymers, Pharmaceutics 2018, 10, 16. A hydrogel may be associated with a solid support through covalent or non-covalent interactions. The hydrogel may further comprise orthogonal conjugation chemistry modalities to support the recode workflow.

The terms "ith", "(i-1)th", etc., refer to an arbitrary position in the macromolecular analyte and it's nearest neighbor.

The term "ligation oligo" (e.g., "ligationOligo") refers to a nucleic acid that becomes ligated to a cycle tag of an immobilized conjugate complex when appropriately directed by a cognate binding agent via hybridization to the recode tag of the cognate binding agent. Ligation oligos may, in certain embodiments, hold information related to amino acid and workflow cycle assembly, and are complementary to the recode tag of a cognate binding agent. It is also recognized that the ligation oligo may be another molecular format that is not a nucleic acid, and that recodes amino acid and workflow cycle information that can be joined with a cycle tag via a chemical reaction. In certain embodiments, ligation oligos may optionally comprise a sequence facilitating ligation, extension:ligation, or chemical ligation of a recode block to another other recode block irrespective of the order of assembly. For example, by including a 3' and/or 5' universal assembly sequence on a plurality of recode blocks such that at least two recode blocks share the same universal assembly sequence, assembly of such recode blocks into a memory oligo, in any given order, is enabled.

The term "linker" or "spacer" refers to a molecule used to join two or more molecules. The composition of the molecule may be a polymer, a monomer or combination of both. A linker may further comprise reactive elements that promote covalent and/or non-covalent conjugation between molecules. Exemplary linkers include those used to join a binding agent to a recode tag, or a cycle tag to other elements of a conjugate complex, e.g. a molecule having a NHS-ester at one end and an azide at the other end of a PEG molecule, or a molecule having a biotin at one end and an maleimide moiety at the other end of a nucleic acid.

The term "linking oligo" (e.g., linkingOligo") refers to a nucleic acid capable of promoting ligation between a recode block associated with a given workflow cycle and a second recode block associated with any other workflow cycle of the recoding process. Linking oligos are useful to complete the assembly of a memory oligo, because they can substitute for errors, e.g., in upstream processes that resulted incomplete or unexpected recode block sequence for one or more workflow cycles, no recode block assembly for one or more workflow cycles, or steric effects that prevent interaction between and assembly of recode blocks. Linking oligos may optionally comprise a sequence complementary to the cycle tag sequence of one workflow cycle and the cycle tag sequence of any other workflow cycle. Ligation of recode blocks via linking oligos may create a lack of information related to the recode block that was skipped in the assembly of the memory oligo. In this case it is recognized that the memory oligo may still be valuable for analysis of macromolecular information, since information may be inferred during analysis that an unknown (or multiple unknown) monomers separate the positions of known monomers, and mapping to references sequence allows macromolecule sequence and identity information. In certain embodiments, linking oligos may optionally comprise a sequence for promoting ligation between a recode block associated with a workflow cycle and a second recode block associate with another workflow cycle of the recoding process. For example, such ligation may be promoted via complementarity between universal assembly sequences of the cycle tag and/or the recode tag.

The term "location linker" refers to any molecule configured to attach a peptide to a solid support, and further configured to bind to a nucleic acid. In some examples, a location linker refers to a molecule with 3 or more functional elements that facilitate the attachment of a peptide, a nucleic acid, and a solid support. In some examples, the nucleic acid can be a UMI that carries code information related to a location of isolation for isolated immobilized PTC-conjugates.

The term "location oligo" (e.g., "locationOligo") refers to a nucleic acid of any suitable length, but typically in the range 10-40 bases, that contains a sequence that represents the x,y,z coordinates of an immobilized macromolecular analyte and is held in proximity to a macromolecule via a location linker. Location oligos are useful to transfer location information to spatially-adjacent immobilized recode blocks.

The terms "macromolecule" and "macromolecular polymer" refer to a high molecular weight molecule composed of subunits. Examples of macromolecules include, but are not limited to, protein complexes such as a photosynthetic reaction center antenna complex, multi-subunit proteins such as a photosynthetic reaction center or a pore protein, single subunit proteins such as cytochrome-c, protein fragments, peptides, polypeptides, nucleic acids, carbohydrates, and polymers such as urethane or acrylamide. "Macromolecule" also describes natural and synthetic combinations of two or more macromolecular types, such as a peptide covalently bound to a nucleic acid, or a lectin bound to a carbohydrate though electrostatic, van der waals forces, or any non-covalent forces.

The term "memory oligo" (e.g., "memoryOligo") refers to a construct that comprises location information, monomer relative positional information, and/or monomer identity information. It is typically assembled by aggregating the information of recode blocks. Typically, a memory oligo comprises information for one associated macromolecular analyte. However, it is recognized that there are embodiments where a memory oligo comprises identifying information for one or more macromolecular analytes. Optionally, a memory oligo may further comprise: sample indexes, UMIs, universal priming sites, linkers, and other identifiers of macromolecule provenance. The length of a memory oligo will typically be between 25 and 25,000 base pairs. When perfectly assembled, the length of the memory oligo equals the sum of the lengths of provenance identifiers plus the lengths of cycle tag and AA tag sequences multiplied by the number of workflow cycles. It is recognized that cycle tag lengths may be different for different workflow cycles. Note that imperfect assembly of a recode block may produce a memory oligo with shorter or longer lengths than the perfectly assembled memory oligos and that are valuable for analysis of the macromolecule, since cycle and amino acid (e.g., monomer) information is transferred to adjacent registers of the memory oligo. It is further recognized that sequential assembly of recode block information into a memory oligo is not required to provide a memory oligo for analysis that is useful for macromolecule analyte analysis.

The term "n" refers to the length of the target macromolecular analyte, or the workflow cycle number. It also refers to terminal subunit of the macromolecular analyte, e.g., nth subunit. Accordingly, the next subunit is denoted as n−1, then the n−2, and so on down the length of the peptide. Theses labels can be assigned starting from the N-terminal or the C-terminal end of a macromolecule.

The terms "n−1", n−2", etc., refer to a cycle prior to the last cycle and, so on. It can also refer to a nearest and a next-nearest subunit molecule to the terminal subunit of a macromolecular analyte.

The term "polynucleic acid" or "polynucleotide" refers to a polymer of deoxyribonucleotides linked by 3'-5' phosphodiester bonds. This also includes polymers with nucleotide analogs and non-natural nucleotides such as Iso-G and Iso-C. This also includes nucleotides linked by thiophosphate bonds or peptidyl bonds such as in PNA. This also covers RNA and polymers with a modified ribose moiety or moieties, such as LNA, XNA, or BNA.

The terms "nucleic acid sequencing", "NGS", or "next generation sequencing" refer to high-throughput methods to determine the sequence of a nucleic acid polymer. These methods are exemplified by commercially available products from Illumina, Pacific Biosciences, and Oxford Nanopore.

The term "peptide" or "polypeptide" refers to a chain of two (2) or more amino acids, and no discrimination in terms of length is implied by the terms: peptide, polypeptide, or protein. Similarly, no discrimination or restriction is implied in terms of 1-, d-, non-natural, or post-translationally modified amino acids monomers that comprise the peptide.

The term "PITC-conjugate" refers to a chemically-reactive conjugate that has not been reacted with an amino acid or a solid support. It is recognized that the qualifier "PITC" is representative terminology to describe any number of molecules (or sets of molecules) that can function similarly to bind to N-terminal or C-terminal amino acids and cleave the terminal subunit.

The terms conjugate complex, "PTC-conjugate", and "PTC-AA-cycle tag-conjugate complex", refer to a chemically-reactive conjugate that has been reacted with an amino acid, but not necessarily been immobilized to a solid support. It is recognized that the qualifier "PTC" is representative terminology to describe any number of alternative molecules (or sets of molecules) that can function similarly to bind to N-terminal or C-terminal amino acids and cleave the terminal subunit. The terms "immobilized conjugate complex," "immobilized PTC-conjugate", and "immobilized PTC-AA-cycle tag-conjugate complex" refer to a chemically-reactive conjugate that has been reacted with an amino acid been immobilized to a solid support. It is recognized that the qualifier "PTC" is representative terminology to describe any number of alternative molecules (or sets of molecules) that can function similarly to bind to N-terminal or C-terminal amino acids and cleave the terminal subunit.

The term "post-translational modification" refers to any modification of an 1-, d-, or non-natural amino acid, either biologically or synthetically. The modifications can occur at the terminal amine, the terminal carboxyl, or any reactive moiety of a peptide. Examples include, but are not limited to, phosphorylation, glycosylation, glycanation, methylation, acetylation, ubiquitination, carboxylation, hydroxylation, biotinylation, pegylation, and succinylation. Further information regarding post-translational modifications may be found in, DOI: 10.1021/acs.biochem.7b00861. Biochemistry 2018, 57, 177-185, which is herein incorporated by reference in its entirety.

The term "recode block" (e.g., "recodeBlock") refers a construct created by interaction between a cycle tag of an immobilized conjugate complex and the recode tag of a cognate binding agent. Typically, a recode block is a chimeric nucleic acid molecule that contains the information relating the workflow cycle and the amino acid, or class of amino acid, composition that comprises the conjugate complex. Further, the recode block holds information to direct assembly of a memory oligo, and/or amplify the recode block. A recode block may be formed by utilizing an extension-ligation method to transfer information from the recode tag to the recode block, or via a ligation reaction under appropriate conditions in the presence of ligase and ligation oligo. The format of a recode block is not necessarily a nucleic acid. It may also take the form of mass tags that could be used to assign identity for cycle and amino acids of the cognate conjugate complex, or other modalities that represent the information of the immobilized conjugate complex, and are amenable to group that information for analysis.

The term "recode tag" (e.g., "recodeTag") refers to a nucleic acid molecule of any length, but typically in the range 15-60 bases, having a sequence comprised of an ith cycle tag complement, an AA tag complement, and an (i-1)th cycle tag complement. It provides identifying amino acid (or monomer subunit) information for its associated binding agent. It may uniquely identify one amino acid or may identify a class of amino acids with structural and/or functional similarity. A recode tag may provide a probabilistic estimate as to the identity of the amino acid component of an immobilized PTC-AA-cycle tag-conjugate complex, and thereby provide sufficient information for analysis. In certain embodiments, a recode tag may optionally comprise the ith cycle tag complement, an AA tag complement, and/or a universal assembly sequence or a complement of the universal assembly sequence, that aids in the assembly of a memory oligo. In certain embodiments, a recode tag may optionally comprise a universal assembly sequence at both the 3' and 5' ends to facilitate memory oligo assembly without regard to the order of assembly of constituent recode blocks. In further embodiments, a recode tag may comprise a sequence facilitating amplification of recode blocks.

The term "sample index" refers to an identifier incorporated during a post-recode preparation of a DNA library for NGS analysis, or an identifier that can be ligated as a component of a memory oligo during its assembly, and used during NGS analysis to identify the provenance of oligonucleotides in the DNA library.

The term "solid support" or "surface" refers to any solid material substrate in planar form, spherical form, or a combination of forms including, but not limited to: a solid bead, a porous bead, a solid planar material, a porous planar material, a patterned or non-patterned solid material, a nanoparticle, or a inorganic or polymeric microsphere, or a capillary. For example, the solid support may comprise a glass slide or wafer, a silicon slide or wafer, a PC, PTC, polyethylene (PE), high density polyethylene (HDPE), or other plastic slide, a teflon, nylon, nitrocellulose membrane, or borosilicate capillary. Particles and beads may be formed from polystyrene, cross-linked polystyrene, agarose, or acrylamide. Beads or nanoparticles may be magnetic or paramagnetic to support separation or purification processes. Solid supports may be passivated with glass, silicon oxide, tantalum pentoxide, DLC diamond-like carbon, or other passivation agents. A "solid support," including membranes, may be passivated or activated via corona or other plasma treatments methods. Solid supports may further be assembled with other components to facilitate fluid transport and/or detection (e.g., flowcell, biochip, a microtiter plate. Solid supports may comprise an associated hydrogel that supports joining components for macromolecule recoding and/or analysis workflows. In certain examples, the term, "solid support" may include any of the described solid supports above further associated with a hydrogel.

The term "splint" refers to a nucleic acid with complementarity to the 5' end of one nucleic acid and the 3' end of another nucleic acid, such that hybridization of the splint to both nucleic acids brings the 5' and 3' ends into proximity to promote either chemical or biological ligation.

The term "strobe sequencing" refers to a method of sequencing (e.g., nucleic acids, peptides, and other polymers) wherein short gapped reads, or interspersed subreads, are generated from a contiguous fragment rather than a single uninterrupted read. Such subreads are referred to as "strobe" or "strobed" reads.

As used in the present disclosure, the term "unique molecular identifier" or "UMI" refers to a nucleic acid molecule of length 10 to 40 bases that can be assembled into, e.g., the memory oligo and provides unique identification for in silico deconvolution of NGS sequencing data as to a specific memory oligo.

The term "universal priming site" or "universal primer" refers to a nucleic acid molecule, which may be used for library amplification and/or during NGS. Exemplary universal priming sequences can include P5, P7, P5', P7', SBS Read 1, and SBS Read 2 primers.

The term "universal sequence" or "universal assembly sequence" or "universal amplification sequence" refers to a common complementary polynucleotide sequence that can be appended to a 3' and/or 5' end of a tag, e.g., a recode tag, for facilitating amplification thereof with common primers or assembly into an oligo, e.g., a memory oligo. In certain embodiments, a universal sequence comprises a repetitive sequence, e.g., a dinucleotide repetitive sequence such as (GT)n, or other relatively short nucleotide motif.

The universal sequence may be silent during sequencing of the oligo to facilitate efficient detection and analysis of the assembled constituents of the oligo.

The term, "workflow cycle" or "cycle" refers to the iteration number of any one of the operations of a process flow or method described herein.

Several references to oligonucleotides may be employed, and are may alternatively be included or named as in Table 2.

TABLE 2

| SEQ ID NO: | Alternate Name |
|---|---|
| 75 | Sys#001, SO or SOC |
| 76 | Sys#001, COM |
| 6 | Sys#001, LO1 |
| 77 | Sys#001, LO2 |
| 78 | Sys#001, SP104 |
| 79 | Sys#001, SP503 |
| 80 | Sys#001, LO1-COM |
| 81 | Sys#001, LO2-COM |
| 82 | Sys#001, PR5 + 3 |
| 83 | Sys#001, PR4 + 1 |
| 84 | Sys#001, LO1, 30 |
| 85 | Sys#001, LO2, 30 |
| 86 | Sys#001, PR6 |
| 87 | Sys#001, PR7 |
| 88 | Sys#001, COM105 |
| 89 | Sys#001, LO1, 30-COM |
| 90 | Sys#001, LO2, 30-COM |
| 91 | Sys#002, SO or SOC |
| 92 | Sys#002, COM |
| 13 | Sys#002, LO1 |
| 93 | Sys#002, LO2 |

TABLE 2-continued

| SEQ ID NO: | Alternate Name |
|---|---|
| 94 | Sys#002, SP104 |
| 95 | Sys#002, SP503 |
| 96 | Sys#002, PR5 + 3 |
| 97 | Sys#002, PR4 + 1 |
| 98 | Sys#002, LO1, 30 |
| 99 | Sys#002, LO2, 30 |
| 100 | Sys#002, PR6 |
| 101 | Sys#002, PR7 |
| 102 | Sys#002, COM105 |
| 103 | Sys#002, LO1, 30-COM |
| 104 | Sys#002, LO2, 30-COM |
| 105 | Sys#002, PR7, 22 |
| 106 | Sys#002, PR3, 25 |
| 107 | Sys#002, PR1, 25 |
| 108 | Sys#003, SO or SOC |
| 109 | Sys#003, COM |
| 20 | Sys#003, LO1 |
| 110 | Sys#003, LO2 |
| 111 | Sys#003, SP104 |
| 112 | Sys#003, SP503 |
| 113 | Sys#003, PR5 |
| 20 | Sys#003, PR4 |
| 114 | Sys#003, LO1, 30 |
| 115 | Sys#003, LO2, 30 |
| 116 | Sys#003, PR6 |
| 117 | Sys#003, PR7 |
| 118 | Sys#003, COM105 |
| 119 | Sys#003, LO1, 30-COM |
| 120 | Sys#003, LO2, 30-COM |
| 121 | Sys#003, PR3, 25 |
| 122 | Sys#003, PR1, 25 |

Note that as used herein and in the appended claims, the singular forms "a," "an," and "the" include plural referents unless the context clearly dictates otherwise. Thus, for example, reference to "an oligo" refers to one or more oligos, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this disclosure belongs. All publications mentioned herein are incorporated by reference for the purpose of describing and disclosing devices, methods and cell populations that may be used in connection with the presently described disclosure.

Where a range of values is provided, it is understood that each intervening value, between the upper and lower limit of that range and any other stated or intervening value in that stated range is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

In this description, numerous specific details are set forth to provide a more thorough understanding of the present disclosure. However, it will be apparent to one of ordinary skill in the art that the present disclosure may be practiced without one or more of these specific details. In other instances, well-known features and procedures well known to those skilled in the art have not been described in order to avoid obscuring the disclosure.

The functionalities described in connection with one embodiment are intended to be applicable to the additional embodiments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of organic chemistry, polymer technology, molecular biology (including recombinant techniques), cell biology, proteomics, biochemistry and sequencing technology, which are within the skill of those who practice in the art. Such conventional techniques include polymer array synthesis, hybridization and ligation of polynucleotides and other polymers, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green et al., Eds. (1999), Genome Analysis: A Laboratory Manual Series (Vols. I-IV); Weiner, Gabriel, Stephens, Eds. (2007), Genetic Variation: A Laboratory Manual; Dieffenbach, Dveksler, Eds. (2003), PCR Primer: A Laboratory Manual; Mount (2004), Bioinformatics: Sequence and Genome Analysis; Sambrook and Russell (2006), Condensed Protocols from Molecular Cloning: A Laboratory Manual; and Sambrook and Russell (2002), Molecular Cloning: A Laboratory Manual (all from Cold Spring Harbor Laboratory Press); Stryer, L. (1995) Biochemistry (4th Ed.) W. H. Freeman, New York N.Y.; Gait, "Oligonucleotide Synthesis: A Practical Approach" 1984, IRL Press, London; Nelson and Cox (2000), Lehninger, Principles of Biochemistry 3rd Ed., W. H. Freeman Pub., New York, N.Y.; Berg et al. (2002) Biochemistry, 5th Ed., W.H. Freeman Pub., New York, N.Y.; all of which are herein incorporated in their entirety by reference for all purposes.

EXAMPLES

The following examples are put forth so as to provide those of ordinary skill in the art with a complete disclosure and description of how to make and use the present disclosure, and are not intended to limit the scope of what the inventors regard as their disclosure, nor are they intended to represent or imply that the experiments below are all of or the only experiments performed. It will be appreciated by persons skilled in the art that numerous variations and/or modifications may be made to the disclosure as shown in the specific aspects without departing from the spirit or scope of the disclosure as broadly described. The present aspects are, therefore, to be considered in all respects as illustrative and not restrictive.

Example 1: Characterization and Validation of Trifunctional Chemically Reactive Conjugate (TCRC) Function A chemically reactive conjugate (CRC) may include (x) a cycle tag (or a moiety for covalent attachment to a cycle tag such an aminoxy group in this example), (y) a reactive moiety (such as PITC in this example) for binding and cleaving the N-terminal amino acid residue of the peptide, exposing a next amino acid residue as an N-terminal amino acid residue on the cleaved peptide, and (z) an immobilizing moiety (such as propargyl in this example) for immobilization to a solid support. The ability to synthesize the trifunctional molecule, bind its reactive moiety to and N-terminal amino acid of an immobilized peptide, cleave the N-terminal amino acid, hybridize to the cycle tag, ligate the cycle tag, and bind the CRC to the solid support through the immobilizing moiety, was demonstrated using PPO, an example of a CRC compound as illustrated in FIG. 32B.

Thus, an example which has been shown to be functional herein is PPO is an example CRC that has been shown here to be functional. PPO (Propargyl-PITC-Oligo): 1-(1-deoxyribonucleotido-indol-3-yl)-N-(12-(4-(3-(4-isothiocyanatophenyl)-3,9-dihydro-8H-dibenzo[b,f][1,2,3]triazolo[4,5-d]azocin-8-yl)-4-oxobutanoyl)-3,6,9,15,18-pentaoxa-12-azahenicos-20-yn-1-yl)-3,6,9,12,15-pentaoxa-2-azaoctadec-1-en-18-amide.

Chemical names of intermediates that may be formed during synthesis, such as the synthesis shown in FIG. 32A-32B, may be as follows:

PDA: N-(propargyl-PEG2)-DBCO-PEG3-Amine (Broadpharm cat #29932)

PDON: N-(12-(4-(11,12-didehydrodibenzo[b,f]azocin-5(6H)-yl)-4-oxobutanoyl)-3,6,9,15,18-pentaoxa-12-azahenicos-20-yn-1-yl)-2,5,8,11,14-pentaoxa-1-azaheptadecan-17-amide PDON-tBOC: PDON tert-butyloxycarbonyl PDO: 1-(1-deoxyribonucleotido-indol-3-yl)-N-(12-(4-(11,12-didehydrodibenzo[b,f]azocin-5(6H)-yl)-4-oxobutanoyl)-3,6,9,15,18-pentaoxa-12-azahenicos-20-yn-1-yl)-3,6,9,12,15-pentaoxa-2-azaoctadec-1-en-18-amide As a preliminary test, in FIG. 26, a ~1 kd model trifunctional molecule that included vanillin in place of an oligonucleotide was generated with: (1) phenyl isothiocyanate, (2) propargyl, and (3) model vanillin at the oligo position to simplify analytical characterization of the base structure: NNN-(Propargyl-PEG2) (6-oxo-6-(dibenzo[b,f]azacyclooct-4-yn-1-yl)-caproic) (PEG3-1-acetamido-4-iso-thiocyanato-benzene). The molecular structure was confirmed using $L_C$ ESI-MS, and its function was tested. The HPLC analysis shows formation of a product with high yield indicating functional activity of the key reactive isothiocyanate moiety. A trifunctional molecule base was created with a modular design, so that each component and linkage may be exchanged for alternative structures, if needed. Its composition was designed for stability under cyclic Edman conditions while retaining downstream functionality:

PEG is inert to acid and base degradation.

The peptide linkages used to connect the modular components are similar to the internal peptide bonds of a protein that are largely unaffected during the Edman degradation process.

1,2,3-triazole is considered stable to anhydrous acid and basic conditions in ranges useful for the protein sequencing described herein.

The same oligonucleotide protecting groups as used during phosphoramidite synthesis may be used. The exposure to trichloroacetic acid (TCA) during synthesis of long oligos exceeds anticipated chemical stress of protein sequencing steps herein.

Synthesis of PPO, a Trifunctional CRC

Synthesis of PDON-tBOC: N-(Propargyl-PEG2)-DBCO-PEG3-Amine, TFA salt (PDA, Broadpharm cat #29932, 4.56 mg, 0.0063 mmol) was dissolved in 200 μL of 100 mM pH 8.65 phosphate buffer and mixed with 15.8 μL of 400 mM carbonate buffer pH 9.6. t-Boc-Aminooxy-PEG4-NHS ester (Broadpharm cat #24429, 10 mg, 0.021 mmol) was dissolved in 100 μL of DMSO. Solutions were combined and mixed by pipette, 200 μL of dimethylsulfoxide (DMSO) was added and the reaction was incubated at room temperature (RT) for 18 hours. The product was purified using high-performance liquid chromatography (HPLC). An electrospray ionization-mass spectrometry (ESI-MS) peak at m/z=969 (positive mode) $[M+H]^+$ indicated successful synthesis.

Synthesis of PDON: PDON-tBOC was evaporated at reduced pressure at 45 C for 3 hrs then redissolved in dichloromethane (100 ul). Trifluoroacetic acid was added (30 μL), and the mixture was incubated at room temperature (RT) for 1.5 hrs, neutralized by adding 180 μL of 4.1M imidazole in acetonitrile/methanol (2:3 v:v) and purified using $HPL_C$. The successful synthesis of the intermediate, PDON, was confirmed through ESI-MS analysis. Specifically, the observation of a peak at m/z=869 $[M+H]^+$ indicated the successful synthesis of PDON.

Synthesis of PDO: PDON was partially evaporated at reduced pressure at 45 C for 3 hrs. The concentration was quantified using optical density measurement at 310 nm (OD=45, 3.4 mM). Sys3 SOC Oligonucleotide (/5Phos/TGAAGGG/iFormInd/TGACCTAGCAATGGTGAAGT-TAATGCAGGTAGTTAAG (SEQ ID NO: 108), Integrated DNA Technology, 178.8 nmol, where iFormInd denotes a formylindole modification for subsequent tethering)) was resuspended in 100 μL 1×SSPE buffer (Sigma), and 10 μL of the oligo solution was added to 10 μL 11.3 mM 5-aminoindole, and 20 μL 390 mM pH 5.5 acetate buffer. To this mixture, 15 μL PDON solution was added, the solution was mixed by pipette, and the reaction was incubated at RT for 18 hr. Following the reaction, the product was purified using high-performance liquid chromatography (HPLC), and then dried at reduced pressure at a temperature of 45° C. for 4 hrs. Electrospray ionization time-of-flight mass spectrometry (ESI-TOF-MS) analysis was conducted on the product, which produced a peak at m/z=14920 $[M+H]^+$, indicating successful synthesis of the compound PDO. In a control experiment, the mass spectrum of the Sys3 SOC oligonucleotide alone was found to have a peak at m/z=14069 $[M+H]^+$.

Synthesis of PPO: PDO was was resuspended in 28 μL milli-Q water (OD260=20, 43 uM). 4-azidophenylisothiocyanate (N3PITC, 1.30 mg, 0.0074 mmol) was dissolved in 1 mL DMSO to form a 7.4 mM solution). 90 μL of the N3PITC solution was added to the PDO solution and pipette mixed. The reaction was incubated at RT for 3 hr. After this incubation period, the product was purified using high-performance liquid chromatography (HPLC), which resulted in two prominent peaks at 14 and 18 minutes. These product peaks were further analyzed using quadrupole time-of-flight mass spectrometry (QTOF MS). This analysis yielded a peak at m/z=15094 $[M]^+$ for the product corresponding to the 14-minute mark in the HPLC analysis. For the product corresponding to the 18-minute mark, a peak at m/z=15095 $[M+H]^+$ was observed, indicating successful completion of the synthesis step. The two peaks may be assumed to be isomers (e.g. regioisomers of the DBCO-azide adduct) due to the same mass and functional testing performance.

Testing of ITC Function

The functionality of the isothiocyanate (ITC) group was examined through solution phase testing of PPO. HPLC-purified fractions of PPO, which were suspended in a solution of 35 mM TEAA with 5% acetonitrile, were used. To each 100 μL aliquot of these purified fractions, 10 μL of 400 mM carbonate buffer (pH 9.6) was added, then 1 μL of a 10 mM solution of FAM-PEG3-NH2 (Broadpharm cat #BP-20958) in DMSO. The reaction mixture was thoroughly mixed using a pipette and subsequently incubated at RT for a period of 1 hr. Following this incubation period, the reaction samples were analyzed using high-performance liquid chromatography (HPLC). FAM-PEG3-NH2, a fluorescent dye, was separately analyzed under the same buffer conditions as the reaction mixture for use as a control. Notably, the HPLC analysis of the reaction samples indicated that the retention times had shifted towards a shorter time from the original retention time. Furthermore, absorbance at 488 nm, corresponding to the FAM fluorophore, was observed in the HPLC chromatogram. These observations were indicative of a successful conjugation of FAM-PEG3-NH2 to PPO, thereby validating the functionality of the ITC group. The ITC group is an example of a reactive moiety for binding an N-terminal amino acid residue or a peptide.

Binding PPO Through the ITC Group to a Surface and to an Oligo Tag

Testing was conducted on the HPLC-purified fractions of PPO, suspended in a solution of 35 mM TEAA and 5% acetonitrile. PPO was combined with Phosphate buffer pH 7.2, 50 mM tris(3-hydroxypropyltriazolylmethyl)amine (THPTA), 10 mM CuSO4, 100 mM sodium ascorbate, 1% 10 μm azide-functional silica beads (Nanocs cat #Si10u-AZ-1). The mixture was mixed by pipette and incubated at RT for an hour. Subsequently, 2 μL of a 10 mM solution of FAM-PEG3-NH2 (Broadpharm cat #20958) in DMSO and 20 μL of a 400 mM carbonate buffer solution (pH 9.6) were added, and the reaction was continued for one hour. The beads were washed 5× with D.I. H2O using a centrifugation method. The beads were analyzed using a fluorescence plate reader (484 nm excitation, 530 nm emission).

Control reactions were performed in parallel, one without the addition of the copper catalyst to the PPO/azide beads, and the other without PPO. The results, shown in FIG. 33, demonstrated fluorescence intensity above background in the beads that had undergone the reaction with PPO in the presence of copper compared to the controls. This indicated the successful functionality of both the solid support binding group and the ITC group, demonstrating the ability to bind and retain the N-terminal model FAM-PEG3-NH2 and conjugate to solid support.

A complementary oligonucleotide tagged with a fluorophore (5'TET/TAACTTCACCATTGC (SEQ ID NO: 124), where TET is tetrachlorofluorescein) was hybridized to the PPO-functionalized beads. This procedure was conducted at room temperature for 5 minutes, using a 1 μM concentration in a 2×PBST buffer. Following the hybridization, the beads underwent a washing process involving 5 rounds of rinse with 1 mL of 2×PBST buffer. The washed beads were subsequently analyzed on a fluorescent plate reader (515 nm excitation and 545 nm emission).

The results, shown in FIG. 34, demonstrated that the beads with the immobilized PPO exhibited a higher fluorescence intensity than the background control beads. This finding confirms the functionality of the cycle tag oligonucleotide on the solid-support-bound CRC, thus validating the trifunctional nature of the CRC.

In another embodiment of a solid support, a borosilicate glass slide underwent an organic solvent and acid bath cleaning procedure. The slide was rinsed copiously with water and dried at 100 degrees Celsius for 10 minutes. The slide was then silanized with a 2.5% by weight solution of 3-aminopropyltriethoxysilane in ethanol at room temperature for one hour. Subsequent rinse with ethanol and drying at 100 degrees Celsius for an hour completed the slide surface preparation. Selected positions of the slide were treated with 10 μL fractions of PPO mixed with 1 μL of 400 mM pH 9.6 carbonate buffer and incubated at room temperature for an hour. The positions were subjected to several water rinses, and each position received 20 μL of a mixture comprising 2 μL 10 mM FAM-PEG4-N3 (Broadpharm cat #BP-23405) in DMSO, 10 μL 10 mM CuSO4 in water, 10 μL 50 mM THPTA in water, 20 μL 200 mM phosphate buffer pH 7.2, and 20 μL 100 mM sodium ascorbate in water. Control wells were prepared using the same solution but excluding CuSO4. The reaction was allowed to proceed for one hour, after which the positions were rinsed copiously with water. Fluorescence analysis was performed using a plate reader (484 nm excitation, 530 nm emission). The results, shown in FIG. 35 indicated that wells incorporating copper produced a more intense fluorescence signal compared to the background control wells. This confirms the capability to use the CRC on multiple embodiments of solid support.

Cleavage of N-Terminal Amino Acid and Exposure of Next Amino Acid Residue

The functional ability of the reactive moiety of the CRC to bind and cleave the N-terminal amino acid was tested, showing cleaving and thereby separating the N-terminal amino acid residue from the peptide, thereby exposing the next amino acid residue as a N-terminal amino acid residue on the cleaved peptide.

PPO Sys1 SOC: PPO was synthesized using Sys1 SOC oligonucleotide (/5Phos/ATGAGTG/iFormInd/AGGGAAATAGCTTCTGGTCGAACTAGTTGTTCGTCAA) (SEQ ID NO: 75) in a similar manner to that described for the Sys3 SOC oligonucleotide.

Azide functional beads: 2 mL of amine-functionalized silica beads (CD Bioparticles cat DNG-F046, 20 um dia, 5 wt % solids, 4 umol amine/g) were subjected to centrifugation at 21,000 ref for 1 min, then resuspended in a 0.5 mL solution of pH 9.6 400 mM carbonate buffer. A separate solution was prepared by dissolving 28 mg of azidoacetic acid NHS ester (141 mmol, Broadpharm BP-22467) in 0.2 mL DMSO. The two solutions were then combined, and an additional 0.5 mL DMSO was introduced to solubilize any precipitate that had formed. The resulting mixture was incubated in an Eppendorf tube on a rotator for 2.5 hr at ambient temperature. The beads were subsequently washed by adding 1 mL volumes of the following solutions in sequence: water, acetonitrile, water, DMSO, water. After each addition, the solution was resuspended by shaking, then centrifuged (21k rcf 1 min), and the supernatant was removed. The beads were finally resuspended in 1.25 mL of water, creating an 8 wt % slurry.

Peptide Functional Beads: The peptide (0.5 mg, 860 g/mol, sequence from N-terminus to C-terminus: {pTyr}{Ser}{Ser}{pTyr}{Ser}-propargyl) was dissolved in 0.5 mL water to create a 1.16 mM solution. Three peptide immobilization reactions were initiated by combining the reactants in Table 3 (volumes in uL). Reaction A was conducted at 50 C for 1 hr on a rotator, while Reactions B and C were left to incubate at ambient temperature on a 600 rpm shaker for 1 hr.

The beads were subsequently washed by adding 1 mL volumes of various solutions in the following order: 100 mM pH 9.6 carbonate buffer, DMSO, water, 100 mM pH 9.6 carbonate buffer, water, DMSO. After each addition, the solution was resuspended through shaking, centrifuged (21, 000 rcf 1 min), and the supernatant was removed. The DMSO solution was incubated with the beads at 57 C for 4 min. This was followed by washing with acetonitrile, water, 100 mM pH 9.6 carbonate buffer, and water. The carbonate buffer was incubated with the beads for 10 min at ambient temperature.

The beads were analyzed using a fluorescent plate reader (545 nm excitation, 586 nm emission).

TABLE 3

| Reaction | A (uL) | B (uL) | C (uL) |
|---|---|---|---|
| 20 um silica beads, 8 wt % functionalized with azide (Abrus Bio) | 150 | 150 | |
| 10 um silica azide functional beads (Nanocs Si10u-AZ01), 1 wt % | | | 300 |
| Peptide solution (1.16 mM) | 30 | 30 | 30 |
| N,N,N',N",N"-pentamethyldiethylenetriamine | 30 | | |
| 400 mM carbonate buffer pH 9.6 | 30 | | |
| Phosphate buffer 200 mM pH 7.2 | | 30 | 30 |
| Sodium ascorbate (80 mg/mL) | 60 | | |
| Sodium ascorbate (20 mg/mL) | | 60 | 60 |
| tris(3-hydroxypropyltriazolylmethyl) amine (THPTA) (50 mM in water) | | 30 | 30 |
| CuSO4 (10 mM in water) | 60 | 30 | 30 |

Immobilization of PPO-System 1 on beads: To each bead aliquot, 100 μL of PPO-Sys1 SOC (OD260=2, ~4 uM) and 20 μL of 400 mM carbonate buffer pH 9.6 were added. The resulting mixture was incubated at ambient temperature for 30 min on a rotator. Afterward, the beads were centrifuged and the supernatant was removed. A second aliquot of 100 uL PPO-Sys1 SOC, 40 μL of 133 mM carbonate buffer pH 9.2, and 120 μL of 1M NaCl were then added. The reaction was again incubated for 30 min on a rotator at ambient temperature.

The beads were washed via centrifugation with 1 mL of water and 1 mL of 2× phosphate-buffered saline with 0.2% Tween 20 (2×PBST). A fluorescent complementary oligo to Sys1 SOC (/5Alex546N/TTCGACCAGAAGCTA) was dissolved in 2×PBST buffer to a concentration of 1 uM, and 0.3 mL of this solution was incubated with the beads for 5 min at ambient temperature.

The beads were subsequently washed thoroughly with 2×PBST. Both the washed beads and the supernatant were analyzed on a fluorescent plate reader (545 nm excitation, 586 nm emission). The beads were dehybridized using NaOH. The beads were washed with water and read on the plate reader, along with the supernatant from the dehybridization. The Cu-catalyzed Huisgen reaction was performed to immobilize PPO on the bead surface for reactions B and C. The incubation was performed for 20 min on a rotator at 37 C.

Edman Degradation: The beads were exchanged into anhydrous acetonitrile (Sigma Aldrich 99.8%, catalog number 271004), and brought to 50% (v/v) trifluoroacetic acid (TFA). The resulting mixture was incubated at 46 C for 25 min. The reactions were subsequently neutralized with 4.1 M imidazole in a 2:3 (v:v) acetonitrile:methanol solution, and exchanged into 133 mM pH 9.2 carbonate buffer.

PPO-Sys3 SOC Immobilization: The beads were added to a solution comprising 100 μL of PPO-system 3 (18 min retention time peak, ~0.5 OD, ~1 uM), 80 μL of 133 mM pH 9.2 carbonate buffer, and 120 μL of 1M NaCl. The reactions were incubated on a rotator at 37 C for 30 min. Subsequently, the beads were exchanged into 2×PBST, and analyzed on the fluorescence plate reader.

The beads were hybridized with a solution of a fluorescent complementary oligo to Sys3 SOC (STET/TAACTTCACCATTGC) (SEQ ID NO: 124) at 2 uM in 2×PBST for 5 min at ambient temperature. The beads were subsequently washed five times with 2×PBST. Both the supernatant and beads were analyzed on a fluorescent plate reader (500 nm excitation, 550 nm emission). Supernatant was removed NaOH was added to dehybridize the beads. The dehybridization solution was analyzed, and the beads were washed copiously with water, resuspended in 2×PBST and analyzed on the fluorescent plate reader.

As demonstrated in FIG. 20, the beads exhibited an increase in fluorescence during the hybridization reactions with the fluorescent complementary oligo to Sys1 SOC. Significant fluorescence was detected in the dehybridization solutions, and the beads subsequently lost most of their fluorescence following the dehybridization treatment. After undergoing Edman degradation, and with the PPO Sys3-SOC immobilization, the hybridization with the fluorescent Sys3 SOC complementary oligo resulted in a fluorescence level akin to that observed during the Sys1 SOC hybridization. Upon dehybridization, the dehybridization solutions again displayed significant fluorescence, and the beads, in turn, lost most of their fluorescence.

These results indicate a chemically-reactive conjugate can be synthesized and contacting an immobilized peptide with a chemically-reactive conjugate, thereby coupling the chemically-reactive conjugate to the N-terminal amino acid of the peptide to form a conjugate complex is viable. These results further indicate that the chemically-reactive conjugate can immobilize the conjugate complex to the solid support via the immobilizing moiety to provide an immobilized amino acid complex. These results further indicate that a chemically-reactive conjugate can cleave and thereby separate the N-terminal amino acid residue from the peptide, thereby exposing the next amino acid residue as a N-terminal amino acid residue on the cleaved peptide.

Example 2: Assembly of a Recode Block

The current example describes an experiment that achieved successful ligation of model recode block oligos using T4 DNA Ligase. In this example, ligation under standard conditions is demonstrated to the 5' and 3' ends of a model cycle tag having a formylindole modification of nucleobase internal to 5' and 3' ends of the oligonucleotide. Formylindole nucleobase modification of a cycle tag oligonucleotide may facilitate synthesis of a CRC having an oligonucleotide moiety. For example, aminoxy-PEG1-azide (ONH2-PEG-N3, broadpharm cat #23596) may be conjugated to a cycle tag oligonucleotide, which has a formylindole modification. The aminoxy group of a aminoxy-PEG1-azide will react with the aldehyde group on the formylindole nucleobase to form an oxime bond. The azide group can be used to generate further linkages, if desired.

Accordingly, 100 mM Aminoxy-PEG1-azide was mixed with a 5 mM solution of 5-aminoindole catalyst at pH 6. An oligo solution of Sys1-SOC oligonucleotide (SEQ ID NO: 75), was prepared at 100 μM. Thes reaction components were mixed and incubated at 40° C. for 24 hrs. An aliquot of the product was reacted with alkyne-FAM under standard Huisgen reaction conditions to confirm the reaction product was formed. HPLC confirmed the product by a shift in the peak of the oligos and association of 488 nm absorption with the oligonucleotide elution peak. In addition to the above samples, a series of controls were prepared, including reactions where the CuSO4 was omitted from the cycloaddition reaction. The product was purified using HPLC, recovered in 35 mm TEAA:acetonitrile, dried and resuspended in SSPE.

Concentration of the purified ssDNA was quantified using the Qubit assay (Thermofisher) to determine appropriate DNA concentration into the ligation reaction. Ligation oligos for the 3' end (SEQ ID NO: 85) and 5' end (SEQ ID NO: 84), splint oligos (SEQ ID NO: 78 and SEQ ID NO: 79), Sys #001 SOC oligo (SEQ ID NO: 75) (with and without out aminooxy-PEG-azide conjugated), T4 DNA Ligase (M0202L, NEB), T4 DNA Ligase buffer 10× (B0202S, NEB), MilliQ water, and a comparator oligo Sys #001 COM-105 (SEQ ID NO: 88) were mixed to create various ligation conditions according to the method provided by New England Biolabs (NEB). The process was initiated in a microcentrifuge tube, which was maintained 4 C. Oligonucleotides were utilized at ~0.2 μM. Following the assembly of the mixture, all the ingredients, excluding the ligase, were vortexed to ensure the homogeneity of the mixture, and subsequently centrifuged. T4 DNA Ligase was added and the components were mixed with gentle pipette mixing and left at RT for 30 mins, followed by a 65 C 10 min. heat-inactivation of the ligation mixture. Ligation products were analyzed (4% agarose) E-Gel Power Snap Electrophoresis System User Guide, "E-Gel EX 4%". A DNA ladder (cat #10597012 from Invitrogen) was prepared, following the indicated procedures, and denatured in 0.1M NaOH before loading on the gel. Gel electrophoresis (FIG. 27) showed the successful creation of the desired product and successful ligation in the presence of modified bases internal to the 5' and 3' ends of the SOC oligonucleotide. In lane 2 are the products from the ligation of the 45-mer oligo with tether arm with a 30-mer ligation oligo on both the 3' (SEQ ID NO: 85) and 5' (SEQ ID NO: 84) ends. In addition, PCR was conducted on ligation output (FIG. 37) showing amplification of ligated oligos both with and without internally modified bases. These results support method described herein to generate recode blocks and memory oligos, and indicates that within each formed affinity complex, a cycle tag or a reverse complement thereof to a recode tag can be joined to form a recode block, thereby creating a plurality of recode blocks, each recode block corresponding with a formed affinity complex as well as two or members of the plurality of recode blocks can be joined to form a memory oligonucleotide.

Example 3: Validate Affinity Binding Capability and Binder Fidelity

In some approaches, binder fidelity plays a role in the sequencing accuracy. An in-silico simulation was conducted to assess the impact of binder fidelity on the accuracy of protein identification. A probability matrix was computed for a set of analyte-ligand complexes using empirically determined binding constants of N-terminal amino acid binding proteins (NAABs from Rodriques et al, see FIG. 36A-36B).

These dissociation constants (Kd) were converted into association constants to represent the affinity between each amino acid pair. Then the partition function was computed for each analyte using principles of thermodynamics. This process accounted for all possible states of each analyte, whether it was unbound or bound to any ligand.

By applying the law of mass action, the steady-state concentrations of each analyte-ligand complex were computed. This computation ensured the total conservation of each analyte's concentration across its potential states, thus allowing us to determine the occupancy rate of bound pairs in a competitive binding system. The calculated bound occupancy rate then served as input for further simulations.

A cohort of proteins randomly selected from the UniProt database was mutated according to the steady-state probabilities in the matrix to simulate a 'measured cohort' using the NAABs. The 'measured cohort' was mapped using an in-house custom alignment algorithm to evaluate the impact of binder infidelity. A custom alignment algorithm was also developed to assess the alignability of the mutated proteins with the reference proteins. This algorithm utilized the Levenshtein distance between pairs of mutated peptide strings and reference proteins. The distance between letters as a function of the inverse of the probability matrix elements was also accounted for. This approach can ensure that likely mutations are perceived as closer to the reference string than unlikely mutations.

The study resulted in compelling evidence of the approach's effectiveness, showing nearly perfect outcomes even when sequencing the first 12 amino acids from the N-terminus (as shown in FIG. 36A-36B). These findings substantiate the potential of the methodologies described herein for accurate alignment to the proteome despite binder variability using existing binders. These simulations demonstrate the potential to accurately identify and quantify proteins against the reference proteome even with the relative affinities of N-terminal acid binders currently developed. N-terminal amino acid binders represent a more difficult case than isolated amino acids as the local environment varies due to different nearest neighbor amino acids, showing clear ability to develop binders for the method described herein.

Experimental validations were carried out to measure binding kinetics using a high-throughput digital benchtop surface plasmon resonance (SPR) system (Nicoya Alto). The measurement includes loading samples and reagents into a 16-Channel Carboxyl disposable digital fluidics cartridge (part #KC-CBX-PEG-16) that contains optical sensors, thermal zones, a bottom plate consisting of electrodes, and a top plate with wells to load reagents. The reagents include cartridge fluid, capture kits (consisting of reagents such as low and high refractive index normalization fluids (4% and 32% glycerol), EDC, NHS, 10 mM HCl, and 1M Ethanolamine, 10 mM Sodium Acetate, and 10 mM MES), and Streptavidin Reagent Kit (part #ALTO—R-STV-KIT). The experiment included adjusting ligand concentration, salt concentrations, and analyte concentrations to provide optimal density for analyte binding on the 48 analyte wells of the 16-Channel Carboxyl disposable cartridge.

For the samples, an off-the-shelf anti-phosphotyrosine antibody (Sigma, 05-321) was used, and its binding to a custom synthesized and immobilized PTH-phosphotyrosine conjugate was observed. The experiment demonstrated strong binding (KD=9.6 nM), with no detectable binding observed for a series of non-cognate conjugates. This indicated suitable discrimination between phosphotyrosine and other amino acids with commercially available antibodies, including post-translationally modified amino acids, using a commercially available anti-phosphotyrosine antibody. The empirical fidelity observed here even surpasses that assumed in the in-silico simulation which was itself sufficient for high fidelity identification of peptides, providing strong evidence of the effectiveness of the methods described herein.

Finally, resilience to variability in Edman degradation efficiency was assessed. Simulations showed that even with degradation efficiencies as low as 70% average for all cleavage cycles, there were no significant issues in alignment to reference proteins. This is because the ordered cleavage still results in unique, alignable "fingerprints." This resilience to variation in Edman degradation efficiency, which can significantly depend on the identity of the N-terminal amino acid, further underscores the robustness and versatility of the methods described herein.

This shows the ability to contact the immobilized amino acid complexes with a binding moiety for preferentially binding to one or to a subset of the immobilized amino acid complexes using existing binders in the art.

Example 4: Recoding

Biologically or synthetically derived samples may be manipulated prior to the recoding process. These manipulations may include lysis, purification, enrichment, protein fragmentation, etc. Serine proteases (or serine endopeptidases) include a broad class of enzymes that cleave peptide bonds in proteins. The trypsin-like proteases cleave peptide bonds following a positively charged amino acid (lysine or arginine), while chymotrypsin-like serine proteases have specificity for hydrophobic residues, such as tyrosine, phenylalanine and tryptophan. Digestions using these reagents include time titration, and controlled protease and protein concentrations to generate peptides in the range of 20 to 200 amino acids. ThermoFisher, Sigma, and others offer a comprehensive and broad range of products to accommodate a variety of sample preparation strategies. Pre-formulated reagents and robust methods for the preparation of high-quality samples that are ready for MS analysis in less than 3 hours are available. See, e.g., Sample Preparation for Mass Spectrometry. ThermoFisher Scientific, 2022. These procedures include methods for protein extractions from lysates, abundant protein depletion, protein digestion, peptide clean-up, and are amenable to recode sample preparation. Timing of procedural steps may be modified to achieve peptide lengths within a desired range. Peptide length distributions may be measured using polyacrylamide gel electrophoresis.

Solid supports for immobilization of peptides, conjugates, and nucleic acid primers may be formed by spin coating 500 μL of hydrogel polymer using a Sigma Chemat precision spin-coater at 500 rpm for 1 minute onto a corning glass slide. Hydrogel polymer can be obtained by co-polymerization of acrylamide with modified acrylate-based monomers having sidechains that include hydrazine, having sidechains that include amine, and having sidechains that include azide. Briefly, a RAFT polymerization of acrylamide and acrylate may follow procedures as described by Palmiero et.al., The RAFT copolymerization of acrylic acid and acrylamide in Polymer (2016), 98, 156-164. The coated substrate is then assembled into a flowcell by sandwiching a SA-S-4L Grace Bio-Labs double-sided adhesive gasket between the coated Corning slide and a cover slide to create a ~500 um channel that facilitates fluid administration.

Peptides are anchored to the hydrogel via an end-terminal or internal carboxyl group using carbodiimide-mediated conjugation. This is the most frequently used technique, since EDC (N-(3-Dimethylaminopropyl)-N'-ethylcarbodiimide) is readily obtained commercially, and protocols are well known (Hermanson, 1996, Bioconjugate Techniques, Academic Press Inc.). Primers are anchored to the hydrogel via an aldehyde modification at the 5' end of the primer oligonucleotides, e.g. P5 and P7 possible containing sample indexes and/or UMIs. The reaction is completed in phosphate-buffered saline (137 mM Na+, 2.7 mM K+, 12 mM phosphate, pH 7.4 at 25° C. for 2 hours.

In one approach, chemically-reactive conjugates may be constructed in multiple steps (e.g., as shown in FIG. 20). Briefly, an aliphatic hydrazine is derivatized to a carbon of the phenyl ring of phenylisothiocyanate. A 3mer reagent with trifunctional orthogonally reactive groups is synthesized using well known phosphoramidite chemical protocols to connect a 1-Ethynyl-dSpacer CE Phosphoramidite (Glen Research, Cat #10-1910) with a 5-Formylindole-CE Phosphoramidite (Glen Research, Cat #10-1934) and S-Bz-Thiol-Modifier C6-dT (Glen Research, Cat #10-1538). Conjugation of the phenylisothiocyanate-hydrazine derivative to the 3mer is accomplished with the derivative in excess under neutral pH conditions at mM concentration at room temperature for 6 hrs. A cycle tag oligo having an internal modified T nucleobase, as described in Table 4, is reacted with a slight molar excess of SPDP-PEG-succinimidyl (NHS) valerate (Broad Pharma Cat #BP-25336) at 1 mM in alkaline conditions (pH 7.2 to 9 borate buffer) at room temperature for 60 minutes. The NHS is preferentially reactive to the primary amine of the modified-dT over amines attached directly to the nucleobases. The molecular weight of BP-25336 is 5000 daltons, thus length is approximately 50 nm. Unreacted NHS-PEG-SPDP crosslinker is removed by hybridization of the complex to complementary immobilized DNA, followed by washing. The SPDP-PEG-cycleTag is elute under basic conditions. Finally, the SPDP group is reacted to phenylisothiocyanate-hydrazine-3mer conjugate in 100 mM sodium phosphate pH 7.2 to 8.0, 1 mM EDTA, at room temperature for 8 to 16 hrs. Fully functional chemically-reactive conjugate complex is separated from impurities by hybridization to DNA complementary to cycle tag sequences immobilized on beads, washed, and eluted for use in the recoding process. It is recognized that multiple routes to produce the conjugate are possible based on modular conjugation chemistries.

In one approach, binding agents are constructed in multiple steps. Briefly, a 5' alkyne-labeled DNA recode tag oligonucleotide is first coupled to azido-PEG8-hydrazide HCl Salt (BroadPharma, Cat #BP-24118) under conditions and using protocols that are well known to form a oligo-azido-PEG8-hydrazide unit (10 mM ascorbic acid, 2 mM PMDETA, and 0.5 mM Cu2+ catalyst, Presolski et al. (2011) Copper-Catalyzed Azide-Alkyne Click Chemistry for Bioconjugation. Current Protocols in Chemical Biology. 3(4), 153-162; Hong et al., (2009) Analysis and Optimization of Copper Catalyzed Azide-Alkyne Cycloaddition for Bioconjugation. Angew. Chem. Int. Ed., 48(52), 9879-9883). This unit is then joined to a binding moiety scFV by expressing the recombinant scFV with an N-terminal serine, treating the scFv under mildly oxidative conditions using periodate to convert the N-terminal serine to aldehyde (Chelius et.al., 2002, Bioconjugate Chem. 2003, 14, 1, 205-211), exchanging buffer into phosphate-buffered saline (137 mM Na+, 2.7 mM K+, 12 mM phosphate, pH 7.4), and then reacting the oligo-azido-PEG8-hydrazide unit with the scFv at 25° C. for 2 hours. It is recognized that multiple routes to produce the binding agents are also possible based on modular conjugation chemistries.

Contacting the N-terminal amino acid of the immobilized peptide with a chemically-reactive conjugate is accomplished in either aqueous or organic solution. Coupling of phenylisothiocyanate (PITC) to the a-amino group of a peptide or protein occurs under many experimental conditions. In 0.4M dimethylallylamine (DMAA) in propanol-water (60:40 v/v) adjusted to pH 9.5 with TFA results in complete coupling in 30 min at 45° C. Aqueous conditions at pH 8 at 45 C have also been reported (Matsudaira, (1993) in A Practical Guide to Protein and Peptide Purification for Microsequencing (Second Edition), pp 104-123).

Unreacted PITC-conjugate is washed from the surface extensively using 5 flowcell volumes of PBS. The solution is exchanged for click reaction buffer (neutral pH PBS, 2 mM PMDETA, 1 mM Cu2+, 10 mM ascorbate) and the alkyne groups of the conjugates react with the surface-bound azide groups (30 min at room temperature).

Cleaving the N-terminal amino acid via cyclization in anhydrous trifluoroacetic acid (TFA) to form the 2-anilino-5-thiazolinone can damage DNA that is not protected. The recode workflow may be inherently compatible with multiple variations of acidic conditions for this step, because precautions to protect the cycle tag oligo are readily incorporated and include: retaining the protecting groups used during nucleic acid synthesis through the first 4 steps shown in FIG. 14. Protecting groups include N(6)-benzoyl A, N(4)-benzoyl C, and N(2)-isobutyryl G, or protecting groups that are removable under more mild conditions, e.g., phenoxyacetyl (Pac) protected dA and 4-isopropyl-phenoxy-acetyl (iPr-Pac) protected dG, along with acetyl protected dC. These are commercially available and meet the desired criteria for ultra-mild deprotection described below.

Repetition of operations 2-4 of the process 300 in FIG. 3 results in a lawn of immobilized PTC-AA-cycleTag conjugates. Deprotection of nucleic acid protecting groups is accomplished with ammonium hydroxide, or 0.4 M sodium hydroxide in methanol/water (4:1) in 2 hours at room temperature, or 4 hours with 0.05M potassium carbonate in methanol.

Amino acid information is associated with cycle information by contacting the immobilized PTC-AA-cycle tag conjugates with binding agents and transferring the recode tag information of the binding agent to the cognate cycle tag of the immobilized conjugate to create an immobilized recode block. Exemplary scFv-recode tag binding conditions include: PBS at neutral pH, EDTA 1 mM, slow annealing from 37 C to 4 C with a ramp of 1 C per minute. Washing excess binding agent is accomplished by exchanging 5 flowcell volumes at 4 C with PBS pH 11, 10 mM $MgCl_2$, 50 g/ml BSA, 0.1% TX-100. The wash step is followed by ligation. Exemplary enzymatic T4 DNA ligation reaction conditions are: PBS pH 7.8, 10 mM $MgCl_2$, 0.1 mM DTT, 1 mM ATP, 50 μg/ml BSA, 0.1% TX-100, 2.0 U/μL T4 DNA ligase (New England Biolabs), 0.1 μM 5' phosphorylated ligation oligo (each) at room temperature for 1 hr. Conditions using HiFi Taq DNA Ligase (New England Biolabs, cat #M0647S) are similar with addition of 1 mM NAD+), and may provide additional fidelity to reduce unintended ligation. Repetition of the binding, wash and ligation steps 10 times drives toward completion of recode block assembly.

Memory oligo assembly is accomplished by adding 5'phosphorylated AA tag oligos having complementary sequence to the AA tag sequence of the recode blocks. Ligation conditions are: PBS pH 7.8, 10 mM $MgCl_2$, 0.1 mM DTT, 1 mM ATP, 50 μg/ml BSA, 0.1% TX-100, 2.0 U/μL T4 DNA ligase (New England Biolabs), 0.1 μM 5' phosphorylated AA tag complements (each) at room temperature for 1 hr.

Linking oligos can remediate incomplete memory oligo assembly. Also, in this step, attachment of nucleic acids having universal primer, sample indexes, and/or UMIs can be added by ligation to the ends of the memory oligo. The primers, indexes, UMIs, etc. may be bound to the solid support or free in solution. Ligation conditions are: PBS pH 7.8, 10 mM $MgCl_2$, 0.1 mM DTT, 1 mM ATP, 50 g/ml BSA, 0.1% TX-100, 2.0 U/μL T4 DNA ligase (New England Biolabs), 0.1 μM 5' phosphorylated linking oligos (each) at room temperature for 1 hr.

Tethers of the recode blocks may be cleaved using 4 mM dithiothreitol (DTT) in neutral pH PBS, 1 mM EDTA, to provide greater freedom for any non-ligated recode blocks or memory oligo fragments to come into proximity. Following cleavage of the SPDP linker and washing using 5 flowcell volumes, ligation using linking oligos can be repeated to ensure memory oligo assembly results in an amplicon that can be analyzed using NGS.

Example 5: Alternative Events During a Recoding Process

The previous Example provides desired outcomes of chronological performance of certain embodiments of the recoding process described herein. The current Example describes alternative events due to incomplete reactions or other causes, process efficiencies, and how alternative events may be addressed.

As a baseline and framework, each operation of the recoding process can be assigned an efficiency value. These target efficiencies are noted below and may be used within a system model to predict overall efficiency. Assuming:

(Operation 2) PITC binding to N-terminal AA (target efficiency: 0.99)

(Operation 3) Immobilization of PTC conjugate to hydrogel (target efficiency: 0.95)

(Operation 4*a*) Edman cleavage (target efficiency: 0.98)

(Operation 4*b*) Nucleotide deprotection (target efficiency: 0.99)

(Operations 5*a,b*) 'Binder' recognition/retention onto a PITC-conjugate—repeated 10× a) Only 20% converted to correct block each attempt b) Assuming 10 iterative cycles of step 5: $1-(1-20\%)^{10}$=(target efficiency: 0.89)

(Operations 5*c,d*) Information transfer to create a 'block', ligation efficiency (0.95)

(Operation 6) Memory oligo assembly (target efficiency: 0.9)

(Operation 7) Linking oligo ligation (target efficiency: 1)

The product of these stepwise efficiencies is referred to as the overall efficiency, and these target values predict that that on average a memory oligo will represent ~80% of the attempted information for ~90% of the immobilized analytes (e.g., peptides).

A recode sequence (memory oligo) may imperfectly represent the true physical sequence of a sample analyte due to alternative events within the recoding process. Thus, as a baseline, it is important to establish that incomplete or probabilistic information associated with an imperfect recode sequence is valuable for the identification of proteins and their concentrations in a sample. As proof, a random sampling of contiguous and non-contiguous 20 amino acid "reads" from an *E. coli* 6-phosphogluconate dehydrogenase sequence in Uniprot allowed unambiguous mapping of 100% of these reads to this specific dehydrogenase, i.e., there were no matches with the sequences of any other proteins in the *E. coli* proteome. In this example, the 20 amino acid identities and their relative sequence were drawn from a set of 30 amino acids from which identity and sequence information was attempted to be drawn, i.e., 30 recode cycles where only 20 successfully provided information. This demonstrates the value of analysis given only partial identification information for a component or components of an associated macromolecule, such as would be represented by imperfectly assembled conjugates, recode blocks, memory oligos, etc. Similarly, probabilistic identification of amino acids, i.e., as belonging to a subset of possible amino acids, and their relative sequence can be used to create an estimate for the identity of a protein. In a similar way, comparison to reference sequence can be used to impute accurate mapping of imperfect recode sequence in the case of insertion, deletion, and mismatch errors. Deep learning algorithms, Bayesian models, Markov models, and artificial intelligence (AI) can aid in accounting for incomplete information, random errors, and systematic errors, to identify and map perfect and imperfect recode sequences to reference. Information quality based on binding moiety discrimination and other factors can be learned and incorporated into these analyses. For more information regarding AI, algorithms, and models as applied to the field of proteomics, see Crook, Chung, and Deane, Challenges and Opportunities for Bayesian Statistics in Proteomics, J. Proteome Res. 2022, 21(4), 849-864, which is herein incorporated in its entirety by reference for all purposes.

Stepwise alternative events are presented below with estimates of frequency, consequences to recode sequence error rate, consequences for recode sequence efficiency, and methods to mitigate or minimize the effects of such events.

Conjugate immobilization. A desired outcome of operation 2 of the recoding process (e.g., process 300) may be that 100% of N-terminal amino acids bind with a PITC conjugate. One alternative event at operation 2 includes incomplete binding of the N-terminal amino acid. Frequency is estimated to be 1% based on literature. A potential consequence to recode sequence error rate is a phasing phenomenon. Phasing may occur wherein the incorrect cycle will be assigned (i+k cycle instead of the ith cycle) where i is the current cycle and k is the number of "skipped" cycles during which a conjugate is not bound to an N-terminal amino acid. This results in an apparent sequence deletion with respect to a reference with a frequency of 1%, without the remediation steps outlined below. A potential consequence for recode sequence efficiency is that n cycles of recoding result in only n−1 piece of sequence information. Mitigation includes: optimizing binding conditions, increasing conjugate concentrations, repeating the step several times to complete the binding, or flooding the surface with free PITC to bind and remove N-terminal amino acid and eliminate phasing.

Another alternative event of operation 2 includes the incomplete wash of conjugate that did not bind a N-terminal amino acid. The frequency is estimated to be 1%. A potential consequence on recode sequence error rate is negligible based on effective mitigation strategy below. These conjugates may bind in operation 3 of process 300 to the support surface, but not necessarily in close enough proximity to react with a N-terminal amino acid in the next recode workflow cycle. A potential consequence for recode sequence efficiency is that n cycles of recoding result in only n−1 piece of sequence information. Mitigation includes: optimizing wash buffers and protocol, repeating the step several times to complete the binding, and in an intervening operation (operation 4*b*) quench immobilized conjugates that are bound to the surface using an amino acid mimic that is not recognized by binding agent in subsequent steps, or is recognized as an error event.

Yet another alternative event at operation 2 of the recoding process is that the N-terminal amino acid could be cleaved prior to immobilization of the conjugate to the solid support. Based on the frequency predicted from literature, this event may be neglected.

Conjugate immobilization. A desired outcome of operation 3 may be that 100% of conjugate complexes become immobilized to the surface. One of the alternative events at operation 3 is thus incomplete immobilization. The frequency is estimated to be low based on the reactivity of Cu-catalyzed click chemistry. The system model places this as 5%. A potential consequence on recode sequence error rate is skipped information, and the consequence for recode sequence efficiency may be that n cycles of recoding result in only n−1 piece of sequence information. Mitigation includes: optimizing reaction buffers and protocol, repeating the step several times to complete the conjugate immobilization.

Conjugate immobilization. A desired outcome of operation 4 of the recoding process is that 100% of N-terminal amino acids are cleaved to reveal new N-terminal AA and a perfect immobilized conjugate complex. Alternative events include: 1) incomplete cleavage of the N-terminal amino acid; 2) termination of recoding, if the cleavage does not occur during operation 4 of a subsequent workflow cycle; and 3) damage to the nucleobases that reduce their effectiveness to carry information in subsequent steps.

Incomplete cleavage is estimated to be about 3%. Phasing phenomenon may occur wherein the current cycle amino acid is associated with the correct cycle, but once cleavage of the N-terminal amino acid does occur (possibly during step 4 of a subsequent workflow cycle) the i+1+kth cycle information is associated with the i+kth amino acid, where i is the current cycle and k is the number of "skipped" cycles during which the N-terminal amino acid is not cleaved. This results in an apparent deletions of sequences with respect to a reference with frequency of about 3%, without performing any of the mitigation steps outlined below. A potential consequence on recode sequence error rate is about 3%, and a consequence on recode sequence efficiency may be that n cycles of recoding result in only n−1 piece of sequence information. Mitigation includes: optimizing conditions, increasing the repeating the reaction.

Termination of recoding has no effect on error rate but reduces recode sequence efficiency by about 3%.

Damage to the nucleobases is estimated to be low since the only oligos present are the protected cycle tag oligos. The effect on error rate and sequence conversion efficiency are complex and dependent on the code space and other NGS related factors. Mitigation includes increasing cycle tag length to compensate for the fraction of bases that are degraded.

Reagent purity. Reagent purity may have an effect on error rates and process efficiency. Preferred methodologies to produce chemically-reactive conjugate include joining multiple components as shown in FIG. 20. Stepwise yield for phosphoramidite synthesis is approximately 99.5%. Purity of the 3mer trifunctional linker can be assured and improved via preparative HPLC purification to remove any truncated products of the phosphoramidite synthesis. The attachment of functional elements to the trifunctional linker may not be complete. Alternative events caused by low purity reagents include conjugates that do not have a cycle tag; They can be removed via a hybridization purification step during production, as described herein. If not removed, the information gap may not show as a sequence deletion, but rather as a unknown amino acid for one analyte at a particular cycle.

The purity of 1-Ethynyl-dSpacer CE Phosphoramidite (Glen Research, Cat #10-1910) is >99.5%, so that ensures capability to bind to the solid support in operation 4*a* over 99.5% of the time Free PITC-hydrazine may interfere at operation 2 of the recoding process by blocking an N-terminal amino acid, and then in operation 4 cleaving that amino acid, making it invisible to the recoding process and creating a sequence deletion. Thus, in some examples, unbound PITC-hydrazine may be removed. This may be accomplished via the hybridization purification, preparative HPLC, and tested for trace PITC using analytical $HPL_C$. Any conjugates lacking PITC will be spectators in operations 2 through 4. A 1% free PITC (or conjugate lacking the alkyne or cycle tag functionality) impurity in operation 2 is estimated to produce a 1% deletion frequency. Note that cross-contamination of cycle tags during manufacture will result in the potential for mismatch errors, where amino acids are erroneously identified. A 1% cross-contamination is estimated to result in about 1% mismatch error.

Conjugate recognition by binding agents. A desired outcome of operation 5*a* is that a cognate binding agent is bound to each immobilized conjugate. Alternative events include: (1) no binding agent is bound; (2) a binding agent with cognate amino acid affinity, but non-cognate cycle tag is bound; (3) a binding agent with non-cognate amino acid affinity, but cognate cycle tag is bound; (4) a binding agent with non-cognate amino acid affinity and non-cognate cycle tag is bound; and (5) a binding agent having either non-cognate or cognate affinity is non-specifically bound (NSB) in proximity to a cycle tag. None of these events by themselves result in sequence insertions, deletions, or mismatch errors at this point in the recoding process. Their effect on error rate will be discussed in context of operation 5*c*. A potential consequence for recode sequence efficiency is related to the number of iterative cycles to push recode block assembly to >90%. The binding of the binding agent relies primarily on the interaction energy of the binding moiety of the binding agent. However, a feature of the binding agent is the hybridization energy of the cycle tag oligo contributes to the overall binding energy through hybridization to complementary DNA of a cognate recode tag.

Alternative event (1) depends on the affinity and concentration of binding agents. Frequency can be tuned to be low by adjusting binding formulation and condition. This may vary depending on the cognate amino acid. When assessing alternative event (2), the differential binding energies between binding agents will determine how frequently a non-cognate binding agent will block the immobilized conjugate, and render it unable to participate in the following ligation step. Alternative events (3) and (4) will be negligible because hybridization energy is low under the experimental wash conditions. They are estimated to be less than 1%. And alternative event (5) may be tuned by adjusting the formulations, conditions, adding passivation components, and/or modifying the hydrogel to reduce NSB. Any alternative events associated with recognition by binding agents may result in the need for high numbers of iterative cycles in operation 5, and may optionally include contacting the solid support with generic binding agents that do not discriminate binding based on amino acid, and have a high binding affinity to any immobilized conjugate. This promotes complete recode block formation, which aids in memory oligo assembly in subsequent steps. This mitigation gives up amino acid identity information, but provides position information even for amino acids whose identity is not determined. As outlined above, this is useful information when mapping to reference sequences for the identification and quantification of analytes in a sample.

Oligo synthesis. Recode tag sequences may be incorrect due to oligo synthesis errors. Typical error rates are approximately 1 per 500 bases. The number of AA tag nucleotides in each memory oligo in this example is 6×30=180. Only off-by-2 errors will result in undetectable mismatch errors, due to the binary error-checking design of the codespace discussed in Example 6. Assuming 30 cycles of recoding and oligo synthesis errors are random, implies that 4.5% of memory oligos will have 1 mismatch error. This contributes 0.15% to the per AA error rate.

Recode block assembly. A desired outcome of operation 5*b* is that 100% of non-cognate binding agents are washed from the surface and do not interact with immobilized conjugates. Alternative events at operation 5*b* include incomplete removal of non-cognate molecules. Similar to operation 5*a*, this does not by itself result in insertion, deletion, or mismatch errors at this point in the recoding process, and does not have an effect on the recode sequence efficiency. Mitigation for incomplete removal includes: optimizing the time, flowrate, temperature, pH, salt, and/or other stringency factors during the wash step. Reducing the hybridization energy by increasing pH is an effective way to dissociate double-stranded DNA. Effective removal of non-cognate DNA is desired, so, binder moiety selection and affinity maturation at elevated pH will be beneficial to aid this wash step. Removal of non-cognate oligos, not held bound by interaction of a binding agent with cognate amino acid affinity to an immobilized conjugate, is presumed to be >0.1%. The off rate of a binding agent may be a factor in maintaining cognate binding agent association with its cognate immobilized target. Tuning the time, formulations, and conditions through and between wash and ligation steps may impact occupancy of immobilized conjugates (i.e., the fraction with a bound binding agent) and thereby the number of iterative cycles required to push recode assembly to >90%. It is estimated that the fraction of conjugates bound to a cognate binding agent in any given iteration is 20%. Under this conservative assumption and further assuming no systematic effects, 10 iterations should achieve 90% recode block assembly.

A desired outcome of operation 5*c* is 100% ligation of the cognate ligation oligo to a recode block. Alternative events include: (1) no binding agent is bound; (2) a binding agent with cognate amino acid affinity, but non-cognate cycle tag is bound; (3) a binding agent with non-cognate amino acid affinity, but cognate cycle tag is bound; (4) a binding agent with non-cognate amino acid affinity and non-cognate cycle tag is bound; (5) a binding agent having either non-cognate or cognate affinity is non-specifically bound (NSB) in proximity to a cycle tag; and 6) incomplete ligation.

Alternative event (1) does not result in recode sequence error. A potential consequence for recode sequence efficiency may be additional time to iterate the bind, wash, and ligation cycles. Similarly, alternative events (3) and (4) do not result in significant recode sequence error. The <0.1% association of non-cognate cycle tags with recode tags is further reduced by sequence differences at the ends of non-cognate cycle tags that do not participate effectively in the ligation. A potential consequence of this alternative event for recode sequence efficiency is additional time to iterate the bind, wash, and ligation cycles. Alternative event (6) may not result in recode sequence error. A potential consequence for recode sequence efficiency is additional time to iterate the bind, wash, and ligation cycles.

Alternative event (2) is binding of a binding agent with cognate amino acid affinity, but non-cognate cycle tag. This may be difficult to remove by washing due to the similar binding energy for a fully cognate binding agent compared to one with cognate amino acid affinity but not the cognate cycle tag. Too stringent a wash could dissociate cognate binding agents, and prevent the fully cognate binding agent from transferring information to the recode block during ligation. Thus, the frequency of the interference by "binding agents" can be estimated to be high, leading to poor per cycle information transfer efficiency. This must be remediated by iterative cycling, and it impacts the process efficiency. Fortunately, the consequence for recode sequence error rate is low since the cycle tag sequences are chosen to not interact and to be especially different at the 3' end to prevent errant ligation. By using high fidelity ligation at high salt concentrations ligation of incorrect oligos is estimated to be >0.1% (Lohman, et.al. (2015) Nucleic Acids Research, 2016, Vol. 44, No. 2). Even through 20 iterative cycles in attempts to find the cognate binding agent this suggests mis-association of cycle with amino acid will add>1% to recode error rate. Mitigation includes: optimization of ligase conditions and formulations, choice of ligase, avoidance of GT base pairing at the 3' end junction, optimization of cycle tag sequence differences, and slow annealing.

Alternative event (5) is non-specific binding (NSB) of binding agents in proximity to immobilized conjugate. Non-cognate binding agents could have complementary recode tag sequence to a cycle tag in the vicinity. Hybridization to the cycle tag produces a viable ligation target. While difficult to quantify, this alternative event has the potential to contribute to the recode error rate. The probability that the errant recode tag outcompetes the recode tag of an associated binding agent is equivalent, if the fully cognate binding agent is bound, and is high if the recode tag of the bound binding agent has a non-complementary recode tag. Mitigation includes stringent wash of the solid support prior to ligation, adding passivation agents to the formulated reagents, and/or modifying the hydrogel to reduce NSB. Recode process efficiency is not affected by alternative event (5).

The analysis of stepwise error rates suggests that >90% of the identity and sequencing information represented in a memory oligo is accurate.

A desired outcome of the operation **5*d* is that 100% of cognate binding moieties are dissociated from cognate PTC-AA binding site of the immobilized conjugate to prepare for the next iteration of information transfer. Alternative events include incomplete removal of the binding agent. There may be no consequence to error rate however, as conjugates that are not free to find a cognate binding agent will be spectators in the next iteration cycle and significant residual binder will increase the number of requisite iterations of operation 5**. Mitigation includes adjusting wash conditions to be longer, higher flowrate, higher temperature, and formulations that include protein denaturing conditions, such as high or low pH, and high detergent concentrations.

Memory oligo assembly. A desired outcome of operation 6 is that 100% of recode blocks are ligated to form a complete memory oligo, which can serve as a template for cluster generation and NGS data collection is subsequent steps. Alternative events include incomplete ligation of recode blocks. The frequency of incomplete memory oligo assembly is estimated to be high due to "missing recode blocks" for some cycles, steric restriction during the assembly process, and incomplete ligation using enzymatic ligation methods. There is no consequence of this event on recode sequence error rate. However, the penalty in terms of the recode efficiency may be significant. Failure to assemble an amplicon results in no information from a given analyte fragment. Assuming recode block assembly rates are governed by the target stepwise efficiencies above, then for 30 recode cycles and without mitigation, the number of memory oligo amplicons capable of being analyzed by NGS would be ~0.1%. This is derived from an 80% probability to have assembled any given recode block, raised to the power of the number of cycles, which in this example is 30. Thus, methods to assemble incomplete sets of recode blocks may be needed.

Mitigation of imperfect assembly to achieve a memory oligo includes the concept described in operation 7 of the recoding process wherein linking oligos are used to ligate any non-ligated recode block or memory oligo fragments. This can be done in multiple steps using subsets of the full complement of linking oligos capable of splinting any recode blocks (or memory oligo fragments) together. In addition, repeating operation 6 and 7 after cleaving the SPDP tethers in operation 8 to allow greater flexibility and accessibility of components can promote complete assembly of memory oligos. Note that ligation of any non-ligated recode block to any other to complete a memory oligo amplicon can result in a valuable memory oligo construct suitable for NGS analysis. Recode blocks can assembled in any order and deconvoluted in silico, since the cycle information is adjacent to the AA tag information in each recode block. In some embodiments the cycle information is flanked by a universal assembly sequence that allows recode block assembly into the memory oligo in any order, and sequence is deconvoluted in silico; and 2) incorrect ligation of recode blocks. As covered in the previous paragraph, the consequence on recode sequence error rate is negligible, and the consequence for recode sequence efficiency is negligible since in the majority of cases the memory oligo will be imperfect, but still represent a significant quantity of analyte information and be suitable for NGS analysis. Shortcuts could cause a fraction of the recode block information to be lost, for example if recode block 1 ligated to recode block 30, and omitted the information of intervening recode blocks. Strategies may be used for stepwise ligation using ligation oligo subpools to maximize information capture.

Sensitivity analysis indicates robustness. The analysis identifies controllable factors to limit errors to acceptable levels and stabilize overall process efficiency. Reagent impurity, incompletely executed steps, binder fidelity, and alternative interactions within the recode process contribute to deletion of sequences, insertion of sequences, and mismatch errors. Degradation of the conjugate complex, recode block, or memory oligo, hydrogel, hydrogel delamination, or other degradation mechanisms may further result in recode sequence error or changes in efficiency. The frequency is controllable by choice of materials, methods, and protecting groups. In the example above second-order propagation of error is neglected, because these are estimated to be negligible.

Example 6: Code Space and Sequence Space

Two considerations when assigning nucleic acid sequences to AA tags and cycle Tags include: 1) the code space, and 2) the sequence space. It is not obvious that code space and sequence space are separable, since the same nucleotides comprise both the physical and digital attributes of AA tags and cycle tags. However, recognizing that code space and sequence space are not same provides a capability to largely deconvolute the physiochemical properties of the sequence space (i.e., the physical system: hybridization temperature and energy, spatial interference, specificity of nucleic acid interaction) from code space (i.e., the in silico recode information). Pragmatically, deconvolution comes through utilizing a sequencing method to identify recoded information wherein only a subset of the nucleotides of the memory oligo are identified through DNA sequencing, and a subset are not identified. This may be achieved by introducing non-fluorescent, non-reversibly-terminated nucleotides into the sequencing reagent mixtures. The value is that one can tune the physiochemical properties without increasing sequencing time, or cost.

In this Example, a customized reagent set is created wherein a solution of nucleotides that contains blocked and fluorescently-labeled nucleotide triphosphates for A and C, and triphosphate nucleotides for G and T (Trilink Cat #: N-2513, and Cat #: N-2512, respectively) is substituted for the nucleotide reagent in a sequencing kit that contains blocked and fluorescently labeled triphosphates. A flowcell (Illumina, San Diego, CA) is seeded with memory oligos, clusters are generated using standard processes, and sequencing ensues. Sequencing proceeds under standard conditions using a commercial sequencing kit (Illumina NextSeq 500/550 High Output Kit v2.5 (300 Cycles) 20024908). At each sequencing cycle polymerase adds cognate nucleotides to the growing SBS oligo, directed by the DNA template in a given sequencing cluster. When a G, or a T, or a stretch of G's or a stretch of T's, or a combination of G and T is encountered, the polymerase during that cycle of sequencing adds as many G's and T's as necessary to get to the next A or C nucleotide. Then the polymerase adds blocked and fluorescently-labeled nucleotide A or C to the SBS oligo, as directed by the template. No further nucleotides may be added during this cycle because of the 3' OH blocking group of the blocked and labeled nucleotide A or C triphosphates. The flowcell is imaged to read the color of the fluorophore attached to A or C for each cluster. At the end of the sequencing run, the resultant FASTQ file records only the information associated with the A and C bases of the memory oligo. Example sequences are shown with their corresponding code in the table below. In this example, an oligo sequence of length 15 bp provides one of 64 binary codes in 6 sequencing cycles. A fraction of the code space, for example, the codes with even parity, can be used, and the remainder unused to provide error checking and mitigate error modes in the processes of recoding and/or sequencing (Gunderson, et.al. Decoding randomly ordered DNA arrays, Genome Res 2004 May; 14(5):870-7). In this example, even parity codes are assigned to cycle tags, and odd parity codes are assigned to AA tags. The FASTQ file can be parsed to identify the amino acid sequence represented by each cluster, and mapped to reference protein sequences to identify proteins and quantify their concentrations.

TABLE 4

Sequence Space and Code Space

| Name | Physical nucleotide sequence | SEQ ID NO: | FASTQ sequence | Code | Parity |
|---|---|---|---|---|---|
| rcn_001 | ATGAGTGTAGGGAAA | 3 | AAAAAA | 000000 | 0 |
| rcn_002 | TAGCTTCTGGTCGAA | 4 | ACCCAA | 011100 | 1 |
| rcn_003 | CTAGTTGTTCGTCAA | 5 | CACCAA | 101100 | 1 |
| rcn_004 | ATTGAGCTGTCGTAA | 6 | AACCAA | 001100 | 0 |
| rcn_005 | TCTCACGTTTGGAGA | 7 | CCACAA | 110100 | 1 |
| rcn_006 | CGCAGCTTGTCTGGA | 8 | CCACCA | 110110 | 0 |
| rcn_007 | TATGCTGTACTTCGA | 9 | ACACCA | 010110 | 1 |
| rcn_008 | GAACGTGTCTTCTGA | 10 | AACCCA | 001110 | 1 |
| rcn_009 | TGAAGTTTGGAGACA | 11 | AAAACA | 000010 | 1 |
| rcn_010 | AATTGCGTGGGAGCA | 12 | AACACA | 001010 | 0 |
| rcn_011 | GGCAAGTTGGGTCCA | 13 | CAACCA | 100110 | 1 |
| rcn_012 | ACAAGGGTGTGTTCA | 14 | ACAACA | 010010 | 0 |
| rcn_013 | TTGTGACTGGCAATA | 15 | ACCAAA | 011000 | 0 |
| rcn_014 | CTCATTGTGAAGGTA | 16 | CCAAAA | 110000 | 0 |
| rcn_015 | TGAAGGGTTGACCTA | 17 | AAACCA | 000110 | 0 |
| rcn_016 | GCAATGGTGAAGTTA | 18 | CAAAAA | 100000 | 1 |
| rcn_017 | ATGCAGGTAGTTAAG | 19 | ACAAAA | 010000 | 1 |
| rcn_018 | CCTGTTGTCAATGAG | 20 | CCCAAA | 111000 | 1 |
| rcn_019 | CTGTACCTTGTGCAG | 21 | CACCCA | 101110 | 0 |
| rcn_020 | CACGGTTTGAATTAG | 22 | CACAAA | 101000 | 0 |
| rcn_021 | ACTGTCGTACGTAGG | 23 | ACCACA | 011010 | 1 |
| rcn_022 | GCATTGGTCACAGGG | 24 | CACACA | 101010 | 1 |
| rcn_023 | ATACGTGTCTCTCGG | 25 | AACCCC | 001111 | 0 |
| rcn_024 | TCCAACATGTGTTGG | 26 | CCAACA | 110010 | 1 |
| rcn_025 | TTTGTCCTCCTGACG | 27 | CCCCAC | 111101 | 1 |
| rcn_026 | GCCTGATTGTCAGCG | 28 | CCACAC | 110101 | 0 |
| rcn_027 | CGAGAGCTGTTTCCG | 29 | CAACCC | 100111 | 0 |
| rcn_028 | GACATTGTACTTTCG | 30 | ACAACC | 010011 | 1 |
| rcn_029 | GAATAGTTGCGAATG | 31 | AAACAA | 000100 | 1 |
| rcn_030 | AAGCGGATTGAAGTG | 32 | AACAAA | 001000 | 1 |
| rcn_031 | TATTCGCTGTACCTG | 33 | ACCACC | 011011 | 0 |
| rcn_032 | CTCTTCTTCGCCTTG | 34 | CCCCCC | 111111 | 0 |
| rcn_033 | TATGTGGTTCCTAAC | 35 | ACCAAC | 011001 | 1 |
| rcn_034 | GAACTCGTGGTGGAC | 36 | AACCAC | 001101 | 1 |
| rcn_035 | TTGTTGGTTCAACAC | 37 | CAACAC | 100101 | 1 |
| rcn_036 | AGTAGTATTGGCTAC | 38 | AAACAC | 000101 | 0 |
| rcn_037 | GTCCTGTTCGATAGC | 39 | CCCAAC | 111001 | 0 |

TABLE 4-continued

Sequence Space and Code Space

| Name | Physical nucleotide sequence | SEQ ID NO: | FASTQ se-quence | Code | Par-ity |
|---|---|---|---|---|---|
| rcn_038 | TCCTTAGTATGAGGC | 40 | CCAAAC | 110001 | 1 |
| rcn_039 | CAATGGTTATGTCGC | 41 | CAAACC | 100011 | 1 |
| rcn_040 | CATGTGTTTCAATGC | 42 | CACAAC | 101001 | 1 |
| rcn_041 | TTCAGGGTCTGTACC | 43 | CACACC | 101011 | 0 |
| rcn_042 | GTGTGTGTCCAAGCC | 44 | CCAACC | 110011 | 0 |
| rcn_043 | AAGTATGTGGGTCCC | 45 | AAACCC | 000111 | 1 |
| rcn_044 | ATCTATCTGTTGTCC | 46 | ACACCC | 010111 | 0 |
| rcn_045 | CGTATGTTCCTGATC | 47 | CACCAC | 101101 | 0 |
| rcn_046 | TGCCACCTGTTTGTC | 48 | CCACCC | 110111 | 1 |
| rcn_047 | CCGTGTGTTTCACTC | 49 | CCCACC | 111011 | 1 |
| rcn_048 | GCAGGTCTCCGTTTC | 50 | CACCCC | 101111 | 1 |
| rcn_049 | GCTTAAGTTGGCAAT | 51 | CAACAA | 100100 | 0 |
| rcn_050 | GACGTGTTCTCCGAT | 52 | ACCCCA | 011110 | 0 |
| rcn_051 | CGTCTGCTTCGTCAT | 53 | CCCCCA | 111110 | 1 |
| rcn_052 | GCGTCTCTTGACTAT | 54 | CCCACA | 111010 | 0 |
| rcn_053 | CTCGGCGTTGCAAGT | 55 | CCCCAA | 111100 | 0 |
| rcn_054 | ATCTCGCTGCTCGGT | 56 | ACCCCC | 011111 | 1 |
| rcn_055 | TACGATTTGCAGCGT | 57 | ACACAC | 010101 | 1 |
| rcn_056 | ACCTGCGTACTTTGT | 58 | ACCCAC | 011101 | 0 |
| rcn_057 | TGAACGATTGGTACT | 59 | AACAAC | 001001 | 0 |
| rcn_058 | CGATAGTTGAGAGCT | 60 | CAAAAC | 100001 | 0 |
| rcn_059 | TAAGTGTTGGAACCT | 61 | AAAACC | 000011 | 0 |
| rcn_060 | ACATGGGTGAAGTCT | 62 | ACAAAC | 010001 | 0 |
| rcn_061 | CTAAGATTGGGCATT | 63 | CAAACA | 100010 | 0 |
| rcn_062 | ACAGCGTTAAGTGTT | 64 | ACACAA | 010100 | 0 |
| rcn_063 | TGAACACTGTGTCTT | 65 | AACACC | 001011 | 1 |
| rcn_064 | AAGAGAGTGAGCTTT | 66 | AAAAAC | 000001 | 1 |

In this example, the recode information is captured in a base-2 (binary) code, using A and C. Other subsets of nucleotides may be preferred in some instances. Subsets include: AGT, ACT, CTG, ACG while using a non-fluorescent, non-reversibly-terminated C, G, A, or T, respectively, in the sequencing reagent mix. In this case, information is coded using a base-3 code space. When choosing to create a code in binary space it is advantageous to choose one purine and one pyrimidine, as it allows tuning the non-coding bases with a ratio of purine to pyrimidine that provides flexibility to adjust % CG, Tm, and other physiochemical properties.

One clear benefit of recoding using a reduced number of nucleotide types is the ability to tune the physiochemical properties of the AA tag and cycle tag sequences relatively independently of the code that they hold. Note that the melting temperature of the physical sequencing in Table 4 is between 35° C. and 45° C. under standard experimental conditions, while that of 6mer sequences that could be used to code the AA tag and cycle tag information is near 0° C. Note also the greater hybridization specificity that can be obtained using the physical sequences, as compared to that which would be obtained by using the code sequences to support the physiochemical process of hybridization.

Another benefit is the ability to design the physical sequences to support conjugation and avoid steric interferences. Note the $8^{th}$ bases in the physical sequences of the example are all "T". Commercially available phosphoramidites exist that allow conjugation through a modified nucleobase "T", making reagent preparation straightforward (Glen Research, Amino-Modifier C6 dT (10-1039) Catalog #: 10-1039, CAS #: 178925-21-8). By placing a conjugation site near the middle of the oligo, steric interference with ligase is avoided during critical steps in the recode block assembly and memory oligo assembly processes. Alternately, 1) an abasic conjugation site can be placed somewhere in middle of the nucleic acid using a compound during oligonucleotide synthesis such as 1-Ethynyl-dSpacer CE Phosphoramidite (Glen Research Cat #10-1910), having an alkyne group in place of the nucleobase, or 2) a 5-Formylindole-CE Phosphoramidite (Glen Research, Cat #10-1934) could serve to enable aldehyde-hydrazine conjugation at an internal site in the nucleic acid cycle tag.

In Example 4, each recode cycle creates a nucleotide long enough to hold the cycle and amino acid identity. The number of codes to differentiate 30 recode cycles is (43=64). This means at least 3 bases are utilized to hold the cycle tag information in some embodiments. The number of nucleotides to support the physiochemical requirement of the recode process may be between 5 and 20 (e.g. 5, 6, 7, 8, 9, 10, 11, 12, 13, 14, 15, 16, 17, 18, 19, 20, or any range thereof). Other numbers may be included that work outside the range of 5 to 20. Similarly, the number of codes to differentiate 20 amino acids is (43=64). This means at least 3 bases hold the AA tag information. Again, the number of nucleotides to support the recode process may be between 5 and 20. Thus, each sequenced amino acid may require 10's of nucleotide bases. If these all needed to be sequenced, it may restrict the length of amino acid sequence that could be ascertained. Typical short-read NGS kits are capable to sequence 2×150 or 2×300 nucleotides. As the analyte grows longer than this, sequencing quality degrades. Thus, another benefit of decoupling code space and sequence space is the ability to reduce DNA sequencing cycles when analyzing the memory oligo using SBS NGS. By using non-labeled and non-blocked nucleotide triphosphates the memory oligo length is not limited to the maximum number of DNA sequencing cycles.

Exemplary rules for code space follow the theories of digital communication error checking and correction, e.g., Hamming, et.al. Binary codes of length 5 are sufficient to code cycle and amino acid information, but a binary code length of 6 is required to check and correct errors due to imperfect recode block formation, memory oligo assembly, ligation of non-cognate information, oligo synthesis errors, or NGS sequencing errors.

Exemplary rules for sequence space include: 1) maximizing the sequence difference at the 3'end of all nucleic acids that are to be ligated during the process, 2) further, the greatest discrimination of the ligase activity may be obtained by excluding nucleic acids with GG,GC,CG, or CC at the 3' end, 3) no shared words greater than 6mer and maximum distance between sequences to avoid cross hybridization 4)

no homopolymer stretches>3mer, 5) a "T" nucleotide near the middle of the nucleic acid to support conjugation and avoid steric interferences with conjugation sites during the recode process, 6) the requisite number of "A" nucleotides and/or "C" nucleotides to create the codes within the sequence, 7) Tm matched, 8) % CG between 40% and 60%, 9) minimized hairpin structures, 10) defined sequence length (can be different for AA tags and cycle tags).

Concepts of Example 6 can effectively break the 1:1 connection between code space and physiochemical properties of the oligonucleotides. This can effectively be used to increase Tm during ligation assembly events, while reducing NGS cycles to obtain the recoded information of the memory oligo.

It is contemplated that memory oligos may have a limited number of unique constituent recode blocks (e.g., sequence blocks) as a result of the number of cycles and number of binding agents in the recoding process. For example, with thirty (30) cycles of sequencing and twenty (20) amino acids, there are only six hundred (600) blocks for identification using available detection modalities (30 cycles×20 different amino acids). As an alternative to NGS sequencing techniques, analysis by hybridization using a combinatorial approach can be used to "decode" the identity of recode blocks in memory oligos, which in certain embodiments, can be 30mer sequences. Again, for decoding techniques, see Gunderson et al., Decoding Randomly Ordered DNA Arrays, Genome Res., 2004 May; 14(5):870-7, which is herein incorporated in its entirety by reference for all purposes. In such embodiments, instead of sequencing each nucleotide base, memory oligo information may be collected by performing sequential hybridization and de-hybridization steps, interspersed with imaging.

Given the proximity of recode blocks to each other for a given macromolecular analyte (e.g., when anchored to a solid support during the recoding process), it is contemplated that recode blocks may be analyzed by hybridization without prior assembly into a memory oligo. This can be carried out at the single molecule level, or following amplification of each individual recode block while maintaining proximity to each analyte anchor position. As described above with reference to FIG. 3-4, localized amplification of recode blocks may be facilitated by primers such as P5 or P7 immobilized within the hydrogel polymer. The point-spread function of high-resolution optical systems is approximately $\lambda/2$, where $\lambda$ is the wavelength of the emitted photon(s), and is typically in the range of 500-800 nm for fluorescent dyes. Accordingly, since the distance between chemically-reactive conjugate anchor points around a central analyte anchor point may be in the order of 10s' of nm to 200 nm, and the optimal distance between analytes is in the order of several 100's of nm, the optical resolution enables isolation between analytes but not between recode blocks of a given analyte. This applies even if the recode blocks are not connected via phosphodiester bonds or other direct covalent linkages, as described herein for assembly of memory oligos.

Thus, while assembly of memory oligos from recode blocks and subsequent amplification of the memory oligos may facilitate signal enhancement during sequencing, single molecule analysis of memory oligos and/or recode blocks (using appropriate instrumentation/systems and dyes) is also contemplated herein. In such embodiments, the memory oligos, and or recode blocks in proximity to one another, can be analyzed using single-molecule imaging techniques, such as single-molecule decode-based imaging techniques. For more information regarding such single-molecule imaging techniques, see Shashkova and Leake, Single-molecule fluorescence microscopy review: shedding new light on old problems, Biosci Rep 2017 Aug. 31; 37(4), which is herein incorporated in its entirety by reference for all purposes.

In addition to the application described herein, this method may be broadly useful in genomics for overcoming some limitations of short read technology. Short-read sequencing, while a powerful tool in genomics, has several limitations that can hinder its utility in certain applications. One issue is limited read length. Short-read sequencing technologies, such as those provided by Illumina, typically generate reads of up to 300 base pairs. This limitation can make it challenging to assemble complex genomes, particularly those with repetitive regions, as the short reads may not span the entire length of the repeat.

Another issue is the difficulty in mapping structural arrangements. Structural variants, such as inversions, deletions, duplications, and translocations, can have significant impacts on gene function and expression. However, these variants can be challenging to detect with short-read sequencing, as the reads may not span the entire length of the variant, making it difficult to accurately map their locations.

Additionally, short-read sequencing can struggle with accurately measuring gene fusions. Gene fusions, which occur when two previously separate genes become joined together, often play a critical role in diseases such as cancer. However, the short length of the reads can make it difficult to accurately identify the breakpoint where the two genes are fused together.

Other issues with short-read sequencing include difficulties in phasing alleles, accurately identifying long repeat expansions, and resolving complex regions of the genome, such as those with high GC content.

The methods described herein may be useful for addressing some of these issues. By skipping certain base pairs during sequencing, it may be possible to sequence farther than traditional short-read sequencing methods, potentially allowing for longer reads. This could help to resolve some of the issues associated with short-read sequencing, such as difficulties in assembling complex genomes and mapping structural variants.

The method may improve the accuracy of gene fusion detection for certain fusions. By sequencing farther, it may be possible to more accurately identify the breakpoint where two genes are fused together, improving the accuracy of gene fusion detection.

Furthermore, the ability of some such methods to sequence farther may help with phasing alleles, identifying long repeat expansions, and resolving complex regions of the genome. By sequencing farther, it may be possible to span the entire length of long repeat expansions or complex regions, improving the accuracy of these analyses.

In RNA sequencing (RNAseq), longer reads can provide a more complete picture of individual transcripts, especially for organisms with complex genomes, or in the study of alternative splicing events. Longer reads can also improve the annotation of novel genes and isoforms. Longer reads may improve mapping accuracy, especially in regions with repetitive sequences. Shorter reads might map to multiple locations, making it difficult to assign them unambiguously. Longer reads may improve the quantification accuracy of expression levels, especially for longer transcripts.

In addition to extracting part of a sequence from a longer than normal segment, this could enable shorter runs. Sequencing with longer reads may be more expensive. The higher cost may limit the number of samples that can be sequenced in a given project, potentially reducing its statistical power.

Finally, use of a customized reagent set, which includes blocked and fluorescently-labeled nucleotide triphosphates for A and C, and standard triphosphate nucleotides for G and T, may be easily incorporated into existing sequencing technology using standard flowcells and other consumables, and standard primary analysis techniques to determine the base pairs read. Kits that use this may include any one, two, or three of the four reversibly terminated nucleotides being substituted for a normal, unblocked base, in addition to non-natural or other synthetic nucleotides being introduced for reading synthetic codes and skipping uninformative regions as previously described. Such kits and methods may be applied to any number of sequencing technologies that utilize reversible terminators, including, but not limited to the sequencers by Element Biosciences (Aviti), Pacific Biosciences (Onso), or others.

Example 7: Deprotection and Reprotection of Oligonucleotides

An exemplary protocol may be used to illustrate protection or reprotection as follows:

For adenine and cytosine bases: dissolve 250 mg of benzoyl chloride in 1 mL of anhydrous DMF, contact the oligonucleotide with the solution at room temperature for 1-3 hours. Wash the surface with DMF to remove unreacted reagents and byproducts.

For guanine bases: dissolve 250 mg of isobutyryl chloride in 1 mL of anhydrous DMF, contact the oligonucleotide with the solution at room temperature for 1-3 hours. Wash the surface with DMF to remove unreacted reagents and byproducts.

In some embodiments, the location of immobilized amino acid complexes may be defined by a nucleic acid that is joined to the solid support in proximity, a "location oligo". It may be useful to transfer the sequence information of the location oligo to a cycle tag, a recode block or a memory oligo. In these cases protection, deprotection and/or reprotection methods described herein may be applicable.

Oligonucleotide protection can be applied broadly in any protein sequencing method where chemical conditions used within the process may impart changes to oligonucleotide structure or function.

While this disclosure is satisfied by embodiments in many different forms, as described in detail in connection with preferred embodiments of the disclosure, it is understood that the present disclosure is to be considered as exemplary of the principles of the disclosure and is not intended to limit the disclosure to the specific embodiments illustrated and described herein. Numerous variations may be made by persons skilled in the art without departure from the spirit of the disclosure. The scope of the disclosure will be measured by the appended claims and their equivalents. The abstract and the title are snot to be construed as limiting the scope of the present disclosure, as their purpose is to enable the appropriate authorities, as well as the general public, to quickly determine the general nature of the disclosure. In the claims that follow, unless the term "means" is used, none of the features or elements recited therein should be construed as means-plus-function limitations pursuant to 35 U.S.C. § 112, ¶6.

The invention claimed is:

1. A sequencing method, comprising:

providing, in a nucleic acid sequencing reaction, an oligonucleotide and a combination of reversibly terminated nucleotides and non-labeled nucleotides that are not reversibly terminated; and performing the nucleic acid sequencing reaction, wherein nucleotides of the oligonucleotide that correspond with the reversibly terminated nucleotides are sequenced, wherein nucleotides of the oligonucleotide that correspond with the non-labeled nucleotides that are not reversibly terminated are not sequenced, and wherein (a) or (b) is true:

(a) the oligonucleotide comprises a non-sequenced region that includes only a subset of nucleotides selected from A, C, G, and T, wherein the subset is not sequenced, and wherein the non-sequenced region is hybridizable to a recode nucleic acid sequence indicative of an amino acid identity, or is hybridizable to a cycle nucleic acid sequence indicative of a workflow cycle; or (b) the oligonucleotide comprises a sequenced region comprising a recode nucleic acid sequence indicative of an amino acid identity and a cycle nucleic acid sequence indicative of a workflow cycle, and wherein the oligonucleotide further comprises a memory oligonucleotide comprising the recode nucleic acid sequence and the cycle nucleic acid sequence.

2. The method of claim 1, further comprising identifying the nucleotides of the oligonucleotide that correspond with the reversibly terminated nucleotides.

3. The method of claim 1, wherein (a) is true, and the subset of nucleotides selected from A, C, G, and T is a subset of 2 nucleotides selected from A, C, G, and T.

4. The method of claim 1, wherein (a) is true, and the subset of nucleotides selected from A, C, G, and T is a subset of 3 nucleotides selected from A, C, G, and T.

5. The method of claim 1, wherein (a) is true, and the non-sequenced region comprises a primer sequence.

6. The method of claim 1, wherein (a) is true, and the non-sequenced region does not include a barcode nucleic acid sequence representing a protein sequence or identity.

7. The method of claim 1, further comprising:

obtaining sequence information of the nucleotides of the oligonucleotide that correspond with the reversibly terminated nucleotides; and not obtaining sequence information of the nucleotides of the oligonucleotide that correspond with the non-labeled nucleotides that are not reversibly terminated.

8. The method of claim 1, wherein the oligonucleotide comprises a contiguous string of nucleotides.

9. The method of claim 5, further comprising using the primer sequence in a nucleic acid amplification reaction.

10. The method of claim 9, wherein the nucleic acid amplification reaction comprises a polymerase chain reaction.

11. The method of claim 1, wherein (a) is true, and the non-sequenced region connects sequenced regions.

12. The method of claim 1, wherein (a) is true.

13. The method of claim 12, further comprising hybridizing the non-sequenced region to the recode nucleic acid sequence, or to the cycle nucleic acid sequence, before performing the sequencing reaction.

14. The method of claim 1, wherein the oligonucleotide comprises a second sequenced region that includes only a subset of nucleotides selected from A, C, G, and T.

15. The method of claim 1, further comprising generating a sequence output comprising the nucleotides that are sequenced.

16. The method of claim 1, wherein (b) is true.

17. The method of claim 16, further comprising determining identity or positional information of an amino acid residue of a peptide based on sequence information of the memory oligonucleotide obtained from the sequencing reaction.

18. The method of claim 17, wherein the workflow cycle indicated by the cycle nucleic acid sequence of the memory oligonucleotide is used to determine the positional information of the amino acid residue of a peptide.

19. The method of claim 17, wherein the amino acid identity indicated by the recode nucleic acid sequence of the memory oligonucleotide is used to determine the identity of the amino acid residue of a peptide.

* * * * *

SEQUENCE LISTING

```
Sequence total quantity: 124
SEQ ID NO: 1            moltype = DNA  length = 29
FEATURE                 Location/Qualifiers
source                  1..29
                        mol_type = other DNA
                        organism = synthetic construct
modified_base           1
                        mod_base = OTHER
                        note = 5' alkyne P5, NA protected nucleotide
SEQUENCE: 1
aatgatacgg cgaccaccga gatctacac                                    29

SEQ ID NO: 2            moltype = DNA  length = 24
FEATURE                 Location/Qualifiers
source                  1..24
                        mol_type = other DNA
                        organism = synthetic construct
modified_base           1
                        mod_base = OTHER
                        note = 5' alkyne P7, NA protected nucleotide
SEQUENCE: 2
caagcagaag acggcatacg agat                                         24

SEQ ID NO: 3            moltype = DNA  length = 15
FEATURE                 Location/Qualifiers
source                  1..15
                        mol_type = other DNA
                        organism = synthetic construct
SEQUENCE: 3
atgagtgtag ggaaa                                                   15

SEQ ID NO: 4            moltype = DNA  length = 15
FEATURE                 Location/Qualifiers
source                  1..15
                        mol_type = other DNA
                        organism = synthetic construct
SEQUENCE: 4
tagcttctgg tcgaa                                                   15
```

-continued

```
SEQ ID NO: 5            moltype = DNA  length = 15
FEATURE                 Location/Qualifiers
source                  1..15
                        mol_type = other DNA
                        organism = synthetic construct
SEQUENCE: 5
ctagttgttc gtcaa                                                    15

SEQ ID NO: 6            moltype = DNA  length = 15
FEATURE                 Location/Qualifiers
source                  1..15
                        mol_type = other DNA
                        organism = synthetic construct
SEQUENCE: 6
attgagctgt cgtaa                                                    15

SEQ ID NO: 7            moltype = DNA  length = 15
FEATURE                 Location/Qualifiers
source                  1..15
                        mol_type = other DNA
                        organism = synthetic construct
SEQUENCE: 7
tctcacgttt ggaga                                                    15

SEQ ID NO: 8            moltype = DNA  length = 15
FEATURE                 Location/Qualifiers
source                  1..15
                        mol_type = other DNA
                        organism = synthetic construct
SEQUENCE: 8
cgcagcttgt ctgga                                                    15

SEQ ID NO: 9            moltype = DNA  length = 15
FEATURE                 Location/Qualifiers
source                  1..15
                        mol_type = other DNA
                        organism = synthetic construct
SEQUENCE: 9
tatgctgtac ttcga                                                    15

SEQ ID NO: 10           moltype = DNA  length = 15
FEATURE                 Location/Qualifiers
source                  1..15
                        mol_type = other DNA
                        organism = synthetic construct
SEQUENCE: 10
gaacgtgtct tctga                                                    15

SEQ ID NO: 11           moltype = DNA  length = 15
FEATURE                 Location/Qualifiers
source                  1..15
                        mol_type = other DNA
                        organism = synthetic construct
SEQUENCE: 11
tgaagtttgg agaca                                                    15

SEQ ID NO: 12           moltype = DNA  length = 15
FEATURE                 Location/Qualifiers
source                  1..15
                        mol_type = other DNA
                        organism = synthetic construct
SEQUENCE: 12
aattgcgtgg gagca                                                    15

SEQ ID NO: 13           moltype = DNA  length = 15
FEATURE                 Location/Qualifiers
source                  1..15
                        mol_type = other DNA
                        organism = synthetic construct
SEQUENCE: 13
ggcaagttgg gtcca                                                    15

SEQ ID NO: 14           moltype = DNA  length = 15
FEATURE                 Location/Qualifiers
source                  1..15
                        mol_type = other DNA
                        organism = synthetic construct
SEQUENCE: 14
acaagggtgt gttca                                                    15
```

-continued

```
SEQ ID NO: 15          moltype = DNA  length = 15
FEATURE                Location/Qualifiers
source                 1..15
                       mol_type = other DNA
                       organism = synthetic construct
SEQUENCE: 15
ttgtgactgg caata                                                          15

SEQ ID NO: 16          moltype = DNA  length = 15
FEATURE                Location/Qualifiers
source                 1..15
                       mol_type = other DNA
                       organism = synthetic construct
SEQUENCE: 16
ctcattgtga aggta                                                          15

SEQ ID NO: 17          moltype = DNA  length = 15
FEATURE                Location/Qualifiers
source                 1..15
                       mol_type = other DNA
                       organism = synthetic construct
SEQUENCE: 17
tgaagggttg accta                                                          15

SEQ ID NO: 18          moltype = DNA  length = 15
FEATURE                Location/Qualifiers
source                 1..15
                       mol_type = other DNA
                       organism = synthetic construct
SEQUENCE: 18
gcaatggtga agtta                                                          15

SEQ ID NO: 19          moltype = DNA  length = 15
FEATURE                Location/Qualifiers
source                 1..15
                       mol_type = other DNA
                       organism = synthetic construct
SEQUENCE: 19
atgcaggtag ttaag                                                          15

SEQ ID NO: 20          moltype = DNA  length = 15
FEATURE                Location/Qualifiers
source                 1..15
                       mol_type = other DNA
                       organism = synthetic construct
SEQUENCE: 20
cctgttgtca atgag                                                          15

SEQ ID NO: 21          moltype = DNA  length = 15
FEATURE                Location/Qualifiers
source                 1..15
                       mol_type = other DNA
                       organism = synthetic construct
SEQUENCE: 21
ctgtaccttg tgcag                                                          15

SEQ ID NO: 22          moltype = DNA  length = 15
FEATURE                Location/Qualifiers
source                 1..15
                       mol_type = other DNA
                       organism = synthetic construct
SEQUENCE: 22
cacggtttga attag                                                          15

SEQ ID NO: 23          moltype = DNA  length = 15
FEATURE                Location/Qualifiers
source                 1..15
                       mol_type = other DNA
                       organism = synthetic construct
SEQUENCE: 23
actgtcgtac gtagg                                                          15

SEQ ID NO: 24          moltype = DNA  length = 15
FEATURE                Location/Qualifiers
source                 1..15
                       mol_type = other DNA
                       organism = synthetic construct
SEQUENCE: 24
```

```
gcattggtca caggg                                                    15

SEQ ID NO: 25          moltype = DNA  length = 15
FEATURE                Location/Qualifiers
source                 1..15
                       mol_type = other DNA
                       organism = synthetic construct
SEQUENCE: 25
atacgtgtct ctcgg                                                    15

SEQ ID NO: 26          moltype = DNA  length = 15
FEATURE                Location/Qualifiers
source                 1..15
                       mol_type = other DNA
                       organism = synthetic construct
SEQUENCE: 26
tccaacatgt gttgg                                                    15

SEQ ID NO: 27          moltype = DNA  length = 15
FEATURE                Location/Qualifiers
source                 1..15
                       mol_type = other DNA
                       organism = synthetic construct
SEQUENCE: 27
tttgtcctcc tgacg                                                    15

SEQ ID NO: 28          moltype = DNA  length = 15
FEATURE                Location/Qualifiers
source                 1..15
                       mol_type = other DNA
                       organism = synthetic construct
SEQUENCE: 28
gcctgattgt cagcg                                                    15

SEQ ID NO: 29          moltype = DNA  length = 15
FEATURE                Location/Qualifiers
source                 1..15
                       mol_type = other DNA
                       organism = synthetic construct
SEQUENCE: 29
cgagagctgt ttccg                                                    15

SEQ ID NO: 30          moltype = DNA  length = 15
FEATURE                Location/Qualifiers
source                 1..15
                       mol_type = other DNA
                       organism = synthetic construct
SEQUENCE: 30
gacattgtac tttcg                                                    15

SEQ ID NO: 31          moltype = DNA  length = 15
FEATURE                Location/Qualifiers
source                 1..15
                       mol_type = other DNA
                       organism = synthetic construct
SEQUENCE: 31
gaatagttgc gaatg                                                    15

SEQ ID NO: 32          moltype = DNA  length = 15
FEATURE                Location/Qualifiers
source                 1..15
                       mol_type = other DNA
                       organism = synthetic construct
SEQUENCE: 32
aagcggattg aagtg                                                    15

SEQ ID NO: 33          moltype = DNA  length = 15
FEATURE                Location/Qualifiers
source                 1..15
                       mol_type = other DNA
                       organism = synthetic construct
SEQUENCE: 33
tattcgctgt acctg                                                    15

SEQ ID NO: 34          moltype = DNA  length = 15
FEATURE                Location/Qualifiers
source                 1..15
                       mol_type = other DNA
                       organism = synthetic construct
```

-continued

```
SEQUENCE: 34
ctcttcttcg ccttg                                                      15

SEQ ID NO: 35          moltype = DNA  length = 15
FEATURE                Location/Qualifiers
source                 1..15
                       mol_type = other DNA
                       organism = synthetic construct
SEQUENCE: 35
tatgtggttc ctaac                                                      15

SEQ ID NO: 36          moltype = DNA  length = 15
FEATURE                Location/Qualifiers
source                 1..15
                       mol_type = other DNA
                       organism = synthetic construct
SEQUENCE: 36
gaactcgtgg tggac                                                      15

SEQ ID NO: 37          moltype = DNA  length = 15
FEATURE                Location/Qualifiers
source                 1..15
                       mol_type = other DNA
                       organism = synthetic construct
SEQUENCE: 37
ttgttggttc aacac                                                      15

SEQ ID NO: 38          moltype = DNA  length = 15
FEATURE                Location/Qualifiers
source                 1..15
                       mol_type = other DNA
                       organism = synthetic construct
SEQUENCE: 38
agtagtattg gctac                                                      15

SEQ ID NO: 39          moltype = DNA  length = 15
FEATURE                Location/Qualifiers
source                 1..15
                       mol_type = other DNA
                       organism = synthetic construct
SEQUENCE: 39
gtcctgttcg atagc                                                      15

SEQ ID NO: 40          moltype = DNA  length = 15
FEATURE                Location/Qualifiers
source                 1..15
                       mol_type = other DNA
                       organism = synthetic construct
SEQUENCE: 40
tccttagtat gaggc                                                      15

SEQ ID NO: 41          moltype = DNA  length = 15
FEATURE                Location/Qualifiers
source                 1..15
                       mol_type = other DNA
                       organism = synthetic construct
SEQUENCE: 41
caatggttat gtcgc                                                      15

SEQ ID NO: 42          moltype = DNA  length = 15
FEATURE                Location/Qualifiers
source                 1..15
                       mol_type = other DNA
                       organism = synthetic construct
SEQUENCE: 42
catgtgtttc aatgc                                                      15

SEQ ID NO: 43          moltype = DNA  length = 15
FEATURE                Location/Qualifiers
source                 1..15
                       mol_type = other DNA
                       organism = synthetic construct
SEQUENCE: 43
ttcagggtct gtacc                                                      15

SEQ ID NO: 44          moltype = DNA  length = 15
FEATURE                Location/Qualifiers
source                 1..15
                       mol_type = other DNA
```

-continued

```
                        organism = synthetic construct
SEQUENCE: 44
gtgtgtgtcc aagcc                                                      15

SEQ ID NO: 45           moltype = DNA  length = 15
FEATURE                 Location/Qualifiers
source                  1..15
                        mol_type = other DNA
                        organism = synthetic construct
SEQUENCE: 45
aagtatgtgg gtccc                                                      15

SEQ ID NO: 46           moltype = DNA  length = 15
FEATURE                 Location/Qualifiers
source                  1..15
                        mol_type = other DNA
                        organism = synthetic construct
SEQUENCE: 46
atctatctgt tgtcc                                                      15

SEQ ID NO: 47           moltype = DNA  length = 15
FEATURE                 Location/Qualifiers
source                  1..15
                        mol_type = other DNA
                        organism = synthetic construct
SEQUENCE: 47
cgtatgttcc tgatc                                                      15

SEQ ID NO: 48           moltype = DNA  length = 15
FEATURE                 Location/Qualifiers
source                  1..15
                        mol_type = other DNA
                        organism = synthetic construct
SEQUENCE: 48
tgccacctgt ttgtc                                                      15

SEQ ID NO: 49           moltype = DNA  length = 15
FEATURE                 Location/Qualifiers
source                  1..15
                        mol_type = other DNA
                        organism = synthetic construct
SEQUENCE: 49
ccgtgtgttt cactc                                                      15

SEQ ID NO: 50           moltype = DNA  length = 15
FEATURE                 Location/Qualifiers
source                  1..15
                        mol_type = other DNA
                        organism = synthetic construct
SEQUENCE: 50
gcaggtctcc gtttc                                                      15

SEQ ID NO: 51           moltype = DNA  length = 15
FEATURE                 Location/Qualifiers
source                  1..15
                        mol_type = other DNA
                        organism = synthetic construct
SEQUENCE: 51
gcttaagttg gcaat                                                      15

SEQ ID NO: 52           moltype = DNA  length = 15
FEATURE                 Location/Qualifiers
source                  1..15
                        mol_type = other DNA
                        organism = synthetic construct
SEQUENCE: 52
gacgtgttct ccgat                                                      15

SEQ ID NO: 53           moltype = DNA  length = 15
FEATURE                 Location/Qualifiers
source                  1..15
                        mol_type = other DNA
                        organism = synthetic construct
SEQUENCE: 53
cgtctgcttc gtcat                                                      15

SEQ ID NO: 54           moltype = DNA  length = 15
FEATURE                 Location/Qualifiers
source                  1..15
```

```
                        mol_type = other DNA
                        organism = synthetic construct
SEQUENCE: 54
gcgtctcttg actat                                              15

SEQ ID NO: 55           moltype = DNA  length = 15
FEATURE                 Location/Qualifiers
source                  1..15
                        mol_type = other DNA
                        organism = synthetic construct
SEQUENCE: 55
ctcggcgttg caagt                                              15

SEQ ID NO: 56           moltype = DNA  length = 15
FEATURE                 Location/Qualifiers
source                  1..15
                        mol_type = other DNA
                        organism = synthetic construct
SEQUENCE: 56
atctcgctgc tcggt                                              15

SEQ ID NO: 57           moltype = DNA  length = 15
FEATURE                 Location/Qualifiers
source                  1..15
                        mol_type = other DNA
                        organism = synthetic construct
SEQUENCE: 57
tacgatttgc agcgt                                              15

SEQ ID NO: 58           moltype = DNA  length = 15
FEATURE                 Location/Qualifiers
source                  1..15
                        mol_type = other DNA
                        organism = synthetic construct
SEQUENCE: 58
acctgcgtac tttgt                                              15

SEQ ID NO: 59           moltype = DNA  length = 15
FEATURE                 Location/Qualifiers
source                  1..15
                        mol_type = other DNA
                        organism = synthetic construct
SEQUENCE: 59
tgaacgattg gtact                                              15

SEQ ID NO: 60           moltype = DNA  length = 15
FEATURE                 Location/Qualifiers
source                  1..15
                        mol_type = other DNA
                        organism = synthetic construct
SEQUENCE: 60
cgatagttga gagct                                              15

SEQ ID NO: 61           moltype = DNA  length = 15
FEATURE                 Location/Qualifiers
source                  1..15
                        mol_type = other DNA
                        organism = synthetic construct
SEQUENCE: 61
taagtgttgg aacct                                              15

SEQ ID NO: 62           moltype = DNA  length = 15
FEATURE                 Location/Qualifiers
source                  1..15
                        mol_type = other DNA
                        organism = synthetic construct
SEQUENCE: 62
acatgggtga agtct                                              15

SEQ ID NO: 63           moltype = DNA  length = 15
FEATURE                 Location/Qualifiers
source                  1..15
                        mol_type = other DNA
                        organism = synthetic construct
SEQUENCE: 63
ctaagattgg gcatt                                              15

SEQ ID NO: 64           moltype = DNA  length = 15
FEATURE                 Location/Qualifiers
```

-continued

```
source                1..15
                      mol_type = other DNA
                      organism = synthetic construct
SEQUENCE: 64
acagcgttaa gtgtt                                                    15

SEQ ID NO: 65         moltype = DNA  length = 15
FEATURE               Location/Qualifiers
source                1..15
                      mol_type = other DNA
                      organism = synthetic construct
SEQUENCE: 65
tgaacactgt gtctt                                                    15

SEQ ID NO: 66         moltype = DNA  length = 15
FEATURE               Location/Qualifiers
source                1..15
                      mol_type = other DNA
                      organism = synthetic construct
SEQUENCE: 66
aagagagtga gcttt                                                    15

SEQ ID NO: 67         moltype = DNA  length = 15
FEATURE               Location/Qualifiers
source                1..15
                      mol_type = other DNA
                      organism = synthetic construct
modified_base         8
                      mod_base = OTHER
                      note = Amine reactive thymine
SEQUENCE: 67
acagaggttt gaagt                                                    15

SEQ ID NO: 68         moltype = AA  length = 10
FEATURE               Location/Qualifiers
source                1..10
                      mol_type = protein
                      organism = synthetic construct
SEQUENCE: 68
MEAGGFLDSL                                                          10

SEQ ID NO: 69         moltype = AA  length = 10
FEATURE               Location/Qualifiers
source                1..10
                      mol_type = protein
                      organism = synthetic construct
SEQUENCE: 69
MESSQHVDSI                                                          10

SEQ ID NO: 70         moltype = AA  length = 10
FEATURE               Location/Qualifiers
source                1..10
                      mol_type = protein
                      organism = synthetic construct
SEQUENCE: 70
MIASQFLSAL                                                          10

SEQ ID NO: 71         moltype = AA  length = 10
FEATURE               Location/Qualifiers
source                1..10
                      mol_type = protein
                      organism = synthetic construct
SEQUENCE: 71
METLSQDSLL                                                          10

SEQ ID NO: 72         moltype = AA  length = 10
FEATURE               Location/Qualifiers
source                1..10
                      mol_type = protein
                      organism = synthetic construct
SEQUENCE: 72
METVVQDSVV                                                          10

SEQ ID NO: 73         moltype = AA  length = 10
FEATURE               Location/Qualifiers
source                1..10
                      mol_type = protein
                      organism = synthetic construct
SEQUENCE: 73
```

-continued

```
METLLGVSLV                                                        10

SEQ ID NO: 74          moltype = DNA  length = 18
FEATURE                Location/Qualifiers
source                 1..18
                       mol_type = other DNA
                       organism = synthetic construct
SEQUENCE: 74
gaagacggca tacgagat                                               18

SEQ ID NO: 75          moltype = DNA  length = 45
FEATURE                Location/Qualifiers
source                 1..45
                       mol_type = other DNA
                       organism = synthetic construct
modified_base          1
                       mod_base = OTHER
                       note = 5' phosphorylated nucleotide
modified_base          8
                       mod_base = OTHER
                       note = Formylindole modified nucleotide
SEQUENCE: 75
atgagtgnag ggaaatagct tctggtcgaa ctagttgttc gtcaa                 45

SEQ ID NO: 76          moltype = DNA  length = 75
FEATURE                Location/Qualifiers
source                 1..75
                       mol_type = other DNA
                       organism = synthetic construct
SEQUENCE: 76
attgagctgt cgtaaatgag tgtagggaaa tagcttctgg tcgaactagt tgttcgtcaa  60
tctcacgttt ggaga                                                  75

SEQ ID NO: 77          moltype = DNA  length = 15
FEATURE                Location/Qualifiers
source                 1..15
                       mol_type = other DNA
                       organism = synthetic construct
modified_base          1
                       mod_base = OTHER
                       note = 5' phosphorylated nucleotide
SEQUENCE: 77
tctcacgttt ggaga                                                  15

SEQ ID NO: 78          moltype = DNA  length = 30
FEATURE                Location/Qualifiers
source                 1..30
                       mol_type = other DNA
                       organism = synthetic construct
SEQUENCE: 78
tttcccttca ctcatttacg acagctcaat                                  30

SEQ ID NO: 79          moltype = DNA  length = 30
FEATURE                Location/Qualifiers
source                 1..30
                       mol_type = other DNA
                       organism = synthetic construct
SEQUENCE: 79
tctccaaacg tgagattgac gaacaactag                                  30

SEQ ID NO: 80          moltype = DNA  length = 60
FEATURE                Location/Qualifiers
source                 1..60
                       mol_type = other DNA
                       organism = synthetic construct
SEQUENCE: 80
attgagctgt cgtaaatgag tgtagggaaa tagcttctgg tcgaactagt tgttcgtcaa  60

SEQ ID NO: 81          moltype = DNA  length = 60
FEATURE                Location/Qualifiers
source                 1..60
                       mol_type = other DNA
                       organism = synthetic construct
SEQUENCE: 81
atgagtgtag ggaaatagct tctggtcgaa ctagttgttc gtcaatctca cgtttggaga  60

SEQ ID NO: 82          moltype = DNA  length = 25
FEATURE                Location/Qualifiers
source                 1..25
```

```
                          mol_type = other DNA
                          organism = synthetic construct
SEQUENCE: 82
tctccaaacg tgagattgac gaaca                                        25

SEQ ID NO: 83             moltype = DNA  length = 25
FEATURE                   Location/Qualifiers
source                    1..25
                          mol_type = other DNA
                          organism = synthetic construct
SEQUENCE: 83
attgagctgt cgtaaatgag tgtag                                        25

SEQ ID NO: 84             moltype = DNA  length = 30
FEATURE                   Location/Qualifiers
source                    1..30
                          mol_type = other DNA
                          organism = synthetic construct
SEQUENCE: 84
cgcagcttgt ctggaattga gctgtcgtaa                                   30

SEQ ID NO: 85             moltype = DNA  length = 30
FEATURE                   Location/Qualifiers
source                    1..30
                          mol_type = other DNA
                          organism = synthetic construct
modified_base             1
                          mod_base = OTHER
                          note = 5' phosphorylated nucleotide
SEQUENCE: 85
tctcacgttt ggagatatgc tgtacttcga                                   30

SEQ ID NO: 86             moltype = DNA  length = 25
FEATURE                   Location/Qualifiers
source                    1..25
                          mol_type = other DNA
                          organism = synthetic construct
SEQUENCE: 86
tcgaagtaca gcatatctcc aaacg                                        25

SEQ ID NO: 87             moltype = DNA  length = 25
FEATURE                   Location/Qualifiers
source                    1..25
                          mol_type = other DNA
                          organism = synthetic construct
SEQUENCE: 87
cgcagcttgt ctggaattga gctgt                                        25

SEQ ID NO: 88             moltype = DNA  length = 105
FEATURE                   Location/Qualifiers
source                    1..105
                          mol_type = other DNA
                          organism = synthetic construct
SEQUENCE: 88
cgcagcttgt ctggaattga gctgtcgtaa atgagtgtag ggaaatagct tctggtcgaa  60
ctagttgttc gtcaatctca cgtttggaga tatgctgtac ttcga                  105

SEQ ID NO: 89             moltype = DNA  length = 75
FEATURE                   Location/Qualifiers
source                    1..75
                          mol_type = other DNA
                          organism = synthetic construct
SEQUENCE: 89
cgcagcttgt ctggaattga gctgtcgtaa atgagtgtag ggaaatagct tctggtcgaa  60
ctagttgttc gtcaa                                                   75

SEQ ID NO: 90             moltype = DNA  length = 75
FEATURE                   Location/Qualifiers
source                    1..75
                          mol_type = other DNA
                          organism = synthetic construct
SEQUENCE: 90
atgagtgtag ggaaatagct tctggtcgaa ctagttgttc gtcaatctca cgtttggaga  60
tatgctgtac ttcga                                                   75

SEQ ID NO: 91             moltype = DNA  length = 45
FEATURE                   Location/Qualifiers
source                    1..45
                          mol_type = other DNA
```

-continued

```
                        organism = synthetic construct
modified_base           1
                        mod_base = OTHER
                        note = 5' phosphorylated nucleotide
modified_base           8
                        mod_base = OTHER
                        note = Formylindole modified nucleotide
SEQUENCE: 91
gaacgtgnct tctgatgaag tttggagaca aattgcgtgg gagca                   45

SEQ ID NO: 92           moltype = DNA  length = 75
FEATURE                 Location/Qualifiers
source                  1..75
                        mol_type = other DNA
                        organism = synthetic construct
SEQUENCE: 92
ggcaagttgg gtccagaacg tgtcttctga tgaagtttgg agacaaattg cgtgggagca  60
acaagggtgt gttca                                                    75

SEQ ID NO: 93           moltype = DNA  length = 15
FEATURE                 Location/Qualifiers
source                  1..15
                        mol_type = other DNA
                        organism = synthetic construct
modified_base           1
                        mod_base = OTHER
                        note = 5' phosphorylated nucleotide
SEQUENCE: 93
acaagggtgt gttca                                                    15

SEQ ID NO: 94           moltype = DNA  length = 30
FEATURE                 Location/Qualifiers
source                  1..30
                        mol_type = other DNA
                        organism = synthetic construct
SEQUENCE: 94
tcagaagtca cgttctggac ccaacttgcc                                    30

SEQ ID NO: 95           moltype = DNA  length = 30
FEATURE                 Location/Qualifiers
source                  1..30
                        mol_type = other DNA
                        organism = synthetic construct
SEQUENCE: 95
tgaacacacc cttgttgctc ccacgcaatt                                    30

SEQ ID NO: 96           moltype = DNA  length = 25
FEATURE                 Location/Qualifiers
source                  1..25
                        mol_type = other DNA
                        organism = synthetic construct
SEQUENCE: 96
tgaacacacc cttgttgctc ccacg                                         25

SEQ ID NO: 97           moltype = DNA  length = 25
FEATURE                 Location/Qualifiers
source                  1..25
                        mol_type = other DNA
                        organism = synthetic construct
SEQUENCE: 97
ggcaagttgg gtccagaacg tgtct                                         25

SEQ ID NO: 98           moltype = DNA  length = 30
FEATURE                 Location/Qualifiers
source                  1..30
                        mol_type = other DNA
                        organism = synthetic construct
SEQUENCE: 98
ttgtgactgg caataggcaa gttgggtcca                                    30

SEQ ID NO: 99           moltype = DNA  length = 30
FEATURE                 Location/Qualifiers
source                  1..30
                        mol_type = other DNA
                        organism = synthetic construct
modified_base           1
                        mod_base = OTHER
                        note = 5' phosphorylated nucleotide
SEQUENCE: 99
```

-continued

```
acaagggtgt gttcactcat tgtgaaggta                                    30

SEQ ID NO: 100         moltype = DNA  length = 25
FEATURE                Location/Qualifiers
source                 1..25
                       mol_type = other DNA
                       organism = synthetic construct
SEQUENCE: 100
taccttcaca atgagtgaac acacc                                         25

SEQ ID NO: 101         moltype = DNA  length = 25
FEATURE                Location/Qualifiers
source                 1..25
                       mol_type = other DNA
                       organism = synthetic construct
SEQUENCE: 101
ttgtgactgg caataggcaa gttgg                                         25

SEQ ID NO: 102         moltype = DNA  length = 105
FEATURE                Location/Qualifiers
source                 1..105
                       mol_type = other DNA
                       organism = synthetic construct
SEQUENCE: 102
ttgtgactgg caataggcaa gttgggtcca gaacgtgtct tctgatgaag tttggagaca  60
aattgcgtgg gagcaacaag ggtgtgttca ctcattgtga aggta                  105

SEQ ID NO: 103         moltype = DNA  length = 75
FEATURE                Location/Qualifiers
source                 1..75
                       mol_type = other DNA
                       organism = synthetic construct
SEQUENCE: 103
ttgtgactgg caataggcaa gttgggtcca gaacgtgtct tctgatgaag tttggagaca  60
aattgcgtgg gagca                                                    75

SEQ ID NO: 104         moltype = DNA  length = 75
FEATURE                Location/Qualifiers
source                 1..75
                       mol_type = other DNA
                       organism = synthetic construct
SEQUENCE: 104
gaacgtgtct tctgatgaag tttggagaca aattgcgtgg gagcaacaag ggtgtgttca  60
ctcattgtga aggta                                                    75

SEQ ID NO: 105         moltype = DNA  length = 22
FEATURE                Location/Qualifiers
source                 1..22
                       mol_type = other DNA
                       organism = synthetic construct
SEQUENCE: 105
tgactggcaa taggcaagtt gg                                            22

SEQ ID NO: 106         moltype = DNA  length = 25
FEATURE                Location/Qualifiers
source                 1..25
                       mol_type = other DNA
                       organism = synthetic construct
SEQUENCE: 106
tgctcccacg caatttgtct ccaaa                                         25

SEQ ID NO: 107         moltype = DNA  length = 25
FEATURE                Location/Qualifiers
source                 1..25
                       mol_type = other DNA
                       organism = synthetic construct
SEQUENCE: 107
gaacgtgtct tctgatgaag tttgg                                         25

SEQ ID NO: 108         moltype = DNA  length = 45
FEATURE                Location/Qualifiers
source                 1..45
                       mol_type = other DNA
                       organism = synthetic construct
modified_base          1
                       mod_base = OTHER
                       note = 5' phosphorylated nucleotide
modified_base          8
                       mod_base = OTHER
```

-continued

```
                        note = Formylindole modified nucleotide
SEQUENCE: 108
tgaagggntg acctagcaat ggtgaagtta atgcaggtag ttaag                     45

SEQ ID NO: 109          moltype = DNA  length = 75
FEATURE                 Location/Qualifiers
source                  1..75
                        mol_type = other DNA
                        organism = synthetic construct
SEQUENCE: 109
cctgttgtca atgagtgaag ggttgaccta gcaatggtga agttaatgca ggtagttaag  60
ctgtaccttg tgcag                                                    75

SEQ ID NO: 110          moltype = DNA  length = 15
FEATURE                 Location/Qualifiers
source                  1..15
                        mol_type = other DNA
                        organism = synthetic construct
modified_base           1
                        mod_base = OTHER
                        note = 5' phosphorylated nucleotide
SEQUENCE: 110
ctgtaccttg tgcag                                                    15

SEQ ID NO: 111          moltype = DNA  length = 30
FEATURE                 Location/Qualifiers
source                  1..30
                        mol_type = other DNA
                        organism = synthetic construct
SEQUENCE: 111
taggtcatcc cttcactcat tgacaacagg                                    30

SEQ ID NO: 112          moltype = DNA  length = 30
FEATURE                 Location/Qualifiers
source                  1..30
                        mol_type = other DNA
                        organism = synthetic construct
SEQUENCE: 112
ctgcacaagg tacagcttaa ctacctgcat                                    30

SEQ ID NO: 113          moltype = DNA  length = 15
FEATURE                 Location/Qualifiers
source                  1..15
                        mol_type = other DNA
                        organism = synthetic construct
SEQUENCE: 113
ctgcacaagg tacag                                                    15

SEQ ID NO: 114          moltype = DNA  length = 30
FEATURE                 Location/Qualifiers
source                  1..30
                        mol_type = other DNA
                        organism = synthetic construct
SEQUENCE: 114
cacggtttga attagcctgt tgtcaatgag                                    30

SEQ ID NO: 115          moltype = DNA  length = 30
FEATURE                 Location/Qualifiers
source                  1..30
                        mol_type = other DNA
                        organism = synthetic construct
SEQUENCE: 115
ctgtaccttg tgcagactgt cgtacgtagg                                    30

SEQ ID NO: 116          moltype = DNA  length = 25
FEATURE                 Location/Qualifiers
source                  1..25
                        mol_type = other DNA
                        organism = synthetic construct
SEQUENCE: 116
cctacgtacg acagtctgca caagg                                         25

SEQ ID NO: 117          moltype = DNA  length = 25
FEATURE                 Location/Qualifiers
source                  1..25
                        mol_type = other DNA
                        organism = synthetic construct
SEQUENCE: 117
cacggtttga attagcctgt tgtca                                         25
```

-continued

```
SEQ ID NO: 118         moltype = DNA  length = 105
FEATURE                Location/Qualifiers
source                 1..105
                       mol_type = other DNA
                       organism = synthetic construct
SEQUENCE: 118
cacggtttga attagcctgt tgtcaatgag tgaagggttg acctagcaat ggtgaagtta  60
atgcaggtag ttaagctgta ccttgtgcag actgtcgtac gtagg                  105

SEQ ID NO: 119         moltype = DNA  length = 75
FEATURE                Location/Qualifiers
source                 1..75
                       mol_type = other DNA
                       organism = synthetic construct
SEQUENCE: 119
cacggtttga attagcctgt tgtcaatgag tgaagggttg acctagcaat ggtgaagtta  60
atgcaggtag ttaag                                                   75

SEQ ID NO: 120         moltype = DNA  length = 75
FEATURE                Location/Qualifiers
source                 1..75
                       mol_type = other DNA
                       organism = synthetic construct
SEQUENCE: 120
tgaagggttg acctagcaat ggtgaagtta atgcaggtag ttaagctgta ccttgtgcag  60
actgtcgtac gtagg                                                   75

SEQ ID NO: 121         moltype = DNA  length = 25
FEATURE                Location/Qualifiers
source                 1..25
                       mol_type = other DNA
                       organism = synthetic construct
SEQUENCE: 121
cttaactacc tgcattaact tcacc                                        25

SEQ ID NO: 122         moltype = DNA  length = 25
FEATURE                Location/Qualifiers
source                 1..25
                       mol_type = other DNA
                       organism = synthetic construct
SEQUENCE: 122
tgaagggttg acctagcaat ggtga                                        25

SEQ ID NO: 123         moltype = DNA  length = 22
FEATURE                Location/Qualifiers
source                 1..22
                       mol_type = other DNA
                       organism = synthetic construct
SEQUENCE: 123
atgcatcgat cgatcgatcg at                                           22

SEQ ID NO: 124         moltype = DNA  length = 15
FEATURE                Location/Qualifiers
source                 1..15
                       mol_type = other DNA
                       organism = synthetic construct
modified_base          1
                       mod_base = OTHER
                       note = Tetrachlorofluorescein modified nucleotide
SEQUENCE: 124
taacttcacc attgc                                                   15
```